(12) United States Patent
Phan

(10) Patent No.: US 10,066,209 B2
(45) Date of Patent: Sep. 4, 2018

(54) ISOLATION AND CULTIVATION OF STEM/PROGENITOR CELLS FROM THE AMNIOTIC MEMBRANE OF UMBILICAL CORD AND USES OF CELLS DIFFERENTIATED THEREFROM

(71) Applicant: CELLRESEARCH CORPORATION PTE LTD, Singapore (SG)

(72) Inventor: Toan-Thang Phan, Singapore (SG)

(73) Assignee: CELLRESEARCH CORPORATION PTE LTD., Singapore (SG)

( * ) Notice: Subject to any disclaimer, the term of this patent is extended or adjusted under 35 U.S.C. 154(b) by 117 days.

(21) Appl. No.: 14/715,342

(22) Filed: May 18, 2015

(65) Prior Publication Data

US 2016/0102292 A1 Apr. 14, 2016

Related U.S. Application Data

(62) Division of application No. 13/652,371, filed on Oct. 15, 2012, now Pat. No. 9,040,299, which is a division of application No. 12/091,018, filed as application No. PCT/SG2006/000301 on Oct. 11, 2006, now Pat. No. 8,287,854.

(60) Provisional application No. 60/729,172, filed on Oct. 21, 2005.

(51) Int. Cl.
| | |
|---|---|
| *C12N 5/077* | (2010.01) |
| *A61L 27/18* | (2006.01) |
| *A61L 27/36* | (2006.01) |
| *A61L 27/38* | (2006.01) |
| *A61L 27/56* | (2006.01) |
| *A61L 27/60* | (2006.01) |
| *C12N 5/073* | (2010.01) |
| *C12N 5/071* | (2010.01) |
| *C12N 5/0775* | (2010.01) |
| *A61K 35/32* | (2015.01) |

(52) U.S. Cl.
CPC ............ *C12N 5/0655* (2013.01); *A61K 35/32* (2013.01); *A61L 27/18* (2013.01); *A61L 27/3633* (2013.01); *A61L 27/3804* (2013.01); *A61L 27/3839* (2013.01); *A61L 27/56* (2013.01); *A61L 27/60* (2013.01); *C12N 5/0605* (2013.01); *C12N 5/0629* (2013.01); *C12N 5/0668* (2013.01); *C12N 5/0676* (2013.01); *C12N 5/0698* (2013.01); *C12N 2501/11* (2013.01); *C12N 2501/115* (2013.01); *C12N 2502/094* (2013.01); *C12N 2502/1323* (2013.01); *C12N 2506/02* (2013.01); *C12N 2506/1369* (2013.01); *C12N 2533/54* (2013.01)

(58) Field of Classification Search
CPC .................................................. C12N 5/0655
See application file for complete search history.

(56) References Cited

U.S. PATENT DOCUMENTS

| | | | |
|---|---|---|---|
| 5,919,702 | A | 7/1999 | Purchio et al. |
| 6,231,879 | B1 | 5/2001 | Li et al. |
| 6,479,875 | B1 | 11/2002 | Gonzalez |
| 2004/0136967 | A1 | 7/2004 | Weiss et al. |

FOREIGN PATENT DOCUMENTS

| | | |
|---|---|---|
| EP | 1314440 A2 | 5/2003 |
| WO | 9602259 A1 | 2/1996 |
| WO | 9623003 A1 | 8/1996 |
| WO | 9830679 A1 | 7/1998 |
| WO | 0073421 A2 | 12/2000 |
| WO | 0115755 A2 | 3/2001 |
| WO | 03089619 A2 | 10/2003 |
| WO | 2006019357 A1 | 2/2006 |

OTHER PUBLICATIONS

Kim et al. (2007, Cloning and Stem Cell, vol. 9(4), pp. 581-594).*
Pittenger et al., 1999, Science, vol. 284, pp. 143-147.*
The Examination Report issued by the EPO in EP 06799864.1 dated Jan. 11, 2016.
Cancedda et al., Tissue engineering and cell therapy of cartilage and bone. Matrix Biol. Mar. 2003;22(1):81-91.
Sanmano et al., Engraftment of umbilical cord epithelial cells in athymic mice: in an attempt to improve reconstructed skin equivalents used as epithelial composite. J Dermatol Sci. Jan. 2005;37(1):29-39.
Office Action issued by SIPO in parallel Chinese application No. 203104895285 dated Nov. 18, 2015—Engl lang transl only.
Miki et al., Stem Cell Chacterisitics of Amniotic Epithelial Cells. Stem Cells. Nov.-Dec. 2005;23(10):1549-1559.
Abe et al., Peripheral Blood Fibrocytes: Differentiation Pathway and Migration to Wound Sites. J Immunol. Jun. 15, 2001;166(12)7556-7562.
Amit et al., Human Feeder Layers for Human Embryonic Stem Cells. Biol Reprod. Jun. 2003;68(6):2150-2156.
Anderson et al., Amniotic membrane transplantation for partial limbal stem cell deficiency. Br J Ophthalmol. May 2001;85(5):567-575.
Bieback et al., Critical Parameters for the Isolation of Mesenchymal Stem Cells from Umbilical Cord Blood. Stem Cells. 2004;22(4):625-634.
Campagnoli et al., Identification of mesenchymal stem/progenitor cells in human first-trimester fetal blood, liver, and bone marrow. Blood. Oct. 15, 2001;98(8):2396-2402.
Covas et al., Isolation and culture of umbilical vein mesenchymal stem cells. Braz J Med Biol Res. Sep. 2003;36(9):1179-1183.
Dice, Cellular and Molecular Mechanisms of Aging. Physiol Rev. Jan. 1993;73(1):149-159.
Draper et al., Culture and characterization of human embryonic stem cell lines. Stem Cells Dev. Aug. 2004;13(4):325-336.

(Continued)

*Primary Examiner* — Thaian N Ton
*Assistant Examiner* — David A. Montanari
(74) *Attorney, Agent, or Firm* — Acuity Law Group, PC; Michael A. Whittaker

(57) ABSTRACT

The present invention relates to the generation of a chondrocyte using mesenchymal stem/progenitor cells obtained from the amniotic membrane of umbilical cord and therapeutic uses of such chondrocytes.

4 Claims, 111 Drawing Sheets

(56) References Cited

OTHER PUBLICATIONS

Endres et al., Osteogenic induction of human bone marrow-derived mesenchymal progenitor cells in novel synthetic polymer-hydrogel matrices. Tissue Eng. Aug. 2003;9(4):689-702.

Erices et al., Mesenchymal progenitor cells in human umbilical cord blood. Br J Haematol. Apr. 2000;109(1):235-242.

Grueterich et al., Ex vivo expansion of limbal epithelial stem cells: amniotic membrane serving as a stem cell niche. Sury Ophthalmol. Nov.-Dec. 2003;48(6):631-646.

Harris and Cooper, Comparison of bone graft matrices for human mesenchymal stem cell-directed osteogenesis. J Biomed Mater Res A. Mar. 15, 2004;68(4):747-755.

Jones et al., A small-scale method for the isolation of insulin-containing secretory granules from islets of Langerhans. Anal Biochem. Oct. 1987;166(1):142-149.

Mareschi et al., Isolation of Human Mesenchymal Stem Cells: Bone Marrow Versus Umbilical Cord Blood. Haematologica. Oct. 2001;86(10):1099-1100.

Mitchell et al., Matrix Cells from Wharton's Jelly Form Neurons and Glia. Stem Cells. 2003;21(1):50-60.

Moran et al., Characterization of polylactic acid-polyglycolic acid composites for cartilage tissue engineering. Tissue Eng. Feb. 2003;9(1):63-70.

Niwa et al., Quantitative expression of Oct-3/4 defines differentiation, dedifferentiation or self-renewal of ES cells. Nat Genet. Apr. 2000;24(4):372-376.

Park et al., Bmi1, stem cells, and senescence regulation. J Clin Invest. Jan. 2004;113(2):175-179.

Paul et al., Stem cells: hype or hope? Drug Discov Today. Mar. 1, 2002;7(5):295-302.

Quan et al., Circulating fibrocytes: collagen-secreting cells of the peripheral blood. Int J Biochem Cell Biol. Apr. 2004;36(4):598-606.

Romanov et al., Searching for Alternative Sources of Postnatal Human Mesenchymal Stem Cells: Candidate MSC-Like Cells from Umbilical Cord. Stem Cells. 2003;21(1)105-110.

Smith, Embryo-Derived Stem Cells: Of Mice and Men. Annu Rev Cell Dev Biol. 2001;17:435-462.

Studeny et al., Mesenchymal Stem Cells: Potential Precursors for Tumor Stroma and Targeted-Delivery Vehicles for Anticancer Agents. J Natl Cancer Inst. Nov. 3, 2004;96(21):1593-1603.

Tan and Desai, Microfluidic patterning of cells in extracellular matrix biopolymers: effects of channel size, cell type, and matrix composition on pattern integrity. Tissue Eng. Apr. 2003;9(2):255-267.

Timper et al., Human adipose tissue-derived mesenchymal stem cells differentiate into insulin, somatostatin, and glucagon expressing cells. Biochem Biophys Res Commun. Mar. 24, 2006;341(4):1135-1140.

\* cited by examiner

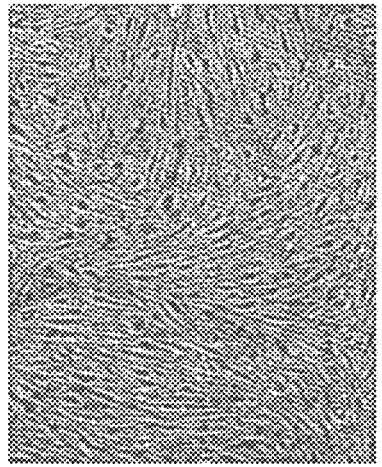
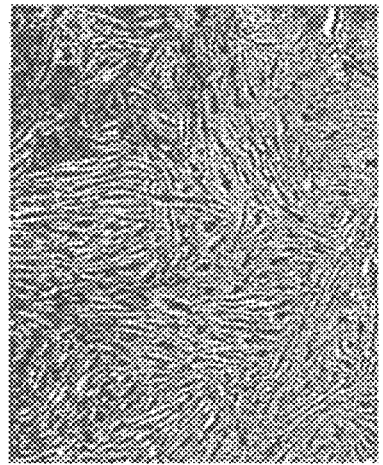
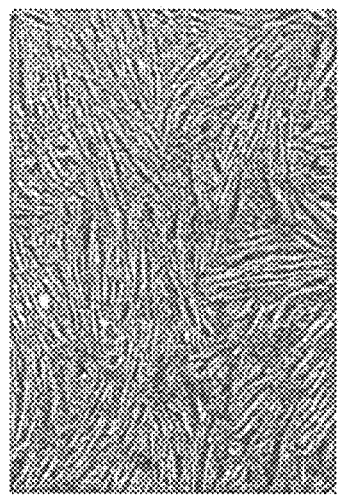
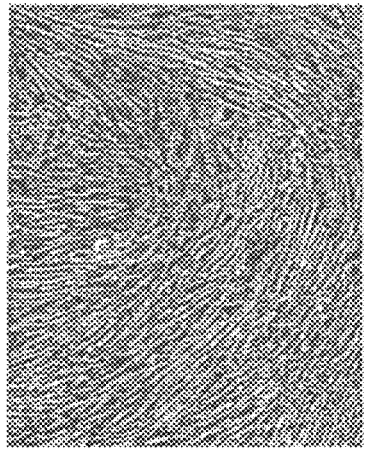

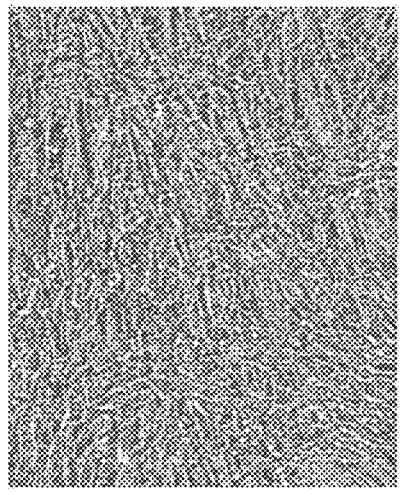
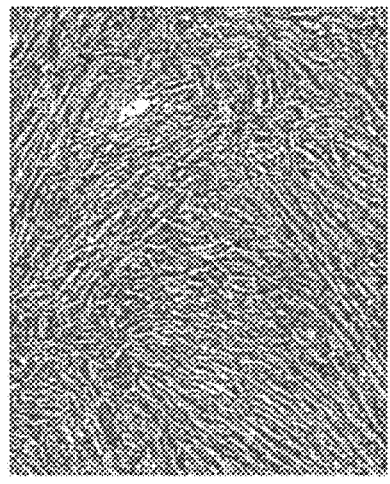
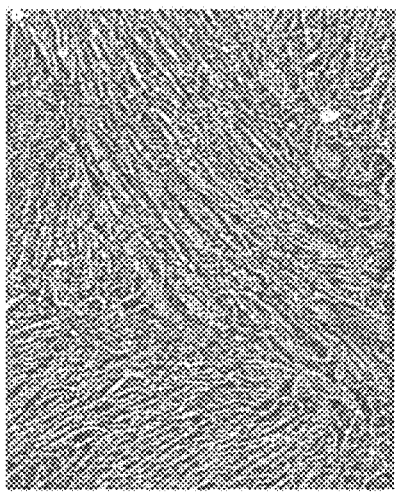
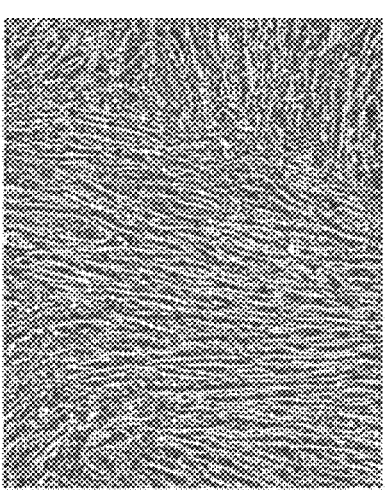

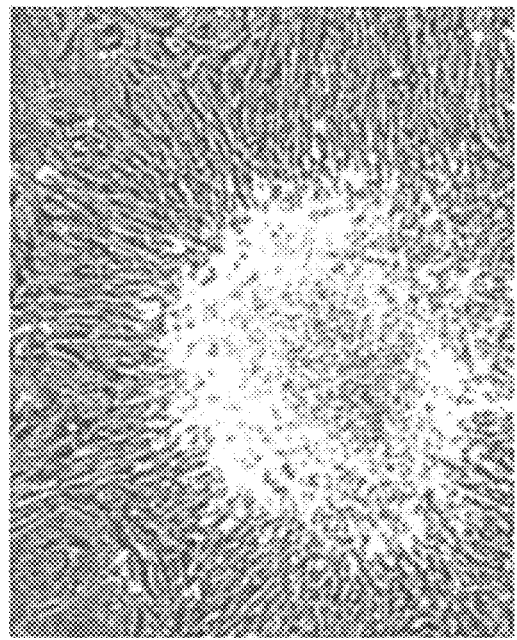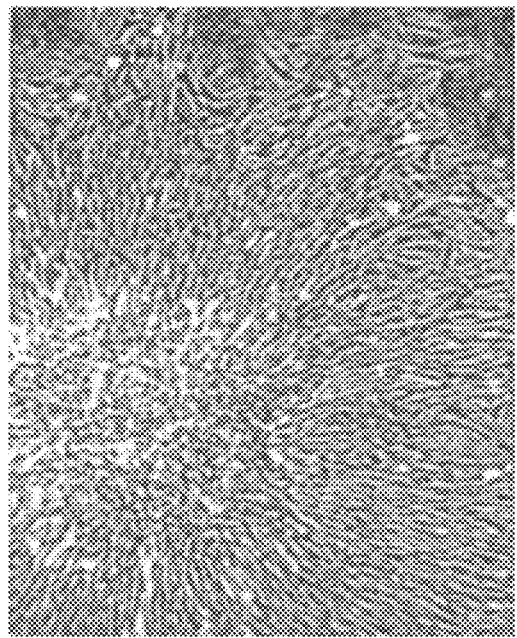
FIG. 6 Colony formation of umbilical cord mesenchymal stem cells cultured in non-feeder layer condition in DMEM/10%FCS. Day 3, Day 7.

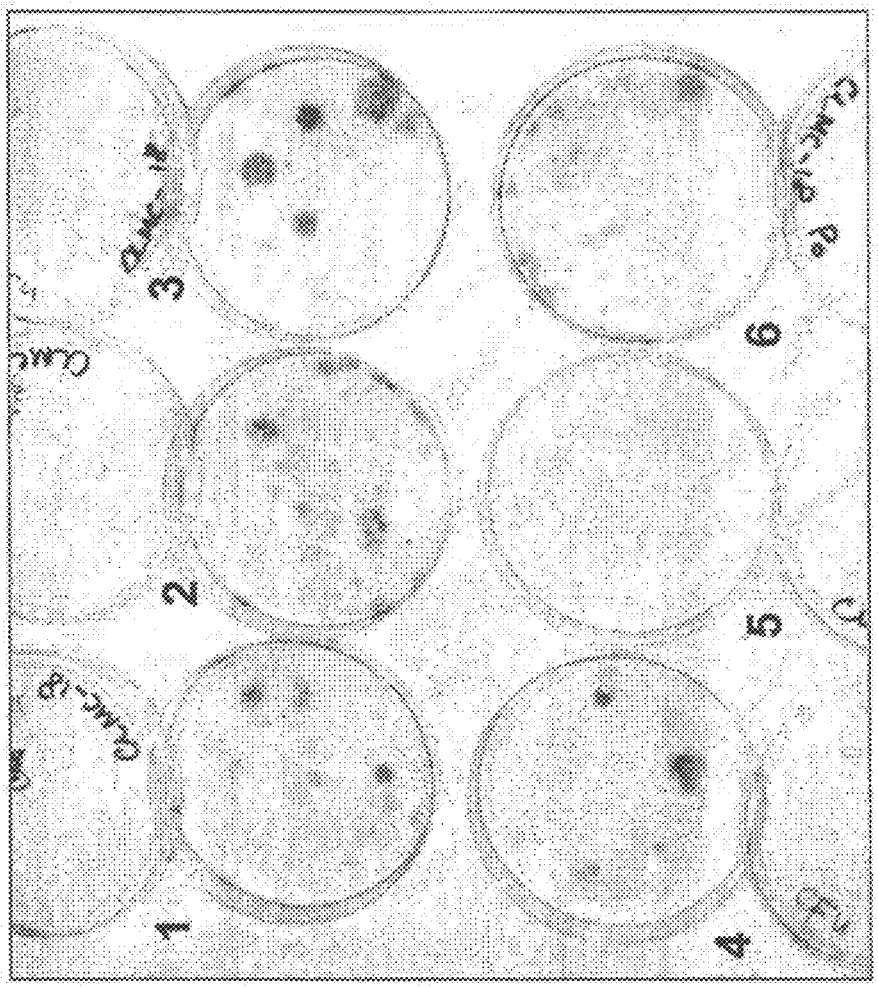
Fig. 9.1a: Oct-4 expression in UCMC colonies (Dish #5 is negative staining)

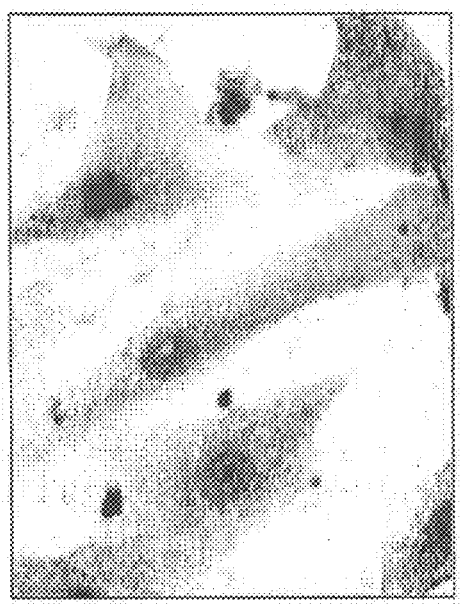
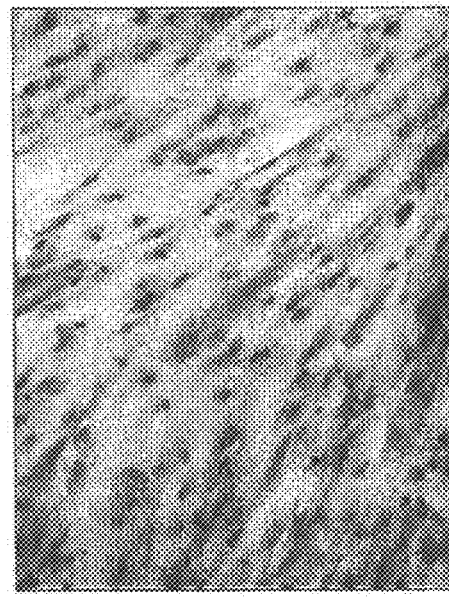
Fig. 9.1b: Oct-4 expression in UCMC cells

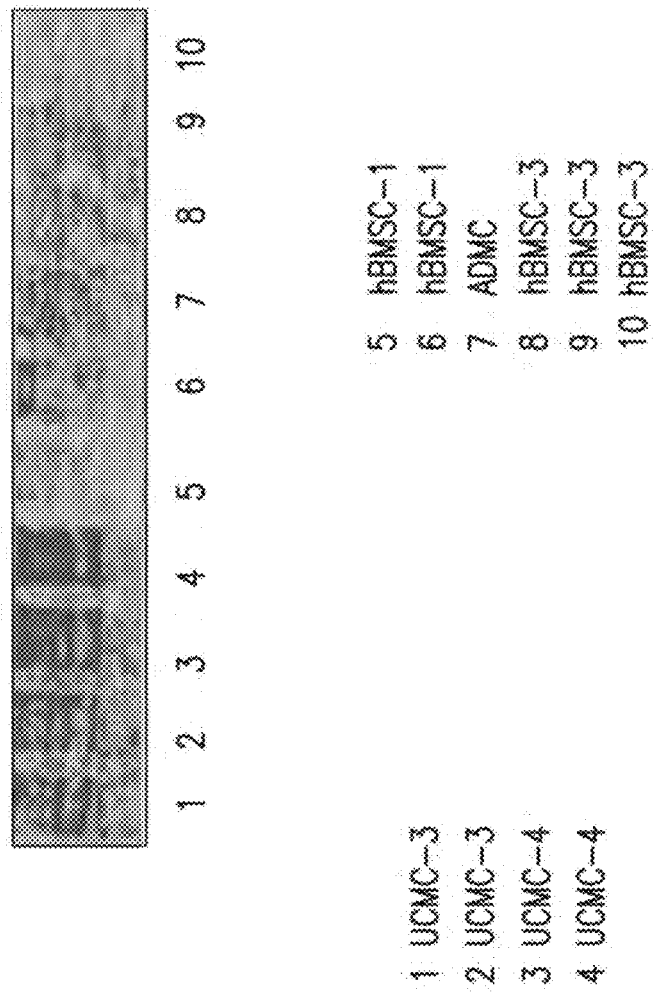

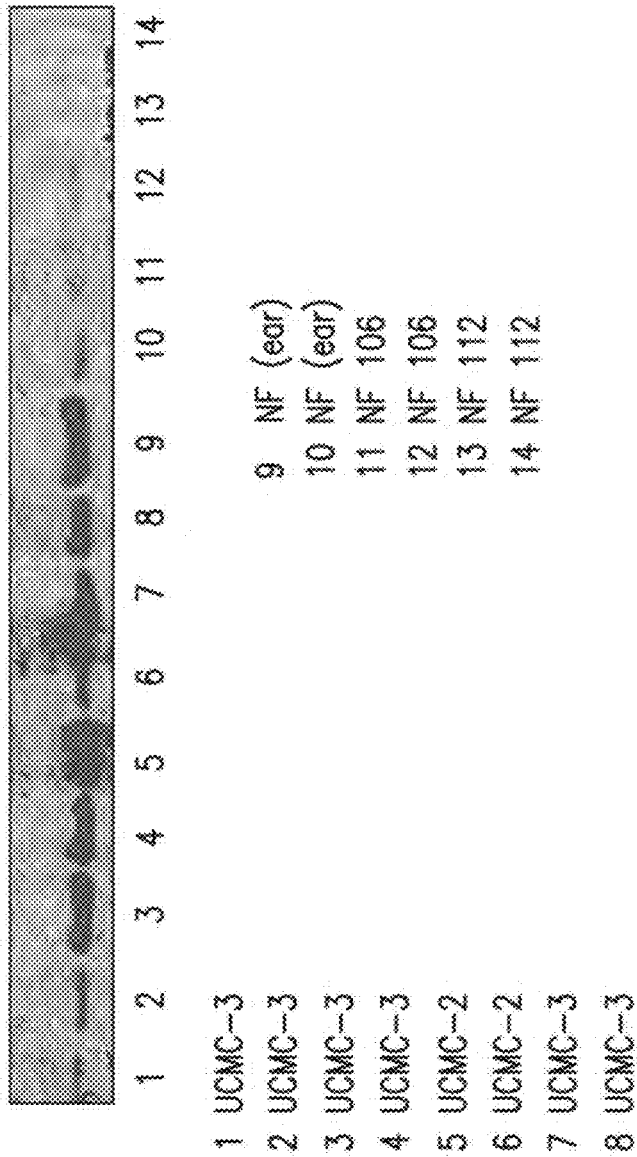

Expression of Fibronectin in Umbilical Cord Mesenchymal Stem Cells (UCMC)

Expression of Stem cell marker Bmi-1 in Umbilical Cord Mesenchymal Stem Cells and Epithelial Stem Cells 1. UCMC-3,
2. UCMC-16
3. UCMC-15
4. UCMC-14
5. UCMC-17
6. UCMC-10
7. NF2
8. hBMSC-3
9. hBMSC-2

Expression of Leukemia Inhibitory Factor (LIF) in Umbilical Cord Mesenchymal Stem Cells and Epithelial Stem Cells (cell culture conditioned media)

1. UCMC-14,
2. UCMC-14
3. UCMC-15
4. UCMC-15
5. UCEC-10
6. UCMC-16
7. UCMC-17
8. UCEC-17
9. UCEC-12
10. UCMC-12

Highly Secreted ActivinA and Follistatin in Umbilical Cord Mesenchymal (UCMC) and Epithelial Stem Cells (UCMC) in Comparison with Bone Marrow (hBMF-3), Adiposed Derived Stem Cells (hMBSC-3), Human Dermal Fibroblasts (NF) and Epidermal Keratinocytes (NK)

| | ActivinA (ng/ml) | Follistatin (ng/ml) |
|---|---|---|
| UCMC-3 | 2.975 | 13.50 |
| UCMC-2 | 6.350 | 14.97 |
| UCMC-3 | 1.161 | 8.65 |
| UCMC-16 | 2.520 | 6.22 |
| hBMF-3 | 0.707 | 8.84 |
| hBMSC-3 | 0.061 | 11.24 |
| PLA-3 | 0.135 | 10.29 |
| NF-109 | <0.010 | 21.80 |
| nscF-1 | 0.032 | 14.95 |
| NF-112 | 0.040 | 11.54 |
| NF | <0.010 | 4.71 |
| NF-113 | <0.010 | 16.54 |
| NF-115 | 0.196 | 5.66 |
| NF-6 | <0.010 | 8.35 |
| UCEC-10 | 1.017 | 87.84 |
| UCEC-12 | 0.722 | 74.02 |
| UCEC-10 | 0.536 | 33.78 |
| UCEC-3 | 0.691 | 32.07 |
| UCEC-3 | 1.032 | 14.04 |
| UCEC-10 | 0.505 | 88.66 |
| UCEC-3 | 0.221 | 5.61 |
| NK-103 | 0.428 | 69.04 |

FIG. 9-30

Spotting of Chip used for Cytokine Array (6.1)

| | A | B | C | D | E | F | G | H | I | J | K | L | M | N |
|---|---|---|---|---|---|---|---|---|---|---|---|---|---|---|
| 1 | POS | POS | POS | POS | Blank | Angiogenin | BDNF | BLC | BMP-4 | BMP-6 | CKb8-1 | CNTF | EGF | Eotaxin |
| 2 | NEG | NEG | NEG | NEG | Blank | Angiogenin | BDNF | BLC | BMP-4 | BMP-6 | CKb8-1 | CNTF | EGF | Eotaxin |
| 3 | Eotaxin-2 | Eotaxin-3 | FGF-6 | FGF-7 | Flt-3 Ligand | Fractalkine | GCP-2 | GDNF | GM-CSF | I-309 | IFN-g | IGFBP-1 | IGFBP-2 | IGFBP-4 |
| 4 | Eotaxin-2 | Eotaxin-3 | FGF-6 | FGF-7 | Flt-3 Ligand | Fractalkine | GCP-2 | GDNF | GM-CSF | I-309 | IFN-g | IGFBP-1 | IGFBP-2 | IGFBP-4 |
| 5 | IGF-I | IL-10 | IL-13 | IL-15 | IL-16 | IL-1a | IL-1b | IL-1ra | IL-2 | IL-3 | IL-4 | IL-5 | IL-6 | IL-7 |
| 6 | IGF-I | IL-10 | IL-13 | IL-15 | IL-16 | IL-1a | IL-1b | IL-1ra | IL-2 | IL-3 | IL-4 | IL-5 | IL-6 | IL-7 |
| 7 | Leptin | LIGHT | MCP-1 | MCP-2 | MCP-3 | MCP-4 | M-CSF | MDC | MIG | MIP-1d | MIP-3a | NAP-2 | NT-3 | PARC |
| 8 | Leptin | LIGHT | MCP-1 | MCP-2 | MCP-3 | MCP-4 | M-CSF | MDC | MIG | MIP-1d | MIP-3a | NAP-2 | NT-3 | PARC |
| 9 | PDGF-BB | RANTES | SCF | SDF-1 | TARC | TGF-b1 | TGF-b3 | TNF-a | TNF-b | Blank | Blank | Blank | Blank | Blank |
| 10 | PDGF-BB | RANTES | SCF | SDF-1 | TARC | TGF-b1 | TGF-b3 | TNF-a | TNF-b | Blank | Blank | Blank | POS | POS |

FIG. 12-6

Spotting of Chip used for Cytokine Array (7.1)

| | A | B | C | D | E | F | G | H | I | J | K | L | M | N |
|---|---|---|---|---|---|---|---|---|---|---|---|---|---|---|
| 1 | POS | POS | POS | POS | Blank | Blank | AgRP | Angiopoietin-2 | Amphiregulin | Axl | bFGF | b-NGF | BTC | CCL-28 |
| 2 | NEG | NEG | NEG | NEG | Blank | Acrp30 | AgRP | Angiopoietin-2 | Amphiregulin | Axl | bFGF | b-NGF | BTC | CCL-28 |
| 3 | CTACK | Dtk | EGF-R | ENA-78 | FAS | FGF-4 | FGF-9 | GCSF | GITR Ligand | GITR | GRO | GRO-a | HCC-4 | HGF |
| 4 | CTACK | Dtk | EGF-R | ENA-78 | FAS | FGF-4 | FGF-9 | GCSF | GITR Ligand | GITR | GRO | GRO-a | HCC-4 | HGF |
| 5 | ICAM-1 | ICAM-3 | IGFBP-3 | IGFBP-6 | IGF-1 SR | IL-1 R4/ST2 | IL-1 RI | IL-11 | IL-12 p40 | IL-12 p70 | IL-17 | IL-2 Rα | IL-6 R | IL-8 |
| 6 | ICAM-1 | ICAM-3 | IGFBP-3 | IGFBP-6 | IGF-1 SR | IL-1 R4/ST2 | IL-1 RI | IL-11 | IL-12 p40 | IL-12 p70 | IL-17 | IL-2 Rα | IL-6 R | IL-8 |
| 7 | I-TAC | Lymphotactin | MIF | MIP-1a | MIP-1b | MIP-3b | MSP-a | NT-4 | Osteoprotegerin | Oncostatin M | PIGF | sgp130 | sTNF RII | sTNF-RI |
| 8 | I-TAC | Lymphotactin | MIF | MIP-1a | MIP-1b | MIP-3b | MSP-a | NT-4 | Osteoprotegerin | Oncostatin M | PIGF | sgp130 | sTNF RII | sTNF-RI |
| 9 | TECK | TIMP-1 | TIMP-2 | Thrombopoietin | TRAIL R3 | TRAIL R4 | uPAR | VEGF | VEGF-d | Blank | Blank | Blank | Blank | Blank |
| 10 | TECK | TIMP-1 | TIMP-2 | Thrombopoietin | TRAIL R3 | TRAIL R4 | uPAR | VEGF | VEGF-d | Blank | Blank | Blank | POS | POS |

FIG. 12-7

UCMC-16 cultured in DMEM/10%FCS, at day 10

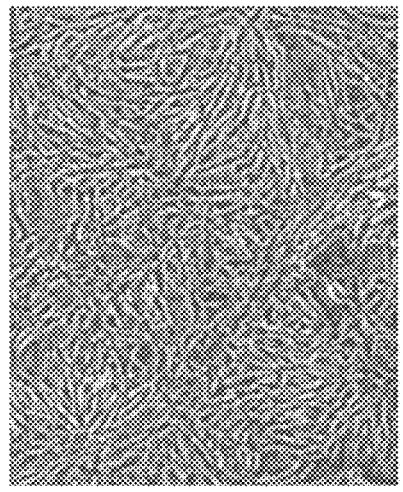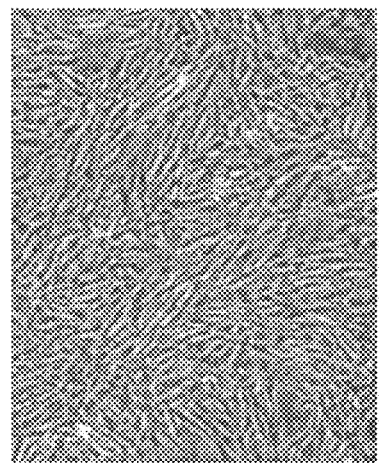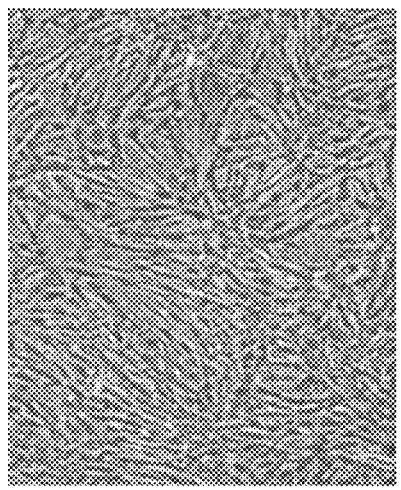
FIG. 13-2
UCMC-15 cultured in PTT-1 medium, day 4

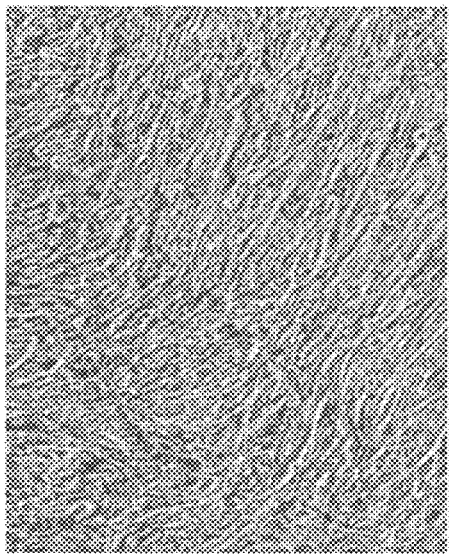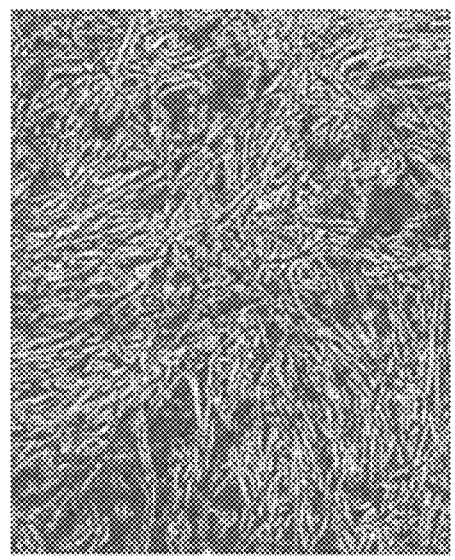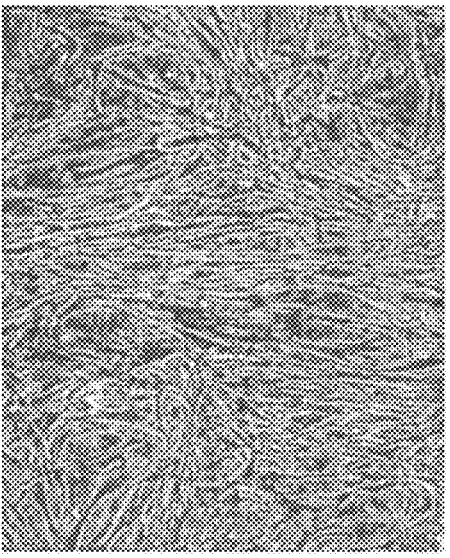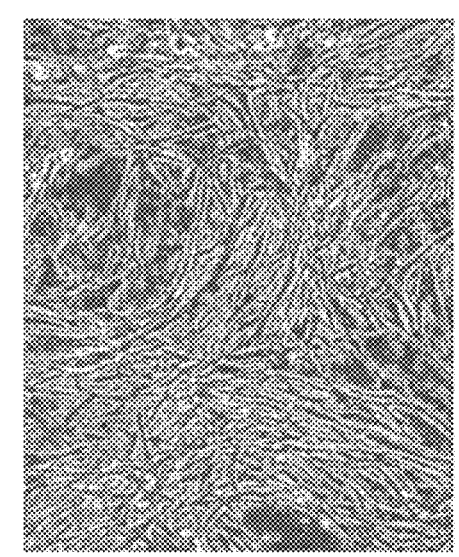
UCMC-16 cultured in PTT-2 at day 10
FIG. 13-4

UCMC-16 cultured in PTT-3 at day 10

Adipose-derived stromal cells cultured in PTT-3 at day 10. Cells did not grow well in serum free medium Bone marrow-derived stromal cells cultured in PTT-3 (MeE) at day 10. Cells did not grow well in serum free medium FIG. 14 - 2
Gene expression present in BOTH, Umbillical
Cord Epithelial and Mesenchymal Stem Cells

- 6 genes in both-cell envelope
- 12 genes in both-cell wall
- 19 genes in both-physiological process
- 36 genes in both-reproduction
- 65 genes in both-response to biotic stimulus
- 78 genes in both-homeostasis
- 83 genes in both-oxygen binding
- 84 genes in both-endosome
- 95 genes in both-peroxisome
- 99 genes in both-responset to endogenous stimulus
- 120 genes in both-translation regulator
- 136 genes in both-neurotransmitter transporter activity
- 140 genes in both-embryonic development
- 146 genes in both-morphogenesis
- 164 genes in both-nuclear membrane
- 176 genes in both-protein modification
- 181 genes in both-viral life cycle
- 198 genes in both-extracellular space
- 205 genes in both-lysosome
- 210 genes in both-ECM
- 215 genes in both-microtubule organizing center
- 223 genes in both-lipid binding
- 283 genes in both-motor activity
- 304 genes in both-response to stress
- 508 genes in both-Golgi apparatus
- 522 genes in both-phosphatase activity
- 532 genes In both-cell adhesion molecules activity
- 554 genes in both-cell growth
- 554 genes in both-lipid metaboloism
- 565 genes in both-cytoskeleton
- 570 genes in both-response to abiotis stimulus
- 575 genes in both-cell proliferation
- 590 genes in both-cell recognition
- 607 genes in both nucleases activity
- 630 genes in both-response to external stimulus

FIG. 14 - 3

Gene expression present in BOTH, Umbilical Cord Epithelial and Mesenchymal Stem Cells

- 663 genes in both—protein binding
- 666 genes in both—cell death
- 747 genes in both—structural molecule activity
- 774 genes in both—extracellular
- 808 genes in both—cell cycle
- 817 genes in both—protein biosynthesis
- 825 genes in both—DNA metabolism
- 899 genes in both—energy pathway
- 926 genes in both—cytoskeleton organization and biogenesis
- 975 genes in both—receptor binding
- 987 genes in both—protein metabolism
- 1048 genes in both—cell-cell signaling
- 1138 genes in both—cell differentiation
- 1317 genes in both—cytosol
- 1364 genes in both—kinase
- 1364 genes in both—protein kinase activity
- 1473 genes in both—host-pathogen interaction
- 1483 genes in both—protein transport
- 1637 genes in both—ion channel activity
- 1667 genes in both—ion transport
- 1774 genes in both—cell organization, biogenesis
- 1774 genes in both—organelle organization biogenesis
- 1968 genes in both—nucleotide binding
- 2067 genes in both—receptor activity
- 2067 genes in both—signal transducer activity
- 2108 genes in both—signal transduction
- 2125 genes in both—cell growth
- 2503 genes in both—transcription regulator activity
- 2906 genes in both—transferase
- 2947 genes in both—transcription
- 3435 genes in both—plasma membrane
- 3436 genes in both—transcription factor activity
- 3509 genes in both—regulation of gen expression
- 3509 genes in both—regulation of gene expression, epigenesis
- 3634 genes in both—DNA binding

FIG. 14 - 4

Gene expression present in BOTH, Umbillical
Cord Epithelial and Mesenchymal Stem Cells

- 3845 genes in both—component unknown
- 3882 genes in both—nucleus
- 3950 genes in both—cell communication
- 4531 genes in both—development
- 6645 genes in both—metabolism
- 7785 genes in both—translation factor activity, nucleic acids
- 10422 genes in both—cell growth or maintainance
- 10458 genes in both—cell

FIG. 14 - 5

Gene expression present UNIQUELY in Umbillical Cord Epithelial Stem Cells (UCEC)

- 3 genes-ECM
- 3 genes-reproduction
- 3 genes-response to stress
- 4 genes-homeostasis
- 4 genes-morphogenesis
- 8 genes-embryonic development
- 8 genes-extracellular space
- 10 genes-cytoskeleton protein binding
- 10 genes-protein binding
- 11 genes-protein biosynthesis
- 12 genes-cell proliferation
- 12 genes-protein metabolism
- 15 genes-cytosol
- 16 genes-cell death
- 16 genes-death
- 17 genes-cytoskeleton
- 17 genes-growth
- 18 genes-structural molecule activity
- 21 genes-response to abiotic stimulus
- 22 genes-cell cycle
- 22 genes-cell recognition
- 23 genes-response to external stimulus
- 24 genes-cell adhesion molecule activity
- 25 genes-cytoskeleton organization, biogenesis
- 26 genes-kinase
- 26 genes-protein kinase activity
- 29 genes-cell organization, biogenesis
- 29 genes-cytoplasm organization, biogenesis
- 29 genes-organelle organization, biogenesis
- 31 genes-defense immunity protein activity
- 32 genes-receptor binding
- 35 genes-extracellular
- 38 genes-cell-cell signaling
- 39 genes-cell differentiation
- 47 genes-transcription
- 54 genes-nucleus
- 54 genes-signal transduction
- 55 genes-host-pathogen interaction
- 56 genes-cell growth
- 62 genes-receptor activity
- 62 genes-signal transducer activity
- 67 genes-DNA binding
- 72 genes-regulation of gene expression, epigenesis
- 78 genes-molecular function unknown
- 81 genes-cellular component unknown
- 82 genes-cytoplasm
- 103 genes-metabolism
- 107 genes-plasma membrane
- 115 genes-development
- 119 genes-cell communication
- 148 genes-RNA binding
- 201 genes-cell growth, maintainance
- 214 genes-cell
- 214 genes-intracellular

FIG. 14 - 6

Gene expression present UNIQUELY in
Umbilical Cord Mesenchymak Stem Cells (UCMC)

- 4 genes-cell wall
- 6 genes-translation regulator
- 9 genes-physiological process
- 12 genes-response to endogenous stimulus
- 21 genes-response to biotic stimulus
- 23 genes-homeostasis
- 25 genes-reproduction
- 40 genes-response to stress
- 45 genes-morphogenesis
- 48 genes-embryonic development
- 48 genes-neurotransmitter activity
- 54 genes-motor activity
- 71 genes-protein biosynthesis
- 87 genes-extracellular space
- 90 genes-ECM
- 95 genes-energy pathway
- 125 genes-cell death
- 125 genes-death
- 126 genes-structural molecule activity
- 133 genes-cell cycle
- 134 genes-DNA metabolism
- 150 genes-cell proliferation
- 157 genes-cytoskeleton
- 157 genes-response to abiotic stimulus
- 164 genes-recognition
- 174 genes-cytoskeleton protein binding
- 174 genes-protein binding
- 174 genes-response to external stimulus
- 184 genes-growth
- 206 genes-cell adhesion molecule activity
- 221 genes-cytoskeleton organization, biogenesis
- 268 genes-cytosol
- 268 genes-defence immunity protein activity
- 294 genes-protein kinase activity
- 297 genes-receptor binding

- 303 genes-cell organization, biogenesis
- 303 genes-organelle organization, biogenesis
- 339 genes-cell differentiation
- 340 genes-extracellular
- 347 genes-cell-cell signaling
- 444 genes-host-pathogen interaction
- 539 genes-transcription regulator activity
- 599 genes-cell growth
- 602 genes-signal transduction
- 604 genes-transcription
- 681 genes-nucleus
- 702 genes-receptor activity
- 702 genes-signal transducer activity
- 712 genes-transcription factor activity
- 747 genes-DNA binding
- 814 genes-regulation of gene expression, epigenetic
- 974 genes-cellular component unknown
- 1026 genes-plasma membrane
- 1120 genes-development
- 1139 genes-cell communication
- 1657 genes-translation factor activity, nucleic acid binding
- 2266 genes-cell growth and maitainance
- 2289 genes-cell

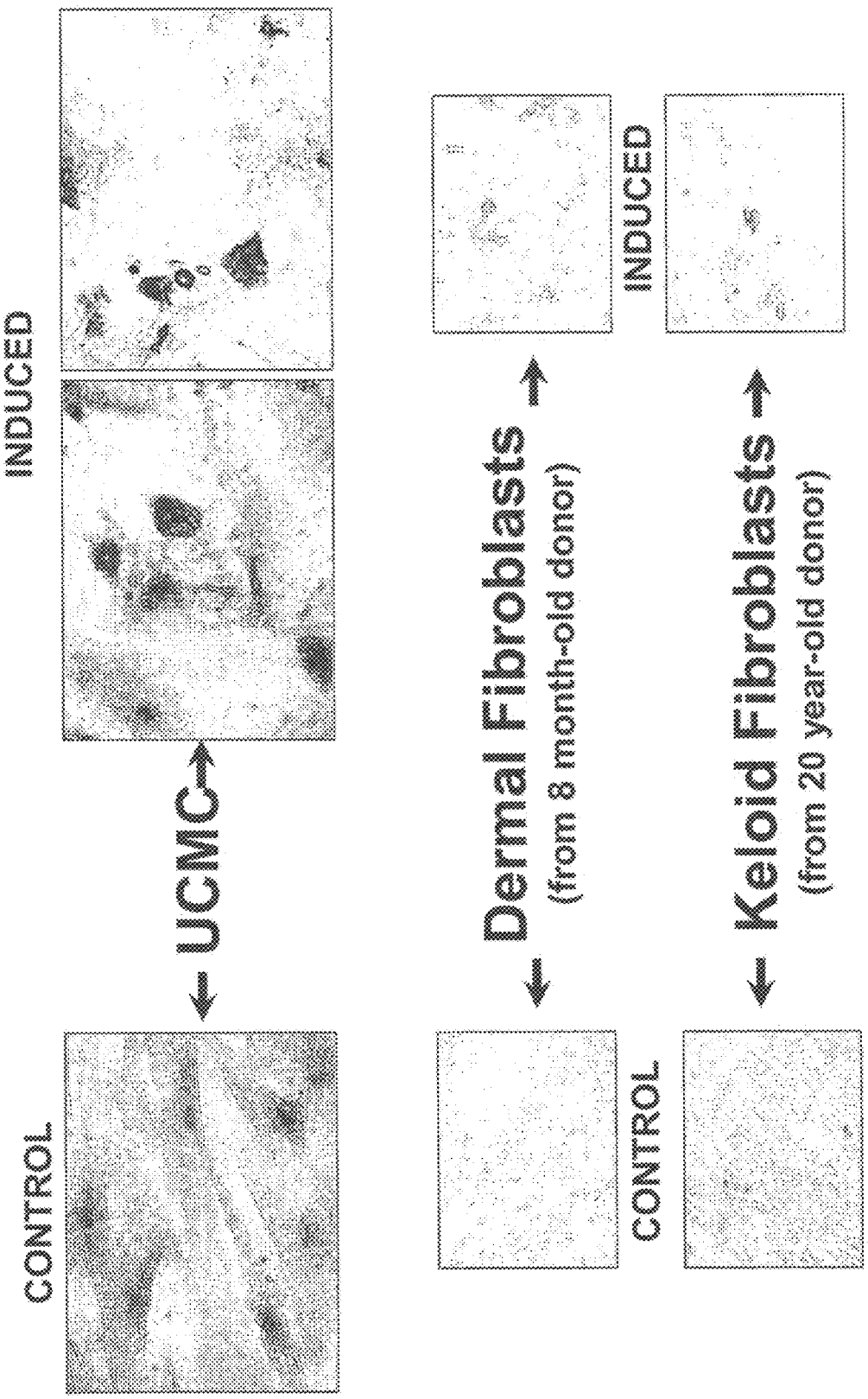
FIGURE 17C: In-vitro Adipogenic Induction of UCMC. Oil Red O staining indicate fat accumulation in UCMC but not in skin derma fibroblasts

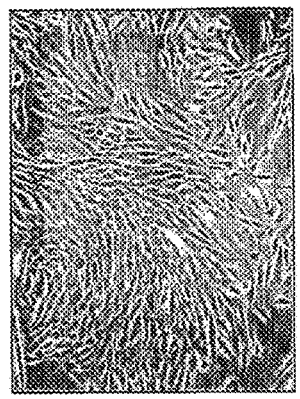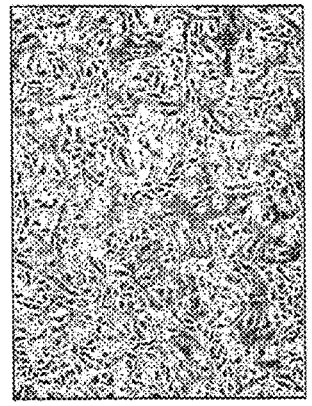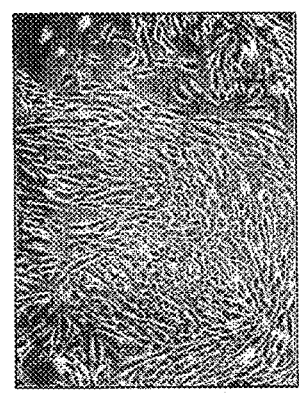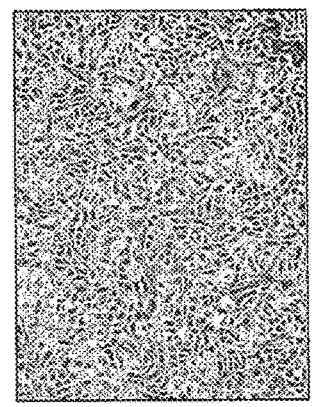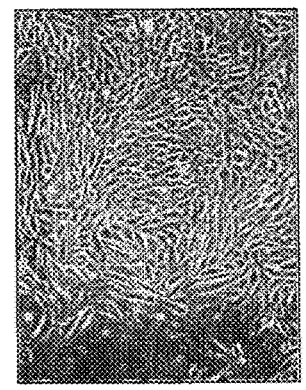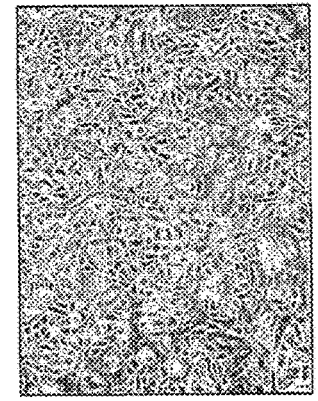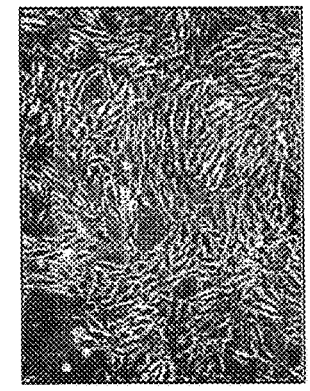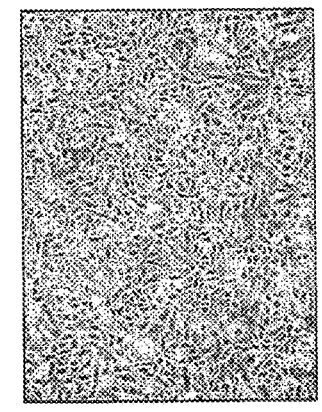
Fig. 18b: UCMC-Derived Skin Fibroblasts
Fig. 18a: UCEC-Derived Skin Keratinocytes

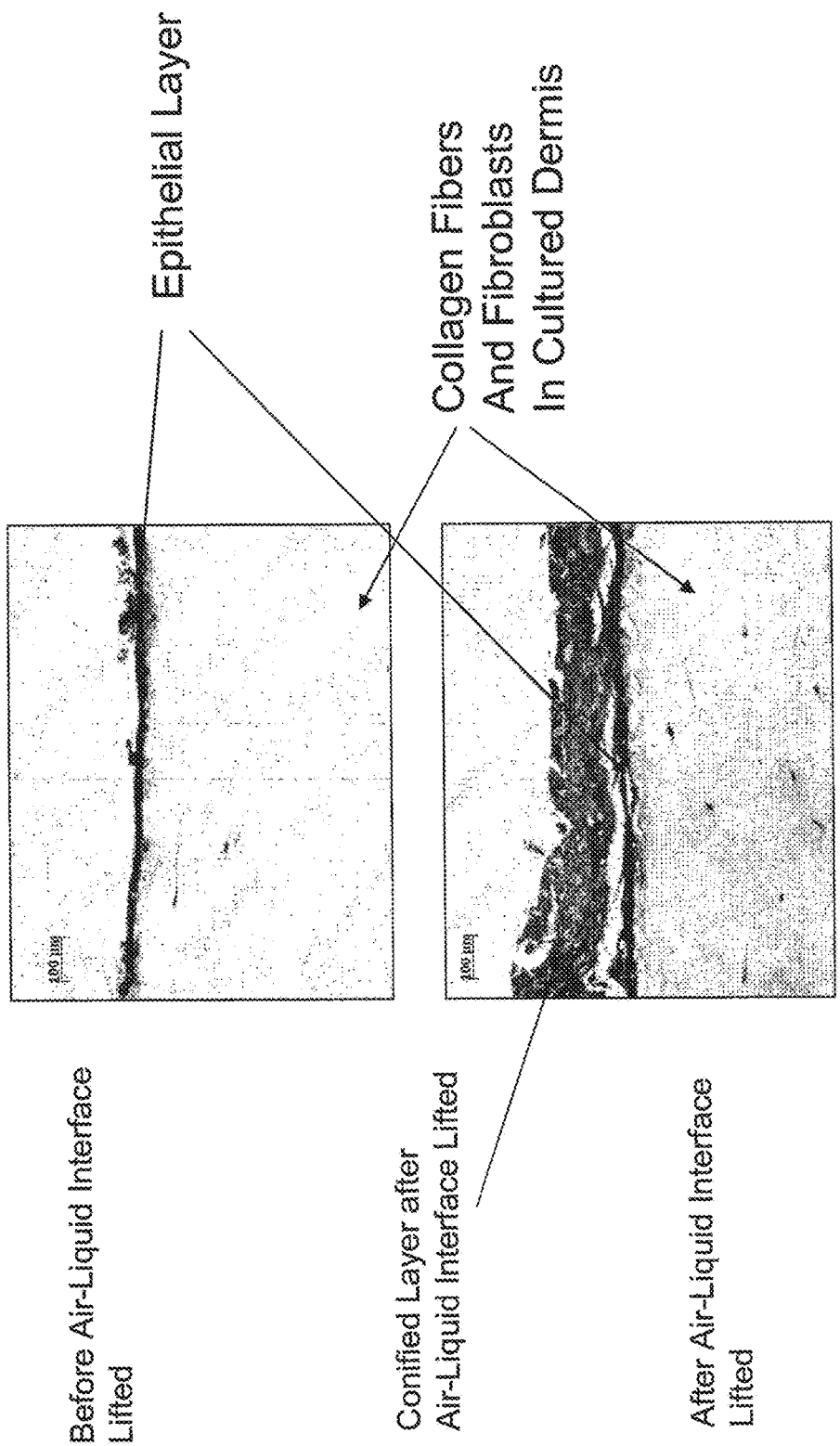
Fig. 19: Cultured Skin Equivalents (CSE-1) Using UCEC and UCMC (H&E Staining)

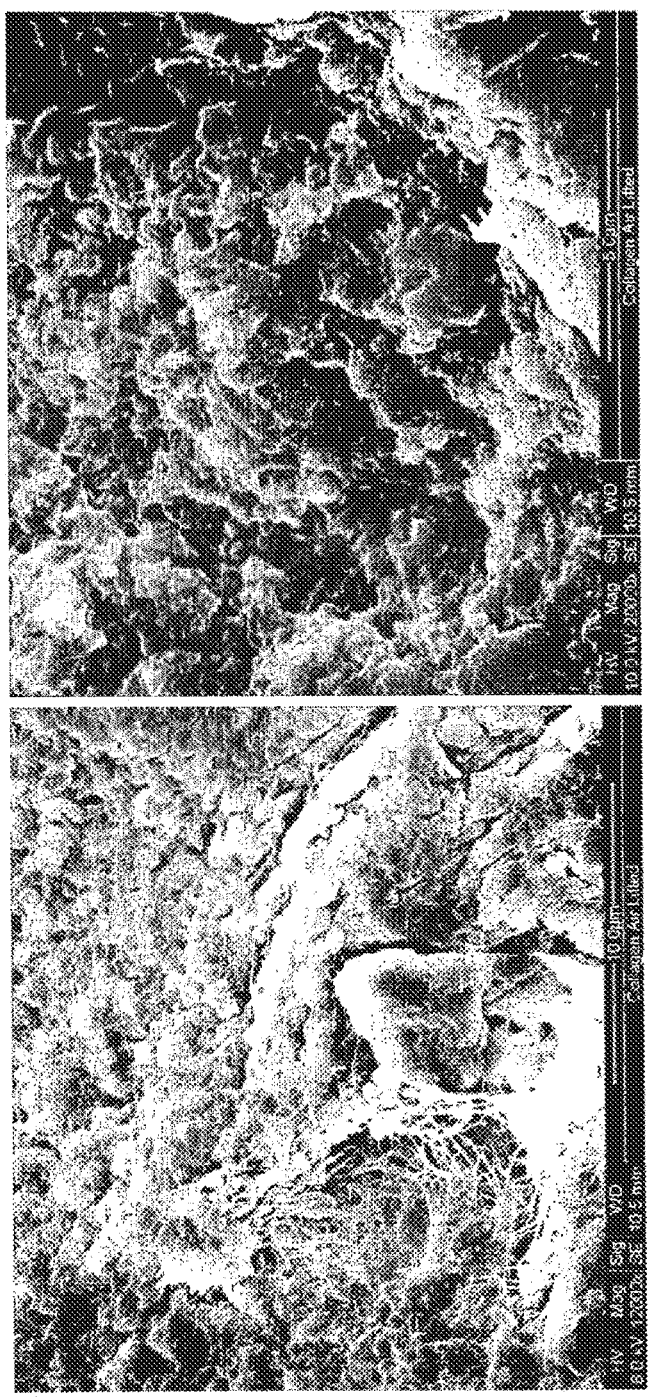
Fig. 20a: Surface appearance of CSE-1 after lifting to air-liquid interface

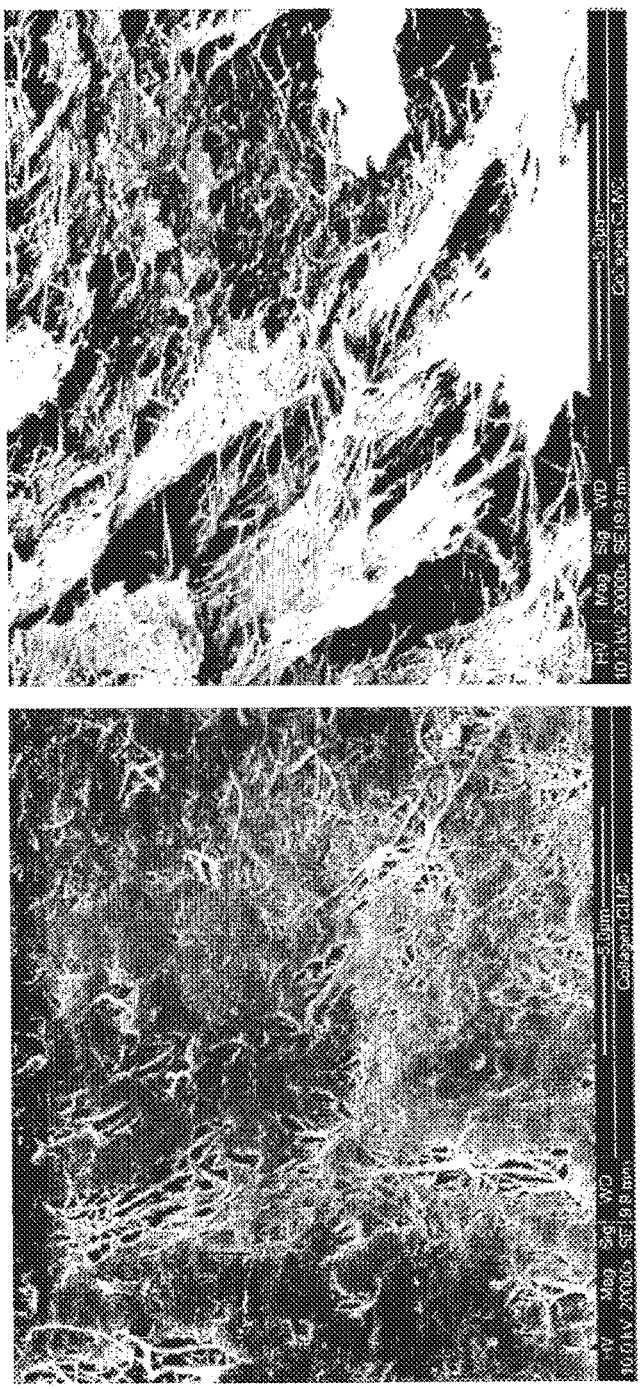
Fig. 20b: Appearance of UCMC populated in collagen lattices of CSE-1

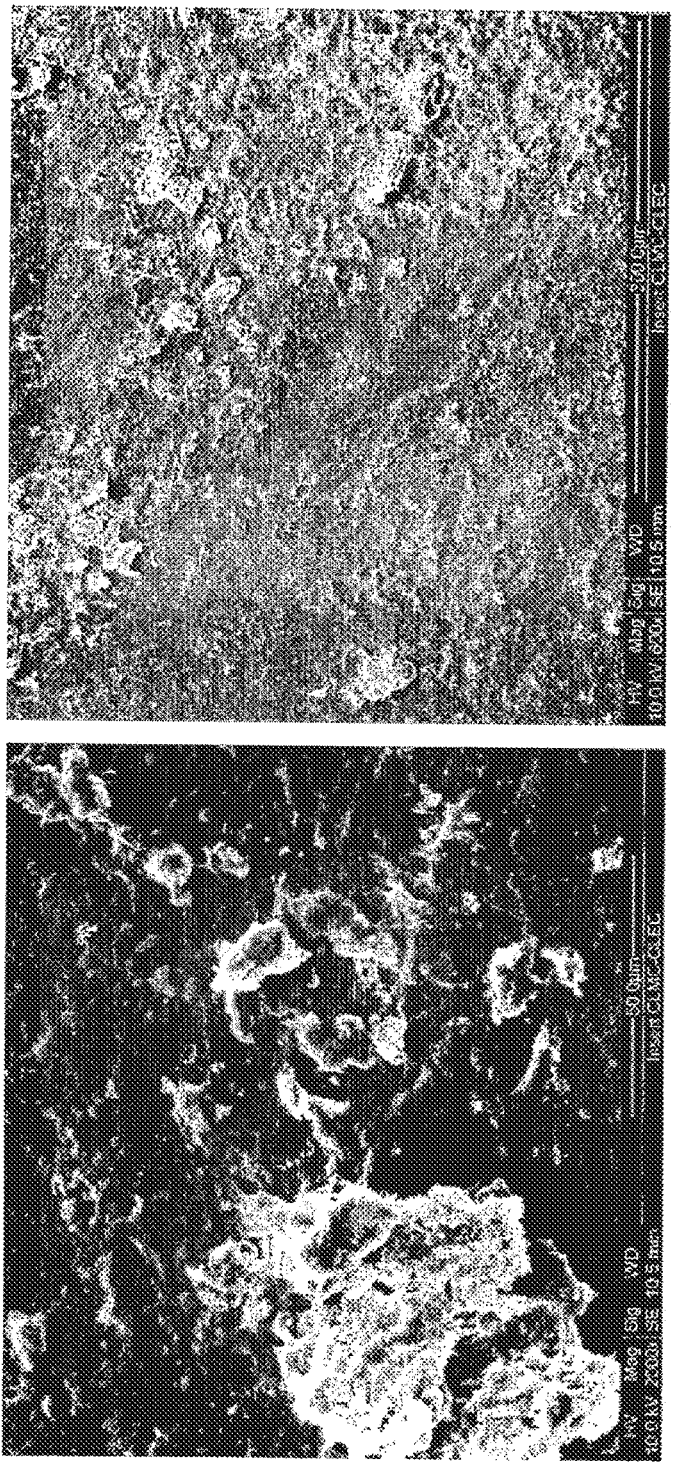
Fig. 21a: Surface appearance of CSE-2 after lifting to air-liquid interface

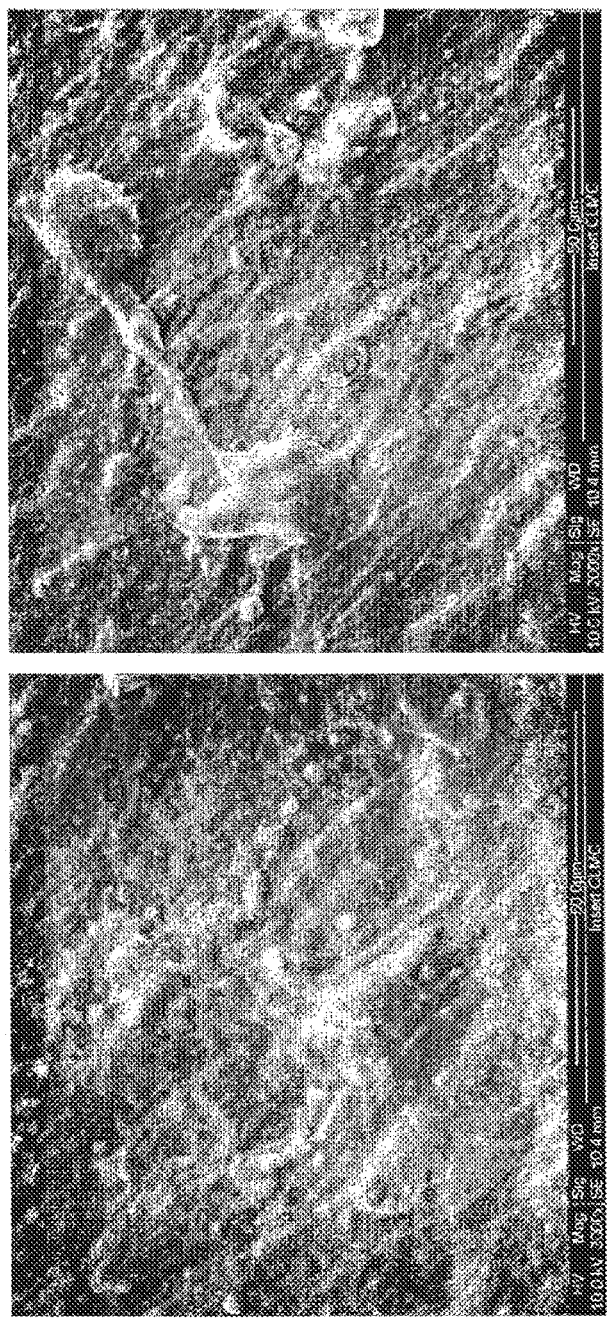
Fig. 21b: Appearance of UCMC cultured in CSE-2

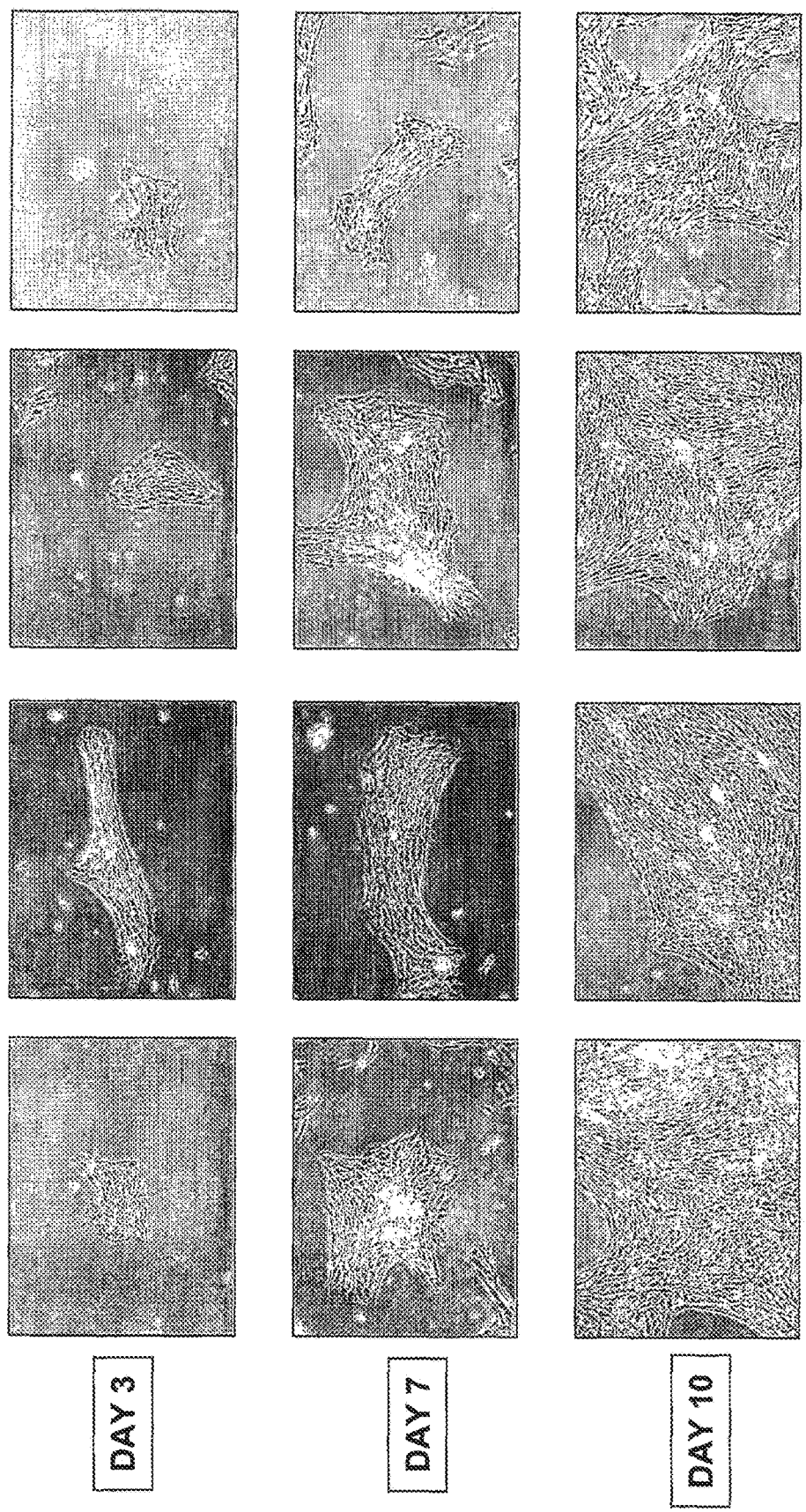

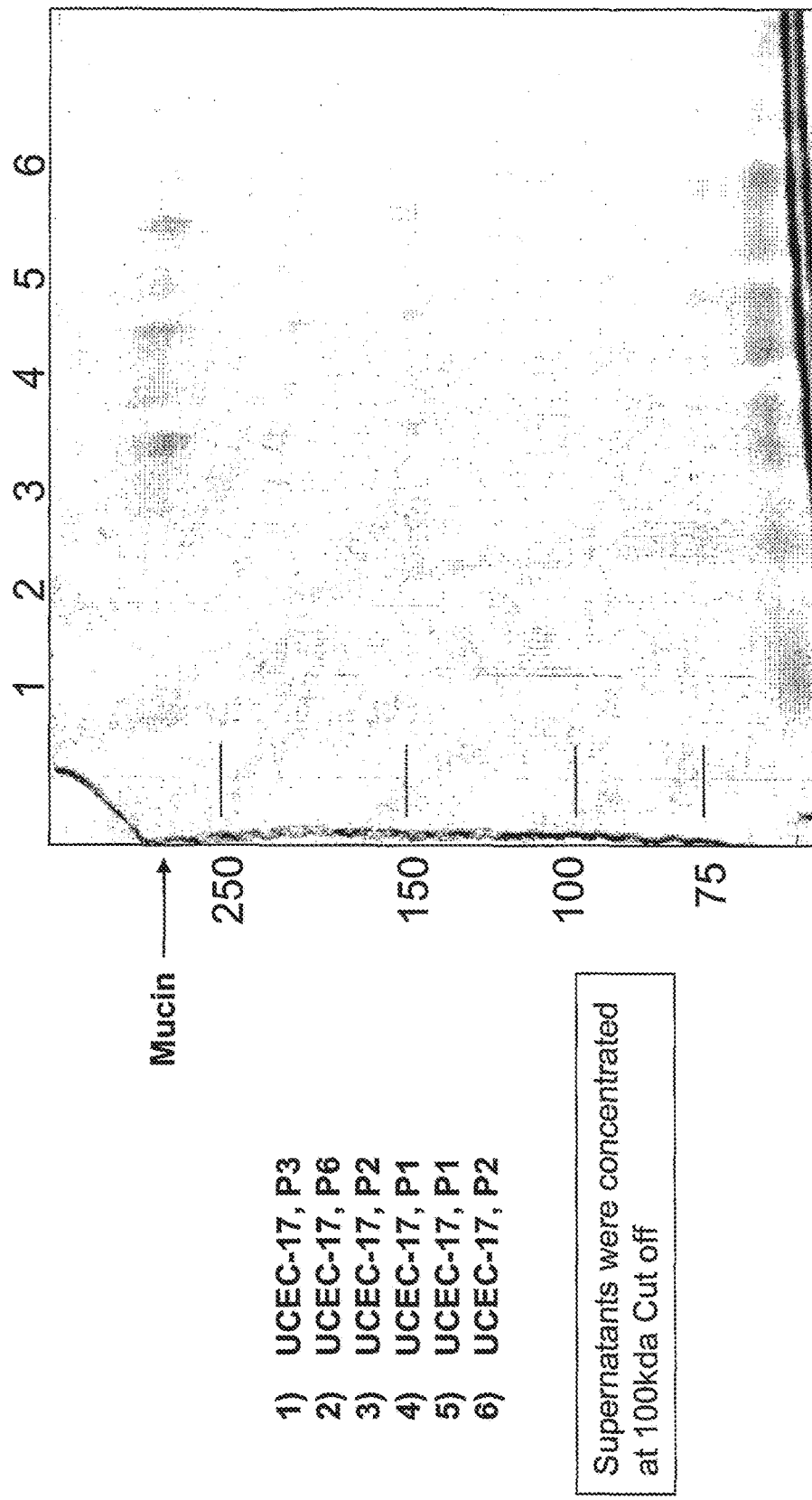

Fig. 23: Beta-islet like structure of UCEC-18 induced by PTT10 supplemented with nicotinamide
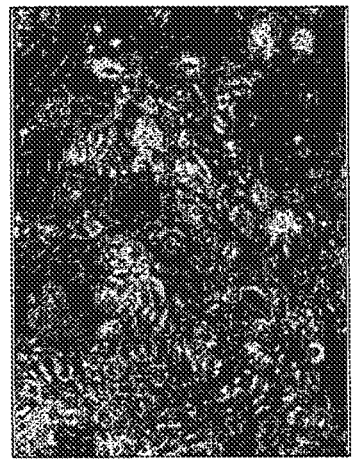
PTT10 only
Fig.23a
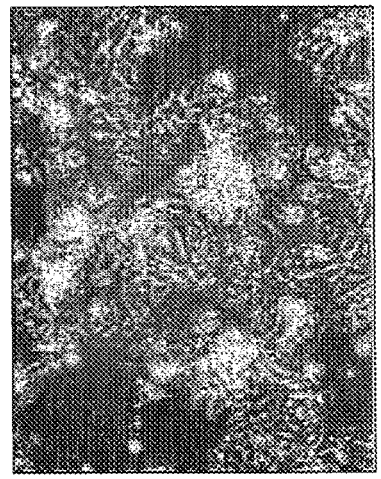
PTT10 + Nicotinamide
Fig.23b
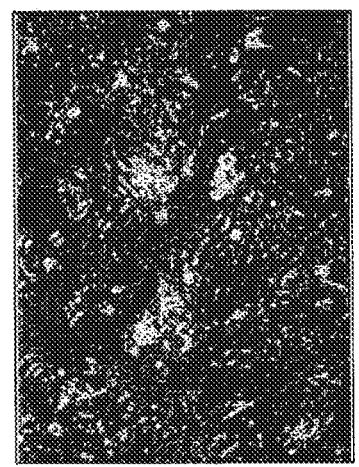
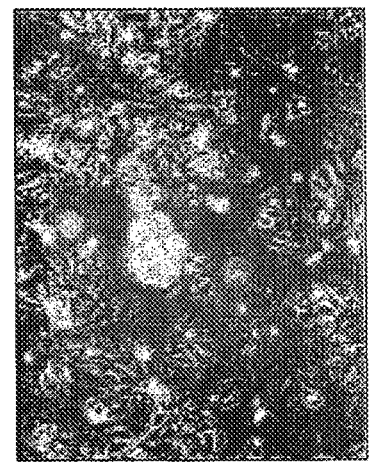

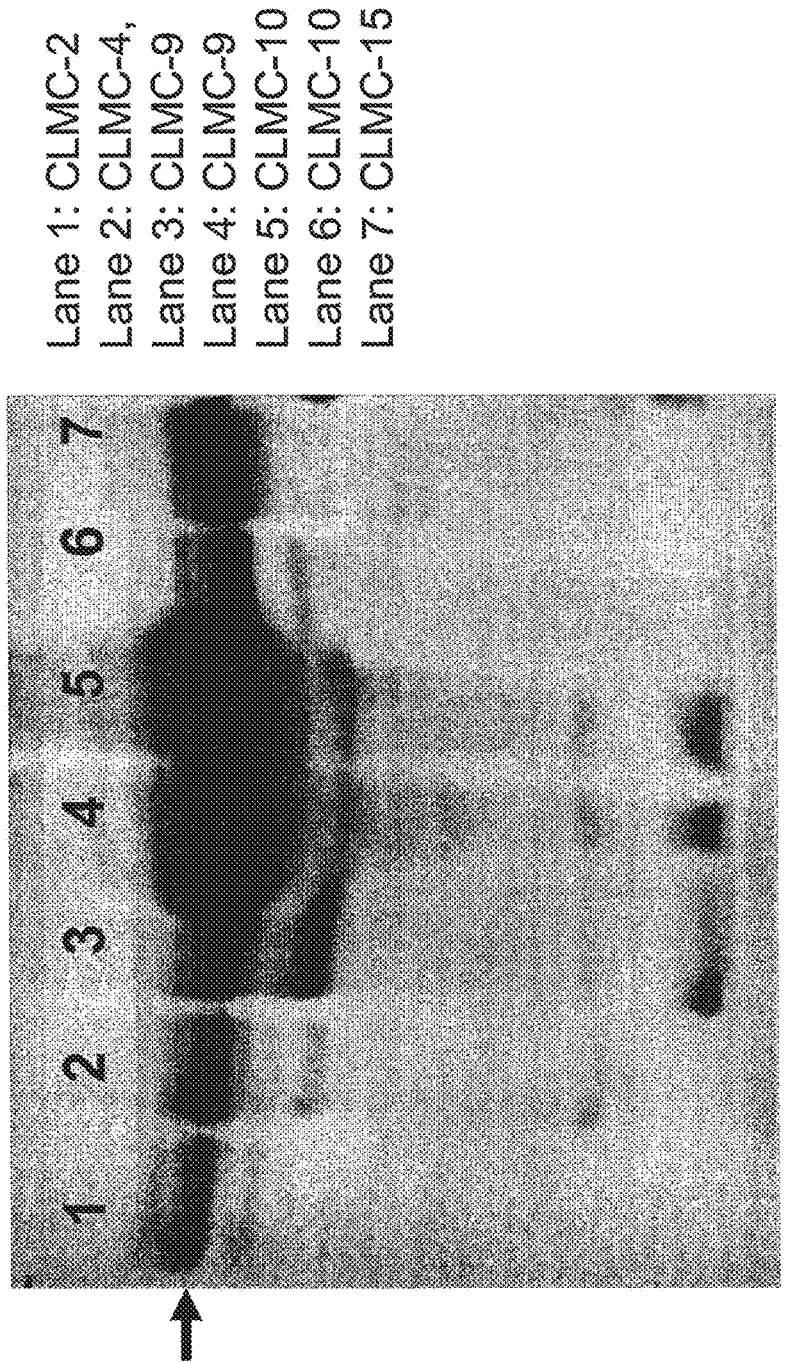

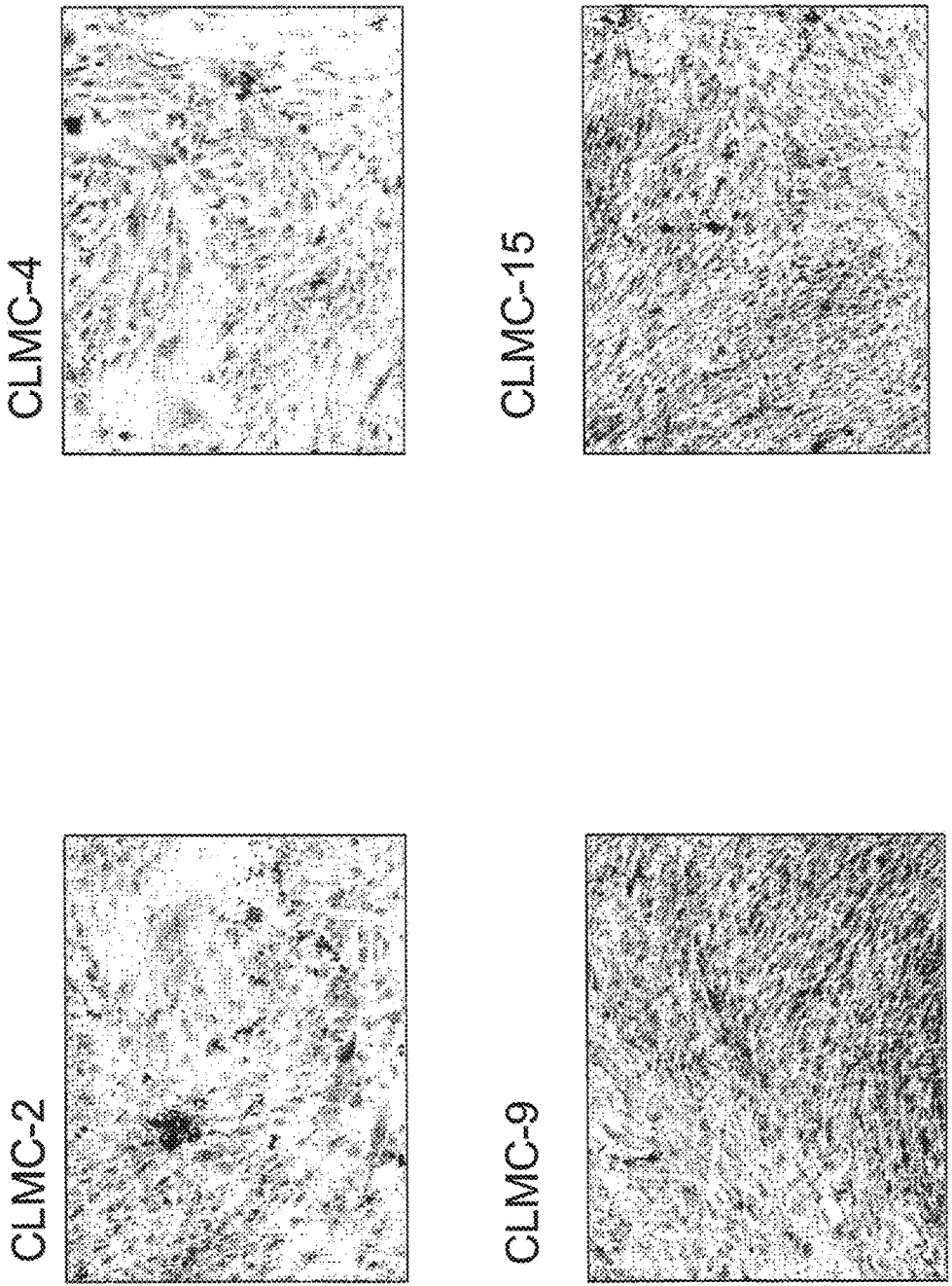

Figure 26C
Negative Control Staining
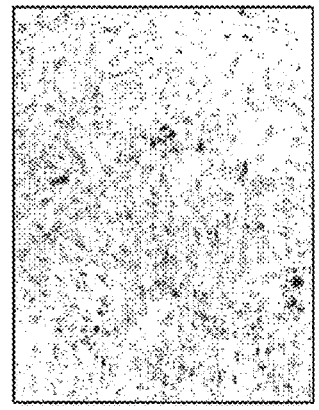
CLMC-4
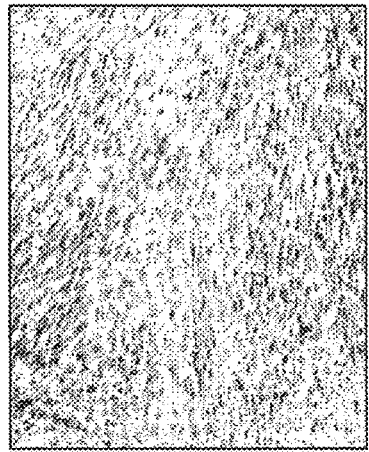
CLMC-15
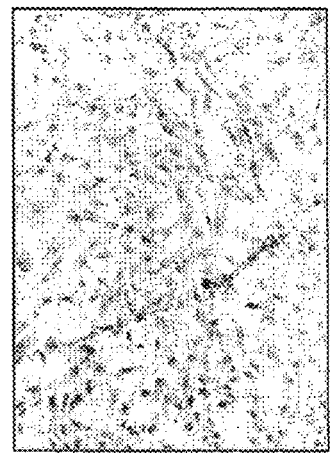
CLMC-2
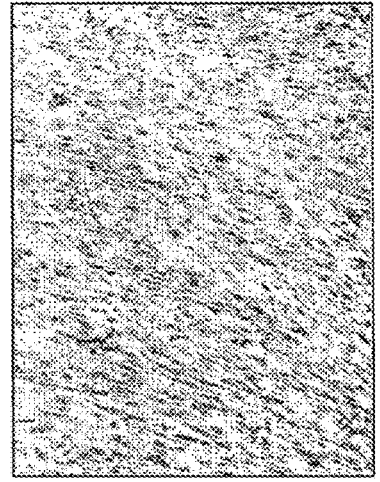
CLMC-9

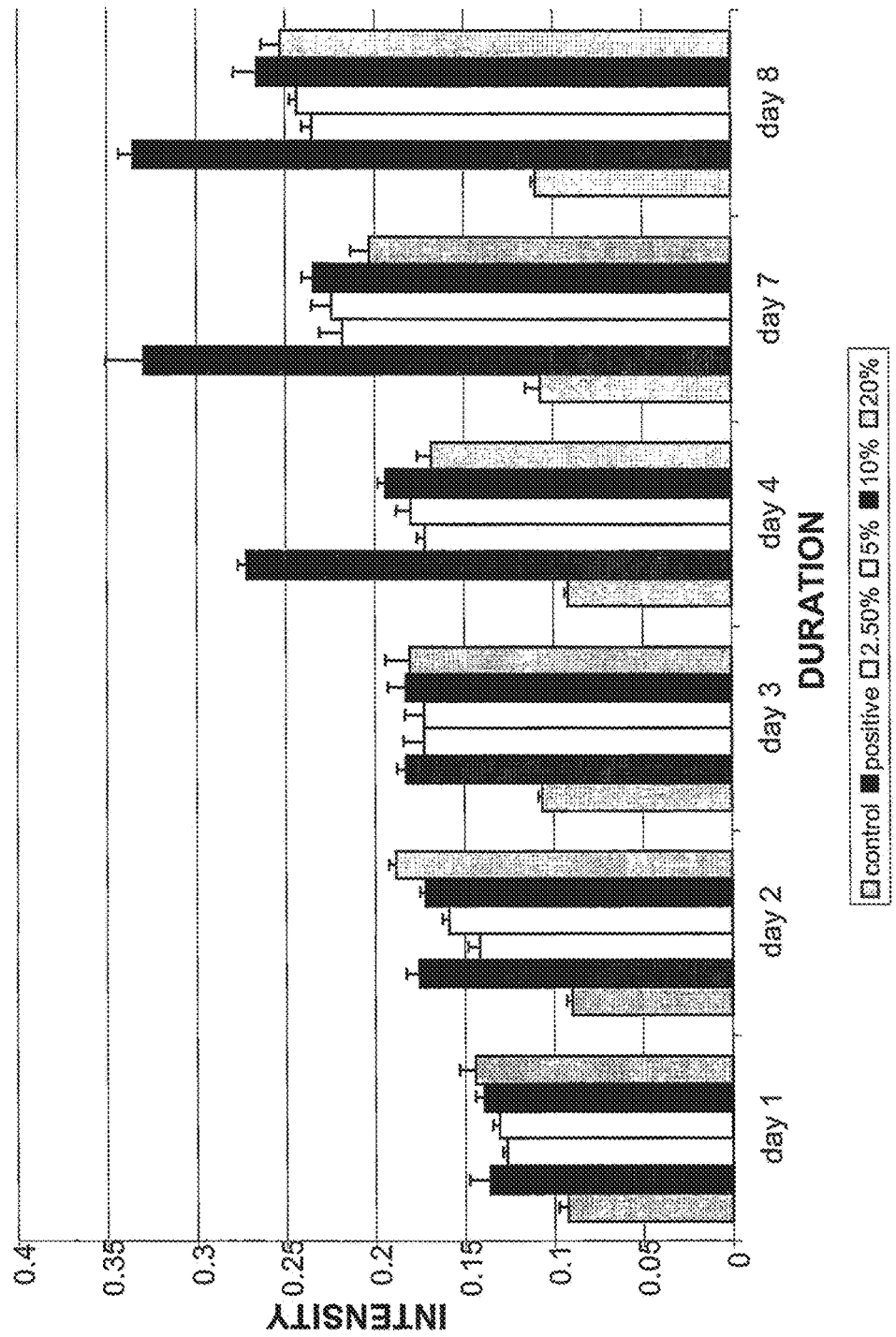

Figure 29A

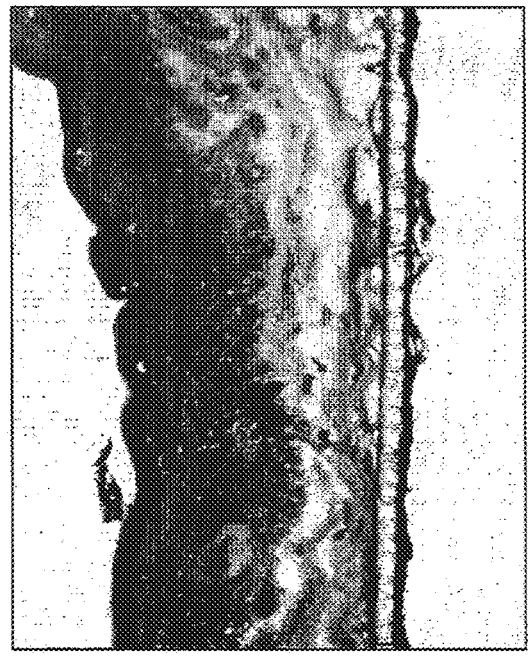
Figure 29B

Figure 30A: CLMC inoculated in TissuFleece Collagen Scaffold
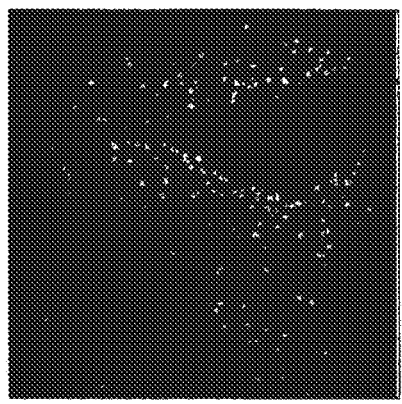
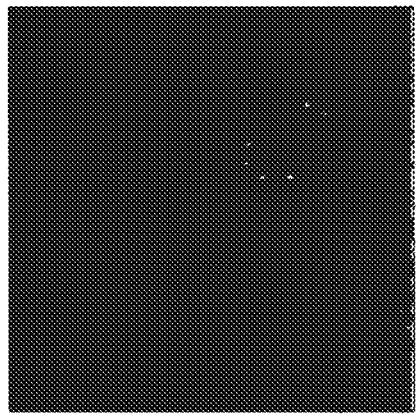
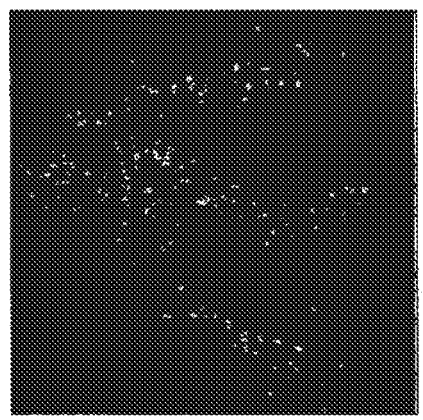
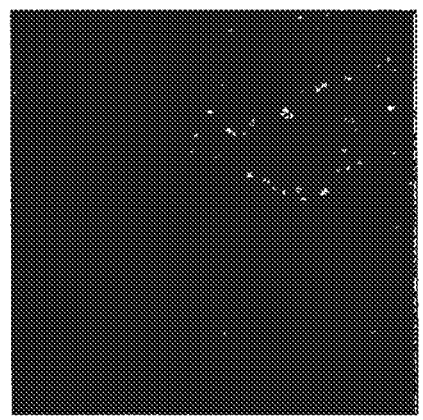

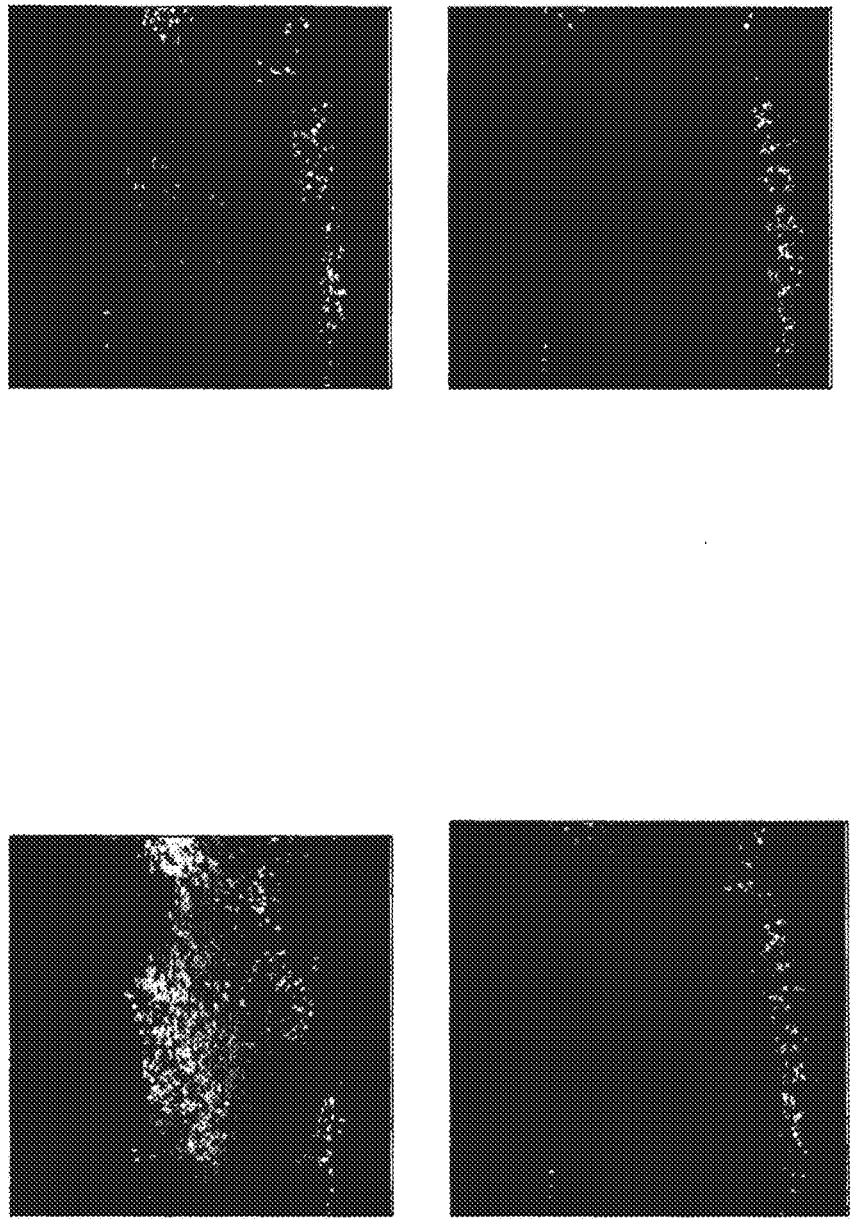

CLMC-populated collagen Lattice at day 21
Figure 31B
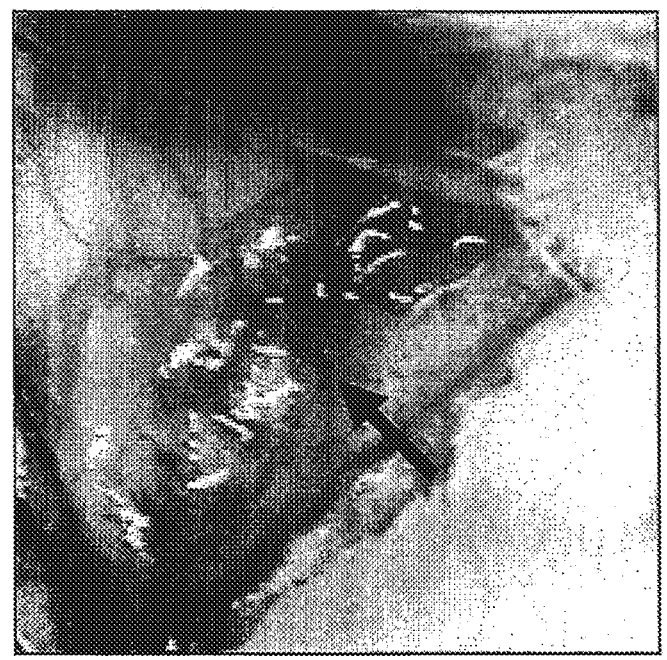
Cell-free collagen lattice at day 21

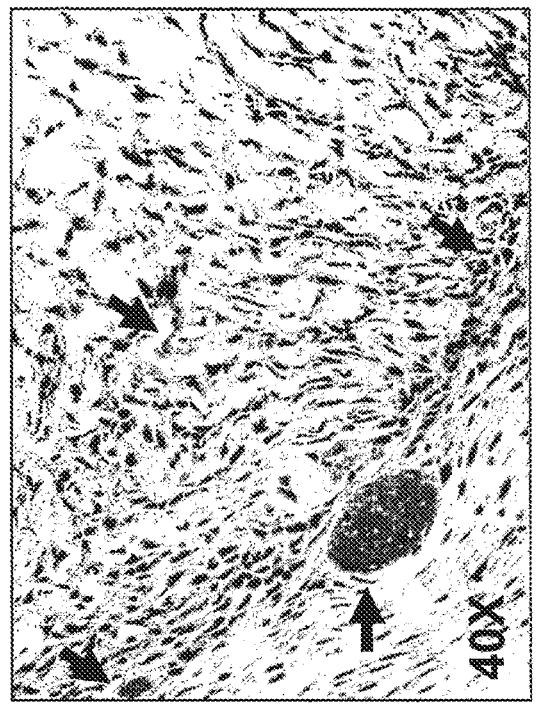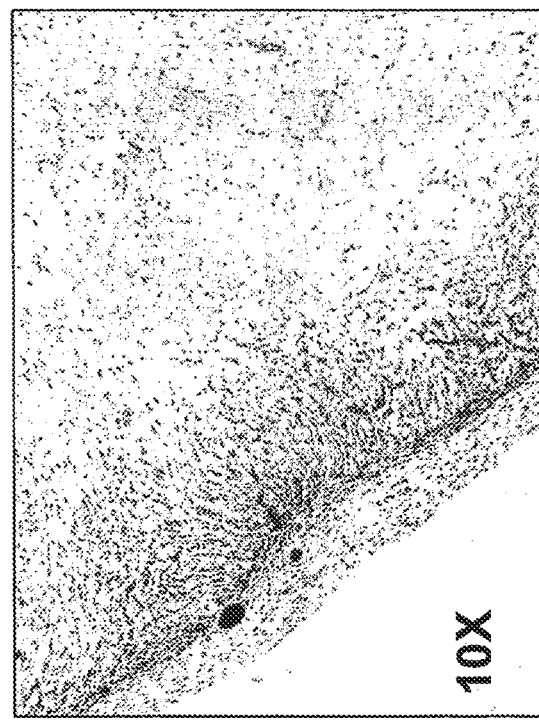
Figure 31C

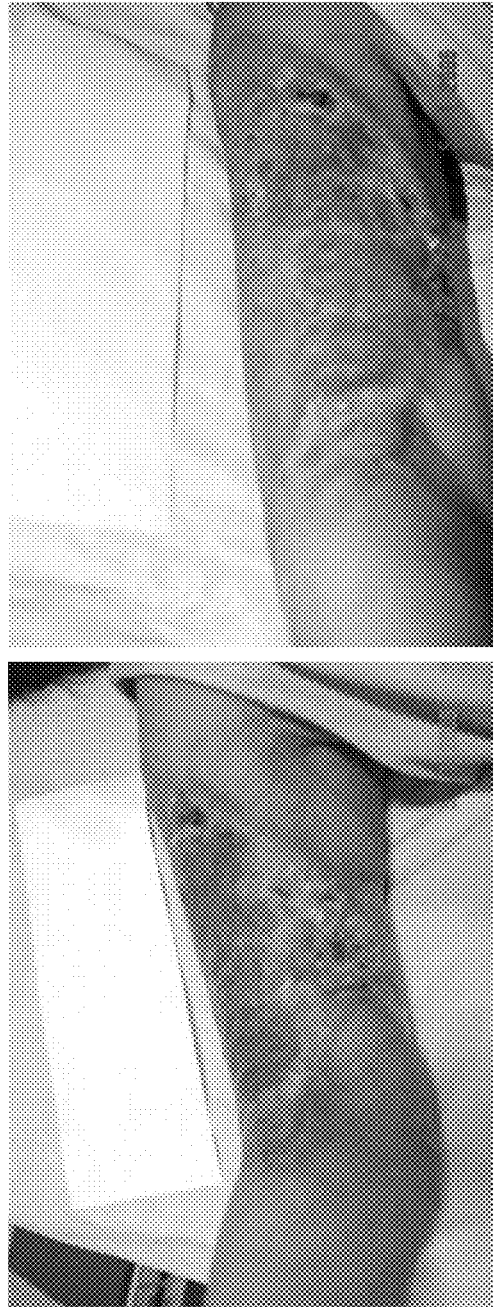
FIG. 32C

Figure 33
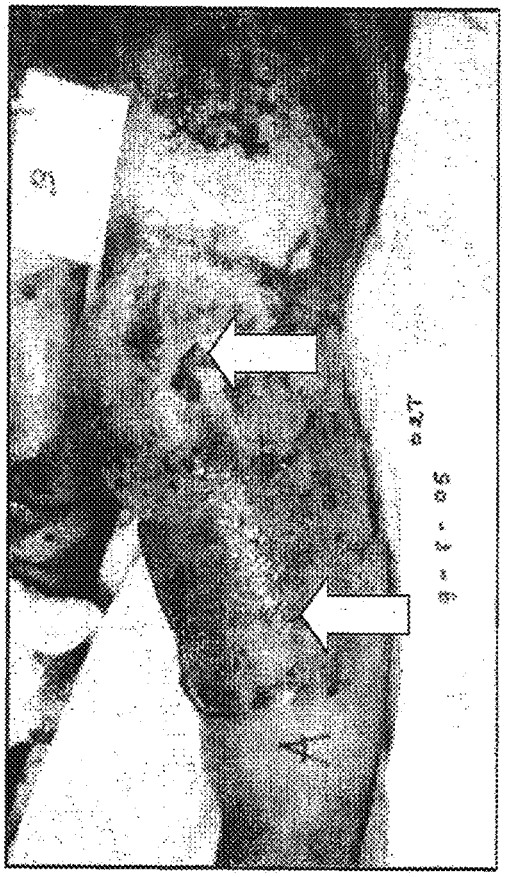
CLMC Transplantation, Case Study #2, 9 Aug 2005 2 year old child, Male*. Partial Thickness – 2nd Degree Burn.
Complete Wound Healing at 3 days, 12 Aug 2005
Area A: CLMC Transplant    Area B: Normal Dressing Control

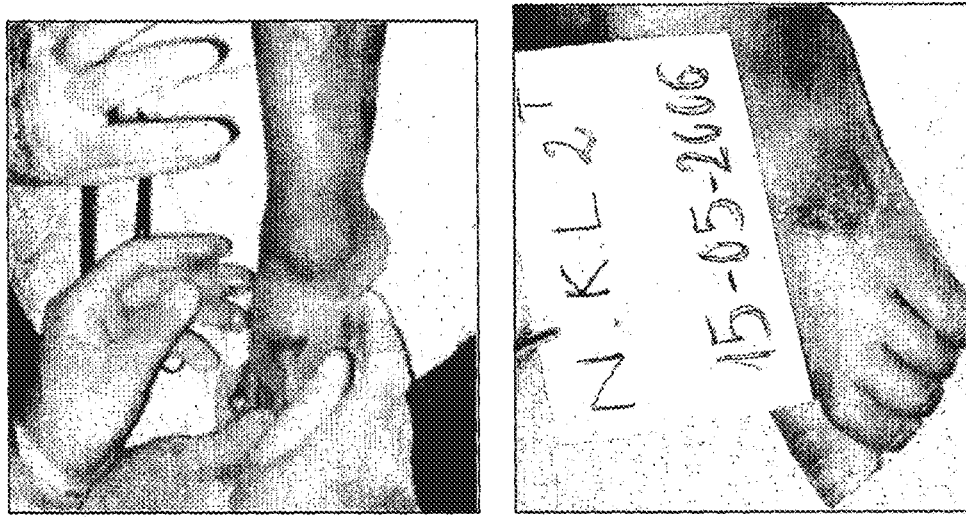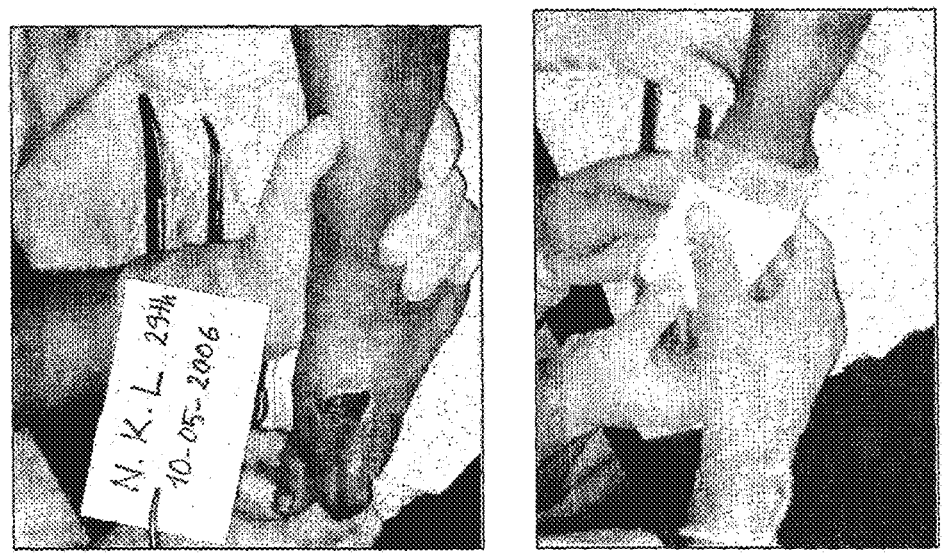
Figure 34

Figure 35 CLMC Transplantation Case Study #3
Radiotherapy for left ankle haemangioma, 1 year-old child

ISOLATION AND CULTIVATION OF STEM/PROGENITOR CELLS FROM THE AMNIOTIC MEMBRANE OF UMBILICAL CORD AND USES OF CELLS DIFFERENTIATED THEREFROM

CROSS-REFERENCE TO RELATED APPLICATIONS

This application is a divisional of U.S. patent application Ser. No. 13/652,371 filed Oct. 15, 2012, which is a divisional of U.S. patent application Ser. No. 12/091,018 filed Apr. 21, 2008, now granted U.S. Pat. No. 8,287,854, which is the United States national stage patent application of International Application No. PCT/SG2006/000301, filed Oct. 11, 2006, which claims the benefit of priority of U.S. provisional application No. 60/729,172, filed Oct. 21, 2005, the contents of which being hereby incorporated by reference it its entirety for all purposes.

FIELD OF THE INVENTION

The present invention relates to a skin equivalent and a method for producing the same, wherein the skin equivalent comprises a scaffold and stem/progenitor cells isolated from the amniotic membrane of umbilical cord. These stem/progenitor cells may be mesenchymal (UCMC) and/or epithelial (UCEC) stem cells, which may then be further differentiated to fibroblast and keratinocytes. Further described is a method for isolating stem/progenitor cells from the amniotic membrane of umbilical cord, wherein the method comprises separating the amniotic membrane from the other components of the umbilical cord in vitro, culturing the amniotic membrane tissue under conditions allowing cell proliferation, and isolating the stem/progenitor cells from the tissue cultures. The invention also refers to therapeutic uses of these skin equivalents. Another aspect of the invention relates to the generation of a mucin-producing cell using stem/progenitor cells obtained from the amniotic membrane of umbilical cord and therapeutic uses of such mucin-producing cells. In yet another aspect, the invention relates to a method for generating an insulin-producing cell using stem/progenitor cells isolated from the amniotic membrane of umbilical cord and therapeutic uses thereof. The invention further refers to a method of treating a bone or cartilage disorder using UCMC. Furthermore, the invention refers to a method of generating a dopamin and tyrosin hydroxylase as well as a HLA-G and hepatocytes using UCMC and/or UCEC. The present invention also refers to a method of inducing proliferation of aged keratinocytes using UCMC.

BACKGROUND OF THE INVENTION

Stem cells are a cell population possessing the capacities to self-renew indefinitely and to differentiate in multiple cell or tissue types. Embryonic stem cells (from approximately days 3 to 5 after fertilisation) proliferate indefinitely and can differentiate spontaneously into all tissue types: they are thus termed pluripotent stem cells (reviewed, for example, in Smith, A. G. (2001) *Annu. Rev. Cell. Dev. Biol.* 17, 435-462). Adult stem cells, however, are more tissue-specific and may have less replicative capacity: they are thus termed multipotent stem cells (reviewed, for example, in Paul, G. et al. (2002) *Drug Discov. Today* 7, 295-302). The "plasticity" of embryonic and adult stem cells relies on their ability to trans-differentiate into tissues different from their origin and, perhaps, across embryonic germ layers.

The ability of stem cells to self-renew is critical to their function as reservoir of primitive undifferentiated cells. In contrast, most somatic cells have a limited capacity for self-renewal due to telomere shortening (reviewed, for example, in Dice, J. F. (1993) *Physiol. Rev.* 73, 149-159). Stem cell-based therapies thus have the potential to be useful for the treatment of a multitude of human and animal diseases.

Stem cells as well as stem/progenitor cells can be derived from different sources. The "multi-lineage" potential of embryonic and adult stem cells has been extensively characterized. Even though the potential of embryonic stem cells is enormous, their use implies many ethical problems. Therefore, non-embryonic stem cells derived from the bone marrow stroma, fat tissue, dermis and umbilical cord blood have been proposed as alternative sources. These cells can differentiate inter alia into chondrocytes, adipocytes, osteoblasts, myoblasts, cardiomyocytes, astrocytes, and tenocytes in vitro and undergo differentiation in vivo, making these stem cells—in general referred to as mesenchymal stem cells—promising candidates for mesodermal defect repair and disease management.

In clinical use, however, harvesting of such mesenchymal stem cells causes several problems. The collection of the cells is a mental and physical burden to the patient as a surgical procedure is required to obtain the cells (for example, the collection of bone marrow is an invasive technique performed with a biopsy needle that requires local or even general anesthesia). Furthermore, in many cases the number of stem cells extracted is rather low. More importantly, no epithelial cells are derived or differentiated from these cells. This prompted the search for other possible sources of stem cells.

Umbilical cord blood has been identified as a rich source of haematopoetic stem/progenitor cells. However, the existence of mesenchymal stem/progenitor cells is discussed controversially. On the one hand, such cells could not be isolated or successfully cultured from term umbilical cord blood (Mareschi, K. et al. (2001) *Haematologica* 86, 1099-1100). At the same time, results obtained by Campagnoli, C. et al. (*Blood* (2001) 98, 2396-2402) as well as Erices, A. et al. (*Br. J. Haematol.* (2000) 109, 235-242) suggest that mesenchymal stem cells are present in several fetal organs and circulate in the blood of pre-term fetuses simultaneously with hematopoietic precursors. Accordingly, International Patent Application WO 03/070922 discloses isolation and culture-expansion methods of mesenchymal stem/progenitor cells from umbilical cord blood and a differentiation method of such cells into various mesenchymal tissues. Isolation efficiencies of about 60% have been reported (Bieback, K. et al. (2004) *Stem Cells* 22, 625-634). In the same study, both the time period from collection of the umbilical cord blood to isolation of the cells and the volume of the blood sample used have been determined as crucial parameters for achieving such a yield. However, it is still a matter of debate whether these stem/progenitor cells are indeed derived of umbilical cord tissue.

Recently, mesenchymal stem/progenitor cells have been successfully isolated from umbilical cord tissue, namely from Wharton's jelly, the matrix of umbilical cord, (Mitchell, K. E. et al. (2003) *Stem Cells* 21, 50-60; U.S. Pat. No. 5,919,702; US Patent Application 2004/0136967). These cells have been shown to have the capacity to differentiate, for example, into a neuronal phenotype and into cartilage tissue, respectively. Furthermore, mesenchymal stem/progenitor cells have also been isolated from the endothelium and the subendothelial layer of the umbilical cord vein, one of the three vessels (two arteries, one vein) found within the umbilical cord (Romanov, Y. A. et al. (2003) *Stem Cells* 21, 105-110; Covas, D. T. et al. (2003) *Braz. J. Med. Biol. Res.* 36, 1179-1183).

However, none of these approaches employed thus far has, for example, resulted in the isolation or cultivation of epithelial stem/progenitor cells as a source for epithelial cell-based therapies such as skin resurfacing, liver repair, bladder tissue engineering and other engineered surface tissues. Skin resurfacing is an especially critical and much needed medical treatment, which still needs a lot of development as can be seen from the numbers available for example for the USA. In the USA alone, there are 100.000 hospital treated burns per year and 600.000 cases of surgical skin excision. The age related problem of non-healing dermal wounds is far larger, with 11 to 12 million patients being treated in the USA. For these pathologies Europe shows approximately the same numbers of patients.

The skin has three layers, the epidermis, the dermis and the fat layer, which all perform specific tasks. The epidermis is generated principally by keratinocytes of epithelial origin, whereas the dermis is populated by fibroblastic cells of mesenchymal origin. The epidermis is the thin, tough, top layer of skin. The outer portion of the epidermis, the stratum corneum, is water-proof and, when undamaged, prevents most bacteria, viruses, and other foreign substances from entering the body. The epidermis also protects the internal organs, muscles, nerves, and blood vessels against trauma. The epidermis also contains islet-cells, which are part of the skin's immune system. The dermis, the next layer of skin, is a thick layer of fibrous and elastic tissue (made mostly of the polymers collagen and fibrillin) that gives the skin its flexibility and strength. The dermis contains nerve endings, glands, hair follicles and blood vessels.

The damage of the epidermis or dermis or of both layers (full thickness wounds) by mechanical force, such as abrasion, surgical wounds associated with the excision of skin cancers, or a loss of skin due to burns or other wounds, such as chronic venous ulcers, requires often the substitution of the skin. Depending on the extent of the damage the substitution with patient's own skin (autografts) taken from non-affected parts of the body is sometimes insufficient due to the extensive loss of skin. Therefore, a need exists to develop substitutes for damaged skin either with help of autologous or allogeneic cells.

U.S. Pat. No. 6,479,875, for example, describes a skin substitute, which consists of a scaffold which incorporates dermis-forming cells consisting of mesenchymal stem cells. However, these mesenchymal stem cells, which are isolated from the bone marrow, are rare and typically 10-20 cc aspirates have to be harvested from a patient in order to obtain enough mesenchymal stem cells.

Thus, there is still a need for methods and reliable sources useful for the isolation and cultivation of epithelial stem/progenitor cells, which can be used for the further development of adequate skin substitutes. Furthermore, rapid and efficient methods which are ethically acceptable and do not pose a biomedical burden on the patient for the isolation of epithelial and mesenchymal stem/progenitor cells are still required in order to provide such cells in a sufficient amount for various applications in regenerative medicine and tissue engineering.

SUMMARY OF THE INVENTION

The invention provides a skin equivalent comprising a scaffold which includes cells derived from stem/progenitor cells isolated from the amniotic membrane of umbilical cord.

In one embodiment of the present invention the cells derived from stem/progenitor cells are mesenchymal stem cells (UCMC: means in other words umbilical cord lining (amniotic membrane) mesenchymal stem cells; also referred to as CLMC) or epithelial stem cells (UCEC: means in other words umbilical cord lining (amniotic membrane) epithelial stem cells; also referred to as CLEC).

The cells used for the skin equivalent of the present invention can be autologous, xenogeneic or allogeneic cells.

Furthermore the cells used for the skin equivalent of the present invention can be of mammalian origin. In one embodiment of the present invention the cells are of human origin.

In another embodiment the scaffold of the skin equivalent can further include additional cell lines, for example, but not limited to, vessel endothelial cells or dermal microvascular endothelial cells. In one embodiment these vessel endothelial cells are derived from the umbilical cord. Depending on the donor the endothelial cells can be of mammalian or human origin.

In one embodiment of the invention the skin equivalent comprises a scaffold, which comprises a biodegradable material. In yet another embodiment this scaffold includes or consist of, but is not limited, to a material such as agarose, polycaprolactone, niobium coated carbon, chitosan, collagen, hyaluronic acid, calcium phosphate, starch, hydroxyapatite, fibrin, alginate, poly-glycolic acid, carbon nano fibres, porous polycarbonate, polytetrafluoroethylene, polylactide and mixtures thereof. In one example of the present invention the scaffold material is polycarbonate.

The present invention further provides a scaffold which scaffold may include at least one extracellular matrix as support for the cells derived from stem/progenitor cells isolated from the amniotic membrane of umbilical cord. The extracellular matrix component may include, but is not limited to one or more of materials such as collagen, elastin, intercellular adhesion molecules, laminin, heparin, fibronectin, proteoglycans, tenascin, fibrillin and mixtures thereof. In one example the extracellular matrix component is collagen. In another embodiment the extracellular matrix is provided by the stem/progenitor cell itself by secretion of the respective extracellular matrix component, e.g. collagen.

In yet another embodiment of the present invention the UCMC and/or UCEC comprised in the skin equivalent of the present invention are able to proliferate and further differentiate in fibroblasts and keratinocytes, respectively.

The invention further provides a method for the production of a skin equivalent comprising:
  providing a scaffold,
  placing cells derived from stem/progenitor cells isolated from the amniotic membrane of umbilical cord in or onto said scaffold, and
  incubating said scaffold in a first medium, which allows said cells to proliferate and further differentiate.

In one embodiment said cells derived from stem/progenitor cells are mesenchymal stem cells (UCMC) or epithelial stem cells (UCEC).

In another embodiment of the present invention said first medium comprises a medium adapted for the cultivation of fibroblast or keratinocytes when said scaffold comprises UCMC and UCEC, respectively.

The invention further provides a method of treating a skin disorder comprising contacting the skin equivalent of the present invention on said skin disorder. The invention further provides the use of a skin equivalent of the present invention or a skin equivalent obtained by the method of the present invention for the manufacture of a pharmaceutical composition as well as the pharmaceutical composition for the treatment of burned skin and an ulcer, to name only a few illustrative examples of skin disorders.

The invention further provides a cell bank comprising a skin equivalent of the present invention or a skin equivalent obtained by a method of the present invention.

The invention also provides a method for the generation of a mucin-producing cell comprising:
  placing umbilical cord amniotic lining membrane epithelial or mesenchymal stem cells (UCEC and UCMC, respectively) in a container, and
  incubating said UCEC or UCMC in a medium adapted for the cultivation of secretory cells. Such mucin-producing cells can be used for treating cells of the ocular surface or the respiratory tracts, which are affected, e.g., by smoke.

The Yet in still another embodiment the present invention provides a method for generating an insulin-producing cell, comprising
  cultivating cells derived from stem/progenitor cells isolated from the amniotic membrane of umbilical cord, and
  proliferating and differentiating said cells in a suitable cultivation medium into β-islet cells.

In yet other embodiments the invention provides insulin-producing cells obtained by a method of the present invention, described above, and treating a disorder associated with an imbalance in the insulin level, comprising administering to a mammal an insulin producing cell obtained by the method of the present invention as described above.

In a further embodiment of the present invention a method of treating a bone disorder comprising administering osteoblasts which are produced from mesenchymal stem cells isolated from the amniotic membrane of the umbilical cord (UCMC) to a patient is provided. Also provided is a method of treating a cartilage disorder comprising administration of chondrocytes, which are produced from mesenchymal stem cells isolated from the amniotic membrane of the umbilical cord (UCMC) to a patient.

Still another embodiment of the present invention provides a method of generating a dopamin and tyrosin hydroxylase producing cell, comprising
  cultivating cells derived from stem/progenitor cells isolated from the amniotic membrane of umbilical cord, preferably UCMC, and
  proliferating and differentiating the cells in a suitable cultivation medium into dopamin and tyrosin hydroxylase producing cells.

In addition, the present invention refers to a method of producing human leukocyte antigen G (HLA-G) or hepatic like cells using UCMC and UCEC, respectively.

In another embodiment of the present invention, it is referred to a method of inducing proliferation of aged keratinocytes comprising
  culturing aged keratinocytes in a suitable growth medium, and adding mesenchymal stem cells (UCMC) of the amniotic membrane of the umbilical cord to the aged keratinocytes to induce proliferation of the aged keratinocytes.

BRIEF DESCRIPTION OF THE DRAWINGS

The invention will be better understood with reference to the detailed description when considered in conjunction with the non-limiting examples and the drawings, in which:

FIG. 5A (40× magnification) depicts the morphology in serum culture condition (DMEM/10% FCS) of normal dermal fibroblasts (NF109 cells). FIG. 5B (40× magnification) depicts the morphology in serum-free culture condition (DMEM) of normal dermal fibroblasts (NF109 cells). FIG. 5C (40× magnification) depicts the morphology in serum culture condition (DMEM/10% FCS) of adipose-derived mesenchymal cells (ADMC). FIG. 5D (40× magnification) depicts the morphology in serum-free culture condition (DMEM) of adipose-derived mesenchymal cells (ADMC). FIGS. 5E and 5G (40× magnification) depict the morphology in serum culture condition (DMEM/10% FCS) of umbilical cord amniotic membrane mesenchymal cells (UCMC) isolated according to the method of the invention. FIGS. 5F and 5H (40× magnification) depict the morphology in serum-free culture condition (DMEM) of umbilical cord amniotic membrane mesenchymal cells (UCMC) isolated according to the method of the invention. Morphology of NF and ADMC cultured in serum starvation conditions (DMEM only) is reflected by flatter cells and less dense cytoplasm as compared with serum rich conditions (DMEM/10% FCS) where cells are more rounded with a dense cytoplasm. No change in morphology was observed in both UCMC groups cultured under identical conditions of serum-free vs. serum rich media, indicating a difference in behavior and physiology of these latter mesenchymal cells.

FIG. 9-2 shows Western blot analysis by which the expression of STAT3 in UCEC and UCMC isolated according to the invention, was compared to the expression of these markers in human dermal fibroblasts (NF), in bone marrow mesenchymal cells (BMSC) and adipose-derived mesenchymal cells (ADMC). FIG. 9-3 shows Western blot analysis by which the expression of STAT3 in UCEC and UCMC isolated according to the invention, was compared to the expression of these markers in human dermal fibroblasts (NF), in bone marrow mesenchymal cells (BMSC) and adipose-derived mesenchymal cells (ADMC). FIG. 9-4 shows Western blot analysis by which the expression of PLGF in UCEC and UCMC isolated according to the invention, was compared to the expression of these markers in human dermal fibroblasts (NF), in bone marrow mesenchymal cells (BMSC) and adipose-derived mesenchymal cells (ADMC). FIG. 9-5 shows Western blot analysis by which the expression of PLGF in UCEC and UCMC isolated according to the invention, was compared to the expression of these markers in human dermal fibroblasts (NF), in bone marrow mesenchymal cells (BMSC) and adipose-derived mesenchymal cells (ADMC). FIG. 9-6 shows Western blot analysis by which the expression of CTGF in UCEC and UCMC isolated according to the invention, was compared to the expression of these markers in human dermal fibroblasts (NF), in bone marrow mesenchymal cells (BMSC) and adipose-derived mesenchymal cells (ADMC). FIG. 9-7 shows Western blot analysis by which the expression of CTGF in UCEC and UCMC isolated according to the invention, was compared to the expression of these markers in human dermal fibroblasts (NF), in bone marrow mesenchymal cells (BMSC) and adipose-derived mesenchymal cells (ADMC). FIG. 9-8 shows Western blot analysis by which the expression of PDGF in UCEC and UCMC isolated according to the invention, was compared to the expression of these markers in human dermal fibroblasts (NF), in bone marrow mesenchymal cells (BMSC) and adipose-derived mesenchymal cells (ADMC). FIG. 9-9 shows Western blot analysis by which the expression of PDGF in UCEC and UCMC isolated according to the invention, was compared to the expression of these markers in human dermal fibroblasts (NF), in bone marrow mesenchymal cells (BMSC) and adipose-derived mesenchymal cells (ADMC). FIG. 9-10 shows Western blot analysis by which the expression of VEGF in UCEC and UCMC isolated according to the invention, was compared to the expression of these markers in human dermal fibroblasts (NF), in bone marrow mesenchymal cells (BMSC) and adipose-derived mesenchymal cells (ADMC). FIG. 9-11 shows Western blot analysis by which the expression of VEGF in UCEC and UCMC isolated according to the invention, was compared to the expression of these markers in human dermal fibroblasts (NF), in bone marrow mesenchymal cells (BMSC) and adipose-derived mesenchymal cells (ADMC). FIG. 9-12 shows Western blot analysis by which the expression of FGF-2 in UCEC and UCMC isolated according to the invention, was compared to the expression of these markers in human dermal fibroblasts (NF), in bone marrow mesenchymal cells (BMSC) and adipose-derived mesenchymal cells (ADMC). FIG. 9-13 shows Western blot analysis by which the expression of FGF-2 in UCEC and UCMC isolated according to the invention, was compared to the expression of these markers in human dermal fibroblasts (NF), in bone marrow mesenchymal cells (BMSC) and adipose-derived mesenchymal cells (ADMC). FIG. 9-14 shows Western blot analysis by which the expression of HDGF in UCEC and UCMC isolated according to the invention, was compared to the expression of these markers in human dermal fibroblasts (NF), in bone marrow mesenchymal cells (BMSC) and adipose-derived mesenchymal cells (ADMC). FIG. 9-15 shows Western blot analysis by which the expression of HDGF in UCEC and UCMC isolated according to the invention, was compared to the expression of these markers in human dermal fibroblasts (NF), in bone marrow mesenchymal cells (BMSC) and adipose-derived mesenchymal cells (ADMC). FIG. 9-16 shows Western blot analysis by which the expression of SCF in UCEC and UCMC isolated according to the invention, was compared to the expression of these markers in human dermal fibroblasts (NF), in bone marrow mesenchymal cells (BMSC) and adipose-derived mesenchymal cells (ADMC). FIG. 9-17 shows Western blot analysis by which the expression of α-SMA in UCEC and UCMC isolated according to the invention, was compared to the expression of these markers in human dermal fibroblasts (NF), in bone marrow mesenchymal cells (BMSC) and adipose-derived mesenchymal cells (ADMC). FIG. 9-18 shows Western blot analysis by which the expression of fibronectin in UCEC and UCMC isolated according to the invention, was compared to the expression of these markers in human dermal fibroblasts (NF), in bone marrow mesenchymal cells (BMSC) and adipose-derived mesenchymal cells (ADMC). FIG. 9-19 shows Western blot analysis by which the expression of fibronectin in UCEC and UCMC isolated according to the invention, was compared to the expression of these markers in human dermal fibroblasts (NF), in bone marrow mesenchymal cells (BMSC) and adipose-derived mesenchymal cells (ADMC). FIG. 9-20 shows Western blot analysis by which the expression of decorin in UCEC and UCMC isolated according to the invention, was compared to the expression of these markers in human dermal fibroblasts (NF), in bone marrow mesenchymal cells (BMSC) and adipose-derived mesenchymal cells (ADMC). FIG. 9-21 shows Western blot analysis by which the expression of syndecan-1 in UCEC and UCMC isolated according to the invention, was compared to the expression of these markers in human dermal fibroblasts (NF), in bone marrow mesenchymal cells (BMSC) and adipose-derived mesenchymal cells (ADMC). FIG. 9-22 shows Western blot analysis by which the expression of syndecan-2 in UCEC and UCMC isolated according to the invention, was compared to the expression of these markers in human dermal fibroblasts (NF), in bone marrow mesenchymal cells (BMSC) and adipose-derived mesenchymal cells (ADMC). FIG. 9-23 shows Western blot analysis by which the expression of syndecan-2 in UCEC and UCMC isolated according to the invention, was compared to the expression of these markers in human dermal fibroblasts (NF), in bone marrow mesenchymal cells (BMSC) and adipose-derived mesenchymal cells (ADMC). FIG. 9-24 shows Western blot analysis by which the expression of syndecan-3 in UCEC and UCMC isolated according to the invention, was compared to the expression of these markers in human dermal fibroblasts (NF), in bone marrow mesenchymal cells (BMSC) and adipose-derived mesenchymal cells (ADMC). FIG. 9-25 shows Western blot analysis by which the expression of syndecan-3 in UCEC and UCMC isolated according to the invention, was compared to the expression of these markers in human dermal fibroblasts (NF), in bone marrow mesenchymal cells (BMSC) and adipose-derived mesenchymal cells (ADMC). FIG. 9-26 shows Western blot analysis by which the expression of syndecan-4 in UCEC and UCMC isolated according to the invention, was compared to the expression of these markers in human dermal fibroblasts (NF), in bone marrow mesenchymal cells (BMSC) and adipose-derived mesenchymal cells (ADMC). FIG. 9-27 shows Western blot analysis by which the expression of Bmi-1 in UCEC and UCMC isolated according to the invention, was compared to the expression of these markers in human dermal fibroblasts (NF), in bone marrow mesenchymal cells (BMSC) and adipose-derived mesenchymal cells (ADMC). FIG. 9-28 shows Western blot analysis by which the expression of LIF in UCEC and UCMC isolated according to the invention, was compared to the expression of these markers in human dermal fibroblasts (NF), in bone marrow mesenchymal cells (BMSC) and adipose-derived mesenchymal cells (ADMC). FIG. 9-29 shows secretion of Leukemia inhibitory factor detected by Western blot analysis in supernatants of umbilical cord mesenchymal and epithelial stem cell culture in comparison with bone marrow, adipose derived stem cells, human dermal fibroblasts and epidermal keratinocytes. FIG. 9-30 shows secretion of highly secreted ActivinA and Follistatin detected by ELISA assay in supernatants of umbilical cord mesenchymal and epithelial stem cell culture in comparison with bone marrow, adipose derived stem cells, human dermal fibroblasts and epidermal keratinocytes. FIG. 9.1*a* and FIG. 9.1*b* describe the result of an experiment in which UCMC were cultured in PTT-4 medium. The colonies in the culture dishes (FIG. 9.1*a*) were fixed and stained with an anti Oct-4 antibody (FIG. 9.1*b*) to confirm expression of the transcription factor (FIG. 9.1.*b*)

FIG. 10-1 shows indirect immunofluorescent analysis of markers of epithelial cells expressed in umbilical cord epithelial stem cells: cytokeratins (CK)-general, CK17, CK6, CK10, CK19, CK18, CK16, CK15. FIG. 10-2 shows indirect immunofluorescent analysis of markers of epithelial cells expressed in umbilical cord epithelial stem cells: Hemidesmosome components-integrin alpha6, integrin beta4; Desmosome components. FIG. 10-3 shows indirect immunofluorescent analysis of markers of epithelial cells expressed in umbilical cord epithelial stem cells: Basement membrane components-laminin1, laminin5, collagen IV, collagen VII. FIG. 10-4 shows indirect immunofluorescent analysis of markers of epithelial cells expressed in umbilical cord epithelial stem cells: extracellular matrix components integrin-beta1 and fibronectin.

FIGS. 11-1 to FIG. 11-4 show cytokine array analysis of secreted cytokines and growth factors by umbilical cord mesenchymal stem cells (UCMC) in comparison with human bone-marrow mesenchymal stem cells. In more detail, FIG. 11-1 shows an expression profile of secreted cytokines and growth factors by umbilical cord mesenchymal cells, FIG. 11-2 also shows an expression profile of secreted cytokines and growth factors by umbilical cord mesenchymal cells, FIG. 11-3 further shows an expression profile of secreted cytokines and growth factors by umbilical cord mesenchymal cells, and also FIG. 11-4 shows an expression profile of secreted cytokines and growth factors by umbilical cord mesenchymal cells.

FIGS. 12-1 to FIG. 12-7 show cytokine array analysis of secreted cytokines and growth factors by umbilical cord epithelial stem cells (UCEC) in comparison with human epidermal keratinocytes. In more detail, FIG. 12-1 shows an expression profile of secreted cytokines and growth factors by umbilical cord epithelial cells, FIG. 12-2 also shows an expression profile of secreted cytokines and growth factors by umbilical cord epithelial cells, FIG. 12-3 shows an expression profile of secreted cytokines and growth factors by human epidermal keratinocytes, FIG. 12-4 also shows an expression profile of secreted cytokines and growth factors by human epidermal keratinocytes, FIG. 12-5 shows an expression profile of secreted cytokines and growth factors by umbilical cord epithelial cells, FIG. 12-6 shows a spotting of a chip used for cytokine array, and FIG. 12-7 also shows a spotting of a chip used for cytokine array.

FIG. 13-1 shows UCMC cells cultured in DMEM supplemented with 10% fetal calf serum (FCS), FIG. 13-2 shows UCMC cells cultured in serum-free media PTT-1. FIGS. 13-3 and 13-4 show UCMC cells cultured in serum-free media PTT-2. FIG. 13-5 shows UCMC cells cultured in serum-free media PTT-3. FIG. 13-6 shows the growth of adipose derived stromal cells in serum free medium PTT-3. FIG. 13-7 shows the growth of bone marrow derived stromal cells in serum free medium PTT-3.

FIGS. 14-1 to 14-6 show global gene expression in umbilical cord epithelial and mesenchymal stem cells analyzed by DNA microarray. UCEC expressed a total of 28055 genes and UCMC expressed a total of 34407 genes. There are 27308 overlapping genes expressing in both cell types. 747 genes expressed were unique to UCEC and 7099 genes expressed were unique to UCMC. The selected genes of interest are presented in this Figure. Both stem cell types expressed 140 genes related to embryonic stem cells and embryonic development.

FIG. 15 shows a schematic illustration of expansion of umbilical cord epithelial and mesenchymal stem cells using repetitive explants of umbilical cord lining membrane tissues.

FIG. 16 depicts a cross section of an umbilical cord demonstrating the umbilical cord amniotic lining membrane (LM), the contained Wharton's jelly (WJ), as well as two umbilical arteries (UA) and one umbilical vein (UV) supported within this jelly.

FIGS. 17B and 17C depict direct in-vitro differentiation of mesenchymal cells isolated from the amniotic membrane of umbilical cord (UCMC) into osteoblasts and adipocytes.

FIGS. 18a and 18b depicts the in vitro differentiation of epithelial cells isolated from the amniotic lining membrane of umbilical cord (UCEC) into skin epidermal keratinocytes (FIG. 18a; pictures taken after 7 days of cell culturing), and in-vitro differentiation of mesenchymal cells isolated from the amniotic lining membrane of umbilical cord (UCMC) into fibroblasts (FIG. 18b; photographs taken after 7 days of cell culturing).

FIG. 19 (200× magnification) depicts a fully developed skin equivalent obtained by the method of the present invention. The epithelial layer is formed by the keratinocytes, which were produced by differentiation and incubation of UCEC in a medium as specified in the method of the present invention. The dermal layer, which is formed by the keratinocytes produced by differentiation and incubation of UCMC in a medium as specified in the method of the present invention, also grows in the extracellular collagen matrix and included in the skin equivalent of the present invention.

FIG. 20a (1200× magnification) depicts the keratinocyte surface appearance of a skin equivalent (CSE-1) produced according to the method described in Example 12—FIG. 20b (2000× magnification) depicts the appearance of UCMC derived fibroblasts in collagen scaffold (lattices), which were obtained according to the method described in Example 12.

FIG. 21a (2000× magnification) depicts the keratinocyte surface appearance of a skin equivalent (CSE-2) produced according to the method described in Example 13. FIG. 21b (3000× magnification) depicts the appearance of UCMC derived fibroblasts in collagen lattices, which were obtained according to the method described in Example 13.

FIG. 22a shows the development of mucin-producing cells after 3, 7 and 10 days of culturing in PTT-6. FIG. 22b shows the mucin produced by UCEC (referred to as pellets 1, 2, 3, 6 (P1, P2 etc.) of UCEC-17) cultured in PTT-6 detected by their molecular weight in a SDS-PAGE. For further details see Example 16.

FIGS. 23a and 23b depicts UCEC which were incubated in PTT-10 together with nicotinamide. As can be seen from the photographs UCEC which were incubated with nicotinamide differentiated into β-islet cells (FIG. 23b), whereas UCEC grown in PTT-10 only did not (FIG. 23a).

FIG. 24B depicts the chondrogenic differentiation of UCMC into chondrocytes for the development of cartilage. Chondrocytes developed from UCMC upon induction with modified PTT-5 (see Example 17) have been stained with Alcian Blue. Positive staining of chondrocytes was observed in.

FIG. 25 shows insulin expression in multiple samples of UCEC under induction of ES Cult medium (Stem Cell Technologies Inc., Vancouver, Canada) or BBRC06 medium as described in Example 15. This experiment shows that UCEC have the potential to differentiate into insulin-producing cells which can be used for the treatment of diabetes.

FIG. 26A and FIG. 26B demonstrate the secretion and expression of tyrosine hydroxylase (TH) and dopamine by differentiated UCMC cells as described in more detail in Example 18. Dopamine is used for the treatment of patient with Parkinson Syndrome. FIG. 26C shows a negative control.

FIGS. 28A, 28B and 28C show the results of the experiment in which the proliferation of aged skin keratinocytes (asK) and human dermal fibroblasts have been induced by UCMC. Skin cells used derived from of 50 or 60 year old patients have been used for this experiment. This experiment demonstrates the proliferative effects of UCMC which can therefore also be used for wound healing, tissue repair, regeneration, rejenuvation, cosmetic and skin care applications.

FIG. 29A shows organotypic coculture of UCMC and UCEC in collagene lattices. Epithelia were observed on these mesenchymal tissue equivalents (MTE) constructs. FIG. 29B shows skin-resemble structures of cultured skin equivalents. UCMC cell-populated collagen lattices support full differentiation of human keratinocyte stem cells. These figures show that UCMC and UCEC can be used to construct organ-like tissue in-vitro for tissue repair and regeneration and drug discovery.

FIG. 30A and FIG. 30B demonstrate that UCMC cells are able to grow into and onto collagen and bone scaffolds of TissueFleece® E (Baxter AG, Austria) and BoneSave® (Stryker Inc., MI, USA). The figures show living UCMC which have been stained and which were grown on the scaffolds as described in Example 2.

FIG. 31B and FIG. 31C refer to an experiment as described in Example 22 demonstrating the angiogenic properties of UCMC populated collagen scaffolds which were implanted in mice. After 21 days, macroscopic as well as microscopic vascularization was observed.

FIGS. 32A to 32C demonstrate the clinical application of UCMC for treatment of full thickness burns wounds ($3^{rd}$ degree). FIG. 32A shows wound bed preparation on full thickness burns of 53 years old female patient. UCMC cells were inoculated onto Biobrane wound dressings (Dow Hickam Pharmaceuticals, Texas, USA). UCMC-Biobrane constructs were transferred onto wounds (FIG. 32B) as described in Example 23. Complete healing was seen at day 7 without skin graft and stable up to 3 month follow-up (FIG. 32C).

FIG. 33 demonstrates the clinical application of UCMC for the treatment of partial-thickness wounds ($2^{nd}$ degree) of 2 years old, male patient as described in example 24. Complete healing of the wound was observed at day 3.

FIG. 34 demonstrates the clinical application of UCMC for the treatment of full thickness burns wounds ($3^{rd}$ degree) of a 2 year old male patient. UCMC were mixed with SoloSite® gel (Smith & Nephew, Hull, UK) and pasted onto wound as described in example 23. Complete healing of the wound with this method was observed at day 5.

DETAILED DESCRIPTION

Figure 1A:
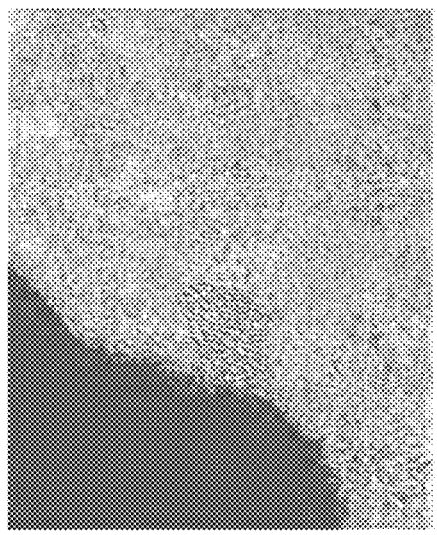
FIG. 1A depicts epithelial cell outgrowth from umbilical cord amniotic membrane by the method of direct tissue explant (40× magnification) at day 2 of tissue culture.
Figure 1C:
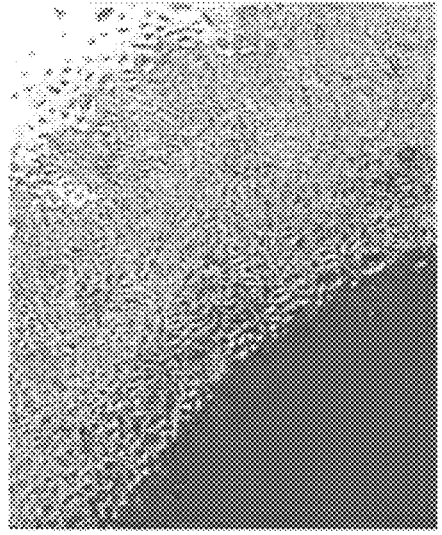
FIGS. 1B and 1C depict epithelial cell outgrowth from umbilical cord amniotic membrane by the method of direct tissue explant (40× magnification) at day 5 of tissue culture. Cell culture plastic surfaces were coated with collagen 1/collagen 4 mixtures (1:2; Becton Dickinson) before placing the amniotic membrane on the surface. The amniotic membrane specimens were submerged in 5 ml EpiLife® medium or Medium 171 (both from Cascade Biologics). Medium was changed every 2 or 3 days and cell outgrowth by explant was monitored under light microscopy. Microphotographs were taken at different time intervals as stated above. The observed polyhedral cell morphology is typical of epithelial cells.

The invention is based on the surprising finding that skin equivalents can be formed using the amniotic membrane of umbilical cord as a source, from which stem/progenitor cells such as mesenchymal and epithelial stem/progenitor cells can be successfully isolated and expanded under in vitro conditions. Using these cells, the invention provides a skin equivalent comprising or consisting essentially of a scaffold including cells derived from stem/progenitor cells derived from the amniotic membrane of umbilical cord. Even more surprising is the finding that these stem/progenitor cells show embryonic stem cell-like characteristics. The amniotic membrane (also called amniotic lining membrane), i.e. thin innermost membranous sac enclosing the placenta and developing embryo of mammals, has recently been used as a natural substrate in ocular surface reconstruction and as a biological substrate for expanding limbal epithelial stem cells (cf., e.g., Anderson, D. F. et al. (2001) Br. J. Ophthal-mol. 85, 567-575; Grüterich, M. et al. (2003) Surv. Ophthalmol. 48, 631-646). However, no methods have been described thus far for the isolation of stem/progenitor cells from the amniotic membrane, at least for humans, nor has the amniotic membrane covering the umbilical cord been reported as a source for stem cells which can be used to produce the skin equivalent of the present invention.

A scaffold is employed as basis for the skin equivalent of the present invention. Scaffolds have been used extensively in the area of tissue engineering either to construct a neo-tissue that can be implanted to repair a defect site in the body or as a cell container in bioartificial devices. Scaffolds form a three dimensional matrix that serves as a template for cell proliferation and ultimately tissue formation. Culturing cells in a scaffold typically involves seeding cells throughout the scaffold and allowing the cells to proliferate in the scaffold for a pre-determined amount of time.

Thus, the present provides a skin equivalent and a method to obtain the same wherein in one embodiment the scaffold includes or is made of a biodegradable material. To use a biodegradable material for the scaffold is advantageous, e.g., for tissue engineering, wherein the scaffolds containing the cells are used to repair defect sites in living tissue, e.g. skin. One useful aspect of the scaffolds used in the present invention is their penetrability for the cell medium that is necessary to transport nutrients and metabolites to and from the cells included into said scaffold. In the present invention, scaffolds further include or are made from materials such as agarose, polycaprolactone (Endres, M. et al., Tissue Engineering, 2003, Vol. 9, No. 4, P. 689-702), niobium coated carbon, chitosan, hydroxyapatite-tricalcium phosphate (Harris, C. T. and Cooper, L. F., Comparison of matrices for hMSC delivery, 2004, P. 747-755), collagen, hyaluronic acid, calcium phosphate, starch, hydroxyapatite, fibrin, alginate, poly-glycolic acid, carbon nano fibres, polytetrafluoroethylene, polylactic acid (Moran, J. et al., Tissue Engineering, 2003, Vol. 9, No. 1, P. 63-70) and mixtures thereof. Foam scaffolds as those described in U.S. Pat. No. 6,231,879 which are based on thermoplastic elastomers, such as polyamide, polyester, polyethylene polyvinylidene fluoride, polyethyurethane or silicone, can also be used in the present invention. In one embodiment, porous polycarbonate is used as scaffold material.

The scaffold in which the cell species are encapsulated may have any regular or irregular (outer) shape. If the scaffolds are, e.g., used in tissue engineering of the skin the shape of the scaffold will fit the shape of the defect site the scaffold will be used for. The scaffold which are used in the present invention are normally about 1 μm to about 5 μm thick and in some embodiments can have a surface area from about 0.5 $cm^2$ to about 20 $cm^2$.

In order to obtain the cells which are used for the skin equivalent of the present invention a method for isolating stem/progenitor cells from the amniotic membrane of umbilical cord is described herein. The method comprises:

(a) separating the amniotic membrane from the other components of the umbilical cord in vitro;

(b) culturing the amniotic membrane tissue obtained in step (a) under conditions allowing cell proliferation; and (c) isolating the stem/progenitor cells.

For isolation of the cells from umbilical cord, the umbilical cord or a part thereof is usually collected immediately after birth (of a child in the case of humans) and for transport to the laboratory transferred in a medium that is suitable for handling of mammalian tissue. Examples of such media include, but are not limited to Leibovitz media which are commercially available from suppliers such as Sigma Aldrich, Saint Louis, Mo. USA or HyClone, Logan, Utah, USA. The umbilical cord is then typically processed under sterile conditions. Processing of the cord typically includes removing the blood that has remained on the surface or within the blood vessels of the umbilical cord by washing with a suitable buffer such as phosphate buffered saline. The umbilical cord is then typically reduced to smaller pieces, for example by cutting, and washed again before separating the amniotic membrane from the other components. In this conjunction, it is noted that it is not necessary to process the umbilical cord of a mammalian donor immediately after birth but it is also possible, to collect the umbilical cord and, optionally after washing under sterile conditions and reducing it into smaller pieces, to preserve the umbilical cord or parts thereof by cryo-preservation and to store the so obtained specimen, for example in liquid nitrogen, for later isolation of the cells from the umbilical cord.

The term "cryo-preservation" is used herein in its regular meaning to describe a process where cells or whole tissues are preserved by cooling to low sub-zero temperatures, such as (typically) −80° C. or −196° C. (the boiling point of liquid nitrogen). Cryo-preservation can be carried out as known to the person skilled in the art and can include the use of cryo-protectors such as dimethylsulfoxide (DMSO) or glycerol, which slow down the formation of ice-crystals in the cells of the umbilical cord.

The term "stem/progenitor cell" as used herein refers to any cell derived of umbilical cord having the capacities to self-renew indefinitely and to differentiate in multiple cell or tissue types such as endothelial cells, epithelial cells, fibroblasts, myocytes or neurons. Not every subject which is in need of a skin equivalent can provide an umbilical cord as source for autologous progenitor/stem cells (i.e. cells obtained from the amniotic membrane of the umbilical cord of the same individual the skin equivalent of the present invention is later used for). Accordingly, the use of xenogeneic (i.e. the case of the present invention stem/progenitor cells isolated from the amniotic membrane of the umbilical cord of a species other than human) or allogeneic (i.e. in the case of the present invention stem/progenitor cells isolated from the amniotic membrane of the umbilical cord of another human) stem/progenitor cells is also contemplated herein. Furthermore, the cells which are used for the skin equivalent and the method of its production according to the present invention may be derived of any mammalian species, such as mouse, rat, guinea pig, rabbit, goat, dog, cat, sheep, monkey or human, with cells of human origin being preferred in one embodiment.

The term "embryonic stem cell-like properties" refers to the ability of the cells derived of umbilical cord that they can—almost like or exactly like embryonic stem cells—differentiate spontaneously into all tissue types, meaning that they are pluripotent stem cells.

The term "amniotic membrane" as used herein refers to the thin innermost membranous sac enclosing the developing embryo of mammals. During pregnancy, the fetus is surrounded and cushioned by a liquid called amniotic fluid. This fluid, along with the fetus and the placenta, is enclosed within a sac called the amniotic membrane, which also covers the umbilical cord. The amniotic fluid is important for several reasons. It cushions and protects the fetus, allowing the fetus to move freely. The amniotic fluid also allows the umbilical cord to float, preventing it from being compressed and cutting off the fetus' supply of oxygen and nutrients derived from the circulating blood within the placental blood vessels. The amniotic sac contains the amniotic fluid, which maintains a homeostatic environment protecting the fetal environment from the outside world. This barrier additionally protects the fetus from organisms (like bacteria or viruses) that could travel up the vagina and potentially cause infection.

Media and reagents for tissue culture are well known in the art (cf., for example, Pollard, J. W. and Walker, J. M. (1997) *Basic Cell Culture Protocols, Second Edition*, Humana Press, Totowa, N.J.; Freshney, R. I. (2000) *Culture of Animal Cells, Fourth Edition*, Wiley-Liss, Hoboken, N.J.). Examples of suitable media for incubating/transporting umbilical cord tissue samples include, but are not limited to, Dulbecco's Modified Eagle Medium (DMEM), RPMI media, CMRL1066, Hanks' Balanced Salt Solution (HBSS) phosphate buffered saline (PBS), and L-15 medium. Examples of appropriate media for culturing stem/progenitor cells according to the invention include, but are not limited to, Dulbecco's Modified Eagle Medium (DMEM), DMEM-F12, RPMI media, CMRL1066, EpiLife® medium, and Medium 171. The media may be supplemented with fetal calf serum (FCS) or fetal bovine serum (FBS) as well as antibiotics, growth factors, amino acids, inhibitors or the like, which is well within the general knowledge of the skilled artisan.

The method for the isolation of stem/progenitor cells can further comprise:

(a") separating these stem/progenitor cells from the amniotic membrane tissue by a enzymatic digestion and/or direct tissue explant technique before cultivation. The term "enzymatic digestion technique" as used herein means that enzymes are added to cleave the cells from the main tissue mass (here the amniotic membrane of the umbilical cord). The separated cells are subsequently collected. The term "direct tissue explant technique" as used herein means that the tissue is first placed in media without enzymes. Then under careful conditions the cells separate from the main tissue mass by itself- and the cells are then harvested for collection.

Methods for separating cells of a particular tissue or organ by treatment with enzymes or by direct tissue explant are well known in the art (cf., for example, Pollard, J. W. and Walker, J. M. (1997) *Basic Cell Culture Protocols, Second Edition*, Humana Press, Totowa, N.J.; Freshney, R. I. (2000) *Culture of Animal Cells, Fourth Edition*, Wiley-Liss, Hoboken, N.J.). Any enzyme catalyzing tissue dissociation may be used for performing this method. In one example, collagenase is used for that purpose. The enzyme may be used as a crude preparation or in purified form. It may be purified from any prokaryotic or eukaryotic organism (with *Clostridium histolyticum* being most preferred) or produced recombinantly by means of gene technology. Any type of collagenase may be employed, i.e. type I, type II, type III, type IV, or any combination thereof. In some examples the use of collagenase type I is being preferred.

In one example, the invention provides a method for isolating stem/progenitor cells that have embryonic stem cell-like properties. These cells can ultimately be differentiated into, but not limited to, by morphology, epithelial or mesenchymal stem cells (UCEC and UCMC, respectively).

Accordingly, in another embodiment, the invention provides a skin equivalent wherein the cells derived from stem/progenitor cells are mesenchymal stem cells (UCMC) or epithelial stem cells (UCEC). These cells (UCMC and UCEC) are obtained in a method for isolating epithelial and/or mesenchymal stem/progenitor cells, wherein in accordance with the above disclosure these cells may have embryonic stem cell-like properties.

Epithelial stem/progenitor cells (UCEC) include any cells exhibiting a epithelial cell like morphology (i.e. a polyhedral shape) that can be differentiated into any type of epithelial cell such as, but not limited to, skin epithelial cells, hair follicular cells, cornea epithelial cells, conjunctival epithelial cells, retinal epithelial cells, liver epithelial cells, kidney epithelial cells, pancreatic epithelial cells, oesophageal epithelial cells, small intestinal epithelial cells, large intestinal epithelial cells, lung and airway epithelial cells, bladder epithelial cells or uterine epithelial cells.

Mesenchymal stem/progenitor cells (UCMC) include any cells exhibiting a mesenchymal cell like morphology (i.e. a spindle-like shape) that can be differentiated into any type of mesenchymal cell such as, but not limited to, skin fibroblasts, chondrocytes, osteoblasts, tenocytes, ligament fibroblasts, cardiomyocytes, smooth muscle cells, skeletal muscle cells, adipocytes, cells derived from endocrine glands, and all varieties and derivatives of neurectodermal cells.

The method for the isolation of stem/progenitor cells can further comprise:
(d) culturing the stem/progenitor cells under conditions allowing the cells to undergo clonal expansion.

The term "clonal expansion" (sometimes also referred to as "mitotic clonal expansion") relates to a process that occurs early in the differentiation program of a cell, by which stem/progenitor cells become committed to a particular lineage and then undergo terminal differentiation. It is well known in the art that the conditions to induce clonal expansion of progenitor cells may vary significantly between different cell types. Without being limited to a particular method, the induction of clonal expansion is generally achieved by cultivating the stem/progenitor cells in a growth medium that has been optimized for cell proliferation. Such media are commercially available from many providers. Non-limiting examples of such media are KGM®-Keratinocyte Medium (Cambrex Corporation, New Jersey, USA), MEGM-Mammary Epithelial Cell Medium (Cambrex Corporation, New Jersey, USA), EpiLife® medium (Cascade Biologics Inc., Oregon, USA), Green's Medium, CMRL 1066 (Mediatech, Inc., Virginia, USA) or Medium 171 (M171; Cascade Biologics Inc., Oregon, USA). Normally, these culture mediums need to be supplemented with reagents inducing cell proliferation, such as growth factors. Such reagents may be admixed in a single solution such as the Human Keratinocyte Growth Supplement Kit (Cascade Biologics Inc., Oregon, USA), to name one example, or may be supplemented individually. Such reagents include, but are not limited to, growth factors (such as epidermal growth factor, insulin-like growth factor-1, platelet-derived growth factor-BB, transforming growth factor-β, keratinocyte growth factor (KGF; also referred to as HBGF-7 or FGF-7), TGF-α, amphiregulin for example), hormones (such as a bovine pituitary extract), hydrocortisone, transferrin and the like in any suitable combination to induce clonal expansion of a given cell type. The term "clonal expansion" also includes cultivation of the cell in vivo, for example, by injection of the cells into mammals such as humans, mice, rats, monkeys, apes to name only a few.

The present invention provides a skin equivalent which mimics the natural composition of the skin with dermal layer and epidermal layer or with only either one of these two skin layers. For this purpose, cells of the present invention such as UCMC and UCEC can be differentiated into fibroblasts and keratinocytes, respectively. Therefore, the invention provides in one embodiment a method for the production of a skin equivalent comprising:
providing a scaffold,
placing cells derived from stem/progenitor cells isolated from the amniotic membrane of umbilical cord in or onto said scaffold, and
incubating said scaffold in a first medium, which allows said cells to proliferate and further differentiate.

As the stem/progenitor cells isolated from the amniotic membrane of umbilical cord of the present invention have the potential to differentiate in UCMC and UCEC, as described above, it is preferred in some embodiments to use UCMC and UCEC derived from the stem/progenitor cells isolated from the amniotic membrane of umbilical cord in the method for the production of a skin equivalent.

In one embodiment of the present invention UCMC extracts obtained as described in Example 20 can be used to induce the growth of cells from cell lines which would under normal growth conditions not proliferate any or much more because of their chronological age. For example, the UCMC extracts described herein can be used to induce the growth of aged keratinocytes (asK) which have been obtained from a 60 year old patient. Other cell lines which growth can be induced by use of UCMC extracts are dermal fibroblast cells (NF) as described in Example 20

Thus, the present invention refers to a method of inducing proliferation of aged keratinocytes comprising culturing aged keratinocytes in a suitable growth medium, and adding mesenchymal stem cells (UCMC) of the amniotic membrane of the umbilical cord to the aged keratinocytes to induce proliferation of the aged keratinocytes. The method can further comprise the isolation of the proliferated aged keratinocytes, and applying them into or onto a scaffold. In one embodiment the aged keratinocytes can be isolated from a subject who is as old or older than 30 years 35 years, 40 years, 50 years, 60 years, 70 years or even more than 80 years. However, it is also possible to isolate the aged keratinocytes from a subject that is younger than 30 years.

Depending on the severity of the wound or disorder affecting the skin, it might be sufficient to replace only one layer, i.e. to provide only an epidermis layer or to provide only a dermis layer onto which keratinocytes forming the epidermis and which already have been cultured or obtained from other sources are placed. To obtain an epidermis layer the UCEC can be differentiated into keratinocytes, and to obtain a dermis layer UCMC can be differentiated into fibroblasts.

Therefore, in the method of the present invention the first medium includes a medium adapted for the cultivation of keratinocyte when said scaffold comprises UCEC in order to proliferate and differentiate said UCEC in keratinocytes.

In this case, this first medium includes a keratinocyte growth medium, a growth factor, insulin, transferrin and selenous acid.

The growth factor can be, for example, an epidermal growth factor (EGF), insulin-like growth factor-1, platelet-derived growth factor-BB (PDGFb), transforming growth factor-β, keratinocyte growth factor (KGF), TGF-α or amphiregulin.

The keratinocyte growth medium can be, for example, the KGM®-Keratinocyte Medium (Cambrex Corporation, New Jersey, USA), MEGM-Mammary Epithelial Cell Medium (Cambrex Corporation, New Jersey, USA), EpiLife® medium (Cascade Biologics Inc., Oregon, USA), Green's Medium, CMRL 1066 (Mediatech, Inc., Virginia, USA), M171 (Cascade Biologics Inc., Oregon, USA), L-15 medium, Dulbecco's Modified Eagle Medium (DMEM), DMEM-F12 or RPMI media.

Figures 1, 9:
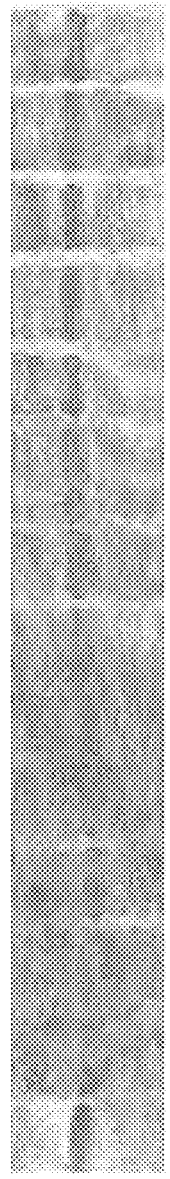
FIG. 9-1 shows Western blot analysis by which the expression of OCT-4 in UCEC and UCMC isolated according to the invention, was compared to the expression of these markers in human dermal fibroblasts (NF), in bone marrow mesenchymal cells (BMSC) and adipose-derived mesenchymal cells (ADMC).
Figures 2, 9:
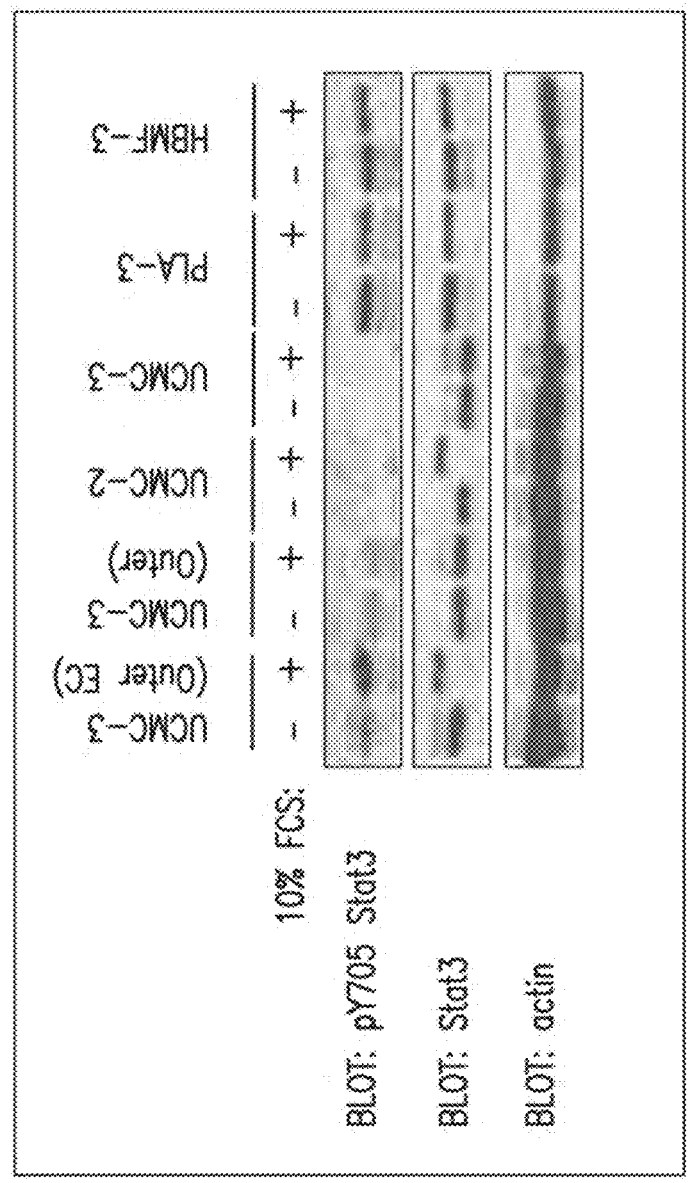
Figures 3, 9:
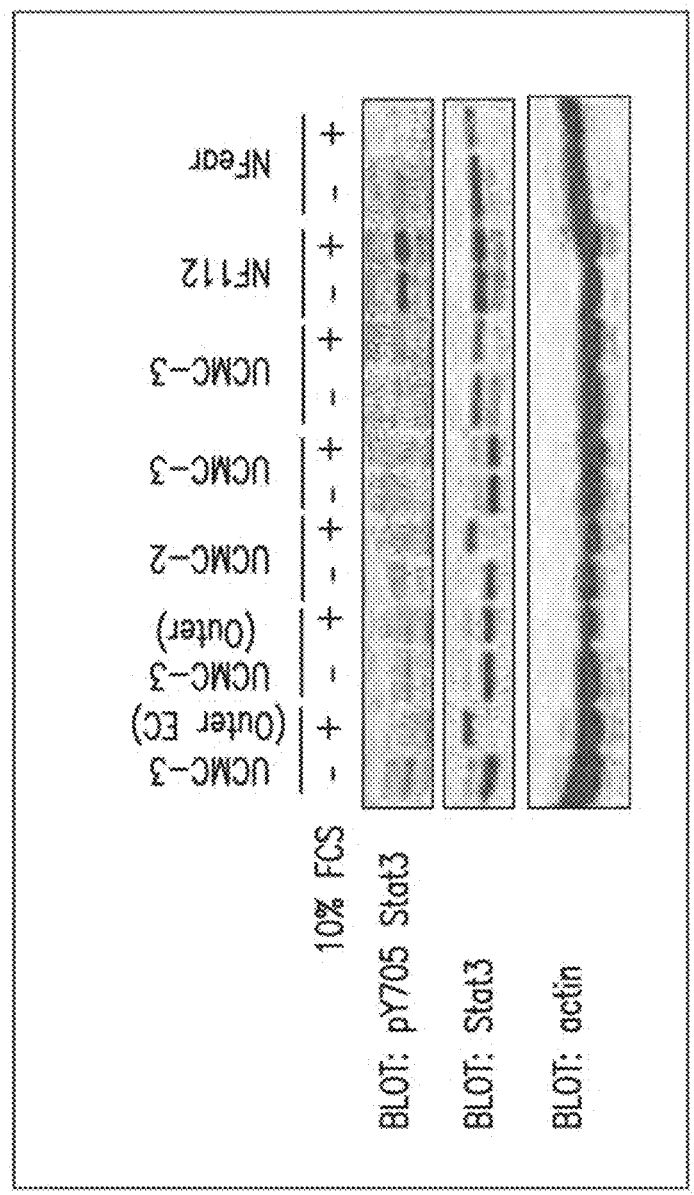
Figures 5, 9:
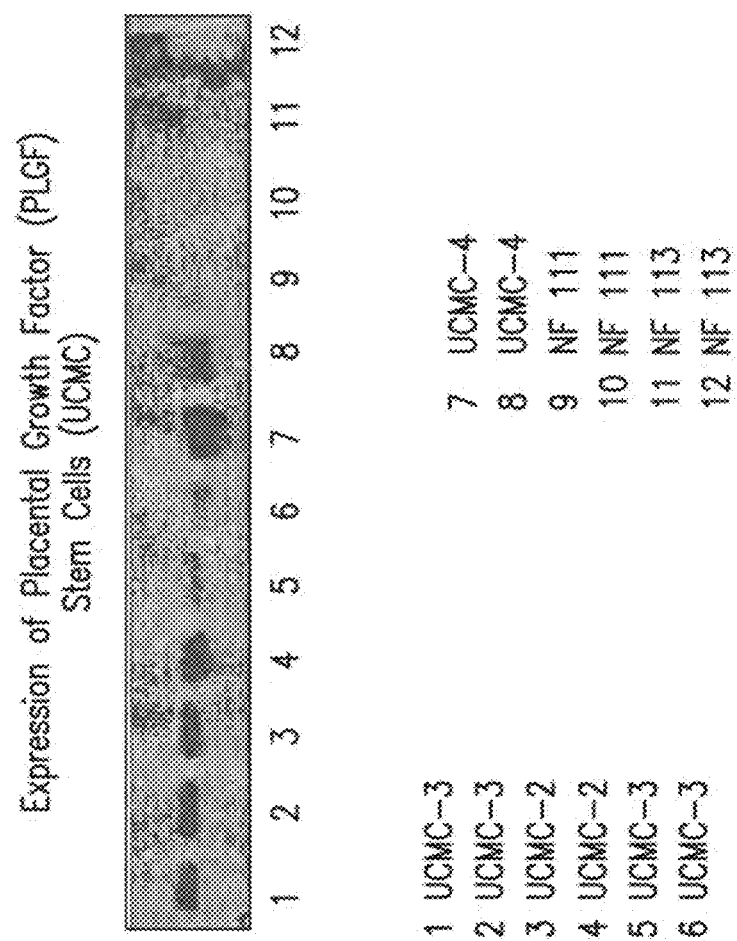
Figures 6, 9:
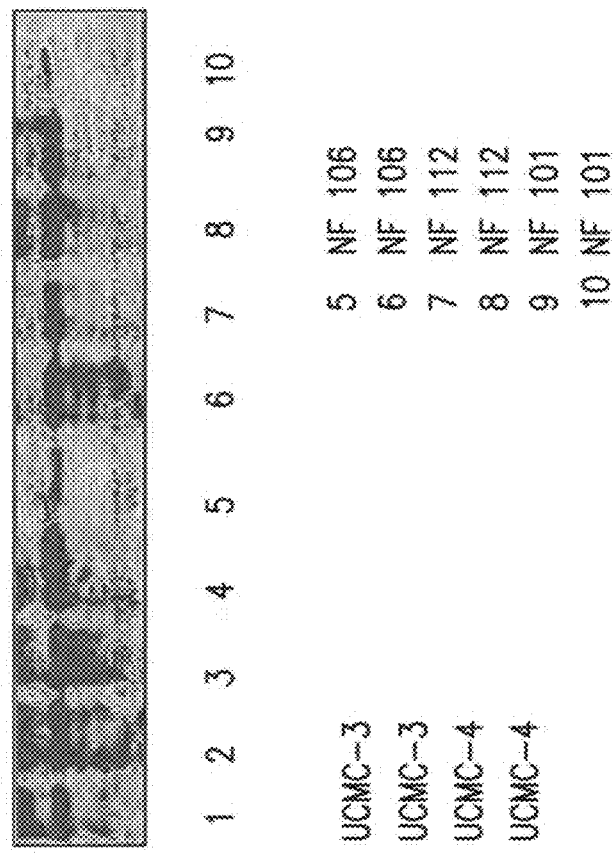
FIG. 6 (40× magnification) depicts UCMC isolated according to the invention cultured in DMEM/10% FCS at days 3 and 7 without a 3T3 feeder layer. The cells are seen to be growing well, and are forming a colony (vertical growth) instead of exhibiting radial spread. Once again, this indicates a difference in behavior of these mesenchymal cells as compared to their more differentiated counterparts.
Figures 7, 9:
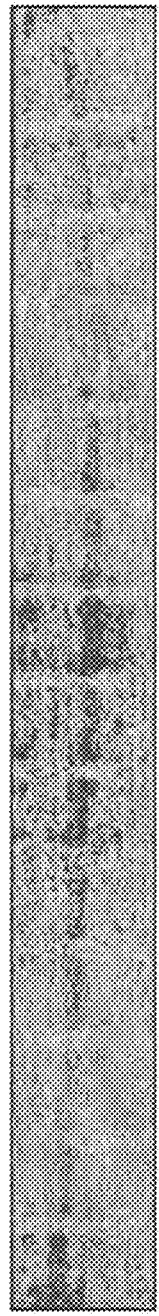
Figures 8, 9:
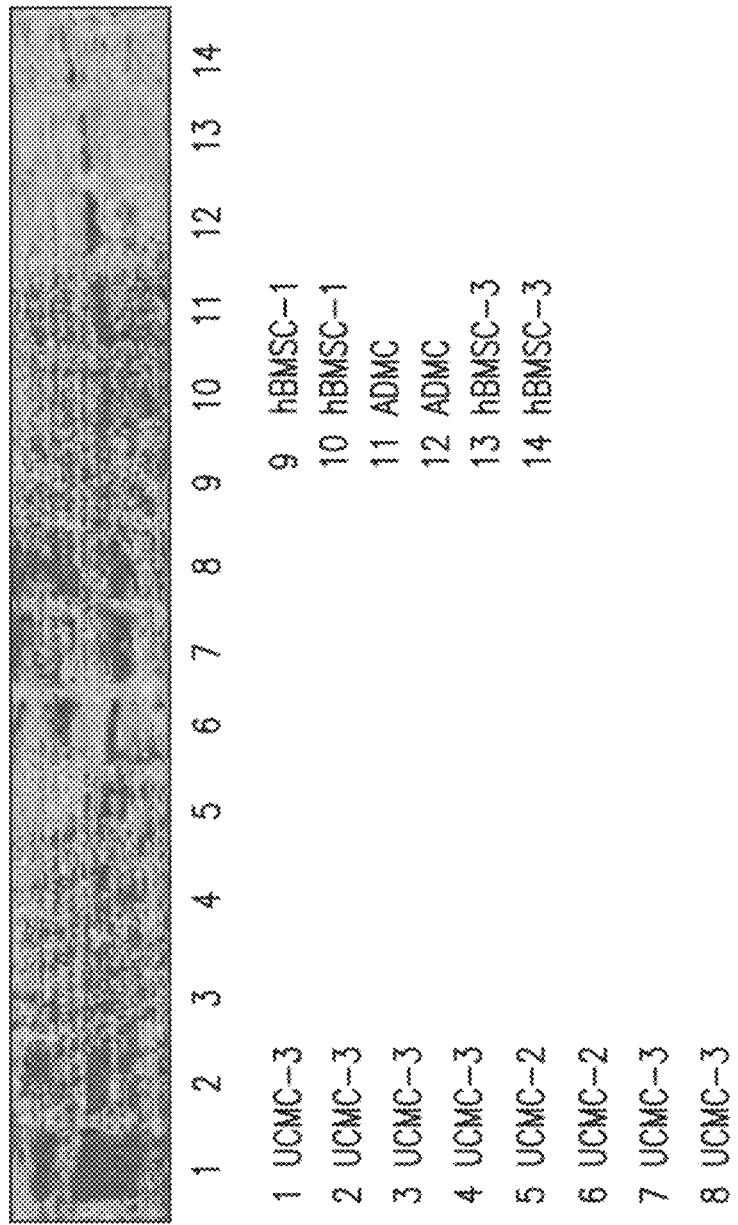
Figure 9:
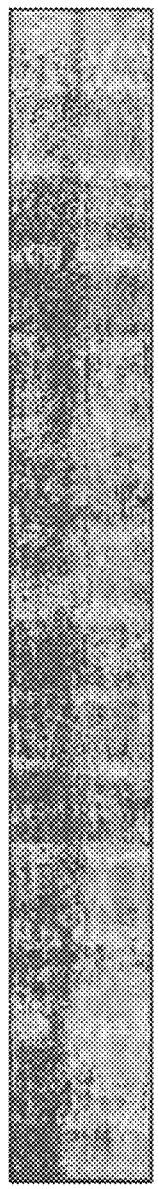
Figures 9, 10:
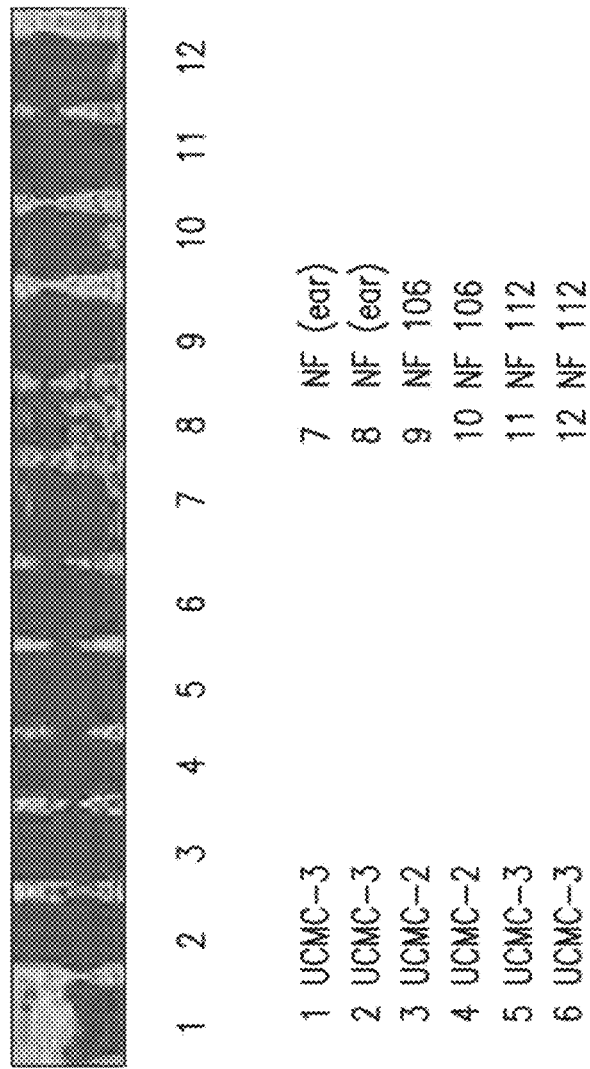
Figures 9, 10, 11:
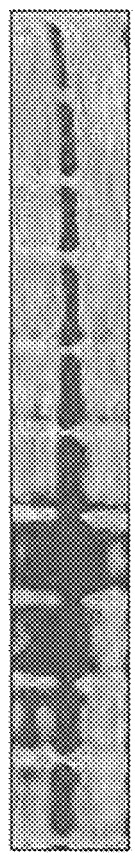
Figures 9, 10, 11, 12:
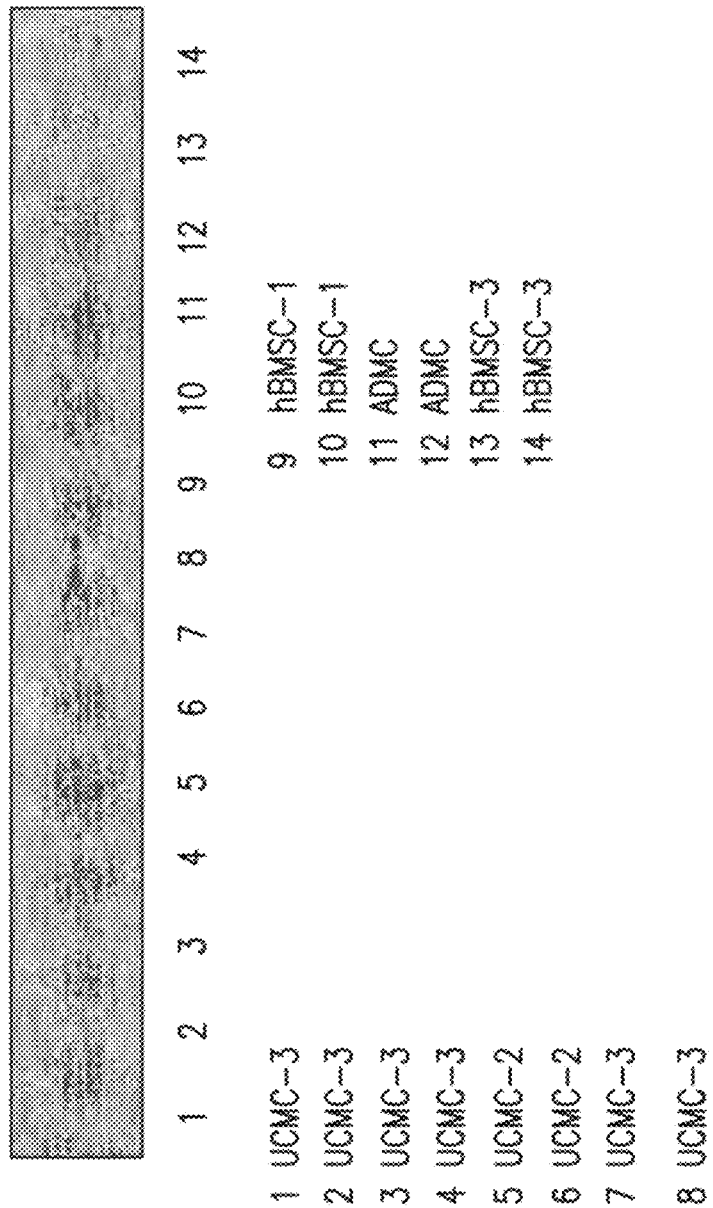
Figures 9, 10, 11, 12, 13, 14:
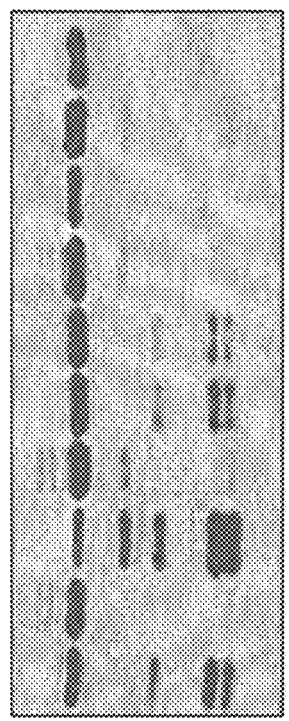

In one embodiment, the first medium adapted for the cultivation of keratinocyte when said scaffold comprises UCEC in order to proliferate and differentiate said UCEC in keratinocytes includes a keratinocyte growth medium, the epidermal growth factor (EGF), insulin, transferrin and selenous acid. In another embodiment, this first medium includes the EpiLife® medium (Cascade Biologics Inc., Oregon, USA), the epidermal growth factor (EGF), insulin, transferrin and selenous acid. In yet still another embodiment, this first medium comprises about 98.8 to about 99.4% (v/v) EpiLife® medium (Cascade Biologics Inc., Oregon, USA), about 0.2 to about 0.4% (v/v) insulin, about 0.2 to about 0.4% (v/v) transferrin, about 0.2 to about 0.4% (v/v) selenous acid and 10 ng/ml epidermal growth factor (EGF). An example for the keratinocytes obtained by use of the method of the present invention can be seen in FIG. 18a.

In another embodiment of the method of the present invention the first medium includes a medium adapted for the cultivation of fibroblast when said scaffold comprises UCMC in order to proliferate and differentiate said UCMC in fibroblasts. In this case, the first medium includes a fibroblast growth medium together with fetal calve serum (FCS) or fetal bovine serum (FBS) in order to proliferate and differentiate said UCMC in fibroblasts. The fibroblast growth medium can be, for example, the KGM®-Keratinocyte Medium (Cambrex Corporation, New Jersey, USA), MEGM-Mammary Epithelial Cell Medium (Cambrex Corporation, New Jersey, USA), EpiLife® medium (Cascade Biologics Inc., Oregon, USA), Green's Medium, CMRL 1066 (Mediatech, Inc., Virginia, USA), M171 (Cascade Biologics Inc., Oregon, USA), L-15 medium, Dulbecco's Modified Eagle Medium (DMEM), DMEM-F12 or RPMI media. In one embodiment, the first medium for the cultivation of fibroblast when said scaffold comprises UCMC in order to proliferate and differentiate said UCMC in fibroblasts includes about 90 to about 95% (v/v) fibroblast growth medium together with about 5 to about 10% fetal or bovine calve serum (FCS). In another embodiment, the first medium comprises about 90 to about 95% (v/v) CMRL1066 (Mediatech, Inc., Virginia, USA) and about 5 to about 10% fetal calve serum (FCS). An example for the fibroblasts obtained by use of the method of the present invention can be seen in FIG. 18b.

Once the UCMC or UCEC are fully differentiated to fibroblast and keratinocytes, respectively, they can be applied to the affected part of the mammalian or human body. Sometimes, however, it may be required to substitute not only the dermis layer or the epidermis layer but both skin layers together. This might be the case, for example, when the epidermis layer as well as the dermal layer of the skin is destroyed due to a burn (full thickness wounds). For this, but also other purposes, the invention provides a method, which includes providing a scaffold,
placing UCMC in or onto said scaffold,
incubating said scaffold in a first medium adapted for the cultivation of fibroblast, which allows said UCMC to proliferate and further differentiate,
placing UCEC in or onto said scaffold, and
incubating said scaffold in a second medium which allows said UCEC to proliferate and further differentiate to keratinocytes.

Using the first medium adapted for the cultivation of fibroblast, which includes the same components as described above for the first medium used to differentiate UCMC into fibroblasts, enables a person skilled in the art to grow a dermis layer comprised of fibroblast in or onto the scaffold. Thereafter, UCEC can be applied in or onto the scaffold already including this dermis layer. Using the second medium, which includes the same components as described above for the first medium used to differentiate UCEC into keratinocytes, it is possible to grow an epidermal skin layer onto the first dermis layer. The skin equivalents of the present invention are thus able to provide a true, morphogenic, multilayer skin equivalent involving UCMC-derived fibroblasts and UCEC-derived keratinocytes. These skin equivalents provide full thickness dermal regeneration as can be seen in FIG. 19, producing accelerated healing and reduced scarring.

The time it requires to develop a functional dermal layer out of UCMC differentiated into fibroblasts is about 4 to 7 days, whereas once the dermal layer is developed and the UCEC are incorporated into the scaffold, it takes another 8 to 10 days until the epidermal layer has been formed from the UCEC-derived keratinocytes. For autologous cultured skin equivalents produced according to the state of the art it takes at least 21 to 35 days, depending on size of biopsy, whereas it requires only between 12 to 18 days using the method of the present invention. Among other reasons, this is due to the fact that the process can be accelerated using the method of the present invention as the cells (xenogeneic or allogeneic) used for the skin equivalent of the present invention are already provided in the cell bank of the present invention or in an off-the-shelf cell culture. The initial concentration, which has been used for the UCMC and UCEC is in exemplary embodiments within a range of about $1 \times 10^5$ to about $1 \times 10^6$ cells/ml. In one embodiment, a concentration of about $5 \times 10^5$ UCMC/ml is used for seeding UCMC into a scaffold and $1 \times 10^6$ UCEC/ml for seeding UCEC.

As described in the background section, the dermis of a natural skin contains not only fibroblasts but also contains nerve endings, glands, hair follicles and blood vessels. To further improve the functionality of the skin equivalent, one embodiment of the method of the present invention thus further includes placing cells of one or more cells lines into or onto the scaffold, which cell lines are able to differentiate into blood vessels or glands. Some glands produce sweat (sweet glands) in response to heat, whereas other glands produce oil (sebaceous glands) to keep the skin moist and soft. This oil also acts as a barrier against foreign substances. The blood vessels of the dermis provide nutrients to the skin and help regulate the body temperature. As these additional cells fulfil important tasks in the skin, one embodiment of the present invention further provides a method, wherein the scaffold further includes vessel endothelial cells or dermal microvascular endothelial cells, to name only a few. In one embodiment the vessel endothelial cells are derived from the umbilical cord of a mammal, and in one embodiment from the umbilical cord of a human. Non-limiting examples of different cell lines, which can be used for the method of the present invention are, for example, human umbilical vessel endothelial cells (HUVEC) or dermal microvascular endothelial cells (DMEC also referred to as DMVEC), to name only two.

Furthermore, research has shown that the functioning of cells is very much influenced by cell extracellular matrix (ECM). As a scaffold, the extracellular matrix forms a three-dimensional pattern which supports cell growth and improves their functionality. Unlike a scaffold as described above, the extracellular matrix consists of natural materials produced by the cells itself, whereas the scaffold as described above can also include or consist of artificial materials, such as, but not limited to, porous polycarbonate. Thus, because of the importance of a matrix for cell growth, it is a major goal of tissue engineering to recreate ECM structures that better mimic this matrix surrounding the cells in vivo, in particular to mimic the matrix of in vivo tissue. Wei Tan, M. S. and T. A. Desai have shown (Tissue Engineering, 2003, Vol. 9, No. 2, P. 255-267) that native collagen and mixtures of collagen with chitosan or collagen, chitosan and fibronectin can be used to create matrices for embedding human lung fibroblasts and human umbilical vein endothelial cells therein.

Thus, the present invention further provides a method wherein in or onto said scaffold at least one extracellular matrix component is placed. This extracellular matrix component shall mimic the ECM matrix normally produced by the cells themselves. Therefore, the ECM component consists of a material, which can also be found in nature where it is produced by the cells themselves. Preferably, this at least one extracellular matrix component is placed in or onto the scaffold together with the cells derived from the stem/progenitor cells described above. If the cells, which are used for the skin equivalent of the present invention and the method to produce them, are able to produce an ECM component on their own, the artificial incorporation of an extracellular matrix component is not required. In one embodiment, UCMC is self-depositing collagen as ECM material after being stimulated with ascorbic acid. If the ECM component is added in addition to the cells used in the present invention, the extracellular matrix component may be chosen from a material such as collagen, elastin, intercellular adhesion molecules, laminin, heparin, fibronectin, proteoglycans, tenascin, fibrillin or mixtures thereof. If collagen is used, it is presently preferred in some embodiments to use type I collagen alone or type I and type III collagen in combination. In one embodiment of the present invention collagen type I is used.

Also described is a method that further includes preserving the isolated stem/progenitor cells or differentiated stem/progenitor cells (e.g. UCMC and UCEC) before their use in the skin equivalent of the present invention.

Methods and protocols for preserving and storing of eukaryotic cells, and in particular mammalian cells, are well known in the art (cf., for example, Pollard, J. W. and Walker, J. M. (1997) *Basic Cell Culture Protocols, Second Edition*, Humana Press, Totowa, N.J.; Freshney, R. I. (2000) *Culture of Animal Cells, Fourth Edition*, Wiley-Liss, Hoboken, N.J.). Any method maintaining the biological activity of the isolated stem/progenitor cells such as epithelial or mesenchymal stem/progenitor cells may be utilized in connection with the present invention. In one example, the stem/progenitor cells are maintained and stored by using cryopreservation.

Accordingly, further described is a progenitor/stem cell derived from the amniotic membrane of umbilical cord by means of the above methods and a cell differentiated from the progenitor/stem cell. In addition, a cell bank comprising or consisting of one or more progenitor/stem cells that have been isolated as described here is also described. This cell bank of progenitor/stem cells may be autologous to an individual or pooled (the latter for subsequent allogeneic transplantation, for example), and subsequently can be employed by further differentiation for regenerative medicine, tissue repair and regeneration, for example.

In accordance with the above, a stem/progenitor cell isolated from the amniotic membrane of umbilical cord by the above described method can also be comprised in a pharmaceutical composition. The pharmaceutical composition can also include a cell differentiated from the stem/progenitor cell. The pharmaceutical composition can be of any kind, and usually comprises the stem/progenitor cells, a cell differentiated therefrom or a cellular secretion or cellular extract thereof together with a suitable therapeutically acceptable carrier/excipient. In case of a cellular secretion, the desired compound(s) can be used in the form of the supernatant into which the compound(s) is/are secreted. In another example, the supernatant might be processed, for example, by purification and concentration prior to be included in a pharmaceutical composition. In some examples, the pharmaceutical composition is adapted for systemic or topical application.

A pharmaceutical composition adapted for topical application may be in liquid or viscous form. Examples thereof include an ointment, a cream, and a lotion and the like. Examples for pharmaceutical compositions that are suitable for systemic use are liquid compositions, wherein the stem/progenitor cells or the cellular extract are dissolved in a buffer that is acceptable for injection or infusion, for example. The preparation of such pharmaceutical compositions is within the knowledge of the person skilled in the art and described in Gennaro, A. L. and Gennaro, A. R. (2000) *Remington: The Science and Practice of Pharmacy*, 20th Ed., Lippincott Williams & Wilkins, Philadelphia, Pa., for example.

Accordingly, a method of treating a subject having a disorder is described. This method comprises administering to the subject an effective amount either of a stem/progenitor cell isolated as explained herein or of a cellular extract derived from such a cell.

In principle, any condition or disorder which is suitable for being treated by means of stem cells/progenitor cells can be treated with a cell or a cellular extract. It is also possible to differentiate cells into a desired type of cell, for example, but not limited to, a skin cell, a bone or cartilage cell, s hepatocyte, an antigen-producing cell, a hormone producing cell such as a beta islet insulin producing cell, and using the differentiated cell therapeutically.

Thus, the present invention also refers to a method for generating an insulin-producing cell, comprising
cultivating cells derived from stem/progenitor cells isolated from the amniotic membrane of umbilical cord, and
proliferating and differentiating said cells in a suitable cultivation medium into β-islet cells.

In one embodiment, the cells derived from stem/progenitor cells are mesenchymal stem cells (UCMC) or epithelial stem cells (UCEC), which can be further differentiated into insulin secreting β-islet cells by including nicotinamide into the cell culture medium.

Besides nicotinamide, the cultivation medium may further include a growth medium for the cultivation of β-islet cells. The cultivation medium may also include a growth factor or fetal serum. The fetal serum may, for example, be of calve or bovine origin. In one embodiment, the cultivation medium can further include insulin, transferrin and selenous acid. The growth factor can, for example, be, but is not limited to, epidermal growth factor (EGF), insulin-like growth factor-1, platelet-derived growth factor-BB (PDGFb), transforming growth factor-β, keratinocyte growth factor (KGF), TGF-α or amphiregulin. The growth medium for the cultivation of β-islet cells can, for example, be, but is not limited to, KGM®-Keratinocyte Medium (Cambrex Corporation, New Jersey, USA), MEGM-Mammary Epithelial Cell Medium (Cambrex Corporation, New Jersey, USA), EpiLife® medium (Cascade Biologics Inc., Oregon, USA), Green's Medium, CMRL 1066 (Mediatech, Inc., Virginia, USA), M171 (Cascade Biologics Inc., Oregon, USA), L-15 medium, Dulbecco's Modified Eagle Medium (DMEM), DMEM-F12 or RPMI media.

In one embodiment of the present invention the media described in Example 15 are used to differentiate UCMC or UCEC into β-islet cells.

In another embodiment, the method includes isolating insulin produced by the β-islet cells, which can afterwards be used for the treatment, e.g., of insulin dependent diabetes mellitus (IDDM), e.g. in a mammal. The mammal can, for example, be a human, a cat, a dog, a sheep, a horse or a pig. The isolation of the insulin can be carried out for example according to, but not limited to, the method described by Jones P. M. and Saermark, T. et al. (Anal Biochem. 1987 Oct.; 166(1):142-9).

Accordingly, the present invention is also directed to an insulin-producing cell obtained by a method for generating an insulin producing cell according to the present invention. The present invention is also directed to a method of treating a disorder associated with an imbalance in the insulin level, comprising administering to a mammal an insulin-producing cell obtained by the method of the present invention. The mammal can, for example, be a human, a cat, a dog, a sheep, a horse or a pig. An example of such a disease is insulin dependent diabetes mellitus (IDDM).

In a further embodiment of the present invention, it is provided a method of generating a dopamin and tyrosin hydroxylase producing cell, comprising cultivating cells derived from stem/progenitor cells isolated from the amniotic membrane of umbilical cord, preferably UCMC, and proliferating and differentiating said cells in a suitable cultivation medium into dopamin and tyrosin hydroxylase (TH) producing cells. Dopamine functions as a neurotransmitter, activating dopamine receptors. Dopamine is also a neurohormone released by the hypothalamus. Its main function as a hormone is to inhibit the release of prolactin from the anterior lobe of the pituitary. Dopamine can be supplied as a medication that acts on the sympathetic nervous system, producing effects such as increased heart rate and blood pressure. Tyrosine hydroxylase is the enzyme responsible for catalysing the conversion of L-tyrosine, an amino acid, to dihydroxyphenylalanine (DOPA), a precursor to Dopamine in the process the body uses to synthesise adrenaline (epinephrin). Thus, in a further embodiment, the method further comprises isolating dopamin and/or tyrosin hydroxylase produced by the dopamin and tyrosin hydroxylase producing cells derived from UCMC.

The present invention also provides a method of generating human leukocyte antigen G (HLA-G). Human leukocyte antigen (HLA)-G is a major histocompatibility complex class I antigen, which is referred to as nonclassical because it displays a tissue-restricted distribution in the placenta, a reduced cytoplasmic domain, a limited polymorphism, and several isoforms. The HLA-G antigen is thought to play an essential role during pregnancy by protecting the semiallogeneic fetus from recognition and destruction by maternal immune cells. HLA-G has been implicated in various immune-mediated diseases and conditions, like organ-, cell transplantation and auto-immune diseases. Examples for such autoimmune diseases are multiple sclerosis, rheumatoid arthritis, type I diabetes mellitus, psoriasis, thyroid diseases, systemic lupus erythematosus, scleroderma or celiac disease. Thus, the present invention provides a method for generating a human leukocyte antigen G (HLA-G) producing cell, comprising cultivating cells derived from stem/progenitor cells isolated from the amniotic membrane of umbilical cord, and proliferating and differentiating this cells in a suitable cultivation medium into HLA-G producing cells. HLA-G producing cells can be generated either from UCEC or UCMC. With the method of the present invention it was shown for the first time that naïve UCEC express and produce HLA-G. Surprisingly, for this method, a specific induction of UCEC for the production of HLA-G is not necessary (see Example 19).

Other disorders, which can be treated using the stem/progenitor cells described herein, are selected from the group consisting of neoplastic disease, accelerated skin aging and skin disorders, tissue disorders, visceral endocrine deficiencies, and neural disorders.

The tissue disorder to be treated can be a congenital or an acquired tissue deficiency. Examples of visceral endocrine deficiency that can be treated with a stem/progenitor cell or a cell derived therefrom include, but are not limited to, testosterone deficiency, anemia, hypoglycemia, hyperglycemia, pancreatic deficiency, adrenal deficiency, and thyroid deficiencies.

Examples of neural disorders that can be treated include, but are not limited to, Alzheimer's disease, Parkinson's disease, Jacob Kreutzfeld's disease, Lou Gehrig's disease, Huntington's disease and neural neoplastic conditions.

The present invention is also directed to the use of mesenchymal stem cells (UCMC) isolated from the amniotic membrane of the umbilical cord for the production of osteoblasts (see Example 10) which are used for the treatment of damages of a bone, or for the production of chondrocytes (see Example 17) which are used for the treatment of damages of cartilage.

Furthermore, the present invention also provides a method of generating hepatocytes, comprising cultivating cells derived from stem/progenitor cells isolated from the amniotic membrane of umbilical cord, preferably UCEC, and proliferating and differentiating said cells in a suitable cultivation medium into hepatocytes. The suitable cultivation medium contains oncostatin-M for inducing the differentiation into hepatocytes. Oncostatin-M (OSM) is a pleitropic cytokine that belongs to the Interleukin-6 group of cytokines. Of these cytokines it most closely resembles leukemia inhibitory factor in both structure and function. However it is as yet poorly defined and is proving important in liver development, haematopoeisis, inflammation and possibly CNS development.

In line with the above discussion, the invention also refers to a method of treating a wound or a skin disorder including applying the skin equivalent of the present invention with a wound or a skin disorder. Accordingly, a skin equivalent of the present invention which has been obtained by a method of the present invention can be used for the manufacture of a pharmaceutical composition. The present invention is further directed to a pharmaceutical composition thus obtained for the treatment of burned skin, an ulcer, radiation and diabetic wounds. The invention is also directed to a cell bank comprising a skin equivalent of the present invention.

An example of a skin disease is a wound or a damaged part of the skin, for example, sun burned skin. Also aging of the skin is considered to be a skin disease herein. Topical or similar delivery of stem/progenitor cells or cellular extracts thereof, for example, as a constituent in lotions or creams or any other suitable vehicle may thus be used for repair of sun damaged skin and in addition may slow also down the aging process of skin (anti-aging properties) by replenishing, and thus fortifying, deficient growth factors and related peptide elements, without which skin aging would be accelerated. A skin equivalent of the present invention can be used accordingly. The stem/progenitor cells may also migrate to injured regions of the body such as surface wounds to form the necessary required cellular elements necessary for the local reparative processes (cf. *The Journal of Immunology*, 2001, 166: 7556-7562; or *International Journal of Biochemical and Cell Biology* 2004; 36: 598-606).

The neoplastic disease may be cancer, in particular as recent studies have demonstrated that stem cells may selectively target neoplastic tumor tissue (*Journal of the National Cancer Institute* 2004; 96 (21): 1593-1603) allowing for directed delivery of antineoplastic agents such as interferon to neoplastic foci. The cancer can be any kind of cancer, including those cancers that are able to form solid tumors, ranging from skin cancer to cancer of the internal organs. Examples of cancers to be treated include, squamous cell carcinoma, breast ductal and lobular carcinoma, hepatocellular carcinoma, nasopharyngeal carcinoma, lung cancer, bone cancer, pancreatic cancer, skin cancer, cancer of the head or neck, cutaneous or intraocular malignant melanoma, uterine cancer, ovarian cancer, rectal cancer, cancer of the anal region, stomach cancer, colon cancer, breast cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemias, solid tumors of childhood, lymphocytic lymphoma, cancer of the bladder, cancer of the kidney or ureter, renal cell carcinoma, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer or any combination of such cancers, including disseminated (metastasising) forms thereof. In case of treatment of a neoplastic disease the umbilical cord amnion derived stem cells and/or their cellular extracts described herein can be administered systemically both as a direct treatment and/or as a carrier vehicle. In the latter case of anti-neoplastic tumor therapy, the cells comprise an anti-neoplastic agent.

In another pharmaceutical use, stem/progenitor cells can be used for gene therapy. For this purpose, the cells can be transformed with a nucleic acid encoding the protein that is to be produced in the cells. The nucleic acid can be introduced into a cells of the invention using any of the various methods that are well known to the skilled person, for example, using a viral vector and/or a lipid containing transfection composition such as IBAfect (IBA GmbH, Göttingen, Germany), Fugene (F. Hoffmann-LaRoche Ltd., Basel, Switzerland), GenePorter® (Gene Therapy Systems), Lipofectamine (Invitrogen Corporation, California, USA), Superfect (Qiagen, Hilden, Germany), Metafecten (Biontex, Munich, Germany) or those ones described in the PCT application WO 01/015755). In a related embodiment, the stem/progenitor cells and cells derived therefrom, after being transformed with a nucleic acid encoding a polypeptide of choice, can be used of recombinantly producing this polypeptide.

As mentioned above, stem cell extracts are rich in a variety of growth factors and peptides that are relevant for normal tissue physiology. Such growth factors and/or peptides may be deficient in exposed parts of the body, such as the skin, which is the surface layer of all human beings protecting the body from external elements for the maintenance of internal homeostasis. Therefore, stem/progenitor cells or cellular extracts thereof are suitable for the treatment and/or maintenance of internal homeostasis.

Furthermore and in line with the above description, the stem/progenitor cells and cells derived therefrom can be used for the production of any biological molecule. The biological molecule can be, for instance, any molecule that is naturally produced in the cells or a molecule the coding nucleic acid of which has been introduced into the cells via recombinant DNA technology. Examples of molecules that can be produced by the cells include, but are not limited to, a protein such as a cytokine, a growth factor such as insulin-like growth factor (IGF), epidermal growth factor (EGF), transforming growth factor beta (TGF-beta), Activin A, a bone morphogenetic protein (BMP), PDGF or a hormone as insulin or erythropoietin or a transporter protein such transferrin, a peptide such a growth factor or hormone (e.g. luteinic hormone (LSH), follicle stimulating hormone (FSH)), a small organic molecule such as a steroid hormone, an oligo- or polysaccharide, for example, heparin or heparan sulfate (cf., example WO 96/23003, or WO 96/02259 in this regard), a proteoglycan, a glycoprotein such as collagen or laminin, or a lipid, to name only a few.

Mucin, which is a glycoprotein, is a complex molecule that can be found in mucous secrets of most epithelial layers (e.g. saliva, gastric juice, chyle, bronchial juice). Mucin carries out lube- and protective functions (e.g. transport of chime, buffering excessive gastric acid, lube function within the synovial fluid of joints). Due to its complex structure and its high molar mass (of about 1-50 million Dalton) it is normally difficult to isolate mucin molecules in their native form.

Thus, the present invention further provides a method for the generation of a mucin-producing cell comprising:
  placing umbilical cord amniotic membrane epithelial stem cells (UCEC) in a container (e.g. culture flask, petri dish), and
  incubating said UCEC in a medium adapted for the cultivation of secretory cells.

These mucin-producing cells cannot only be used to isolate mucin from the cell culture media but also to use these cells in a method of the present invention comprising contacting a tissue comprising cells affected by smoke with a mucin-producing cell generated by the method of the present invention. These affected cells may be cells of the respiratory tracts, e.g. the lung, or the ocular surface.

Furthermore, the mucin-producing cells obtained by the method of the present invention can be used for the treatment of a synovial cell sarcom, a smoke inhalation injury or ocular surface injury. The mucin-producing cells obtained by the method of the present invention can further be used for oesophagus and airway track tissue engineering, for cosmetic applications or as gene/protein delivery system.

To differentiate UCEC as described herein into mucin-producing cells, the invention further provides a medium, wherein said medium includes a growth medium for the cultivation of mucin-producing cells, insulin, transferrin, selenous acid and a growth factor.

The growth factor can, for example, be but is not limited to, epidermal growth factor (EGF), insulin-like growth factor-1, platelet-derived growth factor-BB (PDGFb), transforming growth factor-β, keratinocyte growth factor (KGF), TGF-α or amphiregulin.

The growth medium for the cultivation of mucin-producing cells can, for example, be, but is not limited to, KGM®-

Keratinocyte Medium (Cambrex Corporation, New Jersey, USA), MEGM-Mammary Epithelial Cell Medium (Cambrex Corporation, New Jersey, USA), EpiLife® medium (Cascade Biologics Inc., Oregon, USA), Green's Medium, CMRL1066 (Mediatech, Inc., Virginia, USA), M171 (Cascade Biologics Inc., Oregon, USA), L-15 medium, Dulbecco's Modified Eagle Medium (DMEM), DMEM-F12 or the RPMI media.

In one embodiment the medium adapted for the cultivation of a mucin-producing cell includes a growth medium for the cultivation of mucin-producing cells, the epidermal growth factor (EGF), insulin, transferrin and selenous acid.

In still another embodiment, the medium adapted for the cultivation of a mucin-producing cell includes about 98.8 to about 99.4% (v/v) of a growth medium for the cultivation of mucin-producing cells, about 0.2 to about 0.4% (v/v) insulin, about 0.2 to about 0.4% (v/v) transferrin, about 0.2 to about 0.4% (v/v) selenous acid and about 10 ng/ml epidermal growth factor (EGF).

In another embodiment, the medium adapted for the cultivation of a mucin-producing cell comprises about 98.8 to about 99.4% (v/v) CMRL1066 (Mediatech, Inc., Virginia, USA) or M171 (Cascade Biologics Inc., Oregon, USA), together with about 0.2 to about 0.4% (v/v) insulin, about 0.2 to about 0.4% (v/v) transferrin, about 0.2 to about 0.4% (v/v) selenous acid and about 10 ng/ml epidermal growth factor (EGF).

Mucin-producing cells which are produced by the method of the present invention can be defined by a Mucin-clot-test (see Example 16). This test is also described by Corfield A. P., Glycoprotein method and procotols: The Mucins, page 29-65. Humana Press 2000; Gatter R. A. and Schumacher R. H., A practical handbook of join fluid analysis, page 59-63, Lea & Febiger, 1991, the entire contents of which is incorporated herein by reference. This test is an assessment of the quality and quantity of mucin produced by UCEC cultured in cell culture media as defined above. Briefly, in this test media of cell cultures in which UCEC cells have been incubated according to the method of the present invention is expelled into 7 N glacial acetic acid. The acetic acid causes the mucin to form a clot. Media containing mucin will appear as clear fluid with a tight, ropy clot. Thus, in one embodiment a mucin producing cell as used herein refers to a cell which yields in a positive result when examined using the test and the conditions as described in Example 16.

In accordance with recent approaches (see, for example, Amit, M et al., Human feeder layers for human embryonic stell cells, Biol Reprod 2003; 68: 2150-2156), the stem/progenitor cells described here can be used as feeder layer for the cultivation of other embryonic stem cells, in particular human embryonic stem cells. In one of these embodiments the cells are preferably of human origin, since using human cells as feeder layer minimizes the risk of contaminating the cell culture with animal-derived components such as animal pathogens or immunogens. In this respect, it is to be noted that the stem/progenitor cells and cells derived therefrom can be cultivated under serum free conditions. Accordingly, employing the cells as feeder layer and cultivating the cell culture under with serum free media as the one described herein later, or in Draper et al. (Culture and characterization of human embryonic stem cell lines, Stem Cells Dev 2004, 13:325-336) or in the International patent application WO 98/30679, for example.

Figures 9, 10, 11, 12, 13, 14, 15:
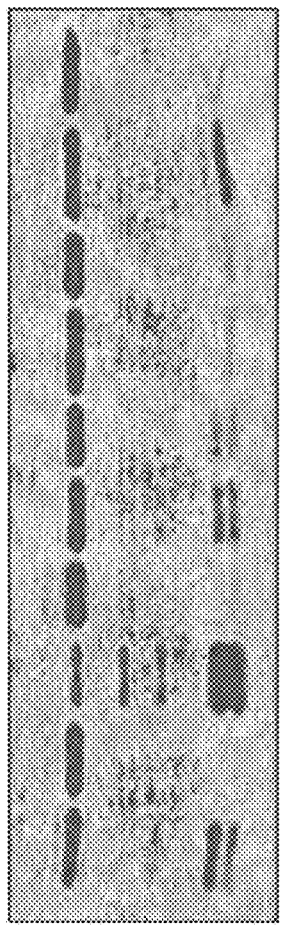

In this connection, it is noted that in transplantation surgery and cell-based therapy high quantities of low passage cells with a minimal proportion of senescent cells (i.e., large proportion of high quality cells) are crucial and are required to be derived within the shortest possible time during cell expansion. For example, mesenchymal stem cells from bone marrow and cord blood are low in quantity and therefore require expansion over many passages for a long period of time in order to achieve the sufficient number of cells required for cell transplant. The high passage cells however tend to deteriorate in quality and may lead to cell senescence or cancerous transformation. It has been found here that high quantities of stem/progenitor cells can be obtained by low passage numbers using a repetitive explanation technique. Thus a method of cultivating stem/progenitors cells is described, wherein this method comprises:

Obtaining a tissue explant from the amniotic membrane of umbilical cord;

Cultivating the tissue explant in suitable cultivation media and cultivation conditions over a suitable period of time, Optionally exposing the tissue explant to fresh cultivation media and continuing the cultivation under suitable conditions over a suitable period of time (cf., FIG. 15).

The cultivation can be carried out in for as many cycles (passages) as wanted and be stopped once the desired number of cells has been obtained. Exposing the tissue explant to fresh cultivation can be carried out by removing the used cell cultivation medium from the vessel used for growing the cells and adding fresh media to that vessel. Instead of replacing the media in the used vessel, exposing to fresh cultivation media can be achieved by transferring the tissue explant to a new vessel which is filled with cultivation media. The tissue explant used for cultivation/propagation of the cells can be obtained by any suitable method, for example by the "direct tissue explant technique" as explained above (in which the tissue is first placed in media without enzymes, and then under careful conditions the cells separate from the main tissue mass by itself, and the cells are then harvested for collection).

The cultivation of the tissue explants can be carried out in any media that is suitable for cultivation of mammalian cells. Examples include the conventional and commercially available media that are given above with respect to the cultivation or the clonal expansion of the stem/progenitor cells and cells derived therefrom such as, but not limited to, KGM®-Keratinocyte Medium (Cambrex Corporation, New Jersey, USA), MEGM-Mammary Epithelial Cell Medium (Cambrex Corporation, New Jersey, USA) EpiLife® medium (Cascade Biologics Inc., Oregon, USA), Medium 171 (Cascade Biologics Inc., Oregon, USA), DMEM, DMEM-F12 or RPMI media. The cultivation is typically carried out at conditions (temperature, atmosphere) that are normally used for cultivation of cells of the species of which the cells are derived, for example, at 37° C. in air atmosphere with 5% $CO_2$. In one embodiment, the cultivation is carried out using serum free, in particular bovine serum free media. The cultivation (in one passage) is performed for any suitable time the cells need for growth, typically, but by no means limited to, for about 1 to several days, for example to about 7 or about 8 days.

The inventions illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

EXAMPLES

Example 1: Collection of Umbilical Cord Tissue

Umbilical cord tissue is collected immediately after delivery of the child. The specimen is rinsed clean and immediately transferred into a 500 ml sterile glass bottle containing culture transport medium (L-15 medium supplemented with 50 IU/ml penicillin, 50 µg/ml streptomycin, 250 µg/ml fungizone, 50 µg/ml gentamicin; all reagents purchased from Invitrogen) prior to transport to the laboratory. In the laboratory, stem cell extraction is conducted in a laminar flow hood under sterile conditions. The specimen is first transferred to a sterile stainless steel tray. All remaining blood in the cord vessels is removed by multiple syringing washes using warm phosphate-buffered saline (PBS) supplemented with 5 IU/ml heparin (from Sigma-Aldrich, Missouri, USA). Plain PBS without heparin is used in the final washes. The umbilical cord tissue specimen is then cut into pieces 2 cm in length and transferred into 10 cm diameter cell culture dishes, where further washing and disinfection is performed with 70% ethanol followed by multiple washes using PBS containing an antibiotic mixture (50 IU/ml penicillin, 50 µg/ml streptomycin, 250 µg/ml fungizone, 50 µg/ml gentamicin; all purchased from Invitrogen Corporation, California, USA) until the solution becomes clear.

Example 2: Cell Separation/Cultivation

Dissection of umbilical cord tissue is first performed to separate the umbilical cord amniotic membrane from Wharton's jelly (i.e. the matrix of umbilical cord) and other internal components. The isolated amniotic membrane is then cut into small pieces (0.5 cm×0.5 cm) for cell isolation. Explant is performed by placing the pieces of umbilical cord amniotic membrane on tissue culture dishes at different cell culture conditions for isolation of either epithelial or mesenchymal stem cells.

For mesenchymal cell separation/cultivation, the explants were submerged in 5 ml DMEM (Invitrogen Corporation, California, USA) supplemented with 10% fetal bovine serum (Hyclone, Utah, USA) (DMEM/10% FBS) and maintained in a $CO_2$ cell culture incubator at 37° C. The medium was changed every 2 or 3 days. Cell outgrowth was monitored under light microscopy. Outgrowing cells were harvested by trypsinization (0.125% trypsin/0.05% EDTA) for further expansion and cryo-preservation using DMEM/10% FBS.

For epithelial cell separation/cultivation, cell culture plastic surfaces were coated with collagen 1/collagen 4 mixtures (1:2) before placing the tissue samples on the surface. The tissue samples were submerged in 5 ml EpiLife medium or Medium 171 (both from Cascade Biologics Inc., Oregon, USA). The medium was changed every 2 or 3 days. Cell outgrowth from tissue culture explants was monitored under light microscopy. Outgrowing cells were harvested by trypsinization (0.125% trypsin/0.05% EDTA) using EpiLife® medium or Medium 171.

For the enzymatic extraction method of cells, umbilical cord amniotic membrane was divided into small pieces of 0.5 cm×0.5 cm and digested in 0.1% (w/v) collagenase type I solution (L. Hoffmann-LaRoche Ltd., Basel, Switzerland) at 37° C. for 6 hours. The samples were vortexed every 15 min for 2 min. Cells were harvested by centrifugation at 4000 rpm for 30 min. Two different approaches were employed to isolate either epithelial or mesenchymal stem cells.

For isolation of epithelial stem cells, cell pellets were resuspended in EpiLife® medium or Medium 171 (both from Cascade Biologics Inc., Oregon, USA) supplemented with 50 µg/ml insulin-like growth factor-1 (IGF-1), 50 µg/ml platelet-derived growth factor-BB (PDGF-BB), 5 µg/ml transforming growth factor-β (TGF-β1), and 5 µg/ml insulin (all obtained from R&D Systems, Minneapolis, USA), counted and seeded on 10 cm tissue culture dishes pre-coated with collagen 1/collagen 4 mixtures (1:2; Becton Dickinson, New Jersey, USA) at density of 1×10$^6$ cells/dish. After 24 hours, attached cells were washed with warm PBS and medium was replaced with supplement-added EpiLife® medium or Medium 171. The medium was changed every 2 or 3 days. Cell growth and expanding clonal formation was monitored under light microscopy. At a confluence of about 70%, cells were sub-cultured by trypsinization (0.125% trypsin/0.05% EDTA) for further expansion and cryo-preservation.

For isolation of mesenchymal stem cells, cell pellets were resuspended in PTT-4 medium, counted and seeded on 10 cm tissue culture dishes at density of 1×10$^6$ cells/dish. The culture medium was changed every 2 or 3 days. Cell growth and expansion was monitored under light microscopy. At a confluence of about 90%, cells were sub-cultured as outlined above.

For cultivation of epithelial and mesenchymal stem cells on feeder layer, umbilical cord lining membrane was digested by collagenase treatment, counted and seeded on 10 cm tissue culture dishes coated with lethally irradiated or Mitomycin C treated 3T3 fibroblasts (feeder layer) in Green's medium. The culture medium was changed every 2 or 3 days. Colony formation was monitored under light microscopy and photographed.

Example 3: Identification of Stem/Progenitor Cells

Figure 1B:
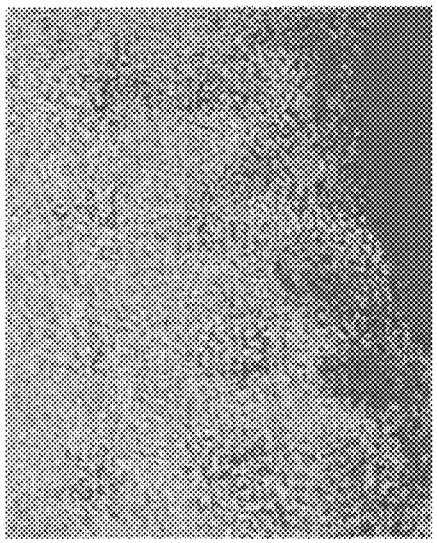
Figure 2A:
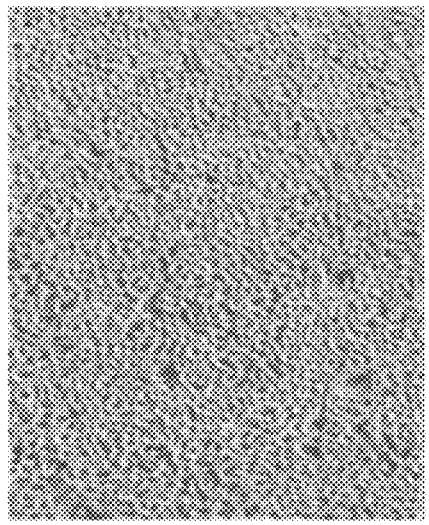
FIGS. 2A and 2C depict enzymatic digestion of the umbilical cord segments yielding similar epithelial (40× magnification) cells at day 2.
Figure 2B:
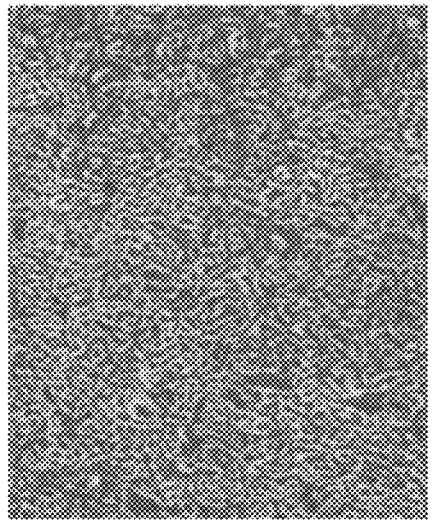
FIGS. 2B and 2D depict enzymatic digestion of the umbilical cord segments yielding similar epithelial (40× magnification) cells at day 5. Umbilical cord amniotic membrane was divided into small pieces of 0.5 cm×0.5 cm and digested in 0.1% (w/v) collagenase type 1 solution (Roche Diagnostics) at 37° C. for 8 hours. The samples were vortexed every 30 min for 3 min. Cells were harvested by centrifugation at 4000 rpm for 30 min. Cell pellets were resuspended in cEpiLife medium or Medium 171 (both from Cascade Biologics) supplemented with 50 µg/ml insulin-like growth factor-1 (IGF-1), 50 µg/ml platelet-derived growth factor-BB (PDGF-BB), 5 µg/ml transforming growth factor-β1 (TGF-β1) and 5 µg/ml insulin (all obtained from R&D Systems), counted and seeded on 10 cm tissue culture dishes pre-coated with collagen 1/collagen 4 mixtures (1:2; Becton Dickinson) at density of $1\times10^6$ cells/dish. After 24 hours, attached cells were washed with warm phosphate buffered saline (PBS) and the culture medium was replaced with EpiLife medium or Medium 171 (both from Cascade Biologics). The medium was changed every 2 or 3 days, and cell outgrowth was monitored under light microscopy. Microphotographs were taken at different time intervals as stated above. Once again the cells demonstrated typical epithelial cell polyhedral morphology.
Figure 2C:
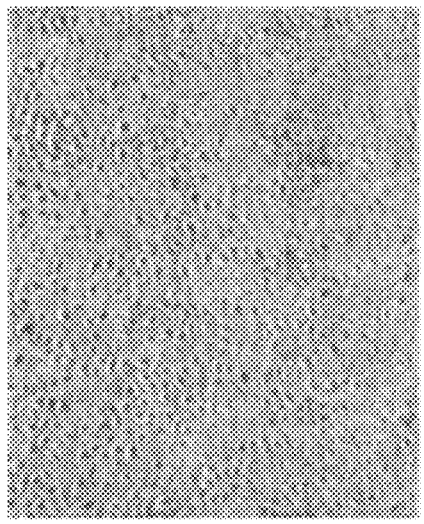
Figure 2D:
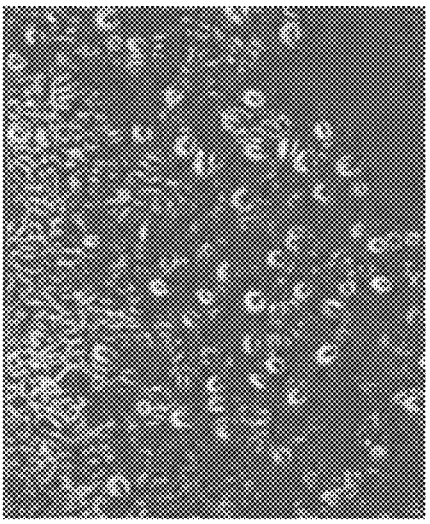
Figure 7:
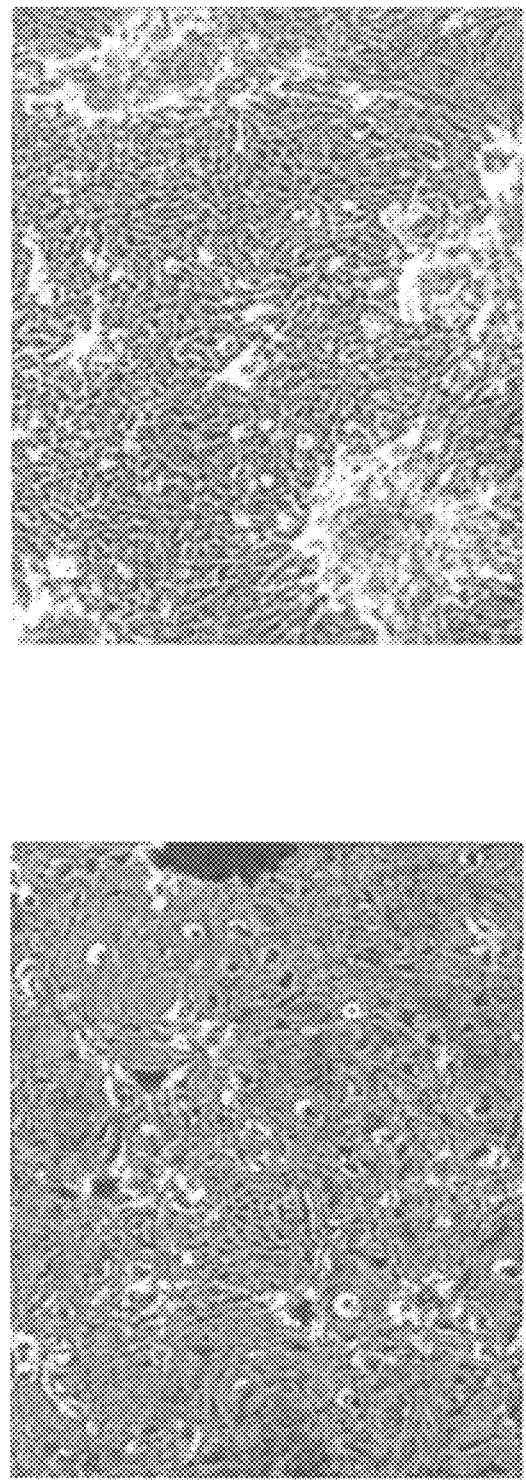
FIG. 7 (40× magnification) depicts colony formation of umbilical cord epithelial cells (UCEC) cultured on a 3T3 feeder layer at days 3 and 7. This appearance is similar to that of normal skin derived epithelial keratinocyte stem cells. In the latter, the 3T3 feeder layer maintains stemness of the cells.
Figure 8A:
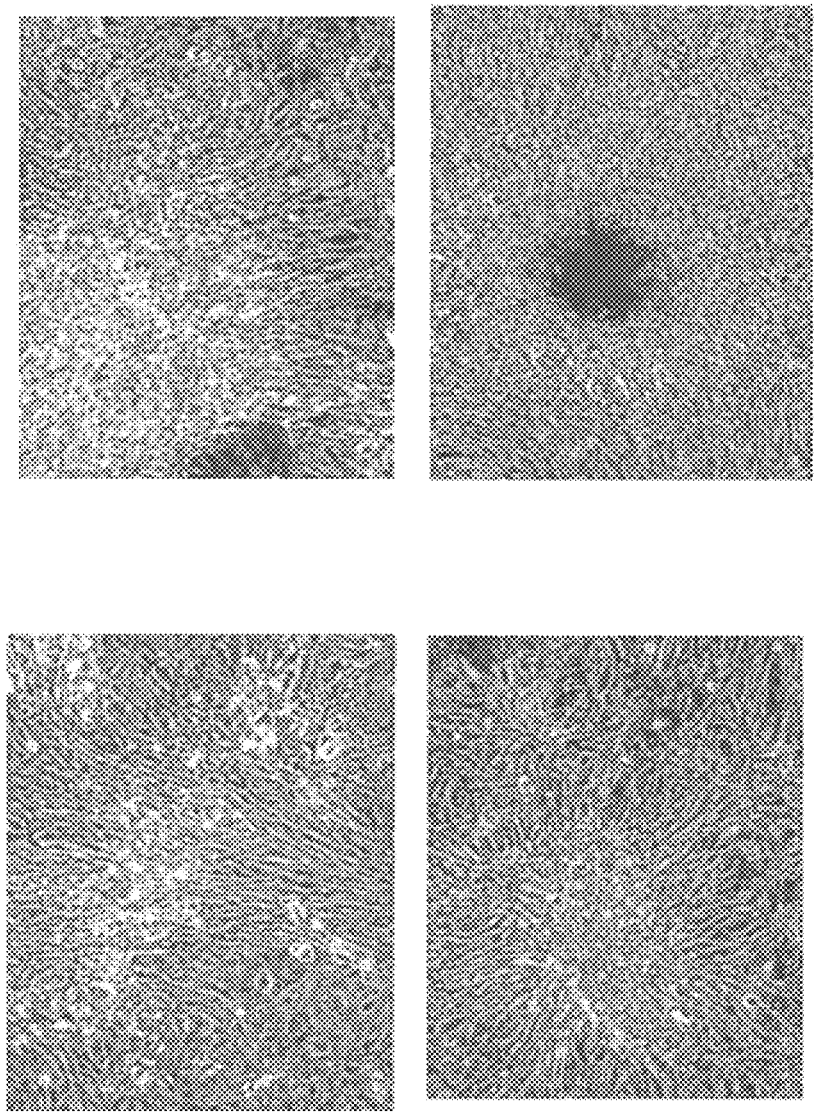
FIG. 8A (40× magnification) depicts obvious colony formation of umbilical cord mesenchymal cells (UCMC) isolated according to the invention cultured on a 3T3 feeder layer at days 3 and 7. The 3T3 feeder layer normally suppresses the growth of differentiated mesenchymal cells as human dermal fibroblasts. Once again, this indicates a difference in behavior of these mesenchymal cells as compared to their more differentiated counterparts.
Figure 8B:
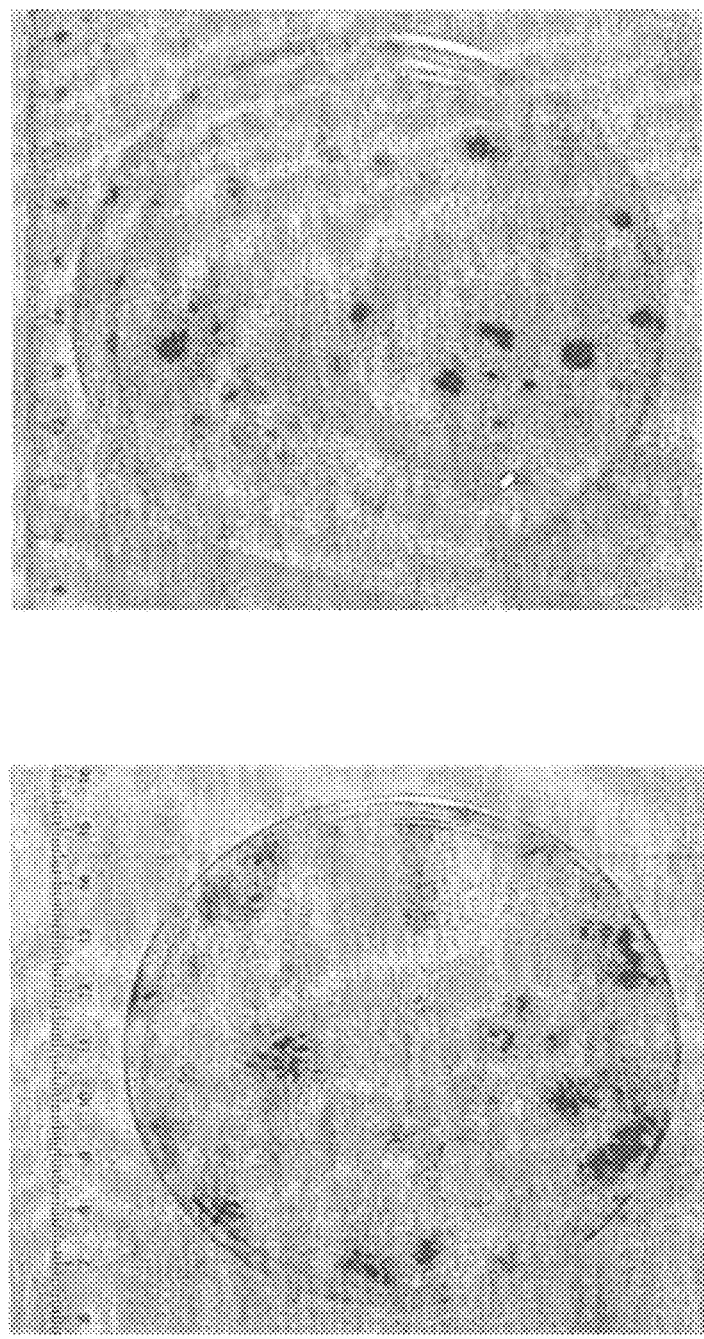
FIG. 8B shows the colony forming efficiency assay of the umbilical cord mesenchymal cells.

Epithelial Cells:
FIG. 1 shows pictures of outgrowing epithelial cells from umbilical cord amniotic membrane prepared by the method using tissue explant (40× magnification). Pictures were taken at day 2 (FIG. 1A) and day 5 (FIG. 1B, C) of tissue culture. Cell morphology analysis demonstrated polyhedral shaped epithelial-like cells. Enzymatic digestion of the umbilical cord segments yielded similar (FIG. 2), epithelial cells at day 2 (FIG. A, C) and day 5 (FIG. B, D) (40× magnification). FIG. 7 shows pictures of colony formation of epithelial stem cells from umbilical cord amniotic membrane cultured on feeder layer using Green's method (40× magnification). A colony of polyhedral shaped epithelial-like cells expanded rapidly from day 3 to day 7.

Figure 3B:
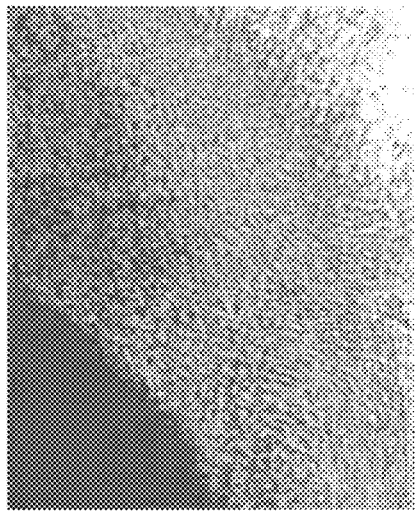
FIGS. 3A, 3B, 3C, and 3D depict outgrowing mesenchymal cells explanted from umbilical cord amniotic membrane. Cellular outgrowth was observed as early as 48 hours after placement in tissue culture dishes using DMEM supplemented with 10% fetal calf serum (FCS) as culture medium (40× magnification). The explants were submerged in 5 ml DMEM (Invitrogen) supplemented with 10% fetal bovine serum (Hyclone) (DMEM/10% FBS). Medium was changed every 2 or 3 days. Cell outgrowth was monitored under light microscopy. Microphotographs were taken at different time intervals. The cells were characterized by their spindle shaped morphology, and migrated and expanded both easily and quickly in vitro, closely resembling fibroblasts.
Figure 3D:
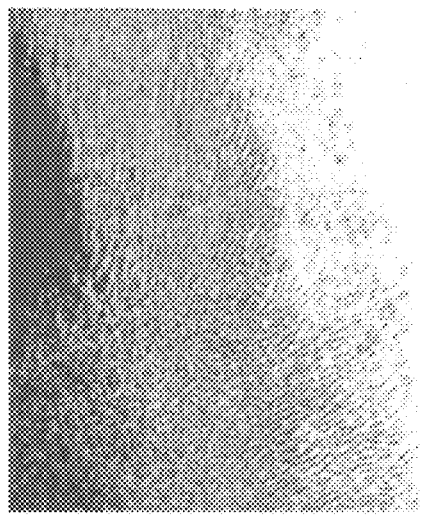
Figure 3A:
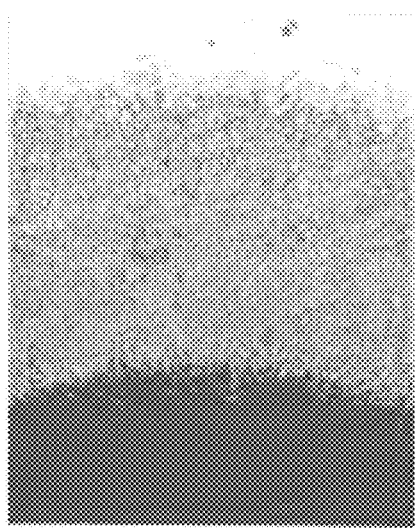
Figure 3C:
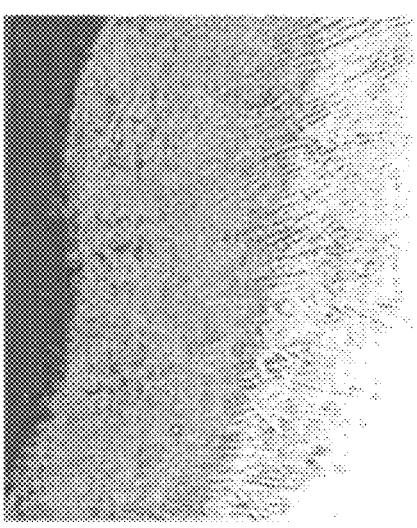
Figure 4B:
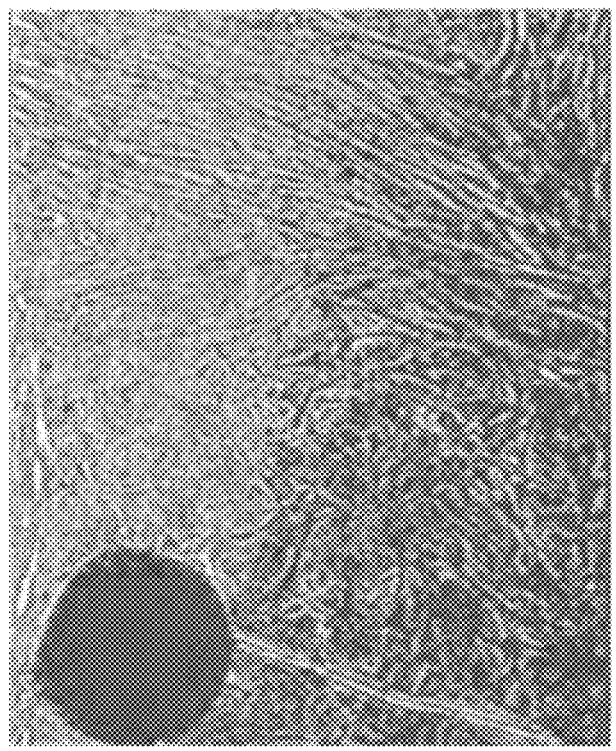
FIG. 4B (40× magnification) depicts mesenchymal cells from umbilical cord amniotic membrane cells isolated by collagenase enzymatic digestion, showing cell proliferation observed at day 5. Umbilical cord amniotic membrane was divided into small pieces of 0.5 cm×0.5 cm and digested in 0.1% (w/v) collagenase type1 solution (Roche Diagnostics) at 37° C. for 6 hours. The samples were vortexed every 15 min for 2 min. Cells were harvested by centrifugation at 4000 rpm for 30 min. Cell pellets were resuspended in DMEM/10% FBS, counted and seeded on 10 cm tissue culture dish at density of 1×10$^6$ cells/dish. Medium was changed every 2 or 3 days. Cell outgrowing was monitored under light microscopy. Microphotographs were taken at different time intervals. Once again, cells demonstrated spindle shaped morphology typical of mesenchymal cells as fibroblasts.
Figure 4A:
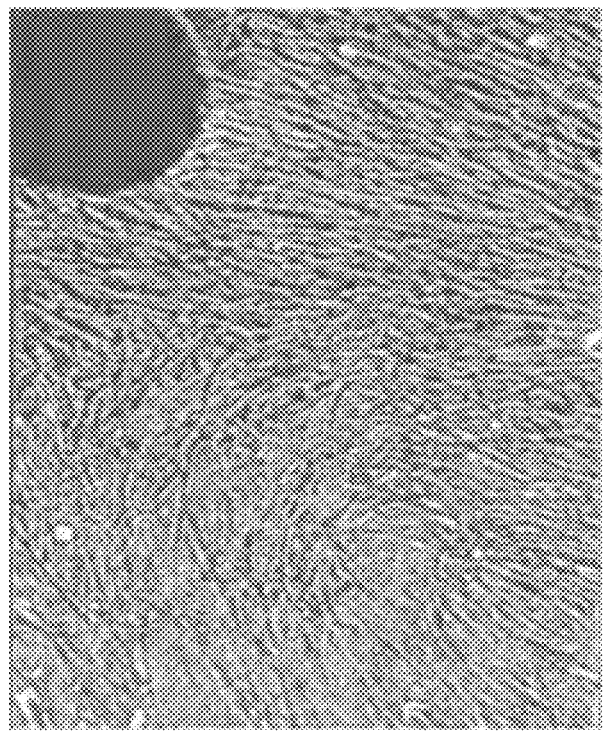
FIG. 4A (40× magnification) depicts mesenchymal cells from umbilical cord amniotic membrane cells isolated by collagenase enzymatic digestion, showing mesenchymal cells isolated from umbilical cord amniotic membrane at day 2.
Figures 1, 10:
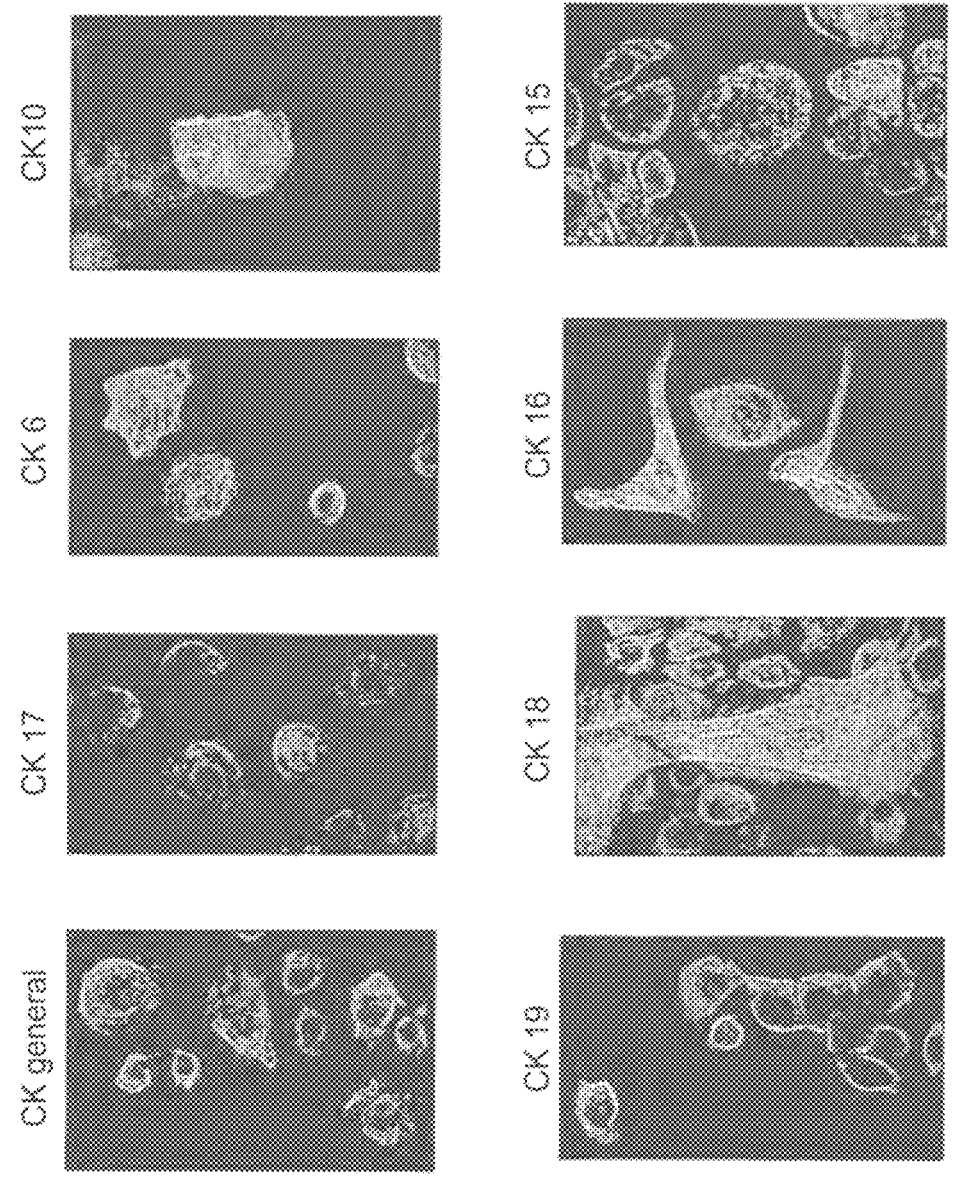
Figures 2, 10:
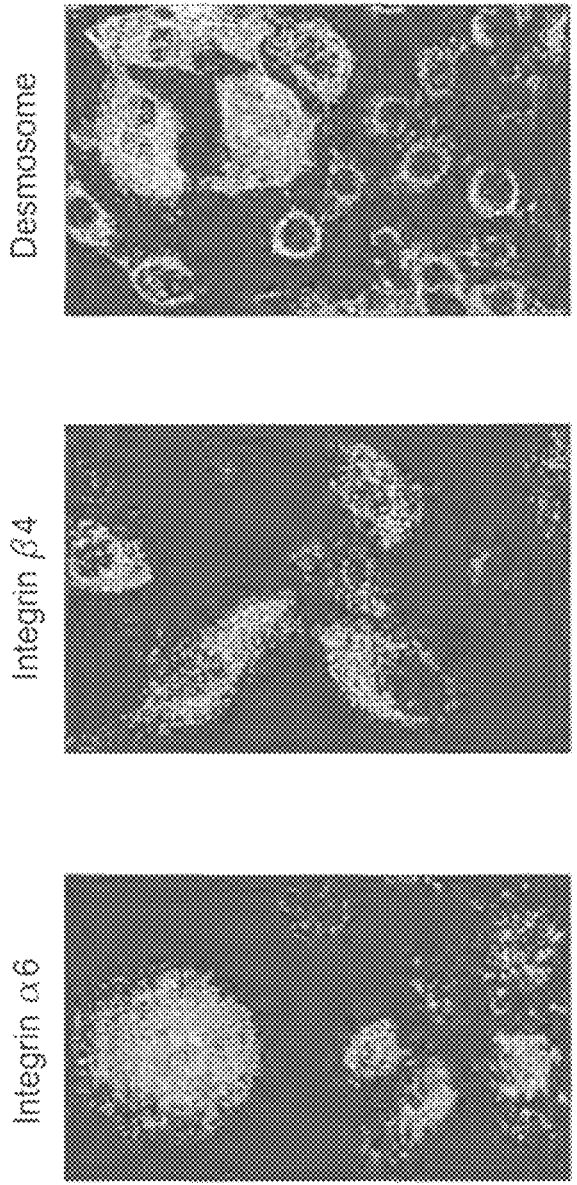
Figures 3, 10:
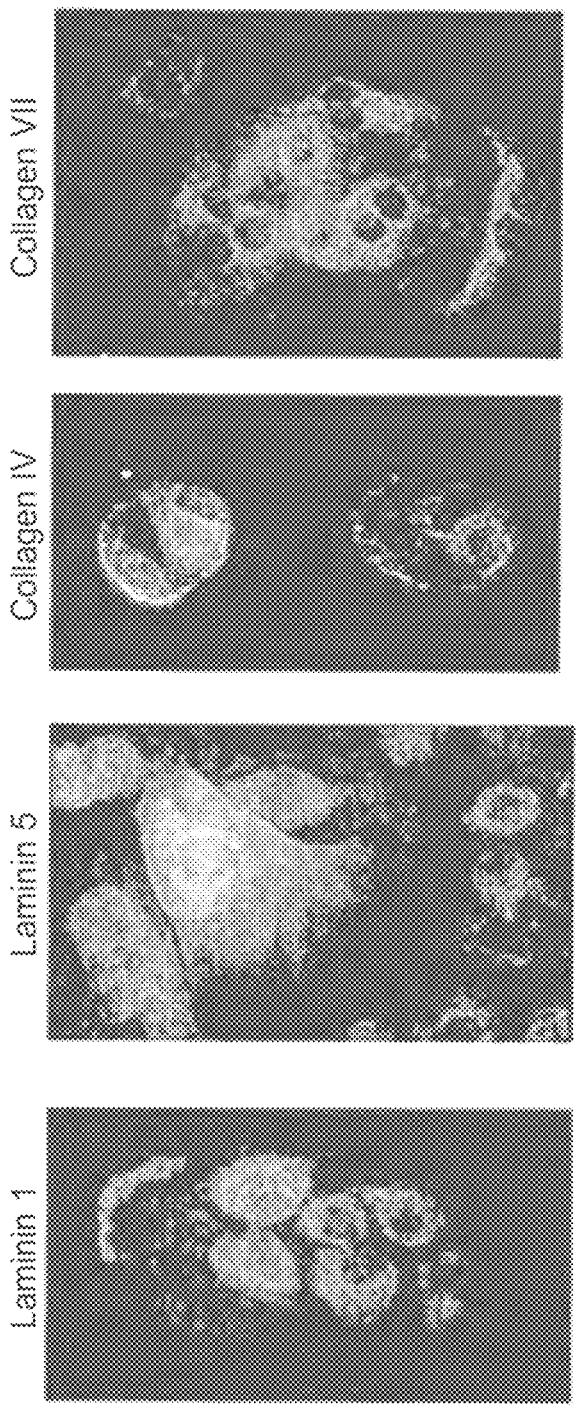
Figures 4, 10:
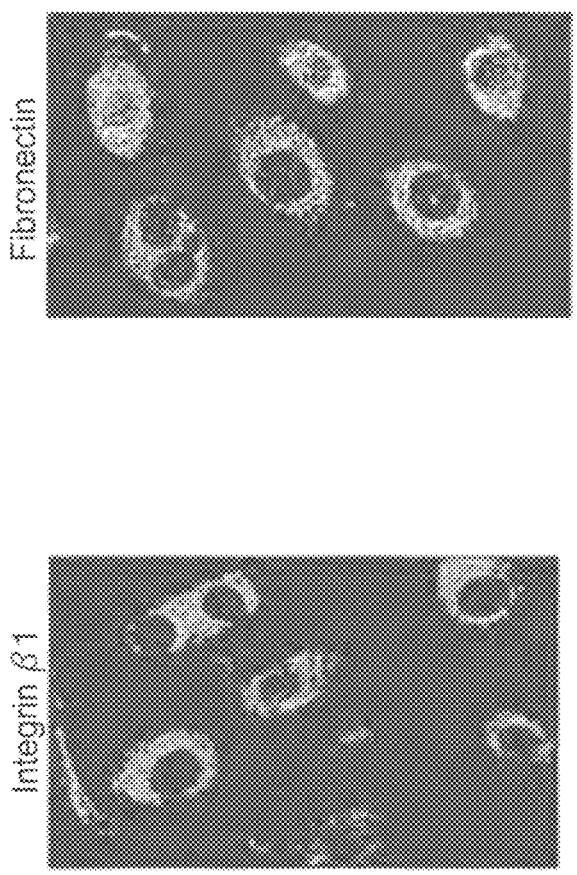
Figures 1, 11:
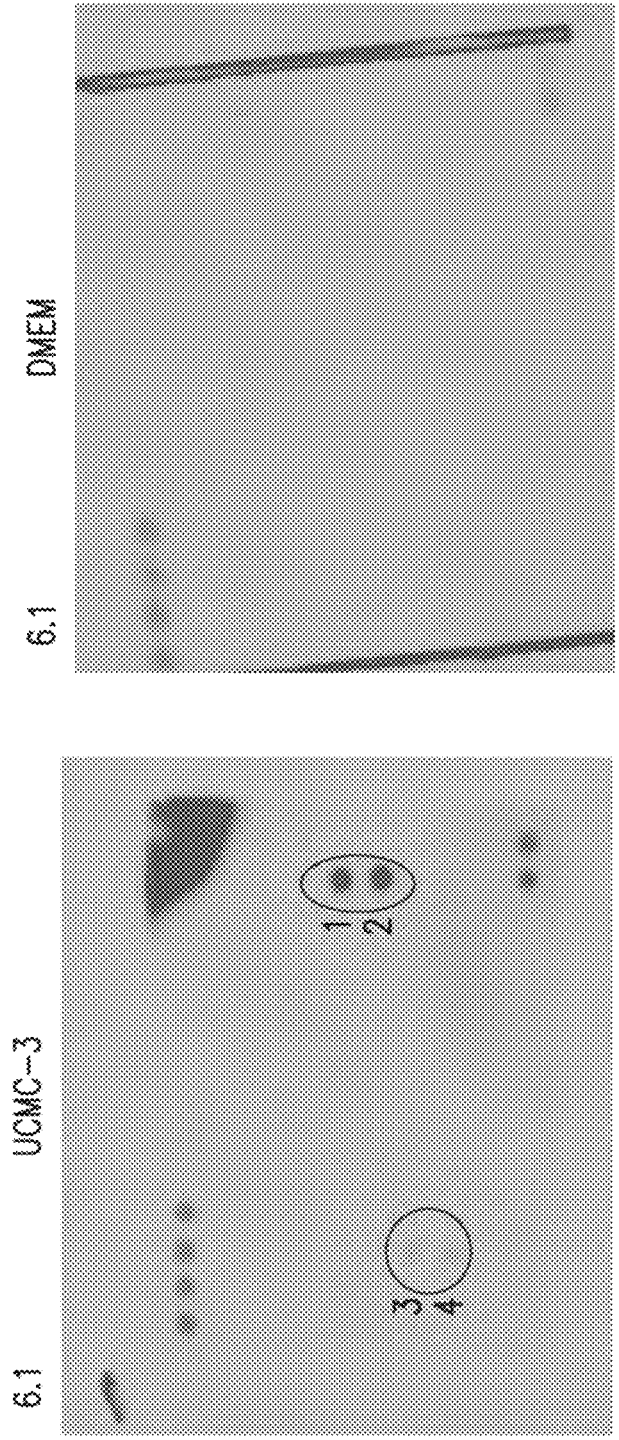
Figures 2, 11:
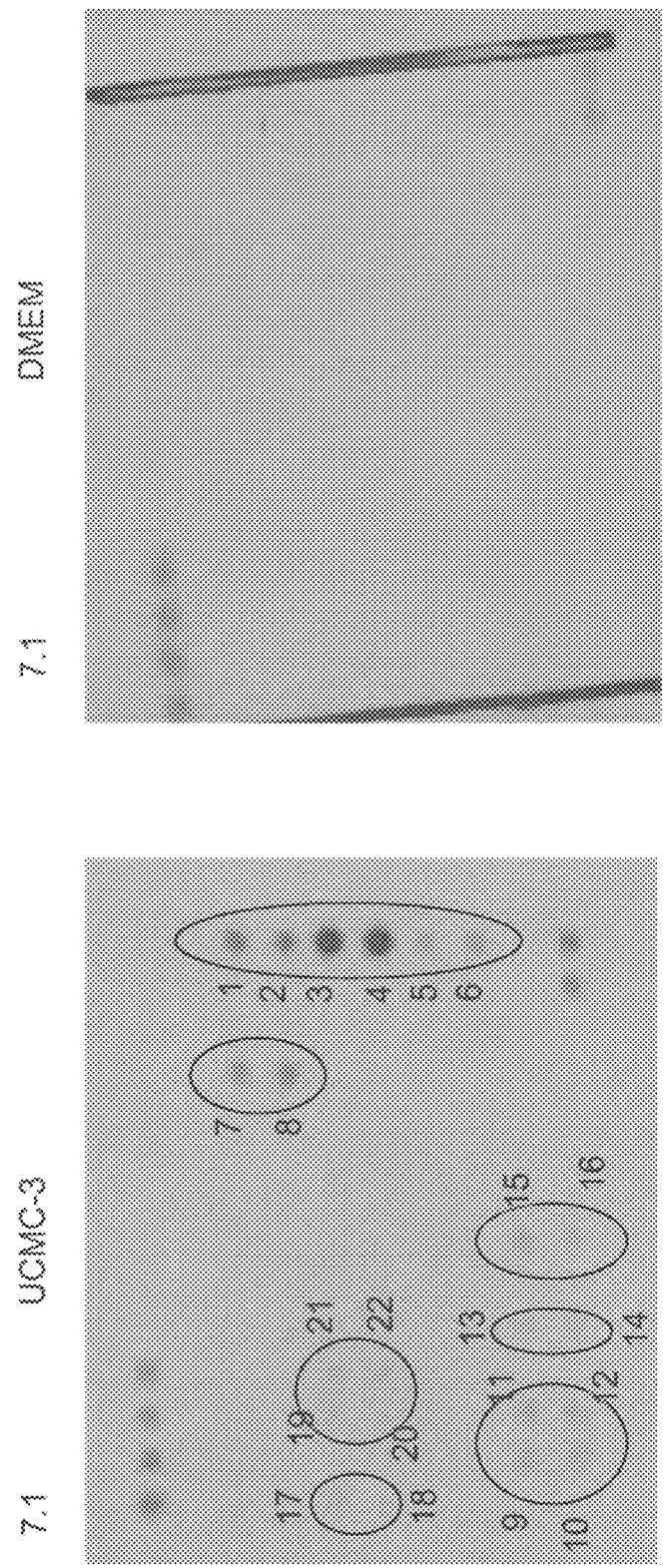
Figures 3, 11:
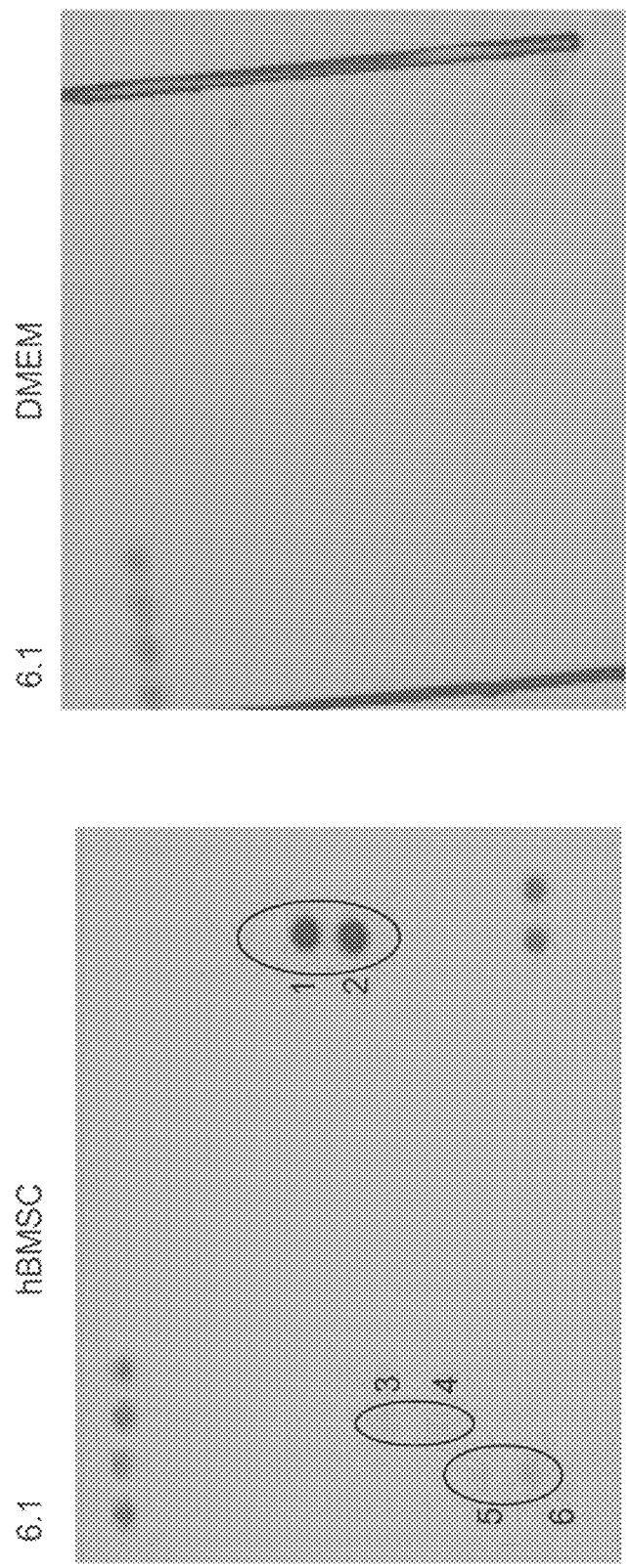
Figures 4, 11:
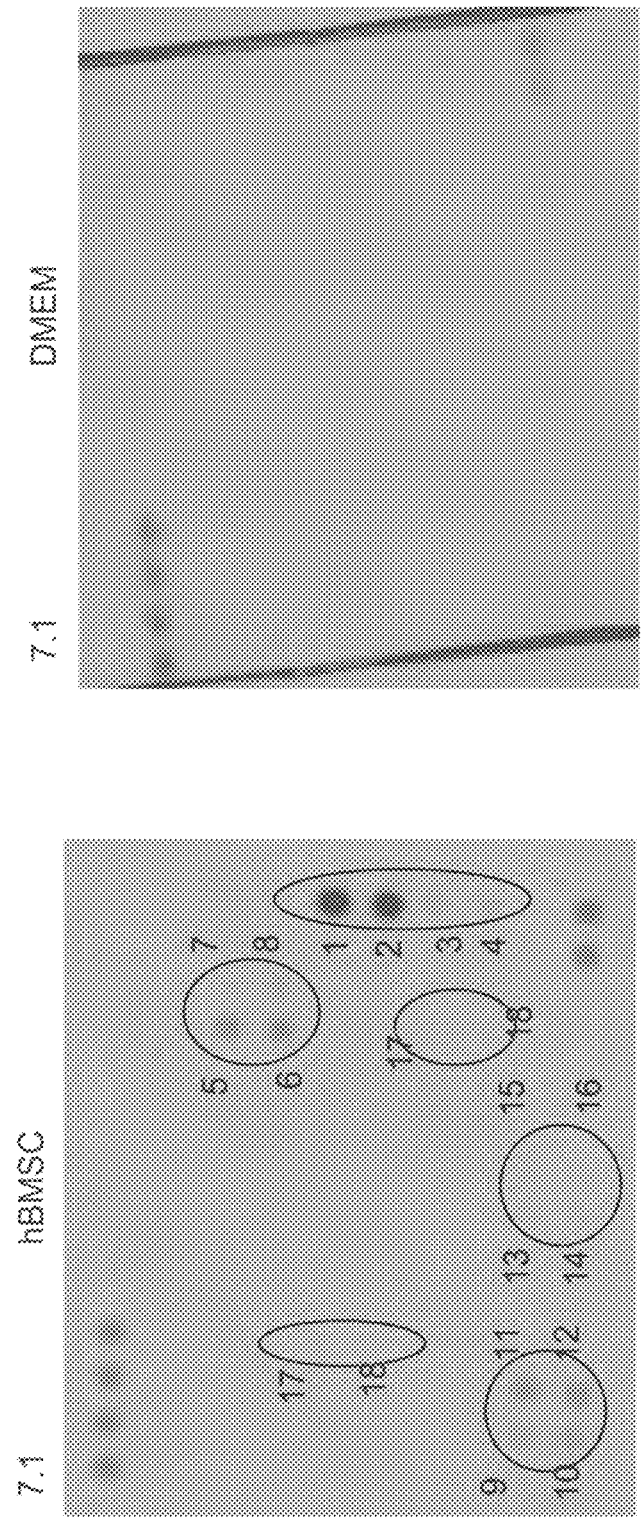
Figures 1, 12:
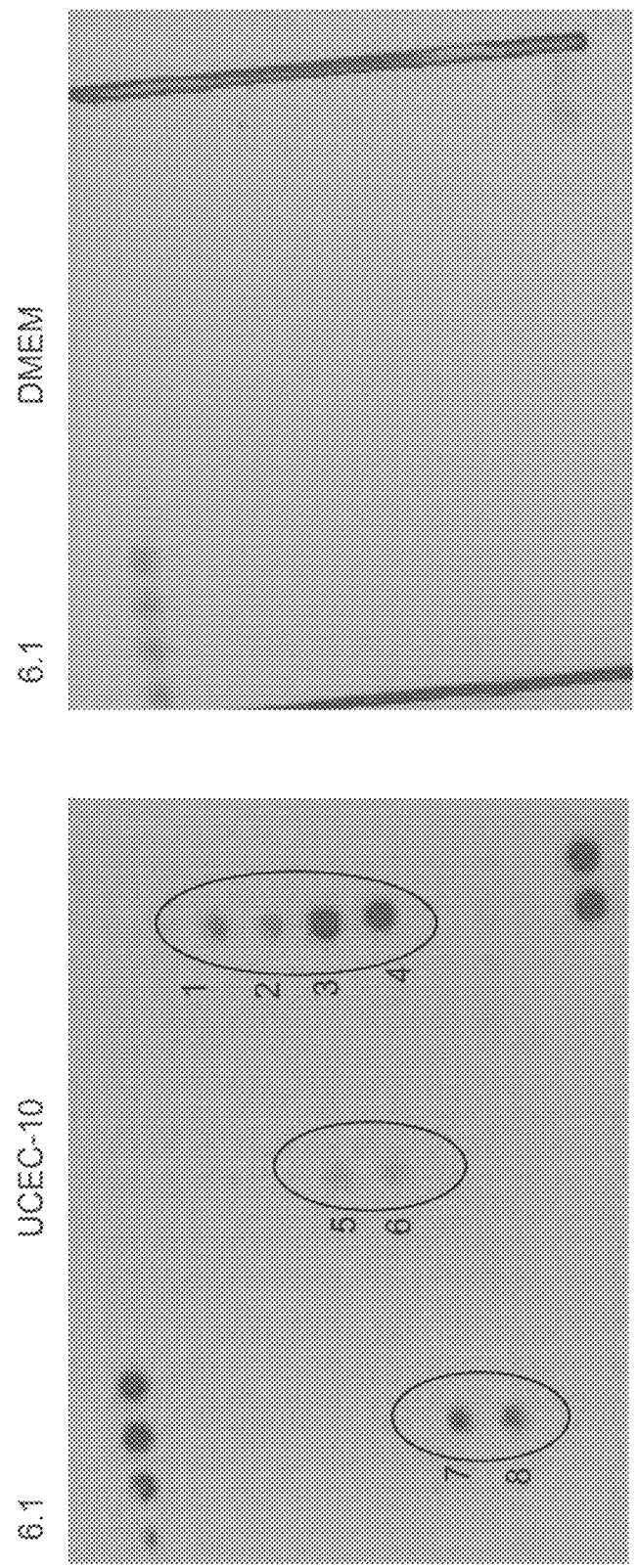
Figures 2, 12:
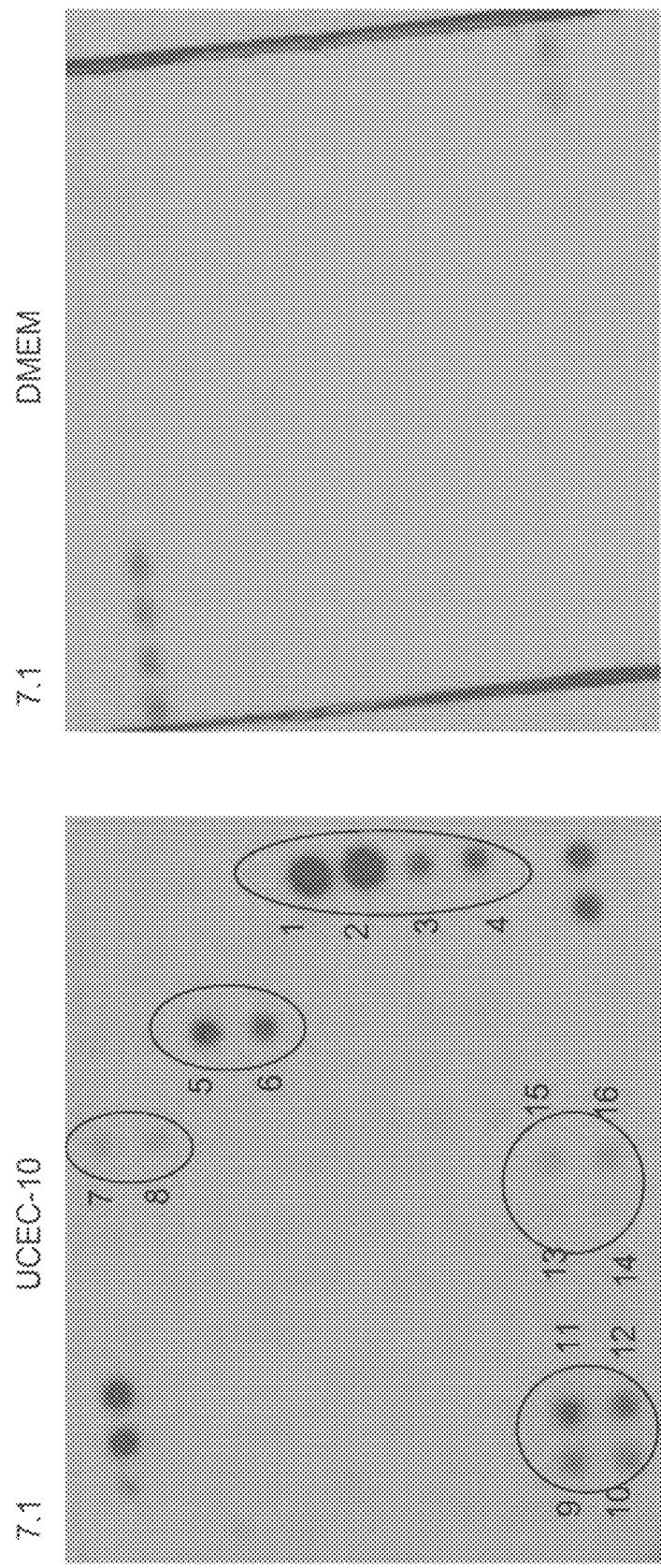
Figures 3, 12:
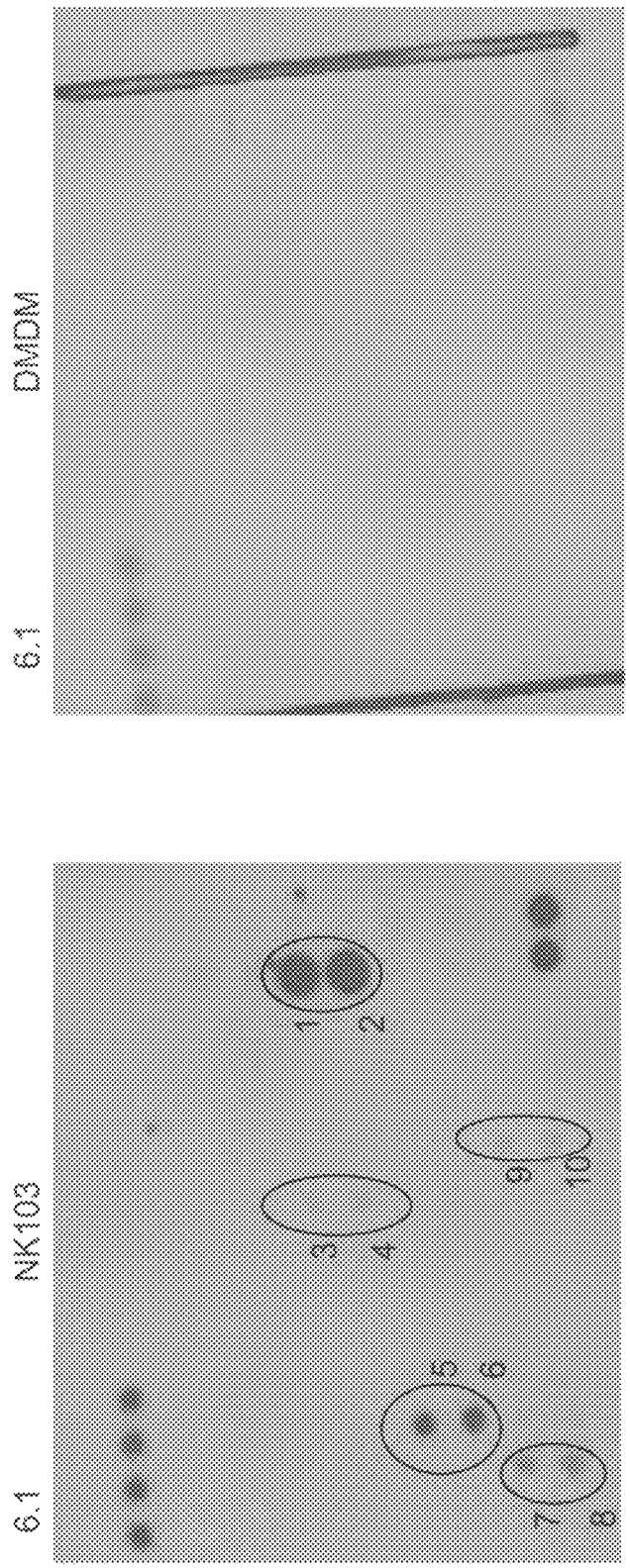
Figures 4, 12:
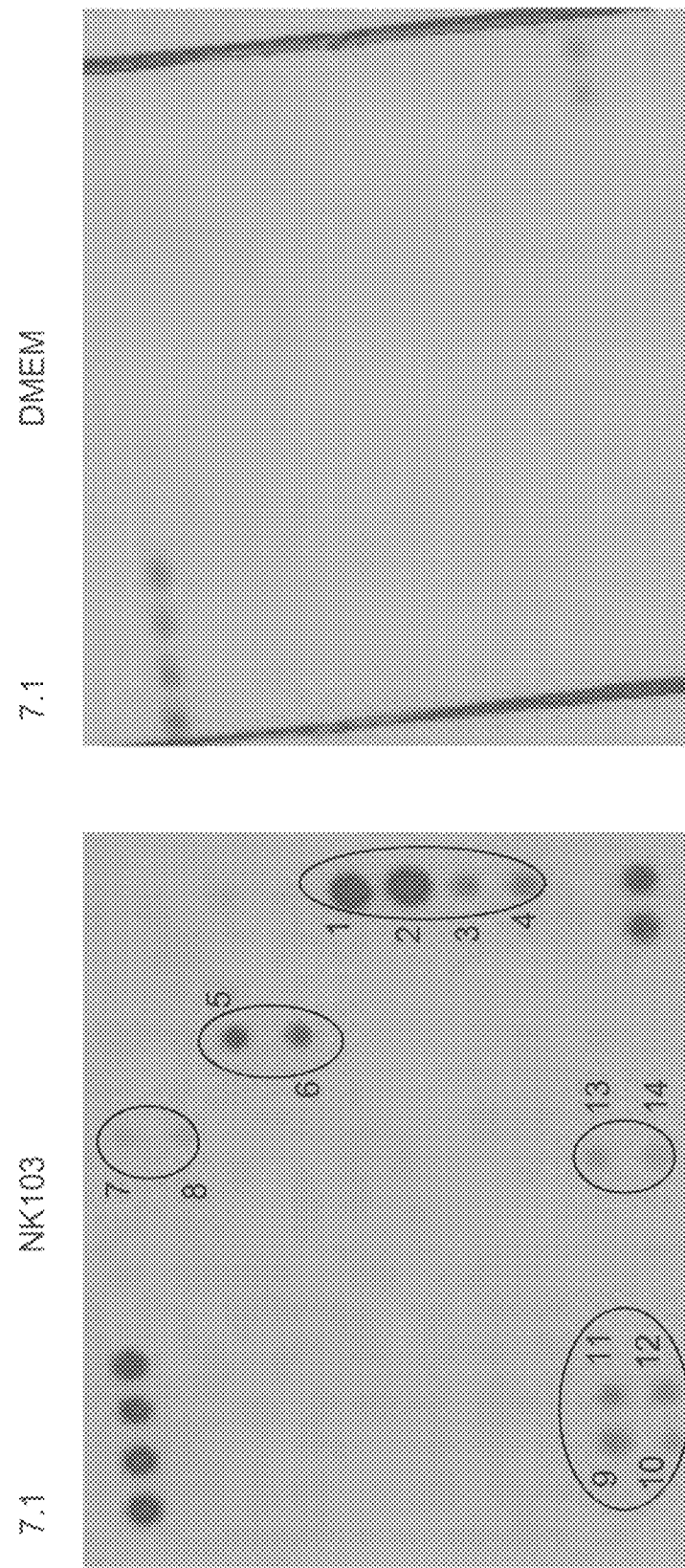
Figures 5, 12:
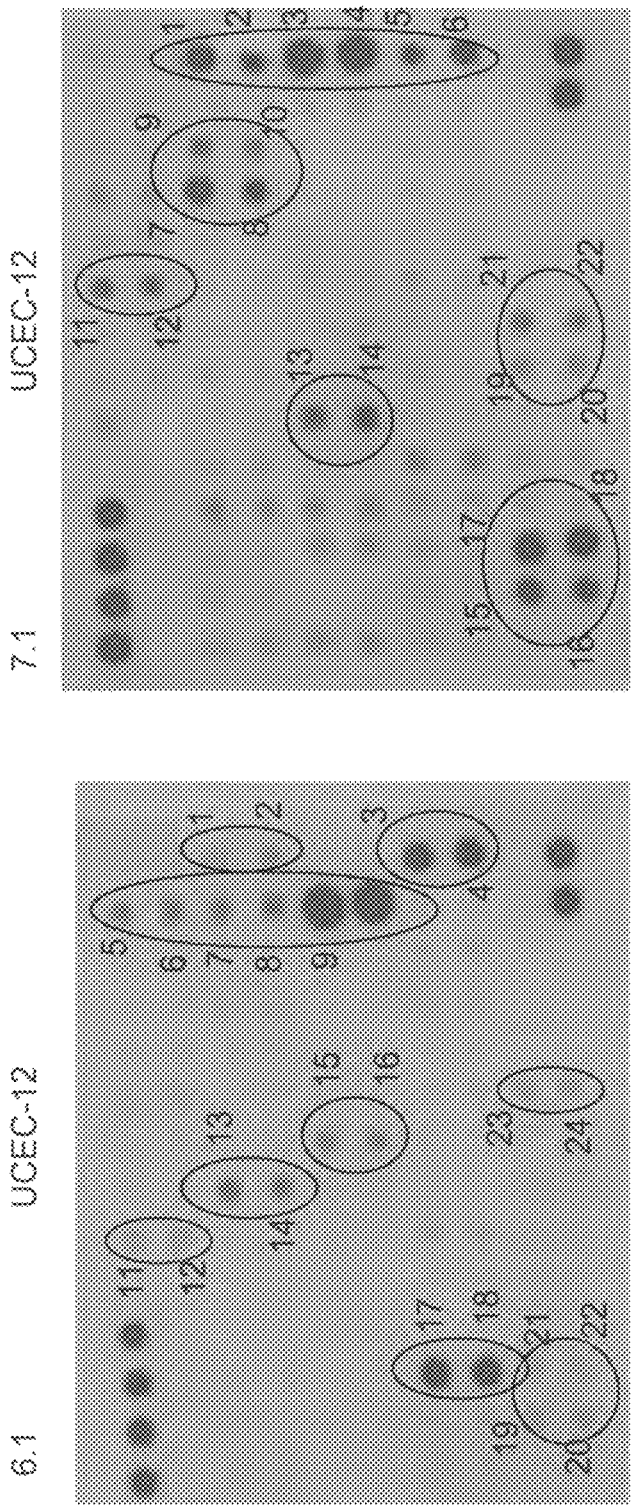
Figure 13:
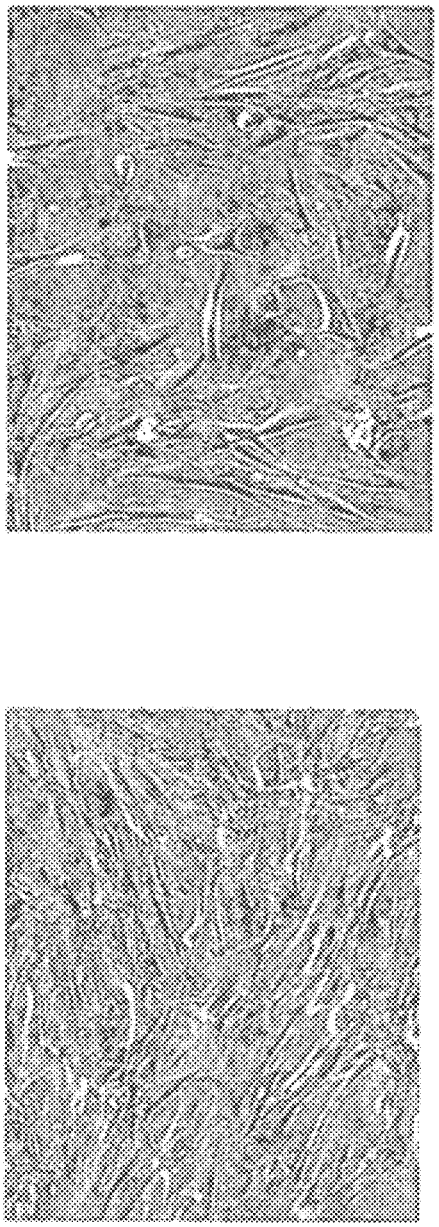
Figure 1:
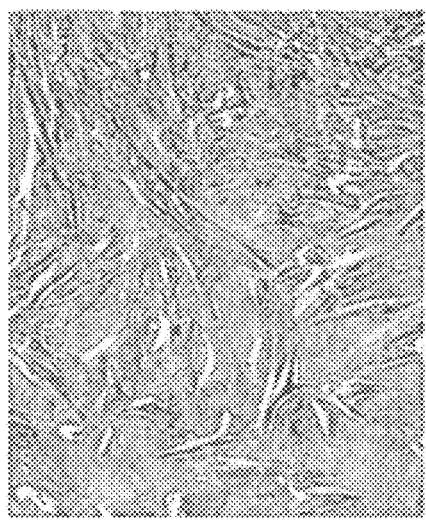
Figure 13:
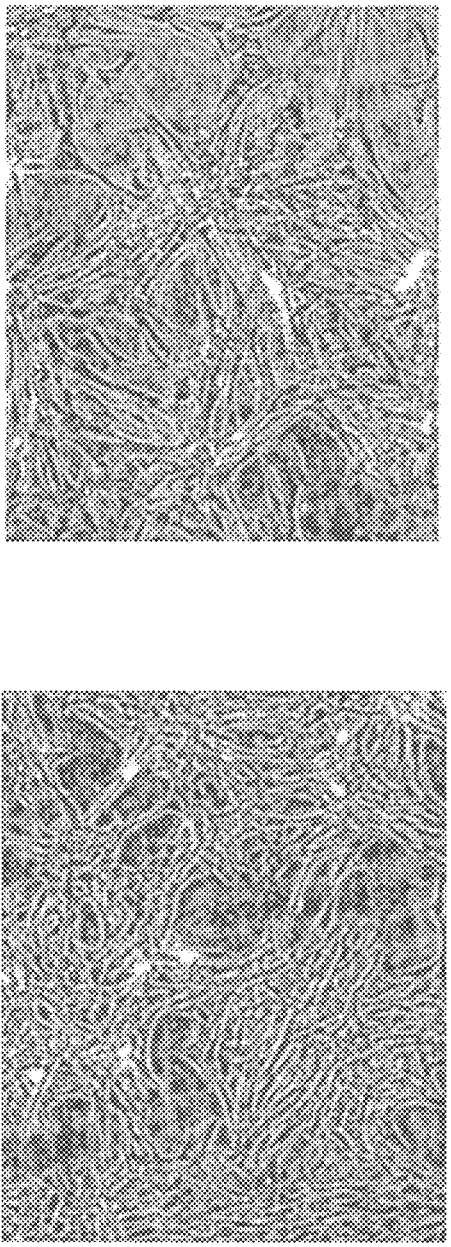
Figure 3:
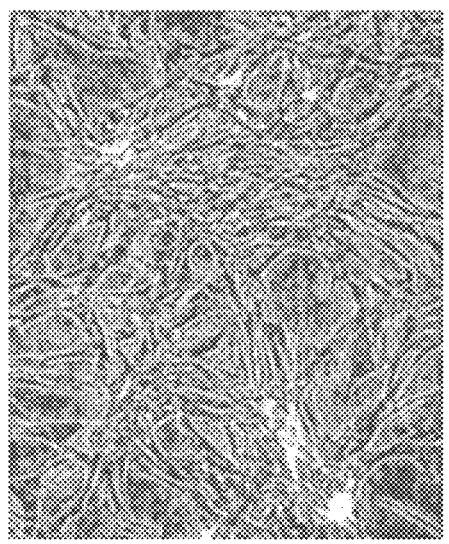
Figure 13:
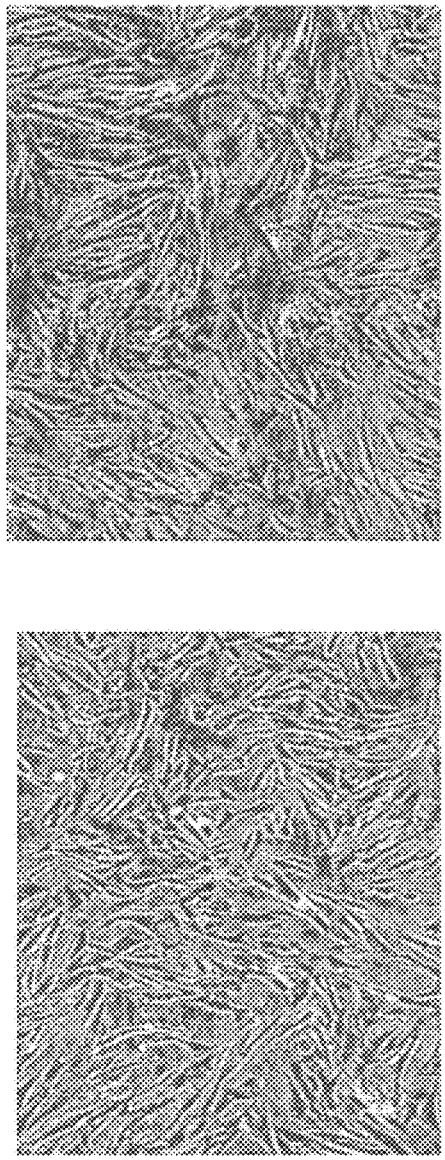
Figure 5:
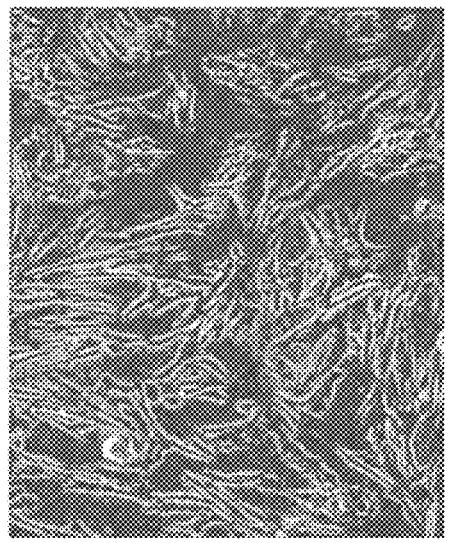
Figure 13:
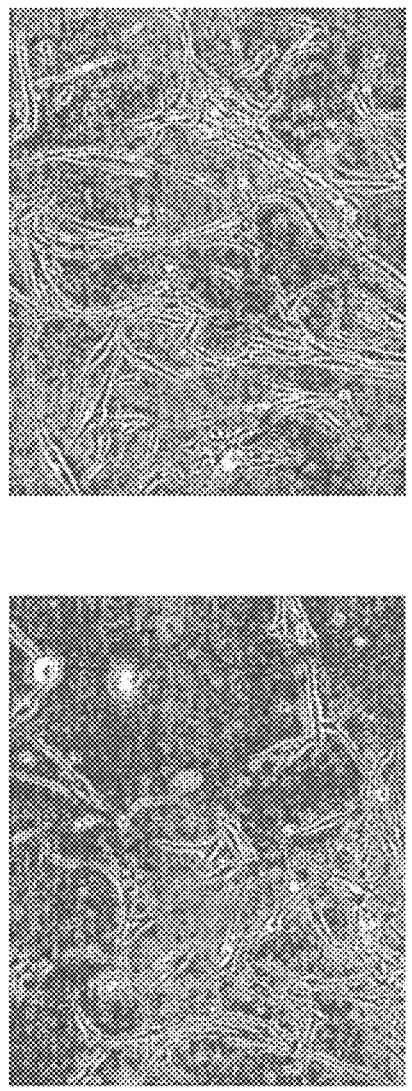
Figure 6:
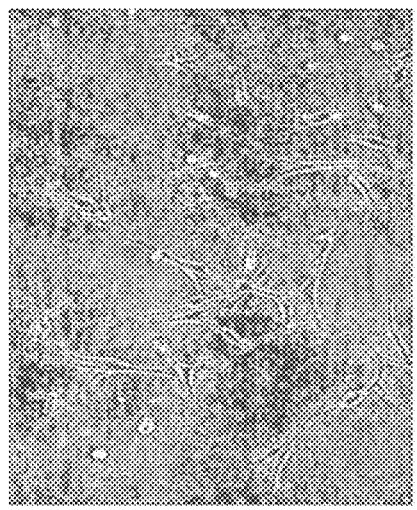
Figures 7, 13:
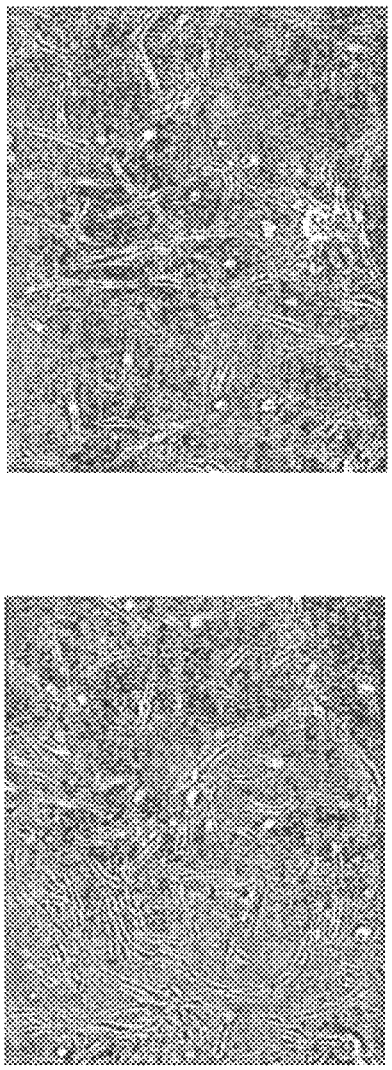
Figures 1, 14:
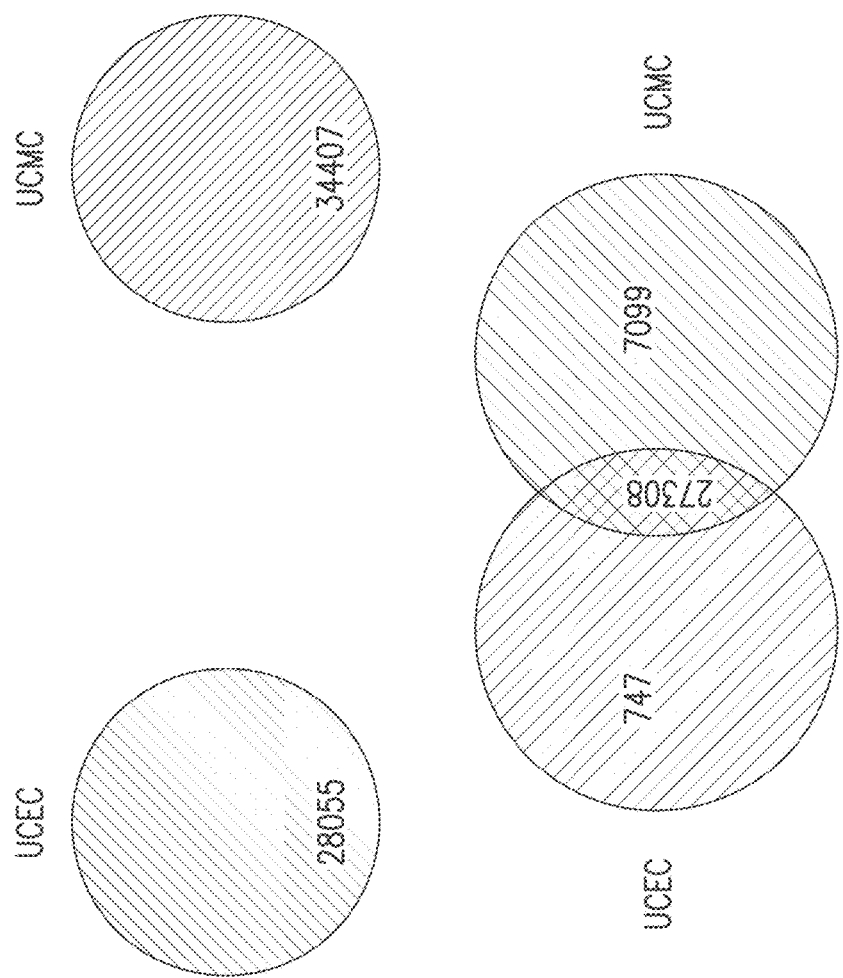
Figure 15:
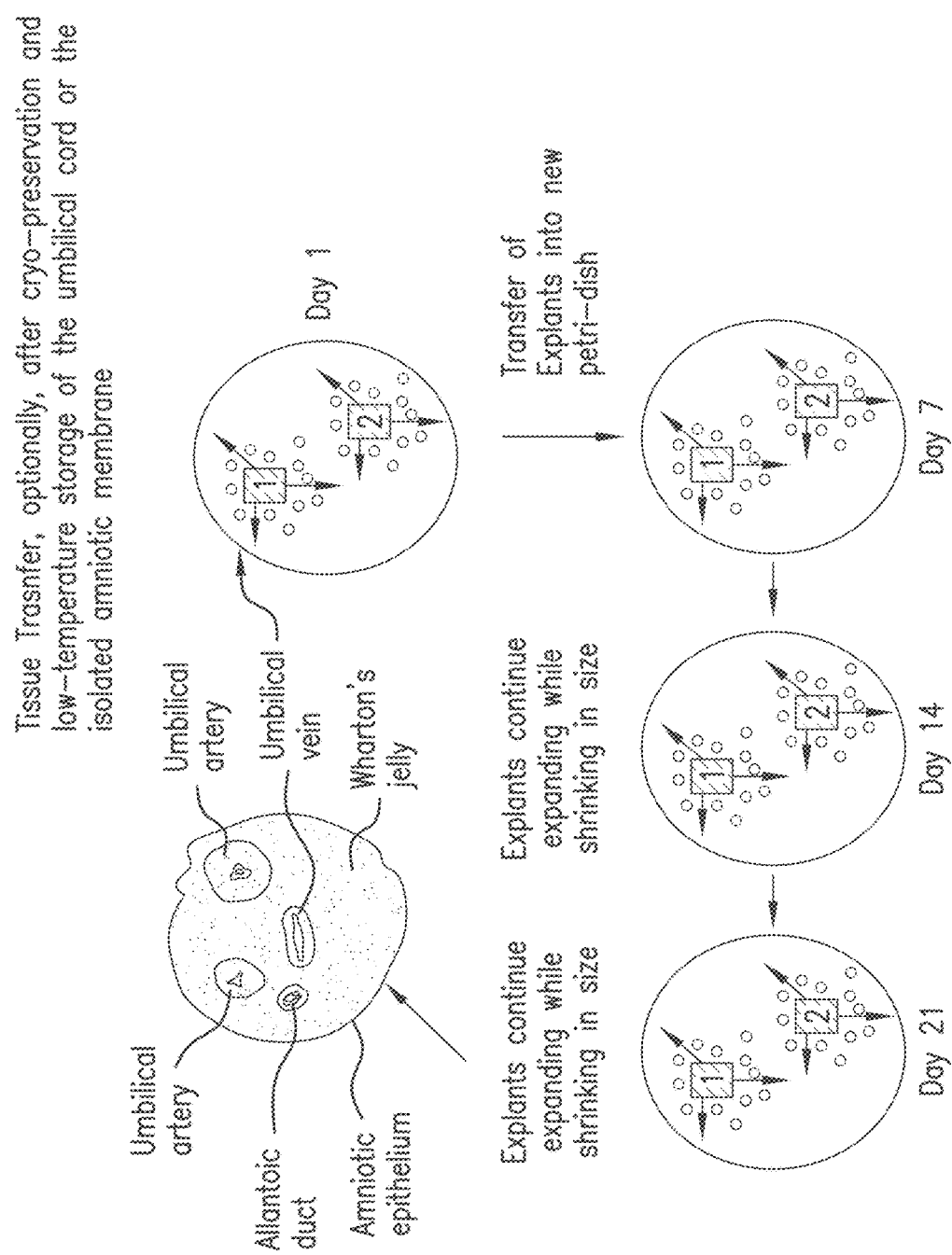
Figure 16:
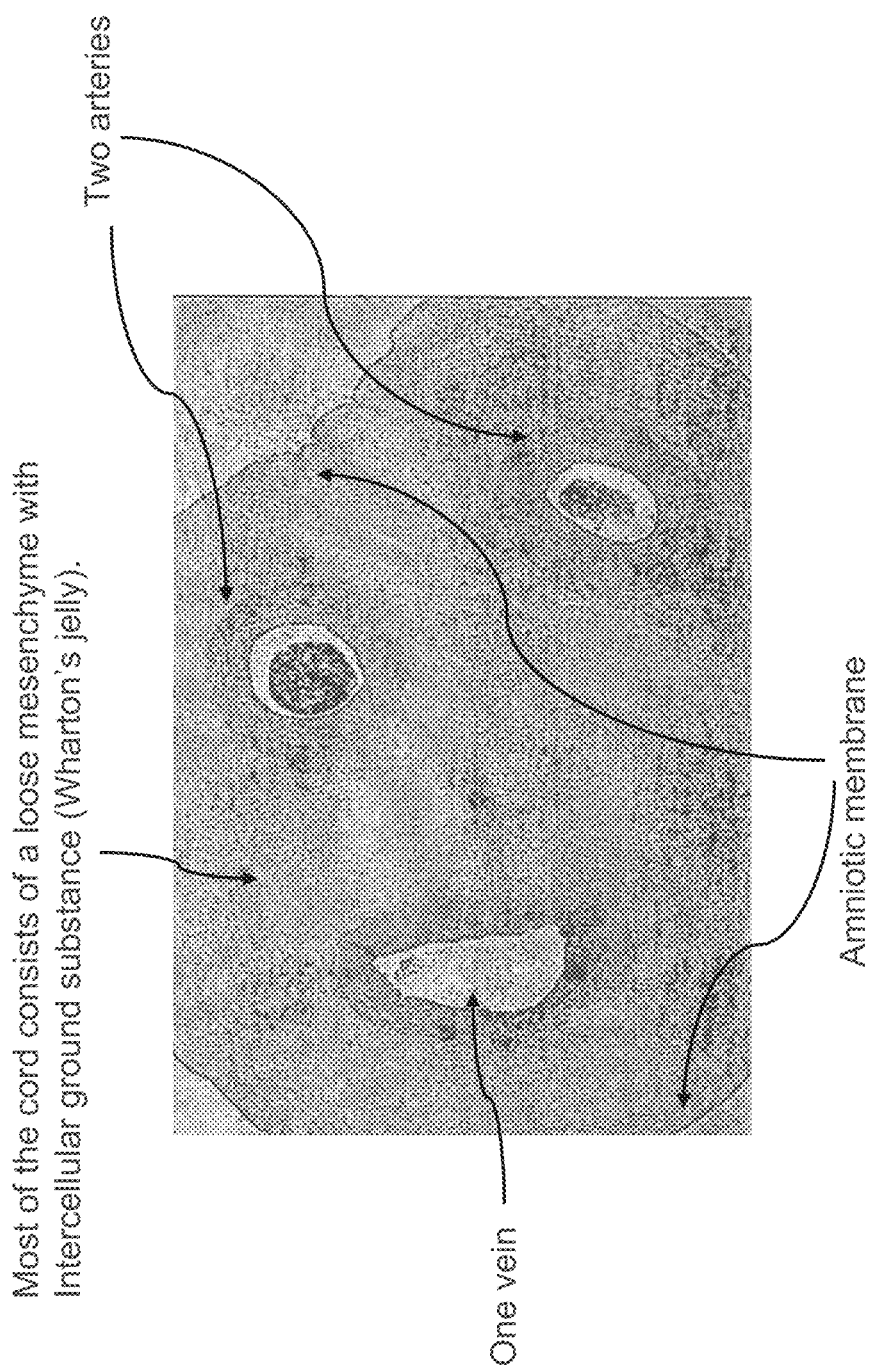

Mesenchymal Cells:

Outgrowth of mesenchymal cells explanted from umbilical cord amniotic membrane was observed as early as 48 hours after placement in tissue culture dishes using CMRL-1066 supplemented with 10% fetal calf serum (FCS) (or PTT-4 medium) as culture medium (FIG. 3A, C) (40× magnification). The cells were characterized by their spindle shaped morphology, and migrated and expanded both easily and quickly in vitro, closely resembling fibroblasts (FIG. 3B, D) (40× magnification). Similar observations were noted in the cell group isolated by collagenase enzymatic digestion (FIG. 4). FIG. 4A shows mesenchymal cells isolated from umbilical cord amniotic membrane at day 2. Cell proliferation was observed at day 5 (FIG. 4B) (40× magnification). FIGS. 6 and 8-1 show pictures of colony formation of mesenchymal stem cells from umbilical cord amniotic membrane cultured on non-feeder layer (FIG. 6) and feeder layer condition (FIG. 8-1, using a 3T3 feeder layer) in PTT-4 medium (40× magnification). The colonies of elongated shaped fibroblastic-like cells expanded rapidly from day 3 to day 7. It is noted in this respect, that the 3T3 feeder layer normally suppresses the growth of mesenchymal cells as human dermal fibroblasts. Once again, this indicates a difference in the behavior of the mesenchymal cells of the invention as compared to more differentiated counterparts.

In further experiments the colony forming ability of the mesenchymal cells of the invention (UCMC) was studied. For colony forming efficiency assay, 100-200 single cells were seeded in 100 mm tissue culture dishes or T75 flasks without feeder layers. Cells were maintained in DMEM/10% FCS for 12 days. Single colony formation was monitored under the inverted light microscope (experiment was carried out in duplicate, experiments termed UCMC-16 and UCMC-17 in FIG. 8-2). Microphotographs were sequentially taken. At day 12, colonies were fixed and stained with Rhodamine. UCMC colony forming units were seen (FIG. 8-2). The multiple large colonies observed, indicated self-renewal of CLSC in-vitro (FIG. 8-2).

Western blot analysis (FIG. 9) shows that mesenchymal stem cells from umbilical cord amniotic membrane (UCMC) and umbilical cord epithelial cells (UCEC) isolated in accordance with the invention expressed the POU5f1 gene which encodes the transcription factor Octamer-4 (Oct-4) a specific marker of embryonic stem cells (cf. Niwa, H., Miyazaki, J., and Smith, A. G. (2000). Nat. Genet. 24, 372-376) (FIG. 9-1). Further results shown in FIGS. 9.1a and 9.1b confirm the expression of Oct-4 in UCMC cells. Briefly, in the experiments leading to the results illustrated in FIGS. 9.1a and 9.1b UCMC were seeded in 100 mm tissue culture dishes at a density of 50 cells/culture dish. The cells were then maintained in PTT-4 (for the composition of PTT-4 see Example 12) for 10 days until some colonies were visible. The colonies were then fixed and incubated with an anti-Oct-4 antibody (ES Cell Marker Sample Kit (Catalog No. SCR002); Chemicon, Temecula, Calif.). One dish (No. 5 in FIG. 9.1a) served as negative control with a secondary antibody staining only. FIG. 9.1b illustrates the morphology of stained UCMC cells that were grown in the above mentioned PTT-4 medium. Thus, this analysis indicates the embryonic-like properties of these stem cells. These mesenchymal and epithelial cells also expressed Bmi-1, a marker that is required for the self-renewal of adult stem cells (cf., Park et al., J. Clin. Invest. 113, 175-179 (2004) (FIG. 9-27) as well as leukemia inhibitory factor (LIF) (FIG. 9-28) that is considered to maintain the pluripotency of stem cells and embryonic cells and has thus, for example been used for isolation and expansion of human neural stem cells. These cells also highly expressed the other growth factors such as connective tissue growth factor (CTGF) (FIGS. 9-6, 9-7), vascular endothelial growth factor (VEGF) (FIGS. 9-10, 9-11), placenta-like growth factor PLGF (FIGS. 9-4, 9-5), STAT3 (FIGS. 9-2, 9-3), stem cell factor (SCF) (FIG. 9-16), Hepatoma-derived Growth Factor (HDGF) (FIGS. 9-14, 9-15), Fibroblast Growth Factor-2 (FGF-2) (FIGS. 9-12, 9-13), Platelet-derived Growth Factor (PDGF) (FIGS. 9-8, 9-9), alpha-Smooth Muscle Actin (α-SMA) (FIG. 9-17), Fibronectin (FIGS. 9-18, 9-19), Decorin (FIG. 9-20), Syndecan-1,2,3,4 (FIGS. 9-21 to 9-26). In FIG. 9, the expression of these genes is compared to human dermal fibroblasts, bone marrow mesenchymal cells (BMSC) and adipose-derived mesenchymal cells (ADMC). FIG. 9-29 shows Western blot data of the secretion of leukemia inhibitory factor (LIF) by both UCEC and UCMC. FIG. 9-30 shows highly secreted Activin A and Follistatin (both of which proteins are well known to promote tissue repair and regeneration, enhanced angiogenesis, and maintain embryonic stem cell culture, so that expression of the respective genes is a sign for the embryonic properties and ability of the cells to differentiate) detected ELISA assay (FIG. 9-30) in supernatants of umbilical cord mesenchymal and epithelial stem cell culture in comparison with bone marrow, adipose derived stem cells, human dermal fibroblasts and epidermal keratinocytes. Also these results indicate that the cells of the invention are promising candidates in therapeutic application of these cells areas such as regenerative medicine, aging medicine, tissue repair and tissue engineering. In addition, FIGS. 9-29 and 9-30 show the capability of the cells to secret an expression product into the culture medium.

Mesenchymal cells were further characterized by analysis of secreted cytokines and growth factors in comparison with human bone-marrow mesenchymal stem cells. The umbilical cord epithelial stem cells (UCEC) were analysed in comparison with human epidermal keratinocytes. This analysis was carried out as follows: Briefly, UCMC, UCEC, dermal fibroblasts, bone-marrow mesenchymal cells, epidermal keratinocytes were cultured in growth media until 100% confluence (37° C., 5% $CO_2$) and then synchronized in starvation medium (serum-free DMEM) for 48 hours. The next day, the medium was replaced the next against fresh serum-free DMEM and the cells then were cultivated for another 48 hours. Conditioned media were collected, concentrated and analyzed using a Cytokine Array (RayBiotech Inc., Gorgia, USA).

The results of this analysis show that UCMC secrete Interleukin-6 (IL-6); (MCP1); hepatocyte growth factor (HGF); Interleukin-8 (IL8); sTNFR1; GRO; TIMP1; TIMP2; TRAILR3; uPAR; ICAM1; IGFBP3; IGFBP6 (FIG. 11), whereas UCEC secrete IGFBP-4; PARC; EGF; IGFBP-2; IL-6; Angiogenin; GCP-2; IL1Rα; MCP-1; RANTES; SCF; TNFβ; HGF; IL8; sTNFR; GRO; GRO-α; Amphiregulin; IL-1R4/ST2; TIMP1; TIMP2; uPAR; VEGF (FIG. 12).

Accordingly, this shows that both cells types secrete large amounts of cytokines and growth factors that play important roles in developmental biology, tissue homeostasis, tissue repair and regeneration and angiogenesis. This further demonstrates the versatility of the cells of the invention for use in the respective therapeutic applications.

In addition, the cells of the invention were further examined with respect to their safety profile using mouse teratoma formation assay as an indicator. Six SCID mice were used in these experiments. A suspension of more than 2 million UCMC was injected with a sterile 25G needle into the thigh muscle of each SCID mouse. Animals were kept up to 6 months and tumor formation was assessed. No tumor formation was observed in these mice (data not shown). This indicates that the cells of the invention are safe and do not have any capability to form tumors, benign or otherwise.

The UCMC were also analysed for their expression of human leukocyte antigen (HLA) molecules. When testing on major histocompatibility complex (MHC) class I molecules, this analysis showed that HLA-A molecules were present in high number (test result in arbitrary unit: 3201), meaning that the cells are HLA-A positive whereas expression of HLA-B molecules was insignificant (test result in arbitrary units: 35), meaning the cells are HLA-B negative. These cells also expressed HLA-G (see Example 19). As HLA-B is mainly responsible for rejection reaction in transplantation, this result indicates that the cells of the invention are not only suitable for autologous transplantation but also for allogeneic transplantation. The cells were tested positive for Class II MHC molecule HLA-DR52 and tested negative for Class II MHC molecule HLA-DRB4. HLA-DRB1 was also found to be present (0301/05/20/22).

Example 4: Cultivation of Stem/Progenitor Cells in Serum Free Media

UCMC cells were cultured in DMEM containing 10 FCS and in serum-free media, PTT-1, PTT-2 and PTT-3. The three media PTT-1, PTT-2 and PTT-3 were prepared by one of the present inventors, Dr Phan. In brief, these 3 media do not contain fetal bovine or human serum, but contain different cytokines and growth factors such as IGF, EGF, TGF-beta, Activin A, BMPs, PDGF, transferrin, and insulin. The growth factor components vary between media to assess differential growth characteristics. The cultivation was carried out as follows: Different proportions of growth factors and cytokines were added in basal media. UCMC were thawed and maintained in these media for 10 days. Cell proliferation was monitored under light microscopy. PTT-2 medium is a mixture of M154 a melanocyte culture medium and EpiLife® (Cascade Biologics Inc., Oregon, USA) at ratio of 3:1. Medium 154 is a sterile, liquid tissue culture medium prepared with 200 µM calcium chloride for the growth of normal human epidermal keratinocytes. Medium 154 is a basal medium containing essential and non-essential amino acids, vitamins, other organic compounds, trace minerals, and inorganic salts. It does not contain antibiotics, antimycotics, hormones, growth factors, or proteins. It is HEPES and bicarbonate buffered and is used in an incubator with an atmosphere of 5% $CO_2$/95% air.

FIG. 13 shows good UCMC growth in the 4 different media groups (FIG. 13-1 to FIG. 13-5), wherein the morphology of UCMC cells is different depending on the ratio or proportion of cytokines or growth factors present in the respective media. In contrast, bone marrow and adipose-derived mesenchymal cells did not grow well in these serum-free media (FIG. 13-6 and FIG. 13-7). Accordingly, the good growth of the UCMC demonstrates the robustness of the cells of the invention and their high viability, indicating that their growth characteristics are superior to conventional sources of mesenchymal stem cells as bone marrow derived and adipose-derived mesenchymal cells. In this respect, it is worth to note that (bovine) serum free medium was used in these experiments and that the majority of human mesenchymal cells do not grow well in serum-free medium systems. Thus, using the cells of the invention in connection with defined serum-free media technologies is a big advantage in cell therapy as the risks of using fetal bovine serum for cell culture and expansion are removed. (Although use of bovine serum has been practiced for a long time and typically optimizes cell growth, concerns of its used have been raised as to the transmission of zoonoses as Bovine Spongiform Encephalopathy (Mad Cow Disease)).

Example 5: Characterization of the Gene Expression Profile of Umbilical Cord Epithelial and Mesenchymal Stem Cells The gene expression profile of umbilical cord (amniotic membrane) epithelial and mesenchymal stem cells was analyzed using a DNA microarray. For this purpose, UCMC and UCEC were cultured in growth media at 37° C., 5% $CO_2$ until 100% confluence. Cells were synchronized in basal media for 48 hours then replaced with fresh basal media for another 48 hours. Total RNA was harvested and sent to Silicon Genetics Microarray Service. Data analysis was performed using GeneSpring 7.2). FIG. 14 summarizes the global gene expression. UCEC expressed a total of 28055 genes and UCMC expressed a total of 34407 genes. There are 27308 overlapping genes expressing in both cell types. 747 genes expressed were unique to UCEC and 7099 genes expressed were unique to UCMC. The selected genes of interest are presented in FIG. 14.

Both stem cell types expressed 140 genes related to embryonic stem cells and embryonic development, further supporting that the cells of the invention have embryonic stem cell-like properties: Nanog; Alpha-fetal protein; Pre-B-cell leukemia transcription factor 3; Laminin alpha 5; Carcinoembryonic antigen-like 1; abhydrolase domain containing 2; Delta-like 3 (*Drosophila*); Muscleblind-like (*Drosophila*); GNAS complex locus; Carcinoembryonic antigen-related cell adhesion molecule 3; Palmitoyl-protein thioesterase 2; Pregnancy specific beta-1-glycoprotein 2; Carcinoembryonic antigen-like 1; Embryonic ectoderm development; Maternal embryonic leucine zipper kinase; Chorionic somatomammotropin hormone 2; Forkhead box D3; radical fringe homolog (*Drosophila*); Kinesin family member 1B; Myosin, heavy polypeptide 3, skeletal muscle, embryonic; Split hand/foot malformation (ectrodactyly) type 3; TEA domain family member 3; Laminin, alpha 1; Chorionic somatomammotropin hormone 1; placental lactogen; Corticotropin releasing hormone receptor 1; thyrotrophic embryonic factor; Aryl-hydrocarbon receptor nuclear translocator 2; Membrane frizzled-related protein; Neuregulin 1'Collagen, type XVI, alpha 1; Neuregulin 1; Chorionic somatomammotropin hormone 1 (placental lactogen); CUG triplet repeat, RNA binding protein 1; Chorionic somatomammotropin hormone 1 (placental lactogen) Bystin-like; MyoD family inhibitor; Retinoic acid induced 2; GNAS complex locus; Pre-B-cell leukemia transcription factor 4; Laminin, alpha 2 (merosin, congenital muscular dystrophy); SMAD, mothers against DPP homolog 1 (*Drosophila*); *Homo sapiens* transcribed sequence with moderate similarity to protein pir:D28928 (*H. sapiens*) D28928 pregnancy-specific beta-1 glycoprotein IB, abortive—human (fragment); Kinesin family member 1B; Bruno-like 4, RNA binding protein (*Drosophila*); Embryo brain specific protein; Pregnancy-induced growth inhibitor; SMAD, mothers against DPP homolog 5 (*Drosophila*); Chorionic somatomammotropin hormone 2; Adenylate cyclase activating polypeptide 1 (pituitary); Carcinoembryonic antigen-related cell adhesion molecule; Laminin, alpha 3; Protein O-fucosyltransferase 1; Jagged 1 (Alagille syndrome); Twisted gastrulation homolog 1 (*Drosophila*); ELAV (embryonic lethal, abnormal vision, *Drosophila*)-like 3 (Hu antigen C); Thyrotrophic embryonic factor; Solute carrier family 43, member 3; Inversin; nephronophthisis 2 (infantile); inversion of embryonic turning; *Homo sapiens* inversin (INVS), transcript variant 2, mRNA; *Homo sapiens* transcribed sequences; Homeo box D8; Embryonal Fyn-associated substrate; ELAV (embryonic lethal, abnormal vision, *Drosophila*)-like 1 (Hu antigen R); Basic helix-loop-helix domain containing, class B, 2; Oxytocin receptor; Teratocarcinoma-derived growth factor 1; Fms-related tyrosine kinase 1 (vascular endothelial growth factor/vascular permeability factor receptor); Adrenomedullin; Nuclear receptor coactivator 6-CUG triplet repeat, RNA binding protein 1; Twisted gastrulation homolog 1 (*Drosophila*); Carcinoembryonic antigen-related cell adhesion molecule 4; Protein tyrosine phosphatase, receptor type, R; Acrg embryonic lethality (mouse) minimal region ortholog; EPH receptor A3; Delta-like 1 (*Drosophila*); Nasal embryonic LHRH factor; Transcription factor CP2-like 1; Split hand/foot malformation (ectrodactyly) type 3; Jagged 2; *Homo sapiens* transcribed sequence; Neuregulin 1; Split hand/foot malformation (ectrodactyly) type 1; Solute carrier family 43, member 3; Hydroxyacyl-Coenzyme A dehydrogenase/3-ketoacyl-Coenzyme A thiolase/enoyl-Coenzyme A hydratase (trifunctional protein), alpha subunit; Fucosyltransferase 10 (alpha (1,3) fucosyltransferase); Acrg embryonic lethality (mouse) minimal region ortholog; Carcinoembryonic antigen-related cell adhesion molecule 7; Nucleophosmin/nucleoplasmin, 2; Fc fragment of IgG, receptor, transporter, alpha; Twisted gastrulation homolog 1 (*Drosophila*); *Homo sapiens* similar to vacuolar protein sorting 35; maternal-embryonic 3 (LOC146485), mRNA; abhydrolase domain containing 2; T, brachyury homolog (mouse); A disintegrin and metalloproteinase domain 10; Ribosomal protein L29; Endothelin converting enzyme 2; ELAV (embryonic lethal, abnormal vision, *Drosophila*)-like 1 (Hu antigen R); Trophinin; Homeo box B6; Laminin, alpha 4; Homeo box B6; hypothetical protein FLJ13456; NACHT, leucine rich repeat and PYD containing 5; ELAV (embryonic lethal, abnormal vision, *Drosophila*)-like 1 (Hu antigen R); Undifferentiated embryonic cell transcription factor 1; Pregnancy-associated plasma protein A, pappalysin 1; Secretoglobin, family 1A, member 1 (uteroglobin); Parathyroid hormone-like hormone; Carcinoembryonic antigen-related cell adhesion molecule 1 (biliary glycoprotein); Laminin, alpha 1.

Both stem cell types also expressed thousands of genes related to developmental biology, cell growth and differentiation, cell homeostasis, cell and tissue repair and regeneration. Examples of such growth factors and their receptors is as follows: (G-CSF, FGFs, IGFs, KGF, NGF, VEGFs, PIGF, Angiopoietin, CTGF, PDGFs, HGF, EGF, HDGF, TGF-beta, Activins and Inhibins, Follistatin, BMPs, SCF/c-Kit, LIF, WNTs, SDFs, OncostatinM, Interleukins, Chemokines and many others); MMPs, TIMPs extracellular matrices (collagens, laminins, fibronectins, vitronectins, tenascins, intergrins, syndecans, decorin, fibromoludin, proteoglycans, sparc/osteonectin, mucin, netrin, glypican, cartilage associated protein, matrilin, hyaluronan, fibulin, ADAMTS, biglycan, discoidin, desmosome components, ICAMs, cadherins, catenins and many others); cytokeratins.

There are groups of genes present only in UCMC. These genes are related to the following: Normal Physiological Processes (Insulin-like growth factor 1 (somatomedin C); Insulin-like 4 (placenta); Relaxin 1; Plasminogen; Insulin-like growth factor 1 (somatomedin C); Insulin-like 5; Insulin-like growth factor 1 (somatomedin C); Insulin-like growth factor 2 (somatomedin A), Homeostasis (Radial spokehead-like 1; Hemochromatosis; Chemokine (C-C motif) ligand 5; Interleukin 31 receptor A; Chemokine (C-X-C motif) ligand 12 (stromal cell-derived factor 1); Nuclear receptor subfamily 3, group C, member 2; Hemochromatosis; Chemokine (C-C motif) ligand 23; Chemokine (C-C motif) ligand 23; Ferritin mitochondrial; Peroxisome proliferative activated receptor, gamma, coactivator 1, alpha; Surfactant, pulmonary-associated protein D; Chemokine (C-C motif) ligand 11; Chemokine (C-C motif) ligand 3; Egl nine homolog 2 (*C. elegans*); Peroxisome proliferative activated receptor, gamma, coactivator 1, beta; Chemokine (C-C motif) ligand 1; Chemokine (C-X-C motif) ligand 12 (stromal cell-derived factor 1); ATPase, Na+/K+ transporting, alpha 2 (+) polypeptide; Chemokine (C motif) ligand 2; Hemopexin; Ryanodine receptor 3), Morphogenesis (Spectrin, alpha, erythrocytic 1 (elliptocytosis 2); Homeo box D3; Eyes absent homolog 1 (*Drosophila*); Ras homolog gene family, member J; Leukocyte specific transcript 1; Ectodysplasin A2 receptor; Glypican 3; Paired box gene 7; Corin, serine protease; Dishevelled, dsh homolog 1 (*Drosophila*); Ras homolog gene family, member J; T-box 3 (ulnar mammary syndrome); Chondroitin beta1,4 N-acetyl-galactosaminyltransferase; Chondroitin beta1,4 N-acetylgalactosaminyltransferase; SRY (sex determining region Y)-box 10; Myosin, heavy polypeptide 9, non-muscle; Luteinizing hormone/choriogonadotropin receptor; radical fringe homolog (*Drosophila*); Secreted frizzled-related protein 5; Wingless-type MMTV integration site family, member 11; Eyes absent homolog 2 (*Drosophila*); Muscleblind-like (*Drosophila*); T-box 5; Mab-21-like 1 (*C. elegans*); Growth arrest-specific 2; Sex comb on midleg homolog 1 (*Drosophila*); T-box 6; Filamin-binding LIM protein-1; Melanoma cell adhesion molecule; Twist homolog 1 (acrocephalosyndactyly 3; Saethre-Chotzen syndrome) (*Drosophila*); Homeo box A11; Keratocan; Fibroblast growth factor 1 (acidic); Carboxypeptidase M; CDC42 effector protein (Rho GTPase binding) 4; LIM homeobox transcription factor 1, beta; Engrailed homolog 1; Carboxypeptidase M; Fibroblast growth factor 8 (androgen-induced); Fibroblast growth factor 18; Leukocyte specific transcript 1; Endothelin 3; Paired-like homeodomain transcription factor 1), Embryonic Development (Pregnancy specific beta-1-glycoprotein 3; ELAV (embryonic lethal, abnormal vision, *Drosophila*)-like 4 (Hu antigen D); G protein-coupled receptor 10; Ectodysplasin A2 receptor; ATP-binding cassette, sub-family B (MDR/TAP), member 4; Pregnancy specific beta-1-glycoprotein 11; Nasal embryonic LHRH factor; Relaxin 1; Notch homolog 4 (*Drosophila*); Pregnancy specific beta-1-glycoprotein 6; pih-2P; *Homo sapiens* pregnancy-induced hypertension syndrome-related protein (PIH2); Oviductal glycoprotein 1, 120 kDa (mucin 9, oviductin); Progestagen-associated endometrial protein; Myosin, light polypeptide 4, alkali; atrial, embryonic; Prolactin; Notch homolog 4 (*Drosophila*); Pre-B-cell leukemia transcription factor 1; radical fringe homolog (*Drosophila*); Corticotropin releasing hormone; Nuclear receptor subfamily 3, group C, member 2; Neuregulin 2; Muscleblind-like (*Drosophila*); Myosin, light polypeptide 4, alkali; atrial, embryonic; *Homo sapiens* cDNA FLJ27401 fis, clone WMCO3071; Extraembryonic, spermatogenesis, homeobox 1-like; Insulin-like 4 (*placenta*); Human processed pseudo-pregnancy-specific glycoprotein (PSG12) gene, exon B2C containing 3' untranslated regions of 2 alternative splice sites C1 and C2;

Fms-related tyrosine kinase 1 (vascular endothelial growth factor/vascular permeability factor receptor); Pre-B-cell leukemia transcription factor 1; Pregnancy specific beta-1-glycoprotein 3; carcinoembryonic antigen-related cell adhesion molecule 1 (biliary glycoprotein); Steroid sulfatase (microsomal), arylsulfatase C, isozyme S; Homeo box B6; Protein O-fucosyltransferase 1; LIM homeobox transcription factor 1, beta; Carcinoembryonic antigen-related cell adhesion molecule 1 (biliary glycoprotein); Follicle stimulating hormone, beta polypeptide; Angiotensinogen (serine (or cysteine) proteinase inhibitor, clade A (alpha-1 antiproteinase, antitrypsin), member 8); Carcinoembryonic antigen-related cell adhesion molecule 6 (non-specific cross reacting antigen); Protein kinase C, alpha binding protein; Collectin sub-family member 10 (C-type lectin); Laminin, alpha 1), the Extracellular Space (Carboxylesterase 1 (monocyte/macrophage serine esterase 1); Fibroblast growth factor 5; Progastricsin (pepsinogen C); Sperm associated antigen 11; Proprotein convertase subtilisin/kexin type 2; Hyaluronan binding protein 2; Sema domain, immunoglobulin domain (Ig), short basic domain, secreted, (semaphorin) 3F; Interleukin 2; Chymotrypsin-like; Norrie disease (pseudoglioma); mucin 5, subtypes A and C, tracheobronchial/gastric; Carboxypeptidase B2 (plasma, carboxypeptidase U); radical fringe homolog (*Drosophila*); Pregnancy specific beta-1-glycoprotein 11; Meprin A, alpha (PABA peptide hydrolase); Tachykinin, precursor 1 (substance K, substance P, neurokinin 1, neurokinin 2, neuromedin L, neurokinin alpha, neuropeptide K, neuropeptide gamma); Fibroblast growth factor 8 (androgen-induced); Fibroblast growth factor 13; Hemopexin; Breast cancer 2, early onset; Fibroblast growth factor 14; Retinoschisis (X-linked, juvenile) 1; Chitinase 3-like 1 (cartilage glycoprotein-39); Dystonin; Secretoglobin, family 1 D, member 2; Noggin; WAP four-disulfide core domain 2; CD5 antigen-like (scavenger receptor cysteine rich family); Scrapie responsive protein 1; Gremlin 1 homolog, cysteine knot superfamily (*Xenopus laevis*); Interleukin 16 (lymphocyte chemoattractant factor); Chemokine (C-C motif) ligand 26; Nucleobindin 1; Fibroblast growth factor 18; Insulin-like growth factor binding protein 1; Surfactant, pulmonary-associated protein A1; Delta-like 1 homolog (*Drosophila*); Cocaine- and amphetamine-regulated transcript; Meprin A, beta; Interleukin 17F; Complement factor H; Cysteine-rich secretory protein 2; Dystonin; WAP four-disulfide core domain 1; Prolactin; Surfactant, pulmonary-associated protein B; Fibroblast growth factor 5; Dickkopf homolog 2 (*Xenopus laevis*); Sperm associated antigen 11; Chemokine (C-C motif) ligand 11; Meprin A, alpha (PABA peptide hydrolase); Chitinase 3-like 2; C-fos induced growth factor (vascular endothelial growth factor D); Chemokine (C-C motif) ligand 4; Poliovirus receptor; Hyaluronoglucosaminidase 1; Oviductal glycoprotein 1, 120 kDa (mucin 9, oviductin); Chemokine (C-X-C motif) ligand 9; Secreted frizzled-related protein 5; Amelogenin (amelogenesis imperfecta 1, X-linked); Relaxin 1; Sparc/osteonectin, cwcv and kazal-like domains proteoglycan (testican); Chemokine (C-C motif) ligand 26; Fibroblast growth factor 1 (acidic); Angiopoietin-like 2; Fms-related tyrosine kinase 1 (vascular endothelial growth factor/vascular permeability factor receptor); Dystonin; Insulin-like 4 (placenta); Transcobalamin II; macrocytic anemia; Chemokine (C-C motif) ligand 1; Insulin-like growth factor binding protein, acid labile subunit; Complement factor H; Pregnancy specific beta-1-glycoprotein 6; Silver homolog (mouse); Proteoglycan 4; Fibroblast growth factor 16; Cytokine-like protein C17; Granulysin; Angiopoietin 2; Chromogranin B (secretogranin 1); Sema domain, immunoglobulin domain (Ig), and GPI membrane anchor, (semaphorin) 7A; Pleiotrophin (heparin binding growth factor 8, neurite growth-promoting factor 1); Chloride channel, calcium activated, family member 3; Secretoglobin, family 1 D, member 1; Fibulin 1; Phospholipase A2 receptor 1, 180 kDa, and the Extracellular Matrix (ADAMTS-like 1; Periostin, osteoblast specific factor; Glypican 5; Leucine rich repeat neuronal 3; Transglutaminase 2 (C polypeptide, protein-glutamine-gamma-glutamyltransferase); A disintegrin-like and metalloprotease (reprolysin type) with thrombospondin type 1 motif, 2; Microfibrillar-associated protein 4; Glypican 3; Collagen, type V, alpha 3; Tissue inhibitor of metalloproteinase 2; Keratocan; Cartilage oligomeric matrix protein; Lumican; Hyaluronan and proteoglycan link protein 3; Statherin; A disintegrin-like and metalloprotease (reprolysin type) with thrombospondin type 1 motif, 3; Spondin 1, extracellular matrix protein; Chitinase 3-like (cartilage glycoprotein-39); Collagen, type IV, alpha 3 (Goodpasture antigen); Wingless-type MMTV integration site family, member 7B; Collagen, type VI, alpha 2; Lipocalin 7; Hyaluronan and proteoglycan link protein 4; A disintegrin-like and metalloprotease (reprolysin type) with thrombospondin type 1 motif, 5 (aggrecanase-2); Fibronectin 1; Matrilin 1, cartilage matrix protein; Hypothetical protein FLJ13710; Chondroitin beta1,4 N-acetylgalactosaminyltransferase; Matrix metalloproteinase 16 (membrane-inserted); Von Willebrand factor; Collagen, type VI, alpha 2; Transmembrane protease, serine 6; Matrix metalloproteinase 23B; Matrix metalloproteinase 14 (membrane-inserted); Leucine rich repeat neuronal 3; SPARC-like (mast9, hevin); Sparc/osteonectin, cwcv and kazal-like domains proteoglycan (testican) 3; Dermatopontin; collagen, type XIV, alpha 1 (undulin); Amelogenin, Y-linked; Nidogen (enactin); ADAMTS-like 2; Hyaluronan and proteoglycan link protein 2; Collagen, type XV, alpha 1; Glypican 6; Matrix metalloproteinase 12 (macrophage elastase); Amelogenin (amelogenesis imperfecta 1, X-linked); A disintegrin-like and metalloprotease (reprolysin type) with thrombospondin type 1 motif, 15; Transmembrane protease, serine 6; A disintegrin-like and metalloprotease (reprolysin type) with thrombospondin type 1 motif, 16; Sparc/osteonectin, cwcv and kazal-like domains proteoglycan (testican); A disintegrin-like and metalloprotease (reprolysin type) with thrombospondin type 1 motif, 20; Collagen, type XI, alpha 1; Hyaluronan and proteoglycan link protein 1; Chondroitin beta1,4 N-acetylgalactosaminyltransferase; Asporin (LRR class 1); Collagen, type III, alpha 1 (Ehlers-Danlos syndrome type IV, autosomal dominant); Secreted phosphoprotein 1 (osteopontin, bone sialoprotein I, early T-lymphocyte activation 1); Matrix Gla protein; Fibulin 5; collagen, type XIV, alpha (undulin); Tissue inhibitor of metalloproteinase 3 (Sorsby fundus dystrophy, pseudoinflammatory); Collagen, type XXV, alpha 1; Cartilage oligomeric matrix protein; Collagen, type VI, alpha 1; Chondroadherin; Collagen, type XV, alpha 1; A disintegrin-like and metalloprotease (reprolysin type) with thrombospondin type 1 motif, 16; Collagen, type IV, alpha 4; Dentin matrix acidic phosphoprotein; Collagen, type IV, alpha 1; Thrombospondin repeat containing 1; Matrix metalloproteinase 16 (membrane-inserted); Collagen, type I, alpha 2; Fibulin 1; Tectorin beta; Glycosylphosphatidylinositol specific phospholipase D1; Upregulated in colorectal cancer gene 1). Cytoskeleton: (Filamin B, beta (actin binding protein 278); Centrin, EF-hand protein, 1; FERM domain containing 3; Bridging integrator 3; Parvin, gamma; Rho guanine nucleotide exchange factor (GEF) 11; Tyrosine kinase 2; Kelch-like 4 (*Drosophila*); Spectrin, beta, erythrocytic (includes spherocytosis, clinical type I); Arg/

Abl-interacting protein ArgBP2; Advillin; Spectrin repeat containing, nuclear envelope 1; Catenin (cadherin-associated protein), delta 1; Erythrocyte membrane protein band 4.1 like 5; Catenin (cadherin-associated protein), alpha 2; Chemokine (C-C motif) ligand 3; Sarcoglycan, gamma (35 kDa dystrophin-associated glycoprotein); Nebulin; Thymosin, beta, identified in neuroblastoma cells; 3-phosphoinositide dependent protein kinase-1; Wiskott-Aldrich syndrome protein interacting protein; Dystonin; Huntingtin interacting protein 1; KIAA0316 gene product; Tropomodulin 4 (muscle); Deleted in liver cancer 1; Villin-like; Syntrophin, beta 1 (dystrophin-associated protein A1, 59 kDa, basic component 1); Protein kinase, cGMP-dependent, type I; Homo sapiens similar to keratin 8; cytokeratin 8; keratin, type II cytoskeletal 8 (LOC345751), mRNA; Adducin 1 (alpha); Protein kinase C and casein kinase substrate in neurons 3; Dystonin; Kell blood group; Filamin A interacting protein 1; Growth arrest-specific 2; Chromosome 1 open reading frame 1; Stathmin-like 2; Spectrin, alpha, erythrocytic 1 (elliptocytosis 2); FKSG44 gene; Kinesin family member 1C; Tensin; Kaptin (actin binding protein); Neurofibromin 2 (bilateral acoustic neuroma); Pleckstrin homology, Sec7 and coiled-coil domains 2 (cytohesin-2); Actin-related protein T1; Wiskott-Aldrich syndrome-like; Kelch-like 4 (Drosophila); Fascin homolog 1, actin-bundling protein (Strongylocentrotus purpuratus); Amphiphysin (Stiff-Man syndrome with breast cancer 128 kDa autoantigen); Polycystic kidney disease 2-like 1; Ankyrin 2, neuronal; CDC42 binding protein kinase alpha (DMPK-like); Hypothetical protein FLJ36144; Arg/Abl-interacting protein ArgBP2; Formin-like 3; Catenin (cadherin-associated protein), beta 1, 88 kDa; Profilin 2; Synaptopodin 2-like; Syntrophin, gamma 2; Phospholipase D2; Engulfment and cell motility 2 (ced-12 homolog, C. elegans); Neurofilament, light polypeptide 68 kDa; Dystonin; Actin-like 7B; Kinesin family member 1C; PDZ and LIM domain 3; Adducin 2 (beta); obscurin, cytoskeletal calmodulin and titin-interacting RhoGEF; Tubulin, beta polypeptide paralog; Filamin A interacting protein 1; Talin 1; Homo sapiens similar to [Segment 1 of 2] Piccolo protein (Aczonin) (LOC375597); CDC42 effector protein (Rho GTPase binding) 4; Syndecan 1; Filamin A, alpha (actin binding protein 280); Profilin 2; Tensin like C1 domain containing phosphatase; Hypothetical protein MGC33407; Rho family GTPase 1; Flavoprotein oxidoreductase MICAL2; Ca2+-dependent secretion activator; Rabphilin 3A-like (without C2 domains); Myosin XVA; Protein kinase, cGMP-dependent, type I; Myosin regulatory light chain interacting protein; Kinesin family member 13B; Muscle RAS oncogene homolog; Spectrin, beta, non-erythrocytic 1; TAO kinase 2; Filamin B, beta (actin binding protein 278); Neurofibromin 2 (bilateral acoustic neuroma); Catenin (cadherin-associated protein), alpha 3; obscurin, cytoskeletal calmodulin and titin-interacting RhoGEF; Coronin, actin binding protein, 1A; Erythrocyte membrane protein band 4.1-like 1; Spectrin, beta, non-erythrocytic 4; Thymosin, beta 4, Y-linked; Tektin 2 (testicular); Ras homolog gene family, member J; Serine/threonine kinase with Dbl- and pleckstrin homology domains; Dystrobrevin, beta; Actin, gamma 2, smooth muscle, enteric; Tara-like protein; Caspase 8, apoptosis-related cysteine protease; Kelch repeat and BTB (POZ) domain containing 10; Mucin 1, transmembrane; Microtubule-associated protein tau; Tensin; Ras homolog gene family, member F (in filopodia); Adducin 1 (alpha); Actinin, alpha 4; Erythrocyte membrane protein band 4.1 (elliptocytosis 1, RH-linked); Bicaudal D homolog 2 (Drosophila); Ankyrin 3, node of Ranvier (ankyrin G); Myosin VIIA (Usher syndrome 1B (autosomal recessive, severe)); Catenin (cadherin-associated protein), alpha 2; Homo sapiens similar to keratin 8, type II cytoskeletal—human (LOC285233); Fascin homolog 3, actin-bundling protein, testicular; Ras homolog gene family, member J; Beaded filament structural protein 2, phakinin; Desmin; Myosin X; Signal-induced proliferation-associated gene 1; Scinderin; Coactosin-like 1 (Dictyostelium); Engulfment and cell motility 2 (ced-12 homolog, C. elegans); Tubulin, beta 4; Ca2+-dependent secretion activator; FERM domain containing 4A; Actin, alpha 1, skeletal muscle; Talin 1; Caldesmon 1; Filamin-binding LIM protein-1; Microtubule-associated protein tau; Syntrophin, alpha 1 (dystrophin-associated protein A1, 59 kDa, acidic component); Adducin 2 (beta); Filamin A interacting protein 1; PDZ and LIM domain 3; Erythrocyte membrane protein band 4.1 like 4B; FYN binding protein (FYB-120/130); Bridging integrator 3). Extracellular: (A disintegrin-like and metalloprotease (reprolysin type) with thrombospondin type 1 motif, 20; SPARC-like 1 (mast9, hevin); Serine (or cysteine) proteinase inhibitor, clade G (C1 inhibitor), member 1, (angioedema, hereditary); Urocortin; Chymotrypsin-like; Platelet-derived growth factor beta polypeptide (simian sarcoma viral (v-sis) oncogene homolog); BMP-binding endothelial regulator precursor protein; Complement factor H; Chorionic somatomammotropin hormone-like 1; Chemokine (C-C motif) ligand 18 (pulmonary and activation-regulated); Fibronectin 1; Pregnancy specific beta-1-glycoprotein 3; A disintegrin-like and metalloprotease (reprolysin type) with thrombospondin type 1 motif, 3; CocoaCrisp; Insulin-like 4 (placenta); Wingless-type MMTV integration site family, member 11; Cartilage oligomeric matrix protein; Transmembrane protease, serine 6; C-fos induced growth factor (vascular endothelial growth factor D); Family with sequence similarity 12, member B (epididymal); Protein phosphatase 1, regulatory subunit 9B, spinophilin; Transcobalamin II; macrocytic anemia; Coagulation factor V (proaccelerin, labile factor); Phospholipase A2, group IID; Tumor necrosis factor, alpha-induced protein 6; Collagen, type XV, alpha 1; Hyaluronan and proteoglycan link protein 3; collagen, type XIV, alpha 1 (undulin); Interleukin 19; Protease inhibitor 15; Cholinergic receptor, nicotinic, beta polypeptide 1 (muscle); Lysyl oxidase-like 3; Insulin-like growth factor binding protein 5; Growth hormone 1; Casein beta; NEL-like 2 (chicken); I factor (complement); Chemokine (C-C motif) ligand 23; Interferon, alpha 2; Matrix metalloproteinase 16 (membrane-inserted); Matrix metalloproteinase 12 (macrophage elastase); Glypican 5; Pregnancy specific beta-1-glycoprotein 3; Fibroblast growth factor 6; Gremlin 1 homolog, cysteine knot superfamily (Xenopus laevis); Protein S (alpha); Chondroitin beta1,4 N-acetylgalactosaminyltransferase; Glycosylphosphatidylinositol specific phospholipase D1; Fibroblast growth factor 1 (acidic); Spondin 1, extracellular matrix protein; Bone morphogenetic protein 1; Surfactant, pulmonary-associated protein B; Dentin matrix acidic phosphoprotein; Lipoprotein, Lp(a); Mucin 1, transmembrane; Mannan-binding lectin serine protease 1 (C4/C2 activating component of Ra-reactive factor); Meprin A, beta; Secretoglobin, family 1D, member 1; Asporin (LRR class 1); Chemokine (C-C motif) ligand 25; Cytokine-like protein C17; Insulin-like 5; Meprin A, alpha (PABA peptide hydrolase); Scrapie responsive protein 1; Fibroblast growth factor 18; Chemokine (C-X-C motif) ligand 9; Inhibin, beta B (activin AB beta polypeptide); Fibroblast growth factor 8 (androgen-induced); Granulysin; Cocaine- and amphetamine-regulated transcript; Collagen, type I, alpha 2; Chemokine (C-C motif) ligand 17; Chemokine (C-C motif) ligand 23; Sparc/osteonectin, cwcv and kazal-like domains proteoglycan (testican) 3; Gamma-aminobutyric acid (GABA) A receptor, beta 3; Defensin, alpha 4, corticostatin; Leucine rich repeat neuronal 3; Glypican 6; Mitogen-activated protein kinase kinase 2; Coagulation factor XI (plasma thromboplastin antecedent); Chemokine (C-C motif) ligand 5; Dystonin; Frizzled-related protein; Coagulation factor XIII, A1 polypeptide; Insulin-like growth factor 1 (somatomedin C); Hypothetical protein MGC45438; Sperm associated antigen 11; Insulin-like growth factor 1 (somatomedin C); Periostin, osteoblast specific factor; Alpha-2-macroglobulin; Gamma-aminobutyric acid (GABA) A receptor, alpha 5; Serine (or cysteine) proteinase inhibitor, clade A (alpha-1 antiproteinase, antitrypsin), member 3; Silver homolog (mouse); Frizzled-related protein; Chondroadherin; Chondroitin beta1,4 N-acetylgalactosaminyltransferase; 5-hydroxytryptamine (serotonin) receptor 3, family member C; Collagen, type VI, alpha 2; Toll-like receptor 9; Amelogenin, Y-linked; Vascular endothelial growth factor B; Radial spokehead-like 1; Fms-related tyrosine kinase 1 (vascular endothelial growth factor/vascular permeability factor receptor); Protease inhibitor 16; Interleukin 2; Clusterin (complement lysis inhibitor, SP-40,40, sulfated glycoprotein 2, testosterone-repressed prostate message 2, apolipoprotein J); Follicle stimulating hormone, beta polypeptide; A disintegrin-like and metalloprotease (reprolysin type) with thrombospondin type 1 motif, 16; Lysozyme (renal amyloidosis); radical fringe homolog (Drosophila); Insulin-like growth factor binding protein 5; Taxilin; Apolipoprotein A-V; Platelet derived growth factor C; Chemokine (C-C motif) ligand 3-like 1; Fibroblast growth factor 16; Collagen, type VI, alpha 2; Serine (or cysteine) proteinase inhibitor, clade C (antithrombin), member 1; Chemokine (C-C motif) ligand 11; Collagen, type IV, alpha 4; Bruton agammaglobulinemia tyrosine kinase; Insulin-like growth factor 2 (somatomedin A); Kazal-type serine protease inhibitor domain 1; Fibrinogen, A alpha polypeptide; Chemokine (C-C motif) ligand 1; Inhibin, beta E; Sex hormone-binding globulin; Collagen, type IV, alpha 1; Lecithin-cholesterol acyltransferase; Cysteine-rich secretory protein 2; Hyaluronan and proteoglycan link protein 1; Natriuretic peptide precursor C; Ribonuclease, RNase A family, k6; Fibroblast growth factor 14; ADAMTS-like 2; Collagen, type IV, alpha 3 (Goodpasture antigen); Angiopoietin 2; Apolipoprotein L, 3; Chemokine (C-X-C motif) ligand 12 (stromal cell-derived factor 1); Hyaluronan binding protein 2; Coagulation factor VII (serum prothrombin conversion accelerator); collagen, type XIV, alpha 1 (undulin); Oviductal glycoprotein 1, 120 kDa (mucin 9, oviductin); Matrilin 1, cartilage matrix protein; mucin 5, subtypes A and C, tracheobronchial/gastric; Tumor necrosis factor receptor superfamily, member 11 b (osteoprotegerin); Transglutaminase 2 (C polypeptide, protein-glutamine-gamma-glutamyltransferase); Keratocan; Collagen, type V, alpha 3; WAP four-disulfide core domain 2; Chemokine (C-X3-C motif) ligand 1; Serine (or cysteine) proteinase inhibitor, clade D (heparin cofactor), member 1; Secretory protein LOC348174; Coagulation factor X; Interleukin 16 (lymphocyte chemoattractant factor); Pancreatic lipase-related protein 2; HtrA serine peptidase 3; Glycine receptor, alpha 3; CD5 antigen-like (scavenger receptor cysteine rich family); Hypothetical protein MGC39497; Coagulation factor VIII, procoagulant component (hemophilia A); Dermatopontin; Noggin; Secreted LY6/PLAUR domain containing 1; ADAMTS-like 1; Alpha-1-B glycoprotein; Chromosome 20 open reading frame 175; Wingless-type MMTV integration site family, member 8B; Fibulin 1; Fibulin 5; Cathepsin S; Nidogen (enactin); Chemokine (C-C motif) ligand 26; Endothelial cell-specific molecule 1; Chitinase 3-like 1 (cartilage glycoprotein-39); Gamma-aminobutyric acid (GABA) A receptor, beta 1; Secretoglobin, family 1 D, member 2; Mannan-binding lectin serine protease 1 (C4/C2 activating component of Ra-reactive factor); ADAMTS-like 1; Sema domain, immunoglobulin domain (Ig), and GPI membrane anchor, (semaphorin) 7A; A disintegrin-like and metalloprotease (reprolysin type) with thrombospondin type 1 motif, 15; Proprotein convertase subtilisin/kexin type 2; Insulin-like growth factor 1 (somatomedin C); Retinoschisis (X-linked, juvenile) 1; A disintegrin-like and metalloprotease (reprolysin type) with thrombospondin type 1 motif, 16; Chemokine (C motif) ligand 2; Fibroblast growth factor 5; Sperm associated antigen 11; Microfibrillar-associated protein 4; Poliovirus receptor; Extracellular signal-regulated kinase 8; Transmembrane protease, serine 6; Protein kinase C, alpha; Chitinase 3-like 2; Interleukin 9; Apolipoprotein L, 6; Surfactant, pulmonary-associated protein A1; Collagen, type VI, alpha 1; Apolipoprotein L, 6; Hypothetical protein FLJ13710; Carboxypeptidase B2 (plasma, carboxypeptidase U); Bactericidal/permeability-increasing protein-like 2; Fibroblast growth factor 5; Secreted phosphoprotein 1 (osteopontin, bone sialoprotein I, early T-lymphocyte activation 1); HtrA serine peptidase 3; Deleted in liver cancer 1; Endothelial cell-specific molecule 1; Von Willebrand factor; A disintegrin-like and metalloprotease (reprolysin type) with thrombospondin type 1 motif, 5 (aggrecanase-2); Sema domain, immunoglobulin domain (Ig), short basic domain, secreted, (semaphorin) 3A; Chemokine (C-X-C motif) ligand 12 (stromal cell-derived factor 1); Statherin; Extracellular signal-regulated kinase 8; Tissue inhibitor of metalloproteinase 3 (Sorsby fundus dystrophy, pseudoinflammatory); Platelet factor 4 (chemokine (C-X-C motif) ligand 4); Surfactant, pulmonary-associated protein D; Complement factor H; Delta-like 1 homolog (Drosophila); WAP four-disulfide core domain 1; Insulin-like growth factor binding protein, acid labile subunit; Breast cancer 2, early onset; Pre-B lymphocyte gene 1; Corticotropin releasing hormone; Hypothetical protein DKFZp434B044; Prolactin-induced protein; RAS guanyl releasing protein 4; Progastricsin (pepsinogen C); Sema domain, immunoglobulin domain (Ig), short basic domain, secreted, (semaphorin) 3F; Upregulated in colorectal cancer gene 1; Proteoglycan 4; Cholinergic receptor, nicotinic, delta polypeptide; Cartilage oligomeric matrix protein; ABO blood group (transferase A, alpha 1-3-N-acetylgalactosaminyltransferase; transferase B, alpha 1-3-galactosyltransferase); Interleukin 12A (natural killer cell stimulatory factor 1, cytotoxic lymphocyte maturation factor 1, p35); Fibroblast growth factor 7 (keratinocyte growth factor); Kin of IRRE like 3 (Drosophila); Cholinergic receptor, nicotinic, alpha polypeptide 2 (neuronal); Palate, lung and nasal epithelium carcinoma associated; Collagen, type XV, alpha 1; Pleiotrophin (heparin binding growth factor 8, neurite growth-promoting factor 1); Angiopoietin-like 2; Norrie disease (pseudoglioma); Chemokine (C-C motif) ligand 3; Chitinase 3-like 1 (cartilage glycoprotein-39); Inter-alpha (globulin) inhibitor H3; Amelogenin (amelogenesis imperfecta 1, X-linked); Epidermal growth factor (beta-urogastrone); Fibroblast growth factor 13; Wingless-type MMTV integration site family, member 7B; Cholinergic receptor, nicotinic, gamma polypeptide; Pregnancy specific beta-1-glycoprotein 6; Matrix metalloproteinase 14 (membrane-inserted); Chemokine (C-C motif) ligand 26; Interferon, alpha 6; Tachykinin, precursor 1 (substance K, substance P, neurokinin 1, neurokinin 2, neuromedin L, neurokinin alpha, neuropeptide K, neuropeptide gamma); Secreted frizzled-related protein 5;

Hyaluronan and proteoglycan link protein 4; Complement component 4B; Matrix metalloproteinase 16 (membrane-inserted); Fibroblast growth factor 7 (keratinocyte growth factor); Apolipoprotein C-II; Chloride channel, calcium activated, family member 3; Tetranectin (plasminogen binding protein); Collagen, type III, alpha 1 (Ehlers-Danlos syndrome type IV, autosomal dominant); KIAA0556 protein; Chemokine (C-C motif) ligand 4; Hemopexin; Inter-alpha (globulin) inhibitor H1; Relaxin 1; Matrix Gla protein; A disintegrin-like and metalloprotease (reprolysin type) with thrombospondin type 1 motif, 2; Interferon (alpha, beta and omega) receptor 2; Acid phosphatase, prostate; Guanine nucleotide binding protein (G protein), gamma 8; Matrix metalloproteinase 23B; Meprin A, alpha (PABA peptide hydrolase); Hyaluronoglucosaminidase 1; Angiotensinogen (serine (or cysteine) proteinase inhibitor, clade A (alpha-1 antiproteinase, antitrypsin), member 8); Cartilage intermediate layer protein, nucleotide pyrophosphohydrolase; Purinergic receptor P2X, ligand-gated ion channel, 7; Glypican 3; Tectorin beta; Interferon, alpha 5; Lipocalin 7; Platelet factor 4 variant 1; Nucleobindin 1; Collagen, type XI, alpha 1; Gastric inhibitory polypeptide; Thrombospondin repeat containing 1; 5-hydroxytryptamine (serotonin) receptor 3 family member D; Collagen, type XXV, alpha 1; Growth differentiation factor 9; Hypothetical protein DKFZp434B044; Endothelin 3; Chemokine (C motif) ligand 2; Prokineticin 2; Tumor necrosis factor receptor superfamily, member 11 b (osteoprotegerin); Tissue inhibitor of metalloproteinase 2; Dystonin; Chromogranin B (secretogranin 1); Hyaluronan and proteoglycan link protein 2; Leucine rich repeat neuronal 3; Lumican; Matrilin 1, cartilage matrix protein; Phospholipase A2, group IIA (platelets, synovial fluid); Carboxylesterase 1 (monocyte/macrophage serine esterase 1); Sparc/osteonectin, cwcv and kazal-like domains proteoglycan (testican); Dickkopf homolog 2 (*Xenopus laevis*); Gamma-aminobutyric acid (GABA) A receptor, alpha 3; Pregnancy specific beta-1-glycoprotein 11; Insulin-like growth factor binding protein 1; Defensin, beta 106; Interleukin 17F; Ligand-gated ion channel subunit; Phospholipase A2 receptor 1, 180 kDa; I factor (complement); Dystonin; LAG1 longevity assurance homolog 1 (*S. cerevisiae*); Prolactin; Testis expressed sequence 264; Sema domain, immunoglobulin domain (Ig), short basic domain, secreted, (semaphorin) 3D; secreted frizzled-related protein 2; secreted frizzled-related protein 4).

There are groups of genes present only in UCEC. These genes are related to the following: Homeostasis (Albumin; Calcium-sensing receptor; Aquaporin 9; Lactotransferrin. Morphogenesis: Homeo box HB9; Epithelial V-like antigen 1). Embryonic Development (Relaxin 2; Carcinoembryonic antigen-related cell adhesion molecule 8; Indoleamine-pyrrole 2,3 dioxygenase; EPH receptor A3; Thyrotrophic embryonic factor; Pregnancy specific beta-1-glycoprotein 1; Laminin, alpha 3), the Extracellular Space (Surfactant, pulmonary-associated protein A1; Pregnancy specific beta-1-glycoprotein 1; Lactotransferrin; TGF-alpha; Albumin; FGF-23; S100 calcium binding protein A9 (calgranulin B)), the Extracellular Matrix (Laminin, beta 4; Laminin, alpha 3; Zona pellucida glycoprotein 4. Structural Molecule Activity: Chromosome 21 open reading frame 29; Laminin, alpha 3; Microtubule-associated protein 2; Laminin, beta 4; Keratin 6B; Ladinin 1; Keratin 6A; Occludin; Loricrin; Erythrocyte membrane protein band 4.1 (elliptocytosis 1, RH-linked); Crystallin, beta A2; eye lens structural protein; Contactin associated protein-like 4; Claudin 19; Hypothetical protein LOC144501; Keratin 6E; Keratin 6L; Lens intrinsic membrane protein 2, 19 kDa), the Cytoskeleton (Microtubule-associated protein 2; Erythrocyte membrane protein band 4.1 like 5; *Homo sapiens* trichohyalin (THH); Keratin 6B; Keratin 6A; Epithelial V-like antigen 1; Hook homolog 1 (*Drosophila*); Loricrin; Erythrocyte membrane protein band 4.1 (elliptocytosis 1, RH-linked); Tropomodulin 1; MAP/microtubule affinity-regulating kinase 1; Keratin 6E; Actin binding LIM protein family, member 2), Cell Adhesion Molecules (Cadherin 19, type 2; Myeloid/lymphoid or mixed-lineage leukemia; Chromosome 21 open reading frame 29; Kin of IRRE like 2; Laminin, alpha 3; Sialoadhesin; CD84 antigen (leukocyte antigen); Lectin, galactoside-binding, soluble, 2 (galectin 2); Epithelial V-like antigen 1; CD96 antigen; Tubulointerstitial nephritis antigen; Carcinoembryonic antigen-related cell adhesion molecule 8; IL-18; Immunoglobulin superfamily, member 1; Integrin, beta 8; Ornithine arbamoyltransferase; Integrin, beta 6; Contactin associated protein-like 4; Collagen, type XVII, alpha 1; Cadherin-like 26; Mucin and cadherin-like), Cell Differentiation proteins (Protein tyrosine phosphatase, receptor-type, Z polypeptide 1; Laminin, alpha 3; CD84 antigen (leukocyte antigen); EDRF2; *Homo sapiens* erythroid differentiation-related factor 2; Tumor protein p73-like; NB4 apoptosis/differentiation related protein; *Homo sapiens* PNAS-133; Similar to seven in absentia 2; Interleukin 24; Keratin 6B; Keratin 6A; Dehydrogenase/reductase (SDR family) member 9; Gap junction protein, beta 5 (connexin 31.1); Iroquois homeobox protein 4; Ventral anterior homeobox 2; Chemokine (C-X-C motif) ligand 10; Tumor necrosis factor receptor superfamily, member 17; Calcium channel, voltage-dependent, beta 2 subunit; Parkinson disease (autosomal recessive, juvenile) 2, parkin; Kallikrein 7 (chymotryptic, stratum corneum); Glial cells missing homolog 2; AP-2 alpha; Protein tyrosine phosphatase, receptor-type, Z polypeptide 1; Troponin T1; Sciellin; Glucosaminyl (N-acetyl) transferase 2, I-branching enzyme; Collagen, type XVII, alpha 1; Suppressor of cytokine signaling 2; Distal-less homeo box 1; Zygote arrest 1; Interleukin 20; Growth differentiation factor 3; FGF-23; Wingless-type MMTV integration site family, member 8A. Extracellular: Chromosome 21 open reading frame 29; Laminin, alpha 3; Laminin, beta 4; Interleukin 24; Pregnancy specific beta-1-glycoprotein 1; Chemokine (C-X-C motif) ligand 11; Surfactant, pulmonary-associated protein A1; Prepronociceptin; 5-hydroxytryptamine (serotonin) receptor 3B; Carcinoembryonic antigen-related cell adhesion molecule 8; Chemokine (C-X-C motif) ligand 10; IL-18 (interferon-gamma-inducing factor); Lactotransferrin; Albumin; Fas ligand (TNF superfamily, member 6); Cholinergic receptor, nicotinic, beta polypeptide 4; Cathelicidin antimicrobial peptide; Airway trypsin-like protease; S100 calcium binding protein A9 (calgranulin B); TGF-alpha; Kallikrein 10; Serine protease inhibitor, Kunitz type 1; WNT1 inducible signaling pathway protein 3; Relaxin 2; Interferon, kappa; Defensin, beta 103A; IL-20; Zona pellucida glycoprotein 4; Growth differentiation factor 3; FGF-23; Wingless-type MMTV integration site family, member 8A; Complement factor H-related 5), Developmental proteins (EPH receptor A3; NIMA (never in mitosis gene a)-related kinase 2; Zinc finger protein 282; TANK-binding kinase 1; MRE11 meiotic recombination 11 homolog A; E2F transcription factor 2; Protein tyrosine phosphatase, receptor-type, Z polypeptide 1; *Homo sapiens* clone 161455 breast expressed mRNA from chromosome X; Laminin, alpha 3; v-myb myeloblastosis viral oncogene homolog (avian)-like 1; Regulator of G-protein signalling 11; Microtubule-associated protein 2; Transmembrane protein 16A; Adenomatosis polyposis *coli* 2; Homeo box HB9; Centromere protein F, 350/400 ka (mitosin); CD84 antigen (leukocyte antigen); EDRF2; *Homo sapiens* erythroid differentiation-related factor 2; Tumor protein p73-like; NB4 apoptosis/differentiation related protein; *Homo sapiens* PNAS-133; Forkhead box P2; *Homo sapiens* gastric-associated differentially-expressed protein YA61P (YA61); Tenascin N; Chromosome 6 open reading frame 49; Zinc finger protein 462; Zinc finger protein 71 (Cos26); SRY (sex determining region Y)-box 7; Triggering receptor expressed on myeloid cells-like 4; Interleukin 24; Pregnancy specific beta-1-glycoprotein 1; Chondroitin sulfate proteoglycan 5 (neuroglycan C); Keratin 6B; Keratin 6A; Dehydrogenase/reductase (SDR family) member 9; Epithelial V-like antigen 1; Gap junction protein, beta 5 (connexin 31.1); G protein-coupled receptor 51; Interferon regulatory factor 6; Neurotrophin 5 (neurotrophin 4/5); CD96 antigen; Iroquois homeobox protein 4; Interleukin 1 receptor-like 1; G-2 and S-phase expressed 1; Nuclear receptor subfamily 2, group E, member 3; Ventral anterior homeobox 2; Zinc finger protein 215; DNA segment on chromosome 4 (unique) 234 expressed sequence; Carcinoembryonic antigen-related cell adhesion molecule 8; Chemokine (C-X-C motif) ligand 10; IL-18; Indoleaminepyrrole 2,3 dioxygenase; Albumin; Calcium-sensing receptor (hypocalciuric hypercalcemia 1, severe neonatal hyperparathyroidism); Fas ligand (TNF superfamily, member 6); TNFR superfamily, member 17; Calcium channel, voltage-dependent, beta 2 subunit; Parkinson disease (autosomal recessive, juvenile) 2, parkin; Kallikrein 7 (chymotryptic, stratum corneum); Glial cells missing homolog 2; TGF-alpha; Thyrotrophic embryonic factor; AP-2 alpha (activating enhancer binding protein 2 alpha); Kallikrein 10; Regulator of G-protein signalling 7; Protein tyrosine phosphatase, receptor-type, Z polypeptide 1; Serine protease inhibitor, Kunitz type 1; WNT1 inducible signaling pathway protein 3; Zic family member 3 heterotaxy 1 (odd-paired homolog, *Drosophila*); TTK protein kinase; Troponin T1, skeletal, slow; Sciellin; TGFB-induced factor 2-like, X-linked; Kallikrein 8 (neuropsin/ovasin); Glucosaminyl (N-acetyl) transferase 2, I-branching enzyme; Ankyrin repeat domain 30A; Relaxin 2; Collagen, type XVII, alpha 1; Gene differentially expressed in prostate; Phosphatase and actin regulator 3; Suppressor of cytokine signaling 2; Nuclear receptor subfamily 4, group A, member 3; Angiotensin I converting enzyme (peptidyl-dipeptidase A) 1; Hypothetical protein MGC17986; Distal-less homeo box 1; LAG1 longevity assurance homolog 3 (*S. cerevisiae*); Zygote arrest 1; Interferon, kappa; IL-20; ICEBERG caspase-1 inhibitor; Growth differentiation factor 3; FGF-23; Testis expressed sequence 15; Wingless-type MMTV integration site family, member 8A; SRY (sex determining region Y)-box 7; Carnitine deficiency-associated, expressed in ventricle 1; Prokineticin 1; CAMP responsive element binding protein 3-like 3; Caspase recruitment domain family, member 15; FLJ23311 protein).

Example 6: Direct Differentiation of Umbilical Cord Lining Epithelial Stem Cells (UCEC) into Skin Epidermal Keratinocytes For differentiation into skin epidermal keratinocytes, umbilical cord epithelial stem cells, UCEC cells, were cultured according to a standard protocol for the cultivation of keratinocytes. Cell isolation techniques were as described above. UCEC were then cultured in serum-free keratinocyte growth media, KGM®, KGM®-2 (Cambrex Corporation, New Jersey, USA), EpiLife® (Cascade Biologics Inc., Oregon, USA) or in Green's medium in the presence of irradiated or Mytomycin-C treated 3T3 mouse embryonic feeder layer at 37° C., 5% $CO_2$). UCEC cell morphology thus differentiated resembled human epidermal keratinocytes. Epithelial cells have similar morphology under light microscope and can be easily turned into fibroblasts using conventional and commercially available media (cf., FIG. 2).

Immunofluorescent analysis shows that the cultivated UCEC also express epidermal keratinocyte molecular markers such as keratins, desmosome, hemidesmosome and basement membrane components (see also FIG. 10 that shows that UCEC are qualified to be epithelial cells in general by expressing a variety of these epithelial cell markers). Accordingly, these results show that umbilical cord epithelial progenitor/stem cells of the present invention can be differentiated into skin cells such as epidermal keratinocytes which can be used for wound healing and have great potential for the development of cultured skin equivalents.

Figures 9, 10, 11, 12, 13, 14, 15, 16:
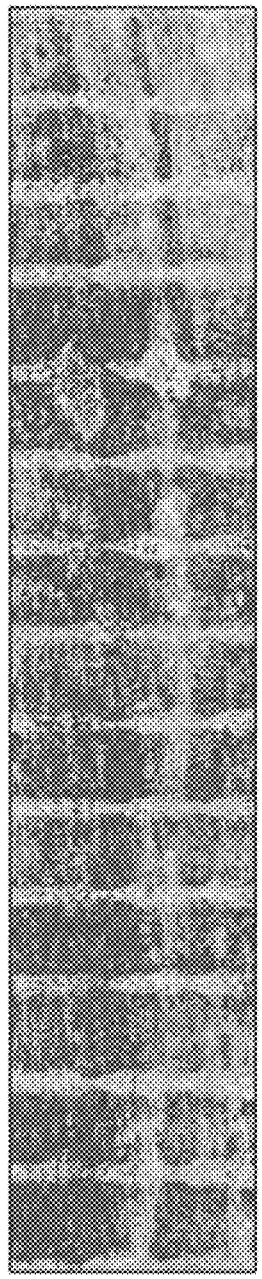

Example 7: Expansion of Umbilical Cord Epithelial and Mesenchymal Stem Cells Using Repetitive Tissue Explants of Umbilical Cord Lining Membrane Tissues Umbilical cord epithelial and mesenchymal stem cells of the invention were expanded using repetitive explants of umbilical cord amniotic membrane tissue as follows. Briefly, at day 1 of process, tissue explants were plated onto tissue culture dishes in growth media (DMEM/10% FCS, EpiLife®, KGM®, KGM®-2 or M171) at 37° C., 5% $CO_2$; media was changed every 2 or 3 days. Cell outgrowths started and continued migrating from the explants for 7 days. After that, tissue explants were transferred to other dishes to allow further cell outgrowth. This process was continued until the explants had diminished in size, preventing further explanation. In this connection it is noted that the explants progressively shrink in size until they are too small for further tissue explant since during the process of cells outgrowing and migrating from tissue explants, the cells produce proteases to digest and break down tissue. FIG. 16 schematically illustrates the rapid and robust expansion process of umbilical cord epithelial and mesenchymal stem cells achieved using this protocol. Thus, this study demonstrates the high yield of UCMC and UCEC cells can be obtained from this source, further reflecting the high viability and pro-growth characteristics off these cells in comparison with other sources of cells as bone-marrow or adipose-derived stem cells. In addition, being a solid tissue, the successful repetitive explant technique used herein demonstrates that the cells of the invention can be uniformly extracted from the entire tissue instead of only certain portions. This allows the maximum number of cells that can be derived at a low passage instead of passing the cells through many generations causing deterioration of cells.

Example 8: Direct Differentiation of Umbilical Cord Lining Mesenchymal Cells (UCMC) into Skin Dermal Fibroblasts For differentiation into skin dermal fibroblasts, umbilical cord mesenchymal stem cells, UCMC cells were cultured according to a standard protocol for the cultivation of fibroblasts. Cell isolation techniques were as described above in Example 6. UCMC were then cultured in DMEM or commercially available fibroblast growth media (FGM). UCMC cell morphology thus differentiated resembled human dermal fibroblasts. Mesenchymal cells have similar morphology under light microscope and can be easily turned into fibroblasts using conventional and commercially available media (cf., FIG. 3).

Example 9: Direct Differentiation of UCEC into Skin Epidermal Keratinocytes

Figures 9, 10, 11, 12, 13, 14, 15, 16, 17:
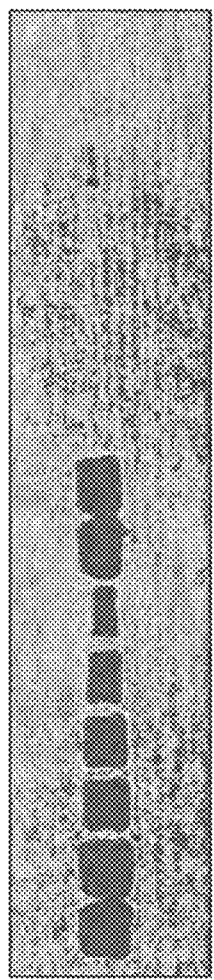
Figures 9, 10, 11, 12, 13, 14, 15, 16, 17, 18:
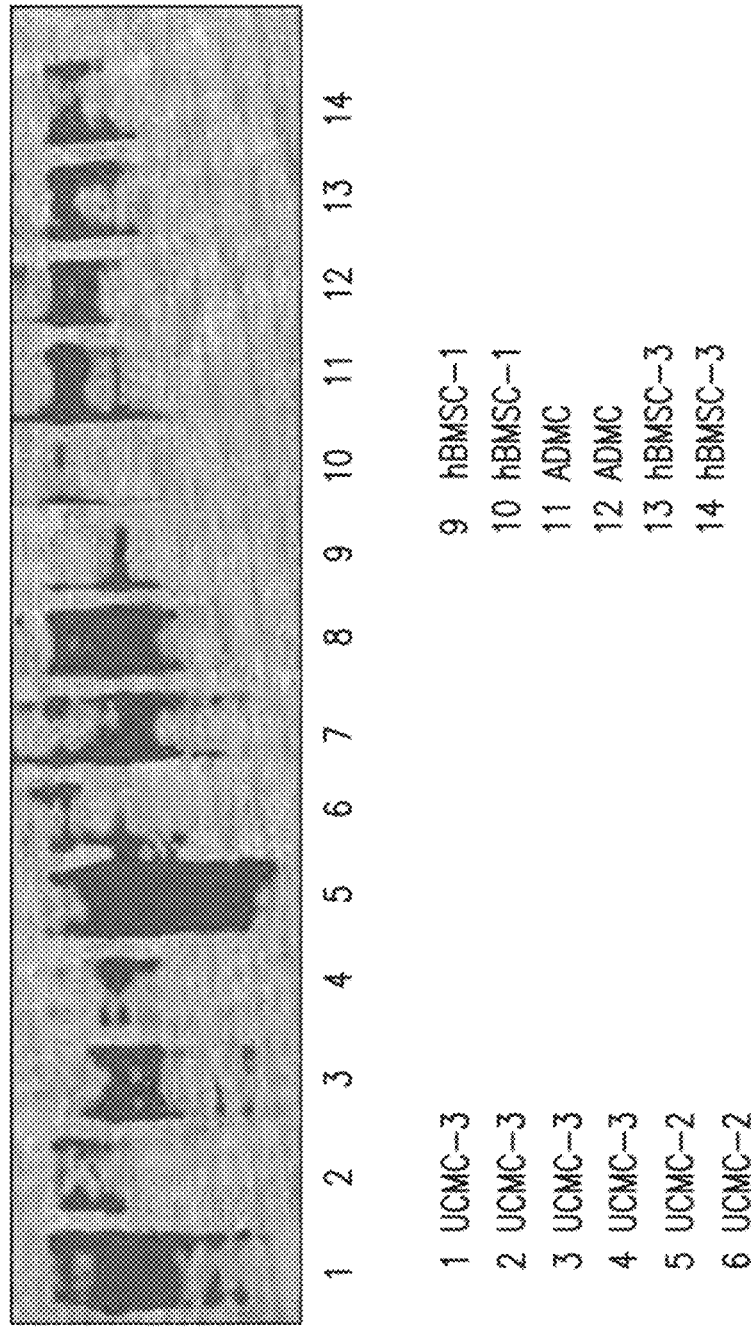
Figures 9, 10, 11, 12, 13, 14, 15, 16, 17, 18, 19:
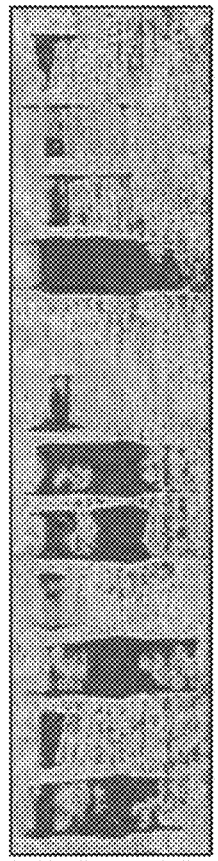
Figures 9, 10, 11, 12, 13, 14, 15, 16, 17, 18, 19, 20:
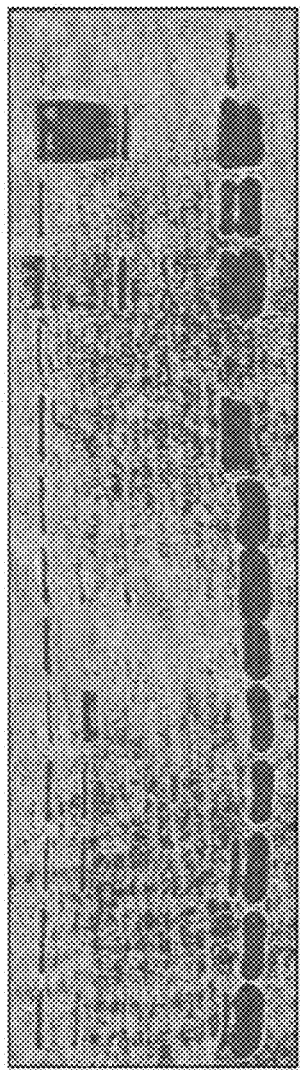
Figures 9, 10, 11, 12, 13, 14, 15, 16, 17, 18, 19, 20, 21:
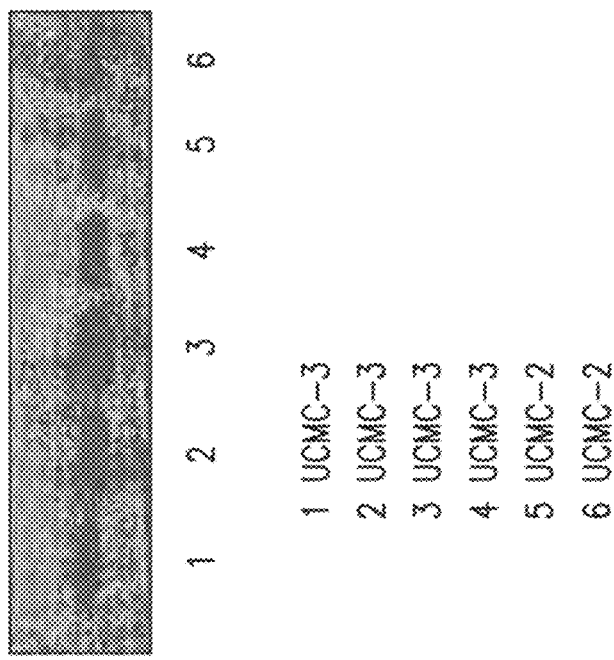
Figures 9, 10, 11, 12, 13, 14, 15, 16, 17, 18, 19, 20, 21, 22:
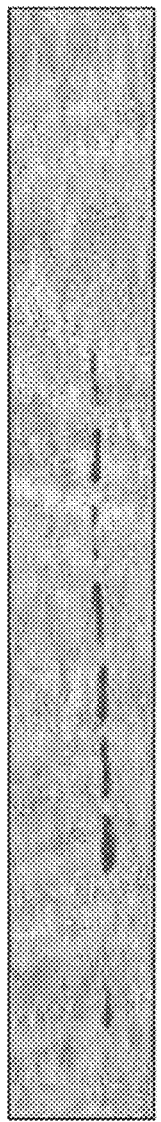

In an approach similar to Example 6, epithelial stem/progenitor cells of the amniotic membrane of the umbilical cord (UCEC) were isolated as described in Example 2. For differentiation of UCEC into epidermal keratinocytes, the cells were cultured in keratinocyte media (EpiLife® or KGM®) until 100% (cultivation after 5 days shown in FIG. 17-A) confluent before changing the media to DMEM/10% FCS for 3 days to form epidermal cell sheets. As shown in FIG. 17-A (in which photographs of two experiments termed "UCEC-10" and UCEC-17 are depicted), after cultivation in DMEM/10% FCS, UCEC, had differentiated into epidermal keratinocytes that formed cell sheets (photograph of FIG. 17-A taken after 10 days). These results thus provide further evidence for the pluripotency of the cells of the present invention.

Example 10: Direct Differentiation of UCMC into Osteoblasts

Mesenchymal cells of the amniotic membrane of the umbilical cord (UCMC) were isolated as described in Example 2. For differentiation of UCMC into osteoblasts, cells were cultured in DMEM/10% FCS until 100% confluent, and then in starvation medium of serum-free DMEM for another 48 hours. UCMC were subjected to osteogenic induction media for 4 weeks before subjecting the cells to von Kossa staining (bone cell staining). The osteogenic induction medium contained DMEM/10% FCS; 1% antibiotic (streptomycin and penicillin)/antimycotic (fungizone); 0.01 µM 1,25-dihydroxyvitamin D3, 50 µM ascorbate-2-phosphate, 10 mM β-glycerophosphate, 1% antibiotic (streptomycin and penicillin)/antimycotic (fungizone).

Figure 17A:
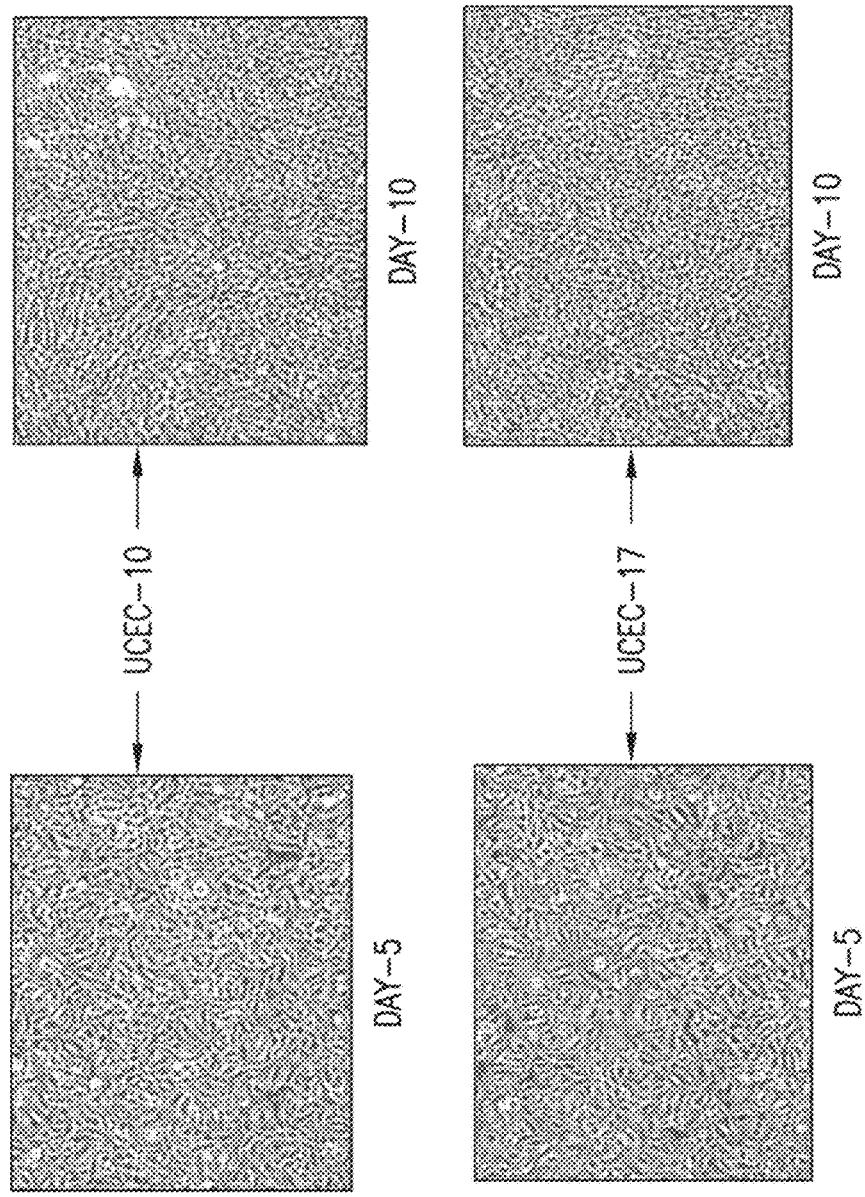
FIG. 17A depicts direct (in-vitro) differentiation of epithelial cells isolated from the amniotic membrane of umbilical cord (UCEC) into skin epidermal keratinocytes.
Figure 17B:
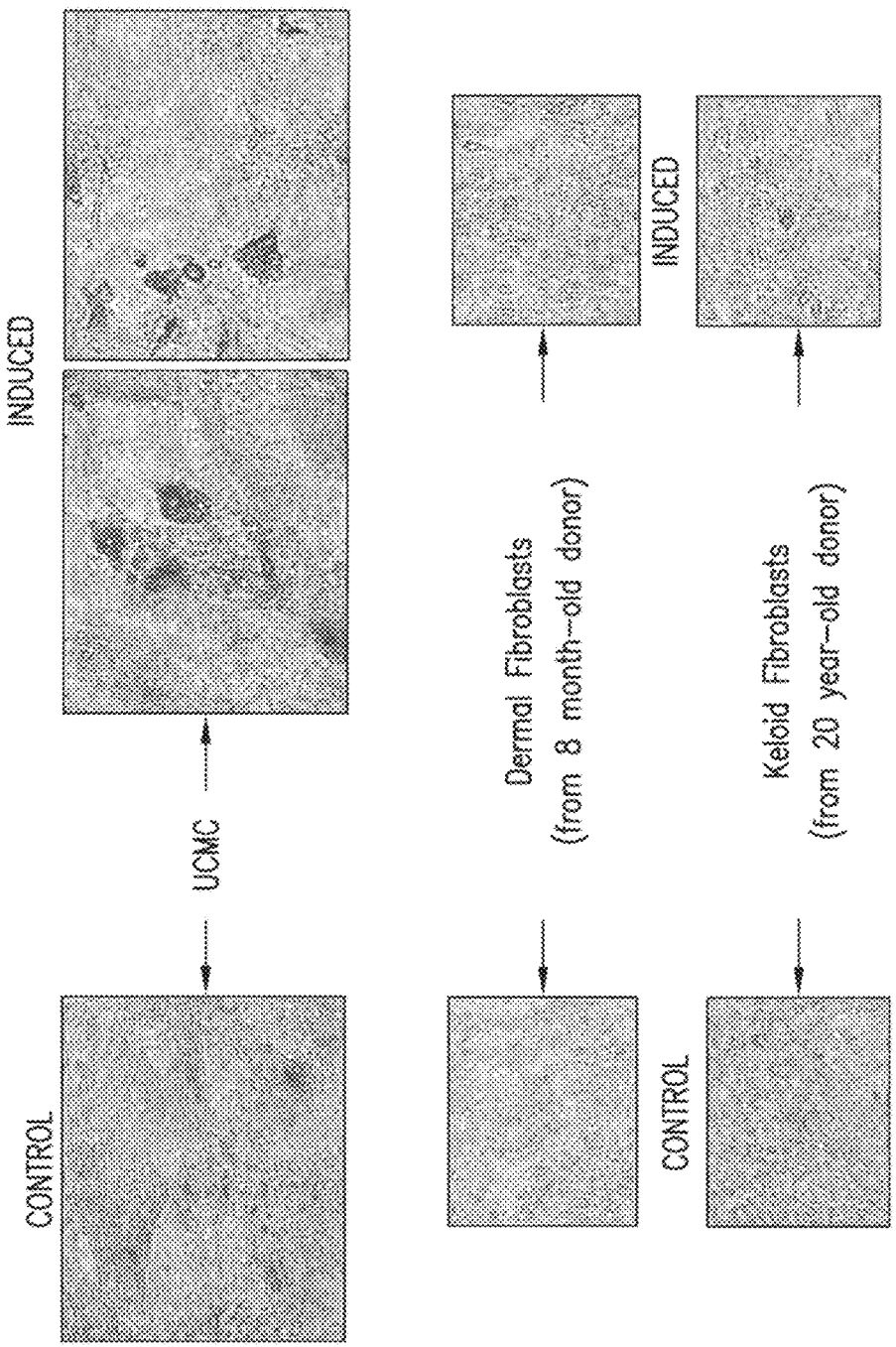

As shown in FIG. 17B, von Kossa staining of UCMC cells that were cultivated in the osteogenic induction medium indicated bone nodule formation in the UCMC and thus differentiation of the UCMC into osteoblasts whereas no such differentiation was indicated in untreated UCMC which were cultured in DMEM/10% FCS without induction under otherwise same conditions as negative control. As a further negative control, dermal fibroblasts from an 8 months old donor and keloid fibroblasts from a 20 year old donor were cultivated under the same conditions as the induced or un-induced UCMC. Both cell types did not yield a positive result using von Kossa staining, which is a further evidence for the pluripotency of UCMC of the present invention and thus to differentiate, for example, also into osteoblasts.

Example 11: Direct Differentiation of UCMC into Adipocytes

Mesenchymal stem/progenitor cells from the amniotic membrane of the umbilical cord (UCMC) were isolated as described in Example 2. For differentiation of UCMC into adipocytes, cells were cultured in DMEM/10% FCS until 100% confluent, and then in starvation medium of serum-free DMEM for another 48 hours. UCMC were subjected to adipogenic induction media for 4 weeks before subjecting the cells to Oil-Red-O staining. The adipogenic induction medium contained DMEM/10% FCS; 1% antibiotic (streptomycin and penicillin)/antimycotic (fungizone)); 0.5 mM isobutyl-methylxanthine (IBMX), 1 µM dexamethasone, 10 µM insulin, and 200 µM indomethacin.

As shown in FIG. 17C, Oil-Red-0 staining of UCMC cells that were cultivated in the adipogenic induction medium indicated fat accumulation in the UCMC and thus differentiation of the UCMC into adipocytes whereas no such differentiation was indicated in untreated UCMC which were cultured in DMEM/10% FCS without induction under otherwise same conditions as negative control. As a further negative control, dermal fibroblasts from an 8 months old donor and keloid fibroblasts from a 20 years old donor were cultivated under the same conditions as the induced or un-induced UCMC. Both cell types did not yield a positive result in the staining with Oil-Red-O, which is a further evidence for the pluripotency of UCMC of the present invention and to differentiate, for example, also into adipocytes.

Example 12: Method to Produce Skin Equivalent Using UCMC and UCEC Together with Collagen as Extracellular Matrix Component To produce an exemplary skin equivalent of the present invention a 6-well tissue-culture tray containing scaffolds made of a 3 µm porous polycarbonate membrane are used (Transwell®, Corning Incorporated, Massachusetts, USA). Such trays can be obtained from Vitaris AG, Baar, Switzerland. For the collagen ECM layer, sterile rat tail acid-extracted collagen (1.0-1.7 mg/ml) in 0.05% acetic acid is used. Further components used for the acellular as well as the cellular ECM medium are 10× minimum essential medium with Earle's salts (Gibco-BRL, Maryland, USA), L-glutamine (200 mM, Gibco-BRL, Maryland, USA), Sodium bicarbonate (71.2 mg/ml), DMEM (Gibco-BRL, Maryland, USA), Fetal bovine serum (FBS, Gibco-BRL, Maryland, USA). For the different cell culture medias PTT-4 and PTT-7 the following components are used:

PTT-4: 90% (v/v) CMRL1066, and 10% (v/v) fetal calve serum.

PTT-7: 99.4% (v/v) EpiLife®, 0.2% (v/v) insulin, 0.2% (v/v) transferrin, 0.2% (v/v) selenous acid and 10 ng/ml epithelial growth factor (EGF).

Mesenchymal and epithelial stem cells from the amniotic membrane of the umbilical cord UCMC and UCEC) were isolated and cultivated as described in Example 2 and 7. UCMC cultured in PTT-4 are shown in FIG. 18b (after 7 days of culture) whereas UCEC cultured in PTT-7 are shown in FIG. 18a (after 7 days of culture).

All components described above should be kept on ice. For generating the extracellular matrix containing no cells (acellular ECM), the acellular ECM medium components are mixed together in the order listed in Table 1. The colour of the medium solution should be straw-yellow to light pink, and any extreme variation in colour may indicate a pH at which the collagen may not gel. After mixing together the acellular ECM medium, add 1 ml of this medium to each scaffold, making sure the mixture coats the entire bottom of the scaffold. Once the collagen gel has been poured, it should not be disturbed in the incubator (37° C., 5% $CO_2$).

Once the acellular ECM has polymerised (which usually takes about 0.5 to about 12 hours after the collagen gel has been poured on the scaffold), UCMC that are in culture can be trypsinised and resuspended thoroughly in PTT-4 cell culture medium to a final concentration of $5 \times 10^5$ cells/ml, ready to mix with collagen solution.

For the cellular ECM medium (see Table 1) all components should be kept on ice. For generating the cell containing extracellular matrix (cellular ECM), the cellular ECM medium components are mixed together in the order listed in Table 1. The UCMC dissolved in PTT-4 should be added last, to ensure that the mix has been neutralised by the addition of collagen, so that the cells are not damaged by an alkaline pH. Mix well and add 3 ml to the scaffolds and allow it to gel in the incubator (37° C., 5% $CO_2$). When the gels are pink and firm (2 to 24 hours later), they are covered with 3 to 4 ml of PTT-4 and incubated for 4 to 7 days, until the gel contraction is stable and complete. The PTT-4 medium allows the cells to differentiate into fibroblasts (FIG. 18b). Another medium that is suitable for differentiating UCMC into fibroblasts is the one described in Example 8. During the interval, there is a 50-fold decrease in the volume of the matrix. The culture medium should be changed every 2 days.

Trypsinise UCEC when they are ready such that up to $1 \times 10^6$ cells in 50 µl of PTT-7 can be plated in each scaffold. The cell suspension can be placed in the central, raised, mesa-like portion of the contracted collagen gel with a 200 µl pipetman.

Do not touch the plates for 2 to 3 hours, while the UCEC adhere in the incubator to the already formed fibroblast layer. After this incubation period, PTT-7 can be added into the well (4 ml) on the top of UCEC (2 ml) and cultured for up to 7 days. The media should be changed every 2 days. The incubation of UCEC with PTT-7 allows the cells to differentiate into keratinocytes (FIG. 18a). Another medium that is suitable for differentiating UCEC into keratinocytes is the one described in Example 6.

At this point, the skin equivalent (CSE-1) is grown at the air-liquid interface using high calcium (0.6 mM) dissolved in PTT-7 culture medium (only 1.5-2 ml) in the well and cultured up to 10 days. The culture medium should be changed every 2 days.

The skin equivalent (CSE-1) is now ready for histological and electron microscopy analysis. It should be noted that CSE-1 growth varies with the strain of UCEC and UCMC used in the method. As can be seen from the photographs in FIG. 19 a dermal layer consisting of fibroblasts and an epithelial layer consisting of keratinocytes have been formed. The photographs in FIG. 20a show the surface appearance of CSE-1 after lifting to air-liquid interface. FIG. 20b shows the appearance of UCMC populated in collagen lattices of CSE-1.

TABLE 1

Components for the ECM medium

| | Acellular ECM medium for 6 ml (1 ml/scaffold) | Cellular ECM medium for 18 ml (3 ml/scaffold) |
|---|---|---|
| 10 x DMEM | 0.59 ml | 1.65 ml |
| L-glutamine | 0.05 ml | 0.15 ml |
| Fetal bovine serum | 0.6 ml | 1.85 ml |
| Sodium bicarbonate | 0.17 ml | 0.52 ml |
| Collagen | 4.6 ml | 14 ml |
| UCMC | — | $5 \times 10^5$ cells in 1.5 ml of PTT-4 medium |

Example 13: Method to Produce Skin Equivalent Using UCMC and UCEC

In general, the following Example is carried out in the same manner as Example 12. However, in contrast to Example 12 no collagen is used as ECM (which in Example 12 is incorporated into the scaffold before seeding UCMC into the scaffold). In the present Example, the UCMC cells themselves secrete collagen type I and form three-dimensional cell sheets, so making the use of an extra collagen layer superfluous. Production of the collagen by UCMC cells is achieved by adding ascorbic acid to the cell medium PTT-4.

First, the UCMC cells are harvested as described in Example 12. UCEC are seeded on the scaffold in a concentration of $1 \times 10^5$ cells/ml and incubated for 3 days (37° C., 5% $CO_2$).

After 3 days the culture medium PTT-4 is supplemented with 50 µg/ml ascorbic acid. The cells are then incubated for another 2 weeks (37° C., 5% $CO_2$). Under these conditions, UCMC will self-deposit collagen type I and form three-dimensional cell sheets, which mimic the extracellular matrix which was separately generated in Example 12.

For the production of the epidermal layer the same experiments as already described in Example 12 are carried out.

The skin equivalent (CSE-2) is now ready for histological and electron microscopy analysis. It should be noted that CSE-2 growth varies with the strain of UCEC and UCMC used for the method. The photographs in FIG. 21a show the surface appearance of CSE-2 after lifting to air-liquid interface. FIG. 21b shows the appearance of UCMC populated in collagen lattices of CSE-2.

Example 14: Method to Produce Skin Equivalent Using UCMC, HUVEC and UCEC Together with Collagen as Extracellular Matrix Component In general, the following example uses the same components and procedure as described in Example 12.

Mesenchymal and epithelial stem cells from the amniotic membrane of the umbilical cord (UCMC and UCEC) were isolated and cultivated as described in Example 2 and 7. Human Umbilical Vessel Endothelial Cells (HUVEC) were cultured from the umbilical cord vessel using collagenase. Briefly, cord vessels were flushed with PBS to remove all blood. Clamped end of the cord: 0.5% collagenase solution was injected into cord vessels and incubated for 20 min at room temperature. Afterwards, the clamps are removed and the cord vessels are flushed with EGM medium (Cambrex Corporation, New Jersey, USA) containing 10% fetal calve serum (FCS) to collect the HUVE-cell suspension. The cell suspension was centrifuged and the cell pellets collected and subsequently cultured in EGM medium (Cambrex Corporation, New Jersey, USA).

Shortly before the carrying out the experiment, HUVEC cells are cultured in EGM medium (Cambrex Corporation, New Jersey, USA) or M131 medium in an incubator (37° C., 5% $CO_2$). The cell purity of these cells is confirmed using immunohistochemical analysis of Factor VIII related antigen or von Willebrand factor (data not shown). Briefly, HUVEC were seeded on cover slips until they reached 80% confluence. Afterwards, they were fixed and incubated with primary antibodies against Factor VIII or antibodies against von Willebrand factor, followed by peroxidase conjugated secondary antibody. The number of positive cells was expressed in percentage of cells marked with Factor VIII or von Willebrand factor. Positive cells were viewed under microscope to check their purity.

All components used for the experiment should be kept on ice. For generating the extracellular matrix containing no cells (acellular ECM), the acellular ECM medium components are mixed together in the order listed in Table 2. For further details see the description in experiment 12.

Once the acellular ECM has polymerised (which takes place about 0.5 to about 12 hours after the collagen gel has been poured onto the scaffold) UCMC and HUVEC that are in culture can be trypsinised and resuspended thoroughly in PTT-4 (for UCMC) and M131 (for HUVEC) cell culture medium to a final concentration of $5 \times 10^5$ cells/ml (UCMC/HUVEC—1:1 mixture), ready to mix with collagen solution.

For the cellular ECM medium (see Table 2) all components should be kept on ice. For generating the cell containing extracellular matrix (cellular ECM), the cellular ECM medium components are mixed together in the order listed in Table 2. The UCMC/HUVEC mixture should be added last, to ensure that the mix has been neutralised by the addition of collagen, so that the cells are not damaged by an alkaline pH. Mix well and add 3 ml to the scaffolds and allow it to gel in the incubator (37° C., 5% $CO_2$). When the gels are firm (30 min later), they are covered with 3 to 4 ml of PTT-4/M131 (1:1) and incubated for 4 to 7 days, until the gel contraction is stable and complete. The PTT-4 medium allows the cells to differentiate into fibroblasts. During the interval, there is a 50-fold decrease in the volume of the matrix. The culture medium should be changed every 2 days.

UCEC are trypsinised when they are ready such that up to $1 \times 10^6$ cells in 50 µl of PTT-7 can be plated in each scaffold. The cell suspension can be placed in the central, raised, mesa-like portion of the contracted collagen gel with a 200 µl pipette.

The plates are left untouched for 2 to 3 hours, while the UCEC adhere in the incubator to the already formed fibroblast layer. After this incubation period, PTT-7 can be added into the well (4 ml) on the top of UCEC (2 ml) and cultured for up to 7 days. The media should be changed every 2 days. The incubation of UCEC with PTT-7 allows the cells to differentiate into keratinocytes.

At this point, the skin equivalent (CSE-3) is grown at the air-liquid interface using high calcium (0.6 mM) dissolved in PTT-7 culture medium (only 1.5 to 2 ml) in the well and cultured up to 10 days. The culture medium should be changed every 2 days.

The skin equivalent (CSE-3) is now ready for histological, confocal, electron microscope and immunological analysis. It should be noted that CSE-3 growth varies with the strain of UCMC, HUVEC and UCEC used in the method.

TABLE 2

Components for the ECM medium

| | Acellular ECM medium for 6 ml (1 ml/scaffold) | Cellular ECM medium for 18 ml (3 ml/scaffold) |
|---|---|---|
| 10 x DMEM | 0.59 ml | 1.65 ml |
| L-glutamine | 0.05 ml | 0.15 ml |
| Fetal bovine serum | 0.6 ml | 1.85 ml |
| Sodium bicarbonate | 0.17 ml | 0.52 ml |
| Collagen | 4.6 ml | 14 ml |
| UCMC | — | $5 \times 10^5$ cells in 1.5 ml of PTT-4/M131 mixture medium |

Example 15: Differentiation of UCEC and UCMC, Respectively, into n-Islet Like Cells Mesenchymal and epithelial stem cells from the amniotic membrane of the umbilical cord (UCMC and UCEC) were isolated as described in Example 2.

UCMC are incubated in PTT-4 medium (for the composition of PTT-4 (90% (v/v) CMRL1066, 10% (v/v) FCS, supra) or PTT-10 medium. PTT-10 medium contains 99.4% (v/v) CMRL-1066 and 0.2% (v/v) insulin, 0.2% (v/v) transferrin and 0.2% (v/v) selenous acid.

UCEC are incubated in PTT-7 medium (for the composition of PTT-7, supra) or PTT-5 and PTT-6 medium. PTT-5 medium contains 98.8% (v/v) CMRL-1066, 0.4% (v/v) insulin, 0.4% (v/v) transferrin, 0.4% (v/v) selenous acid and 10 ng/ml epidermal growth factor (EGF). PTT-6 medium contains 99.4% (v/v) M171, 0.2% (v/v) insulin, 0.2% (v/v) transferrin, 0.2% (v/v) selenous acid and 10 ng/ml epidermal growth factor (EGF).

The differentiation of UCEC and UCMC, respectively, is induced by adding 1 mM nicotinamide to the respective cell culture medium in which the cells are cultivated. The cell culture medium should be changed every 2 or 3 days.

Figures 9, 10, 11, 12, 13, 14, 15, 16, 17, 18, 19, 20, 21, 22, 23:
Figures 9, 10, 11, 12, 13, 14, 15, 16, 17, 18, 19, 20, 21, 22, 23, 24:
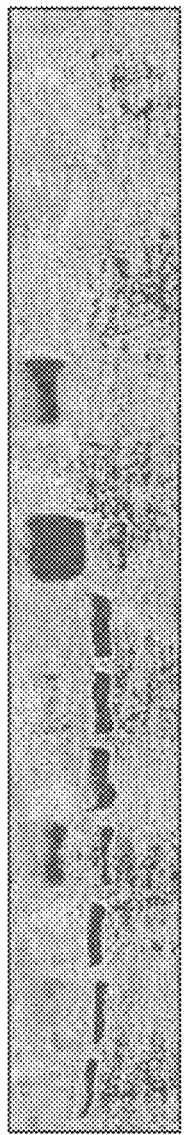

The appearance of beta-islet like cells is observed under microscope (FIG. 23; UCEC in PTT-10 with and without the inductor, i.e. nicotinamide). The β-islet like cells are collected for microscopic analysis. To determine if the cells obtained according to the method of the present invention are indeed β-islet like cells one of the methods that is described in the Technical Manual of StemCell Technologies Inc., Title: In-vitro differentiation of murine ES cells into pancreatic islet-like clusters, or "Epithelial-to-mesenchymal transition generates proliferative human islet precursor cells", Science, 2004, 306, p. 2261-2264 was used.

In the following it is described an alternative method for the induction of insulin-producing cell differentiation of UCEC (CLEC). UCEC have been incubated with one of the media as described above (PTT-5, PTT-6 or PTT-7 medium). For the induction of differentiation of UCEC into insulin-producing cells these cells have been exposed to ESCult medium (purchased from StemCell Technologies Inc., Vancouver, Canada) or BBRC06 medium for 7 days.

ESCult medium (StemCell Technologies Inc., Vancouver, Canada) contains 100 microgram/ml nicotinamide added in together with 20 ml/l B27 and 10 ml/l N2 supplements.

BBRC06 medium contains serum-free DMEM/F12 medium with 17.5 mM, glucose in the presence of nicotinamide 10 mM, activin-A 2 nM, exendin-4, 10 nM, hepatocyte growth factor 100 µM, and pentagastrin 10 nM (Sigma-Aldrich, Missouri, USA) as well as B-27 serum-free supplement, N-2 Supplement (StemCell Technologies Inc., Vancouver, Canada), and 1% penicillin/streptomycin 5000 U/L (Biochem. Biophys. Res. Commun. 2006, Mar. 24; 341(4) p. 1135-40).

After the incubation for 7 days in ES Cult medium or BBRC06 medium, the total RNA were harvested using RNeasy® extraction kits from QIAGEN® (Hilden, Germany) for RNA extraction and purification and single samples were subjected to RT-PCT assays to detect insulin gene expression. An insulin primer was used as a positive control as described in Timper K., Seboek D. et al., Biochem Biophys Res Commun., 2006 Mar. 24, 341(4), p. 1135-40.

Figures 9, 10, 11, 12, 13, 14, 15, 16, 17, 18, 19, 20, 21, 22, 23, 24, 25:
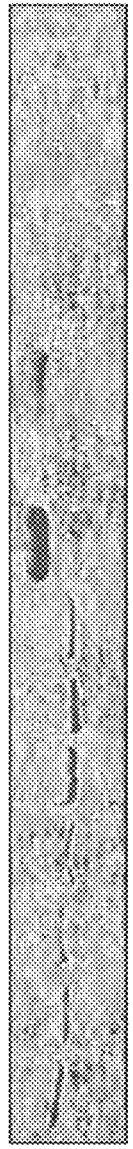
Figures 9, 10, 11, 12, 13, 14, 15, 16, 17, 18, 19, 20, 21, 22, 23, 24, 25, 26:
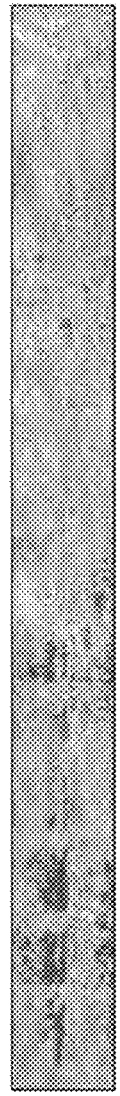
Figures 9, 10, 11, 12, 13, 14, 15, 16, 17, 18, 19, 20, 21, 22, 23, 24, 25, 26, 27:
Figures 9, 10, 11, 12, 13, 14, 15, 16, 17, 18, 19, 20, 21, 22, 23, 24, 25, 26, 27, 28:
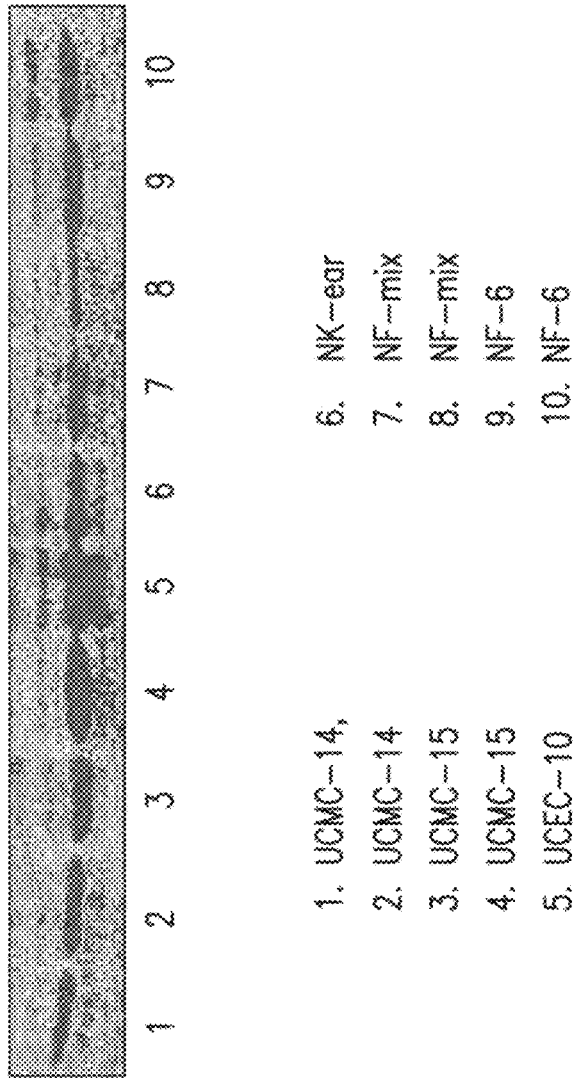
Figures 9, 10, 11, 12, 13, 14, 15, 16, 17, 18, 19, 20, 21, 22, 23, 24, 25, 26, 27, 28, 29:
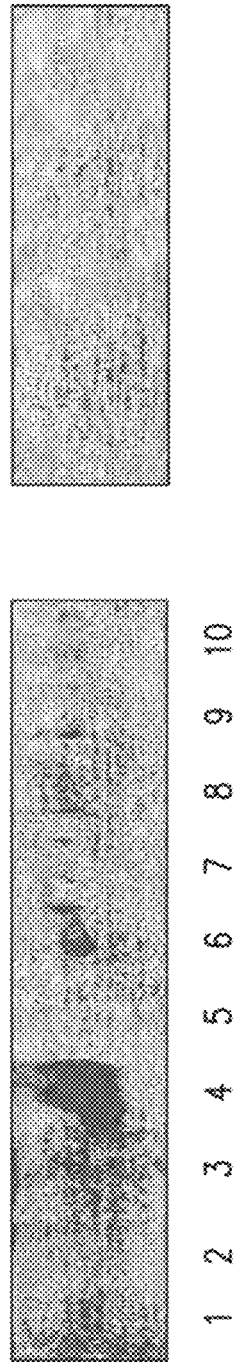

FIG. 25 shows the results of this alternative induction method. FIG. 25 shows insulin expression in multiple samples of UCEC under induction of ES Cult medium or BBRC06 medium. Samples designated with CLEC25, 28 and 30 indicate different samples derived from different donors of umbilical cords. Samples designated with CLEC30(1) and CLEC30 (2) indicate duplicates of the same sample. Thus, it is proved that UCEC have the potential to differentiate into insulin-producing cells which can be used for the treatment of diabetes.

Example 16: Differentiation of UCEC into Mucin-Producing Cells

Epithelial stem cells from the amniotic membrane of the umbilical cord (UCEC) were isolated as described in Example 2.

The isolated UCEC are grown in the cell culture medium PTT-5 or PTT-6 (37° C., 5% $CO_2$) which composition has already been described in Example 15. It was the surprising finding of the present invention that UCEC produce mucin using PTT-5 and PTT-6 to culture UCEC (see FIG. 22a). During the course of pipetting and changing media viscosity of the cell culture supernatants was observed.

Mucin Clot Test:

The mucin clot test is an assessment of the quality and quantity of mucin produced by UCEC cultured in PTT-5 or PTT-6. This test is also described in general by Corfield A. P., Glycoprotein method and procotols: The Mucins, page 29-65. Humana Press 2000; Gatter R. A. and Schumacher R. H., A practical handbook of join fluid analysis, page 59-63, Lea & Febiger, 1991. Within this test, UCEC cell culture conditioned media is expelled into 7N glacial acetic acid. The acetic acid causes the mucin to form a clot. UCEC cell culture conditioned media containing normal mucin appeared as clear fluid with a tight, ropy clot.

To quantify the amount of mucin produced by UCEC a SDS-PAGE and subsequently a Coomassie staining are carried out (see FIG. 22b). For the SDS-PAGE, 2,5 ml of cell culture media collected from UCEC cell culture were concentrated using 100 kDa cut-off membrane Centrisart® I (Sartorius AG, Germany). 100 µl concentrated supernatants were loaded into 6% SDS-PAGE for electrophoresis. Gels were then stained with Coomassie and photographs were taken.

Example 17: Direct Differentiation of UCMC into Chondrocytes (Chondrogenic Lineage)

Similar to the development of UCMC in osteoblasts (see Example 10) they also have the ability to develop into chondrocytes which make up the cartilage.

For the development of cartilage, mesenchymal cells of the amniotic membrane of the umbilical cord (UCMC) were isolated as described in Example 2. For differentiation of UCMC into chondrocytes, cells were cultured in DMEM/10% FCS until 100% confluent. They were then exposed to PTT-5 medium supplemented with 10 ng/mL transforming growth factor-β3 (TGF-β3; R&D Systems, Minneapolis, USA), 100 nM dexamethasone, 50 mg/mL ascorbic acid, 100 mg/mL sodium pyruvate, 40 mg/mL proline (Sigma-Aldrich, Missouri, USA), for 4 weeks. Cell layers were stained with Alcian Blue (it stains acid mucopolysaccharides and glycosaminoglycans)

Figure 24B:
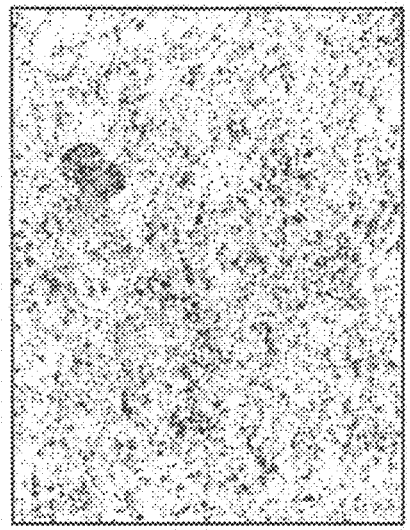
Figure 24A:
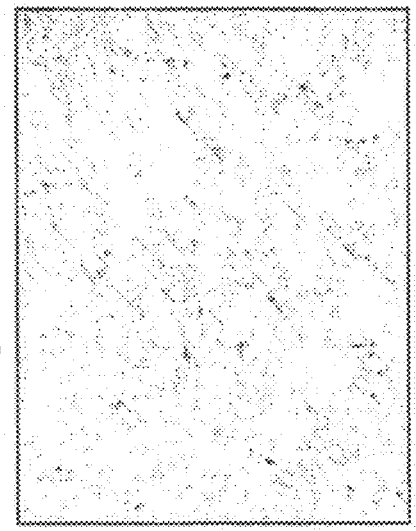
FIG. 24A depicts negative staining observed with undifferentiated UCMC cells.
Figure 25:
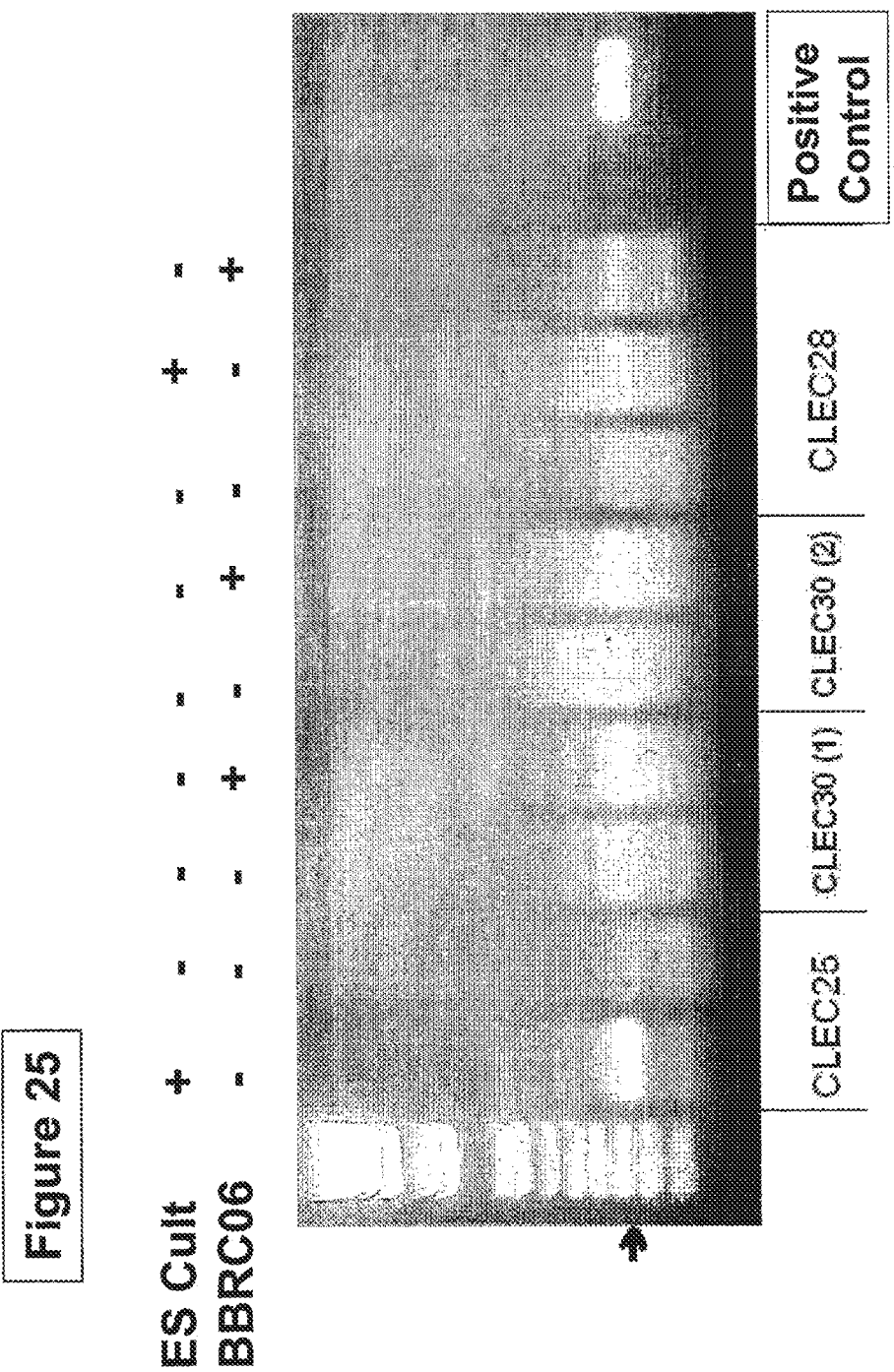

Positive staining of chondrocytes or a chondrogenic lineage with Alcian Blue was observed in FIG. 24B in comparison with the control in which no such differentiation was indicated (FIG. 24A). The control consisted of untreated UCMC which were cultured in DMEM/1% FCS without induction with supplemented PTT-5 (supra) under otherwise same conditions. The results show that UCMC have the potential to form the chondrocytes of the cartilage for cartilage repair and regeneration. Cells can be applied to the body by use of a scaffold, e.g. TissueFleece® (Baxter AG, Austria; described in Example 21) or a hydrogel.

Example 18: Differentiation of UCMC into Dopamine-Producing Cells

This example describes the differentiation of UCMC into dopamine and tyrosine hydroxylase (TH)-producing cells.

For the development of dopamine and TH, mesenchymal cells of the amniotic membrane of the umbilical cord (UCMC) were isolated as described in Example 2.

UCMC were cultured in 100 mm tissue culture dishes at a density of 200000 cells and maintained in PTT-4 medium for 5 days until 80% confluent. The cells were then exposed to PTT-2 medium for another 48 hours. After incubation the cell culture supernatants were collected for analysis. PTT-2 medium is a mixture of M154 a melanocyte culture medium and EpiLife® (Cascade Biologics Inc., Oregon, USA) at ratio of 3:1.

UCMC cells or conditioned media (supernatant, supra) were subjected to Western blot or immunohistochemistry (IHC) analysis. FIG. 26A shows TH secretion of CLMC (UCMC) cells into conditioned media. More TH secretion was observed in lane 4 and 5 when exposed to PTT-2 medium. FIG. 26B shows the expression of Dopamine by CLMC (UCMC) cells. FIG. 26C shows negative control. These UCMC cells are coaxed with dopamine. They are remained undifferentiated, but a high amount of dopamine can be detected. Indication: UCMC have potential to produce Dopamine and Dopamine precursor-TH.

Example 19: Differentiation of UCMC and UCEC into HLA-G-Producing Cells

This example describes the differentiation of UCMC and UCEC into HLA-G-producing cells. HLA-G is a HLA class I antigen which is mainly expressed in the placenta where it presumably protects the fetus against attacks of the immune system of its mother. HLA-G is a special HLA and has been implicated in various immune-mediated diseases and conditions, like organ-, cell transplantation and auto-immune diseases. Examples for such autoimmune diseases are multiple sclerosis, rheumatoid arthritis, type I diabetes mellitus, psoriasis, thyroid diseases, systemic lupus erythematosus, scleroderma or celiac disease. Specific variants have been reported as associated with risks of miscarriage, and preeclampsia. HLA typing is critical for matching donor and recipients for bone marrow transplantation; the use of well-matched donors increases survival and decreases graft vs. host disease. HLA typing is also important for solid organ transplantation, as well as other areas of use.

For the development of HLA-G, epithelial and mesenchymal cells of the amniotic membrane of the umbilical cord (UCEC and UCMC, respectively) were isolated as described in Example 2.

Figure 27A:
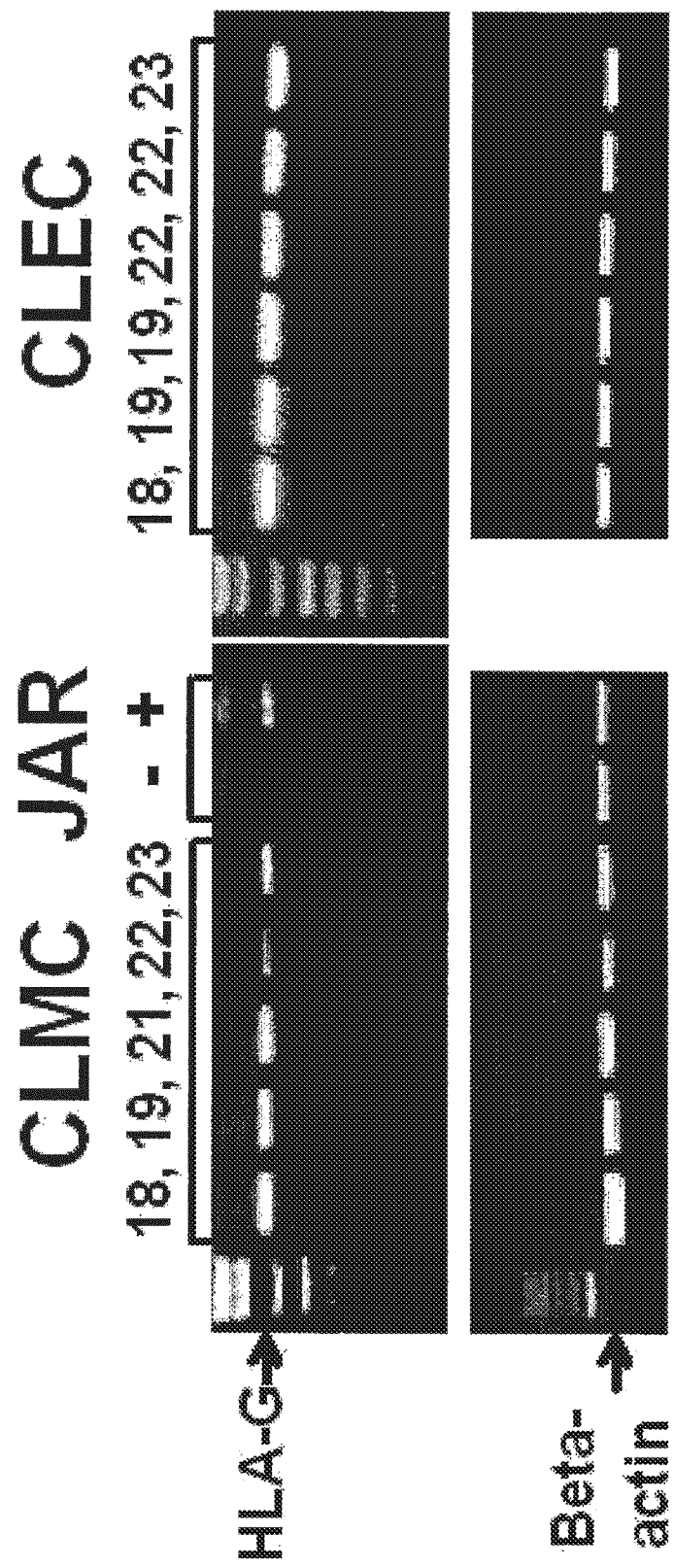
FIG. 27A and FIG. 27B demonstrate secretion and expression of HLA-G by differentiated UCMC and UCEC cells as described in Example 19.
Figure 27B:
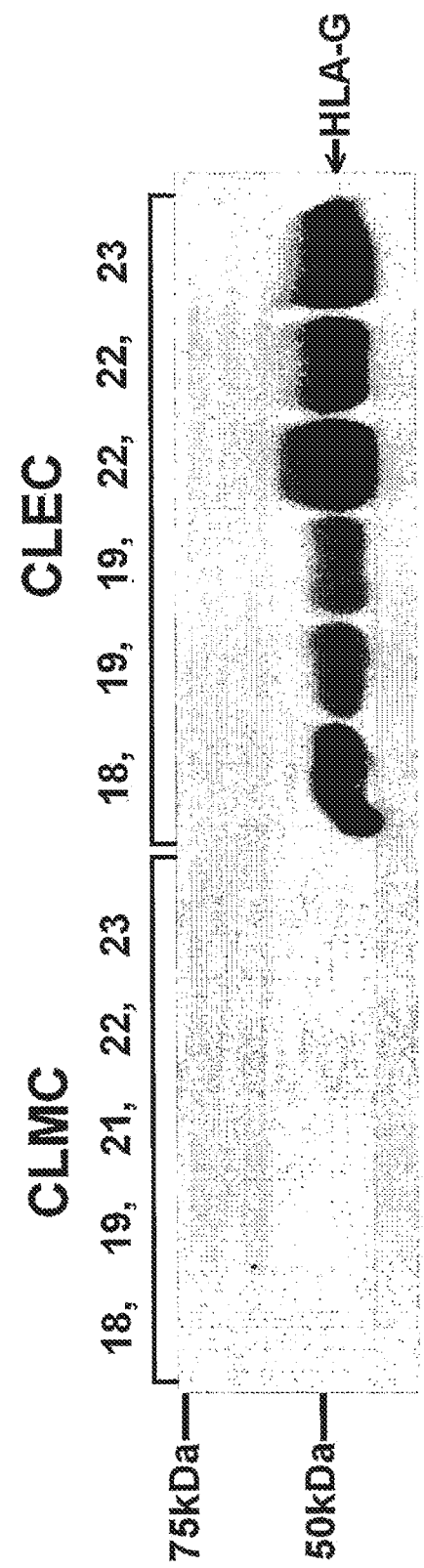

Total RNA and conditioned media were collected from UCMC and UCEC cells and subjected to RT-PCR and Western blot analysis. FIG. 27A shows expression of HLA-G mRNA in both UCMC and UCEC. JAR trophoblast cells served as positive control for HLA-G expression. FIG. 27B shows secretion of the HLA-G protein by UCEC cells in conditioned media.

This experiment shows for the first time that naïve UCEC express and produce HLA-G. A specific induction of UCEC for the production of HLA-G is not necessary. The HLA-G producing UCEC and UCMC cells have good immunosuppressive properties. These cells are low immunogenic and good candidates for allogenic transplantation.

Example 20: Induction of Proliferation of Aged Skin Keratinocytes (asK) Using UCMC In the following example it is demonstrated how UCMC can induce cell proliferation of aged skin keratinocytes (asK) and humand dermal fibroblasts (NF).

Figure 28A:
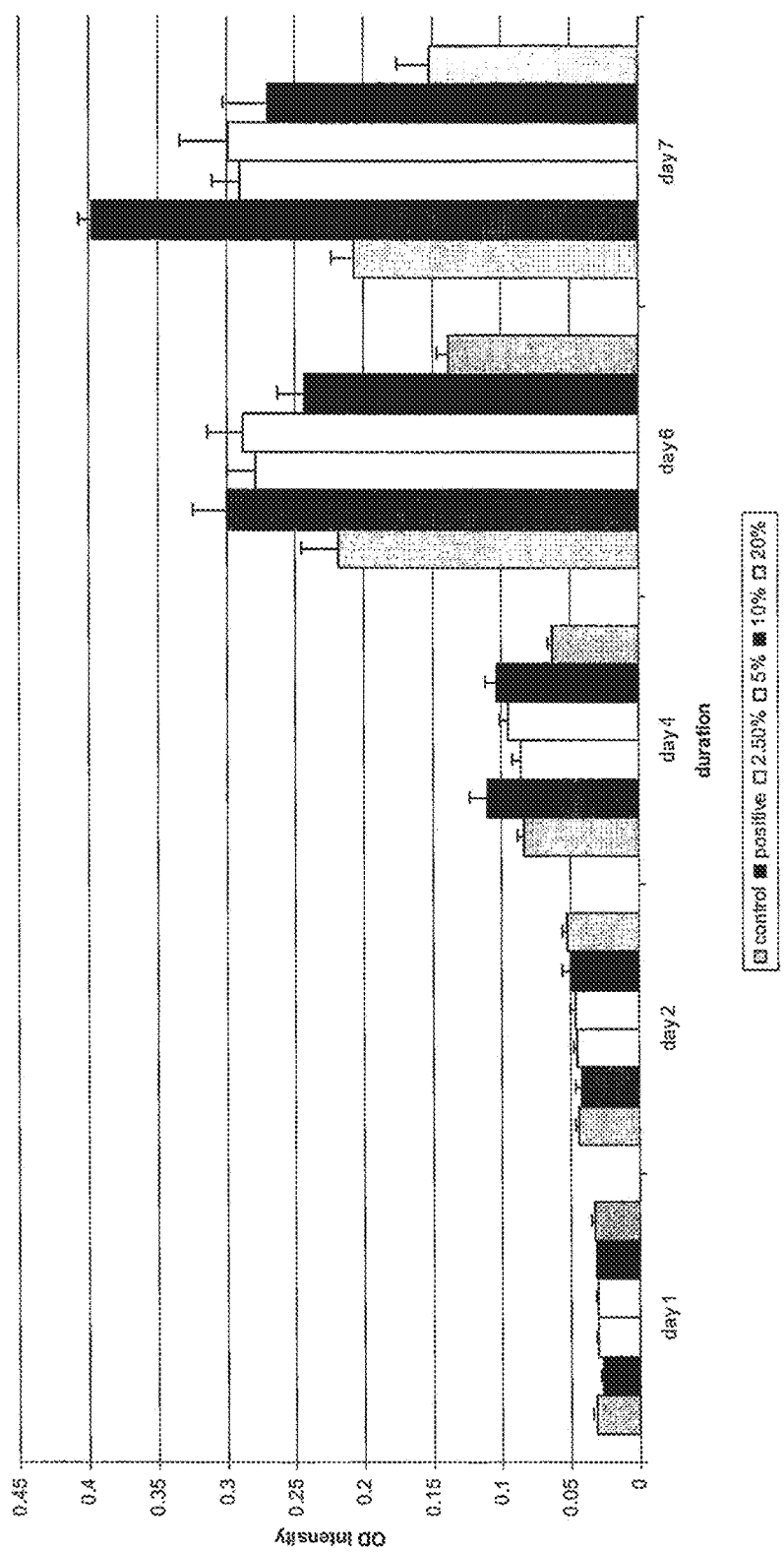
Figure 28C:
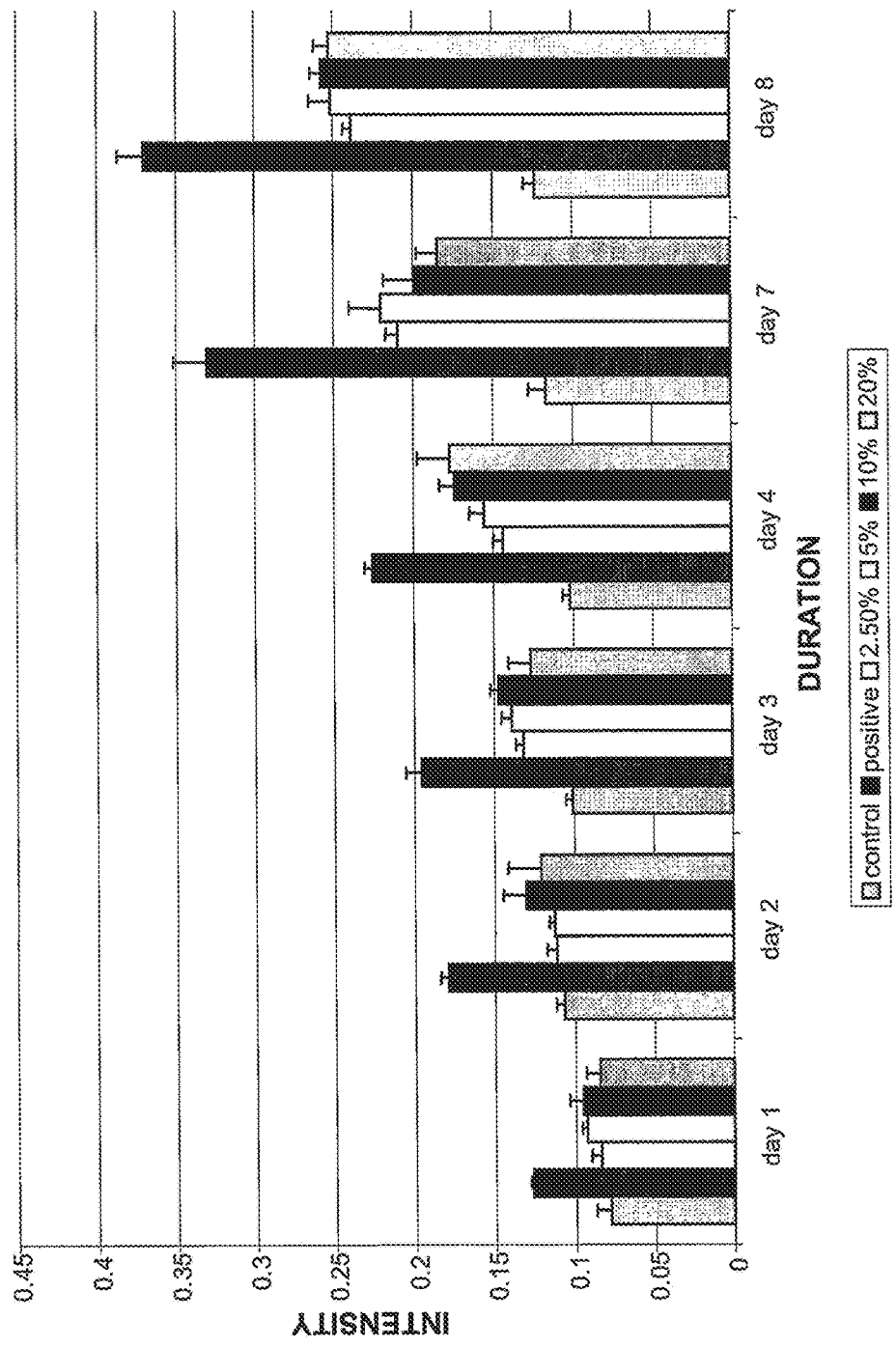

Mesenchymal cells of the amniotic membrane of the umbilical cord (UCMC) were isolated as described in Example 2. UCMC were cultured in PTT-4 medium until 80% confluent. Afterwards, the cells were harvested and centrifuged at 1200 rpm for about 10 min. After centrifugation, hypotonic water was added to the cell pellets with a ratio of 1 ml hypotonic water for 8 million cells. Total cell lysates were centrifuged at 4000 rpm for 30 min at 4° C. The clear phase of "UCMC extracts" were collected and stored in −30° C. Aged skin keratinocytes (asK) were isolated from chronological aged skin (patient who was more than 60 years old). asK cells were seeded in 24 well plates at a density of 4000 cells/well and maintained in growth EpiLife® medium (Cascade Biologics Inc., Oregon, USA) for 24 h. asK cells were then exposed to basal EpiLife® medium (Cascade Biologics Inc., Oregon, USA) for 48 h before adding in the UCMC extract at different dilutions of 2.5%, 5%, 10%, and 20% diluted in basal EpiLife® medium. Standard MTT assays were performed at different time intervals. FIG. 28A shows that an UCMC extract induced asK cells proliferation at concentrations at 2.5%, 5% and 10% at day 6 and 7. The "control" sample bar displayed in FIG. 28A represents aged skin keratinocytes maintained in basal EpiLife® medium without addition of UCMC extract or growth factors. The term "asK 10(1) p3" refers to aged-skin keratinocytes which have been passaged three times. The "positive" sample bar displayed in FIG. 28A represents cells which were maintained in optimal condition of growth media (basal medium EpiLife®+growth factors) without UCMC extract. Similarly, different cell lines of humand dermal fibroblasts (NF125 and NF119, respectively) were treated with "UCMC extract" as described above. The results of these experiments are shown in FIGS. 28B and 28C.

As "UCMC extract" has positive effects on skin keratinocytes and fibroblasts, the extract can be prepared for promoting wound healing, skin repair, regeneration and rejuvenation.

Example 21: Use of Different Scaffold Materials for Cultivation of UCMC

In a first experiment, mesenchymal tissue equivalents (MTE) were prepared byUCMC cell-populated in collagen lattices. To prepare organotypic coculture constructs, MTE were transferred onto Transwell inserts (Corning Inc.). CLEC or human skin keratinocytes were seeded onto MTE at density of 100,000 cells/cm² and maintained in EpiLife medium. The organotypic coculture constructs were then raised to air-liquid interface for 3 weeks. The constructs were then subjected to H&E staining for histological analysis (see FIGS. 29 A and 29B).

A second experiment carried out demonstrates the ability of UCMC to be inoculation in commercially available biomaterial scaffolds such as TissuFleece® (Baxter AG, Austria), INTEGRA Bilayer Matrix Wound Dressing™ (Neuro Sciences, New Jersey, USA), BoneSave® (Stryker Inc., MI, USA) or Synthese (AO).

The active ingredient of TissueFleece® E (Baxter AG, Austria) is a scaffold that consists of free-dried horse skin collagen. 1 cm² of TissuFleece® contains 2.8 mg of native collagen fibrils. Generally, the contact of collagen with blood results in the aggregation of thrombocytes which then adhere in great numbers to the collagen matrix, disintegrate, and release coagulation factors which, in combination with plasma factors, lead to the formation of fibrin. The collagen matrix additionally enhances the coagulum. Owing to its structure, TissuFleece® collagen fleece is capable of absorbing large quantities of liquid. By way of this merely mechanical process, the UCMC are absorbed. Consequently, the formation of granulation tissue is accelerated.

INTEGRA Bilayer Matrix Wound Dressing™ (in the following only referred to as Integra®) is a scaffold that is comprised of a porous matrix of cross-linked bovine tendon collagen and glycosaminoglycan and a semi-permeable polysiloxane (silicone) layer. The semi-permeable silicone membrane controls water vapor loss, provides a flexible adherent covering for the wound surface and adds increased tear strength to the device. The collagen-glycosaminoglycan biodegradable matrix provides a scaffold for cellular invasion and capillary growth.

BoneSave® (Stryker Inc., MI, USA) is a scaffold that consists of calcium phosphate ceramic.

ChronOS® (Synthes GmbH, Switzerland) is a scaffold that consists of beta-tricalcium phosphate.

For the experiment mesenchymal cells of the amniotic membrane of the umbilical cord (UCMC) were isolated as described in Example 2. UCMC were cultured in PTT-4 medium until 80% confluent. Cells were harvested and centrifuged at 1200 rpm for about 5 min to obtain cell pellets. To inoculate UCMC in TissuFleece®, Integra®, BoneSave® (Stryker Inc., MI, USA) and ChronOS® (Synthes GmbH, Switzerland), cell pellets were suspended in PTT-4 medium at a ratio of 8 million cells per 1 ml medium. UCMC cell suspension was then seeded on TissuFleece® or Integra® sheets at a density of 100000 cells/cm². Bone graft granules of BoneSave® (Stryker Inc., MI, USA) or ChronOS® (Synthes GmbH, Switzerland) were submerged and mixed well in UCMC cell suspension. UCMC cell inoculated biomaterials were maintained in PTT-4 medium for 48 hours in cell culture incubator at 37° C. and subjected to confocal microscopy analysis after staining with FDA and propidium iodide. Living UCMC cells were inoculated in TissuFleece® (FIG. 30A) and BoneSave® (Stryker Inc., MI, USA) (FIG. 30B), incubated as described above, afterwards stained with FDA and propidium iodide (PI), and then subjected to confocal microscopy analysis. The results are shown in FIGS. 30A and 30B. Cells stained with PI appear red (indicated by "R" in FIGS. 30A and 30B) and cells stained with FDA appear green (indicated by "G" in FIGS. 30A and 30B).

Both Fluorescein diacetate (FDA) (50 µg/ml) and PI (25 µg/ml) were prepared using 1×PBS. For staining of the cells, they were taken out from incubator and washed twice with 1×PBS. Afterwards they have been incubated with FDA (50 µg/ml)] in a 37° C. incubator for 15 minutes. After this, the cells were rinsed 2 times with 1×PBS. This was followed by counter staining with PI (25 µg/ml) at room temperature for 5 minutes. Then, the cells were washed 2 times with 1×PBS and the samples were kept in 1×PBS to prevent drying. After this, the cells were observed under confocal microscope as described above.

The results of this experiment show that UCMC are growing on different kind of scaffolds. Thus, UCMC can be used to engineer living soft and hard tissue for repair and regeneration.

Figure 31A:
FIG. 31A shows the UCMC populated scaffolds in growth medium before the implantation.

Example 22: Implantation of UCMC-Populated Collagen Scaffolds into Immuno-Competent Mice This experiment demonstrates the angiogenic property of UCMC. The cells were seeded into the scaffolds as previously described in Example 12. FIG. 31A shows appearance of UCMC-populated collagen lattices (scaffold) in vitro.

FIG. 31B shows implanted control cell-free collagen lattices and UCMC-populated collagen lattices in mice at day 21. No sign of immuno-rejection was observed. Macroscopic vascularization was observed in implanted UCMC-populated collagen lattice at day 21. FIG. 31C shows microscopic vascularization (indicated by arrows) of UCMC-populated collagen lattices.

This experiment clearly demonstrates the angiogenic property of UCMC. These cells can thus be used to enhance angiogenesis in tissue repair and regeneration, and to treat ischemic disorders.

Example 23: Clinical Application of UCMC for the Treatment of Full Thickness Burns Wounds This experiment shows the treatment of a 53 year old female patient who suffered from full thickness burns. In general, these kind of wounds require a skin graft to heal completely.

For the experiment mesenchymal cells of the amniotic membrane of the umbilical cord (UCMC) were isolated as described in Example 2.

Figure 32A:
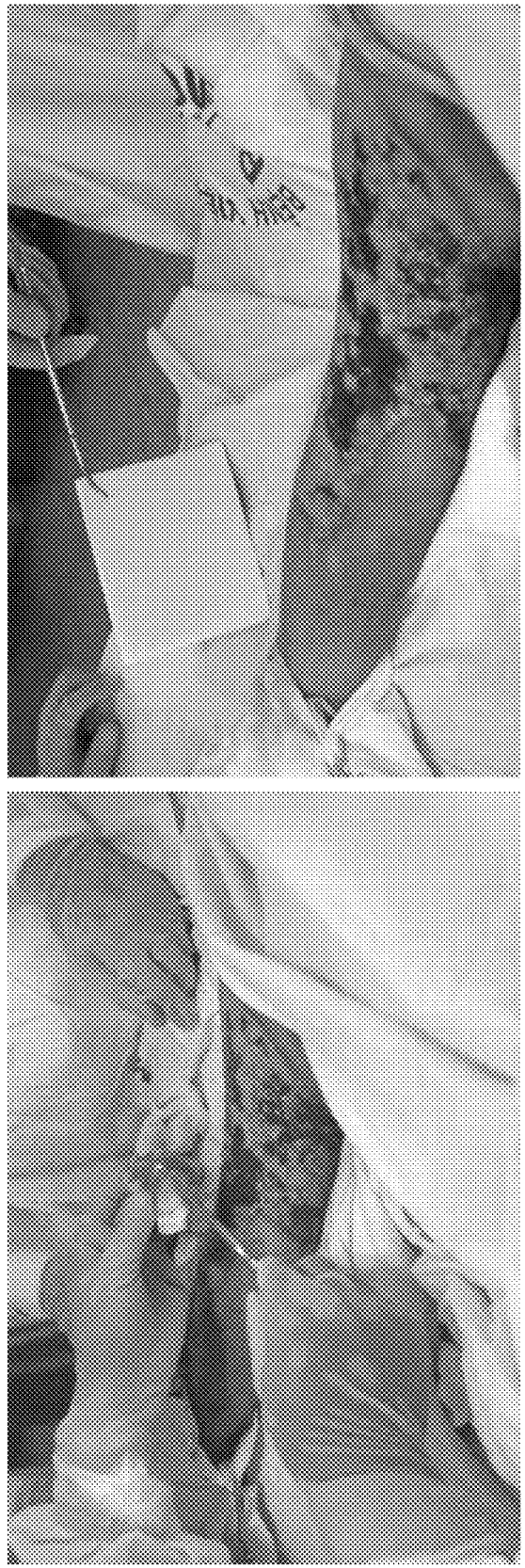
Figure 32B:

For this experiment the patient to be treated was first put under general anesthesia and then the burn necrotic tissue was surgically excised using surgical currets before applying the UCMC populated Biobrane®-L nylon membrane (Dow Hickam Pharmaceuticals, Texas, USA) to the wound of the patient (see FIG. 32B).

In the present experiment the Biobrane®-L nylon membrane was cut into round pieces to fit into 32 mm tissue culture dishes. UCMC were cultured in 150 mm tissue culture dishes and harvested by cell scraping, centrifuged and counted as previously described herein. Membrane pieces (see FIG. 32B, first picture) were wetted with DMEM medium for 48 hours before seeding UCMC with a density of 100000 cells/cm$^2$ on the membrane.

FIG. 32A shows wound bed preparation on full thickness burns (3rd degree) of 53 years old female patient. UCMC were inoculated onto Biobrane®-L wound dressings (Dow Hickam Pharmaceuticals, Texas, USA). UCMC-Biobrane constructs were transferred onto wounds (FIG. 32B). Complete healing was seen (FIG. 32C) at day 7 without skin graft and stable up to 3 month follow-up. This case shows that UCMC may have healing power of stem cells to heal this kind of burn wounds without using a skin graft, indicating that this technology may replace autologous skin graft in the future.

In FIG. 34 the treatment of full-thickness burns wound of 2 years old male patient is shown. The experiment was conducted similar to the one described above. UCMC were cultured on tissue culture dishes in DMEM/10% FCS until confluent. Cells were then harvested by scraping and mixed with SoloSite® gel (Smith & Nephew, Hull, UK) and pasted onto wound at density of 1 million cells/cm$^2$. SoloSite® is a hydrogel wound dressing with preservatives which comprises a water swellable polymer that remains gel-like until saturated. It can donate moisture to rehydrate non-viable tissue. It absorbs exudate while retaining its structure in the wound. Complete healing with this method was observed at day 5 without skin graft.

Example 24: Clinical Application of UCMC for the Treatment of Partial-Thickness Wounds This experiment demonstrates the clinical application of UCMC for the treatment of partial-thickness wounds ($2^{nd}$ degree) of a 2 year old, male patient. The experiment (wound preparation and preparation of the wound dressing etc.) was carried out as described in Example 23. UCMC were cultured on Tegaderm® wound dressing (3M Health Care, Minnesota, USA) and transferred onto wound.

The Tegaderm® wound dressing is a fast wicking, non-swelling polyurethane foam with a highly breathable film backing which prevents wound exudate strike-through and is a barrier to outside contamination while the dressing remains intact without leakage. The wound dressing consists of a urethane film backing (5-10 wt.-%), polyurethane foam (90-95 wt.-%) and a small amount of ink (0.1-1 wt.-%).

A complete healing of the partial-thickness wound was observed at day 3 (see FIG. 33). The left arrow in FIG. 33 indicates area A, i.e. the part of the wound that was treated with UCMC-loaded Tegaderm® wound dressing. The right arrow indicates area B, i.e. the part of the wound that was treated by use of the conventional method.

Figure 35:
FIG. 35 demonstrates the clinical application of UCMC for the treatment of a non-healing radiation wound in a 1 year old child, who had hemangioma. The original wound did not heal over a period of 90 days with conventional wound treatment. UCMC were cultured onto Tegaderm® wound dressing and transferred onto wounds as described in example 25. The radiation wound was healed completely over a period of 20 days of UCMC cell therapy.

Example 25: Clinical Application of UCMC for the Treatment of a Non-Healing Radiation Wound This example demonstrates the clinical application of UCMC for the treatment of a non-healing radiation wound in a 1 year old child, who had hemangioma. The original wound did not heal over a period of 90 days with conventional wound treatment. The experiment was carried out as described in Example 23. UCMC were cultured onto Tegaderm® wound dressing at density of 100000 cells/cm$^2$ and transferred onto wounds twice a week. The radiation wound was healed completely over a period of 20 days of UCMC cell therapy as can be seen in FIG. 35.

Figure 36:
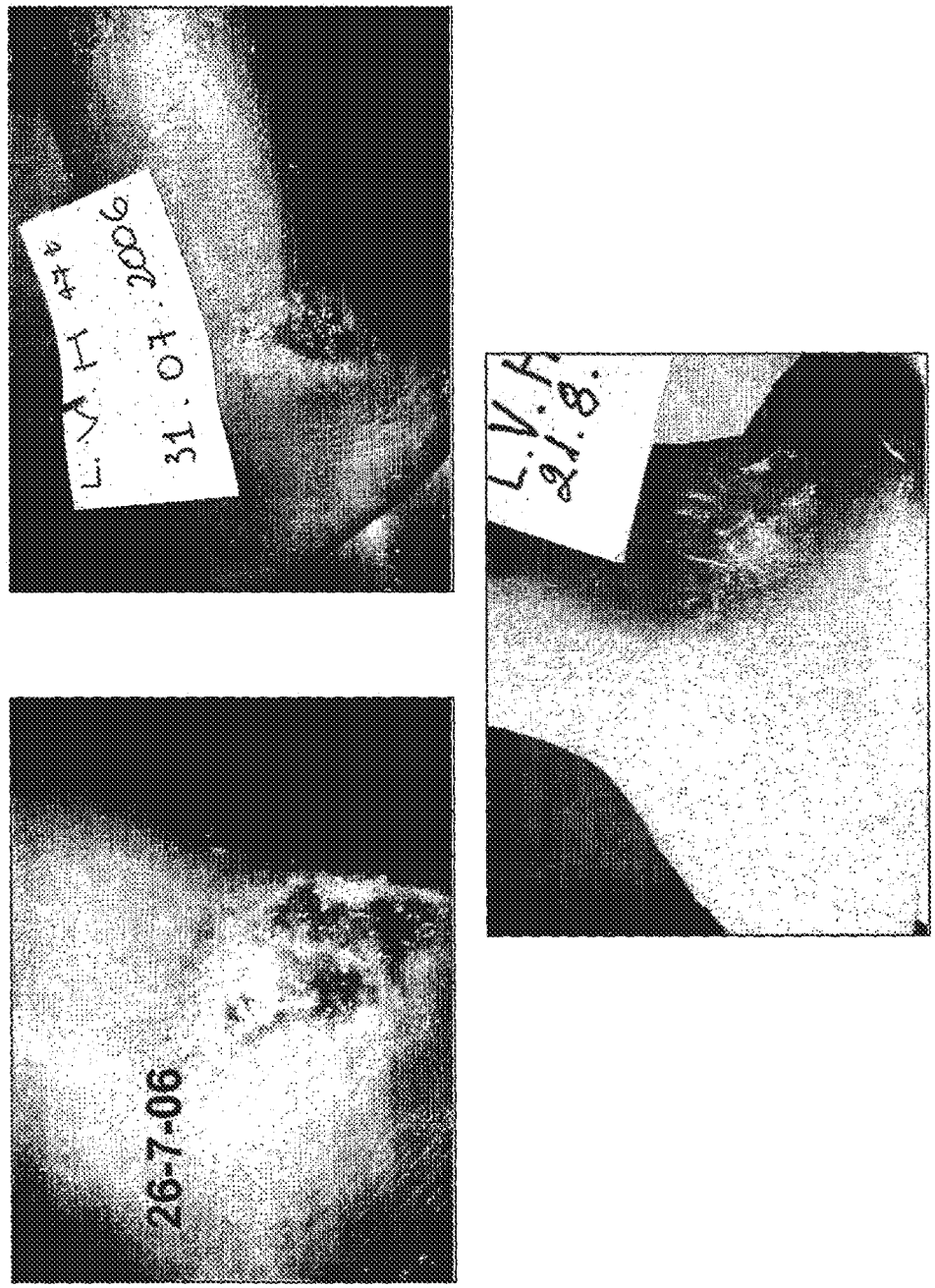
FIG. 36 and FIG. 37A and FIG. 37B demonstrate the clinical application of UCMC for treatment of a non-healing diabetic wound (FIG. 36), a non-healing diabetic food wound (FIG. 37B) and a failed skin flap donor site wound (FIG. 37A). The latter two were failed to heal under conventional treatment over a period of 6 years. UCMC were cultured and mixed with SoloSite® gel (Smith & Nephew, Hull, UK) as described in Example 26.
Figure 37A:
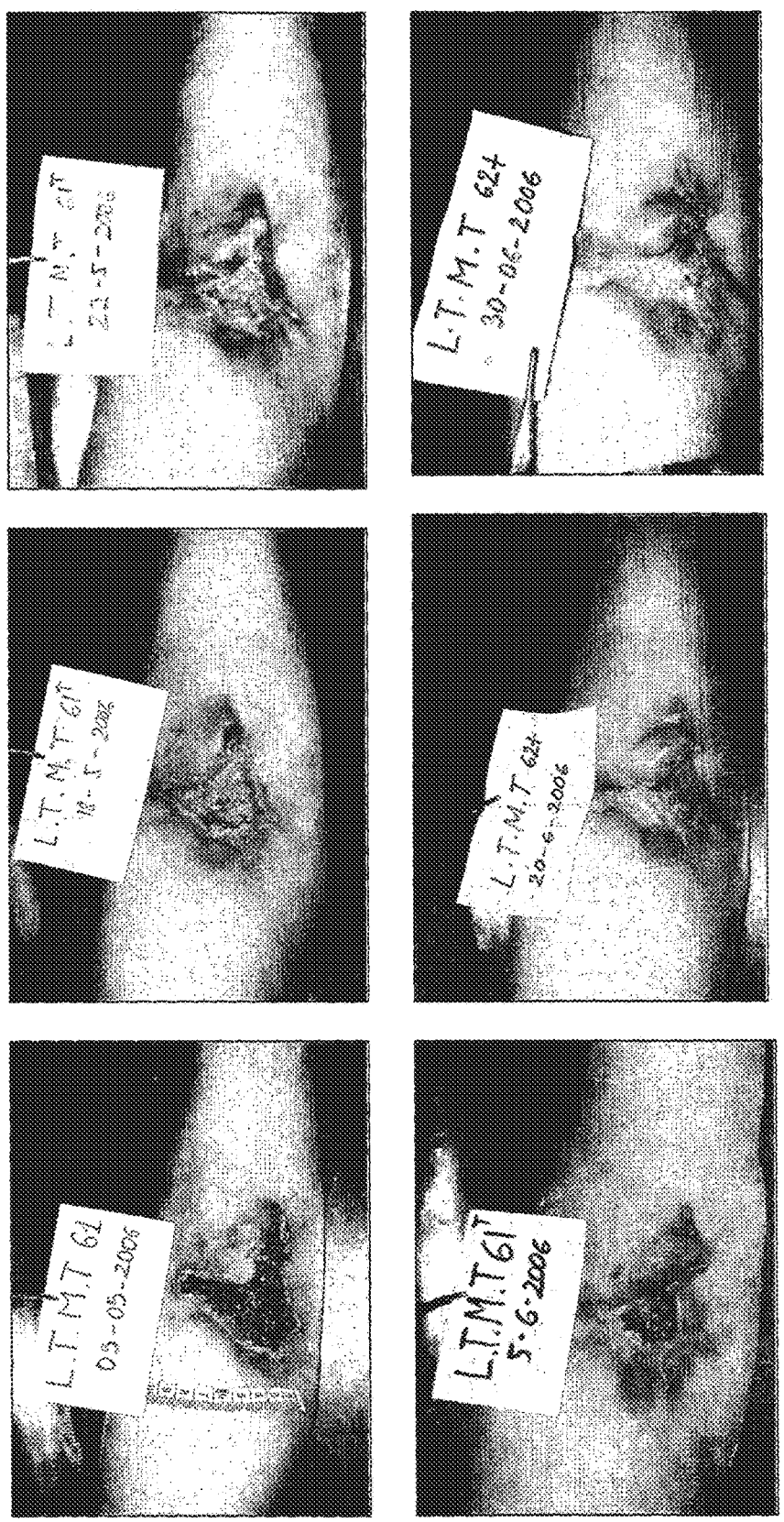
Figure 37B:

Example 26: Clinical Application of UCMC for Treatment of Non-Healing Diabetic Wound and Non-Healing Diabetic Food Wound These experiments demonstrate the clinical application of UCMC for treatment of a non-healing diabetic wound (FIG. 36), a non-healing diabetic food wound (FIG. 37B) and a failed skin flap donor site wound (FIG. 37A). The latter two were failed to heal under conventional treatment over a period of 6 years.

UCMC were cultured and mixed with SoloSite® gel (Smith & Nephew, Hull, UK) as described in example 23. The UCMC/SoloSite® gel mixture was pasted onto the wounds at a density of 1 million cells/cm$^2$. The application to the wounds was performed once a week. Complete healing of the non-healing diabetic wound was observed at day 26 (FIG. 36) whereas in case of the non-healing diabetic food wound (FIG. 37B) and the failed skin flap donor site wound (FIG. 37A) a progress of wound healing could be observed.

Example 27: Direct Differentiation of UCEC into Hepatocytes

Epithelial stem/progenitor cells from the amniotic membrane of the umbilical cord (UCEC) were isolated as described in Example 2. For differentiation of UCEC into hepatocytes, the cells were exposed to BBRC06H medium containing Oncostatin-M (50 µg/ml) (BBRC06H medium is modified version of BBRC06 as decribed in example 15 without addition of nicotinamide and with addition of Oncostatin-M at 50 µg/ml).

Figure 38:
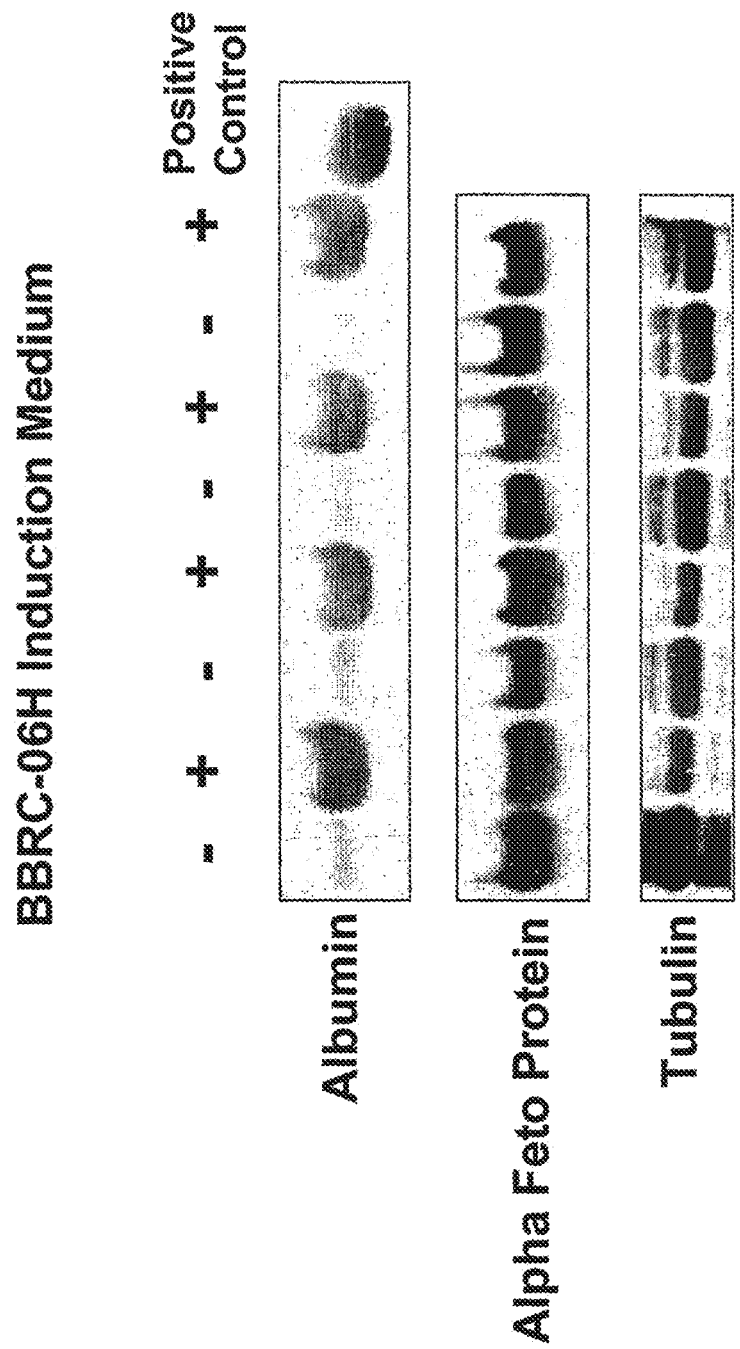
FIG. 38 shows albumin expression of UCEC under induction of BBRC06H medium (BBRC06H medium is modified version of BBRC06 as described in example 15 without addition of nicotinamide and with addition of Oncostatin-M at 50 μg/ml). This experiment shows that UCEC have potential to differentiate into hepatocytes, which can be used for the treatment of liver diseases or in-vitro models for testing cytotoxicity of new drugs.

FIG. 38 shows albumin expression of UCEC after induction with BBRC06H medium containing Oncostatin-M (50 µg/ml). Alpha Feto Protein is a stem cell marker of hepato stem/progenitor cells. When induced by induction medium, UCEC differentiate into mature hepatocytes producing more albumin. Tubulin is a house-keeping gene to show equal loading in western blot assay. This experiment shows that UCEC have the potential to differentiate into hepatocytes, which can be used for the treatment of liver diseases or in-vitro models for testing cytotoxicity of new drugs.

What is claimed is:

1. A method of generating a chondrocyte comprising:
   placing umbilical cord amniotic membrane mesenchymal stem cells (UCMC) in a container;
   culturing the UCMC in a growth medium allowing cell proliferation of the UCMC without differentiation of the UCMC; and
   culturing the UCMC in a growth medium for differentiating the UCMC into chondrocytes comprising insulin, transferrin, selenous acid, epidermal growth factor, transforming growth factor-β3, dexamethasone, ascorbic acid, sodium pyruvate, and proline to differentiate the UCMC into a chondrocyte.

2. The method of claim 1, wherein the growth medium for differentiating the UCMC into chondrocytes contains about 10 ng/mL transforming growth factor-β3, about 100 nM dexamethasone, about 50 mg/mL ascorbic acid, about 100 mg/mL sodium pyruvate, and about 40 mg/mL proline.

3. The method of claim 1, wherein the differentiation into chondrocytes is determined by staining with Alcian Blue.

4. The method of claim 1, wherein the UCMC are cultured in the growth medium for differentiating the UCMC into chondrocytes for about 4 weeks.

* * * * *